US012734521B2

(12) United States Patent
Biz et al.

(10) Patent No.: US 12,734,521 B2
(45) Date of Patent: Sep. 15, 2026

(54) APPARATUS AND METHOD FOR CONTROL OF CELL PROCESSING SYSTEM

(71) Applicant: Cellares Corporation, South San Francisco, CA (US)

(72) Inventors: Tony Biz, South San Francisco, CA (US); Vladimir Azersky, San Jose, CA (US); Adam Newton Wold, San Francisco, CA (US); Brian Alexander Pesch, San Francisco, CA (US)

(73) Assignee: Cellares Corporation, South San Francisco, CA (US)

( * ) Notice: Subject to any disclaimer, the term of this patent is extended or adjusted under 35 U.S.C. 154(b) by 0 days.

(21) Appl. No.: 19/295,488

(22) Filed: Aug. 8, 2025

(65) Prior Publication Data

US 2025/0367660 A1 Dec. 4, 2025

Related U.S. Application Data

(60) Continuation of application No. 18/799,963, filed on Aug. 9, 2024, now Pat. No. 12,491,512, which is a (Continued)

(51) Int. Cl.

| | |
|---|---|
| ***A61L 2/04*** | (2006.01) |
| ***A61L 2/20*** | (2006.01) |

(Continued)

(52) U.S. Cl.

CPC ........... *B01L 3/502715* (2013.01); *A61L 2/04* (2013.01); *A61L 2/20* (2013.01); *A61L 2/206* (2013.01);

(Continued)

(58) Field of Classification Search

CPC ............... B01L 3/502715; B01L 13/00; B01L 2200/027; B01L 2300/049; B01L 2200/04;

(Continued)

(56) References Cited

U.S. PATENT DOCUMENTS

| | | | |
|---|---|---|---|
| 3,728,227 | A | 4/1973 | Elson et al. |
| 4,138,999 | A | 2/1979 | Eckhart et al. |

(Continued)

FOREIGN PATENT DOCUMENTS

| | | | |
|---|---|---|---|
| CN | 104203333 | A | 12/2014 |
| CN | 108660060 | A | 10/2018 |

(Continued)

OTHER PUBLICATIONS

ChargePoint (2021). Aseptic split butterfly valve 10-6 sterility assurance, located at https://www.thechargepoint.com/products/aseptic-split-butterfly-valve-10-6-sterility-assurance/, 2 total pages.

(Continued)

*Primary Examiner* — Jason Holloway

(74) *Attorney, Agent, or Firm* — Cooley LLP

(57) ABSTRACT

Disclosed herein are cell processing systems, devices, and methods thereof. A system for cell processing may comprise a plurality of instruments each independently configured to perform one or more cell processing operations upon a cartridge, and a robot capable of moving the cartridge between each of the plurality of instruments.

14 Claims, 132 Drawing Sheets

Related U.S. Application Data continuation of application No. 18/244,051, filed on Sep. 8, 2023, now Pat. No. 12,551,887, which is a division of application No. 17/579,478, filed on Jan. 19, 2022, now Pat. No. 11,872,557, which is a continuation of application No. 17/198,134, filed on Mar. 10, 2021, now Pat. No. 12,157,119.

(60) Provisional application No. 63/093,038, filed on Oct. 16, 2020, provisional application No. 62/987,745, filed on Mar. 10, 2020.

(51) Int. Cl.

| | |
|---|---|
| ***A61L 2/206*** | (2026.01) |
| ***A61L 2/208*** | (2026.01) |
| ***B01J 19/00*** | (2006.01) |
| ***B01L 3/00*** | (2006.01) |
| ***C12M 1/00*** | (2006.01) |
| ***C12M 1/36*** | (2006.01) |
| ***C12M 3/00*** | (2006.01) |
| ***C12N 5/00*** | (2006.01) |
| *A61L 2/08* | (2006.01) |

(52) U.S. Cl.

CPC ............ *A61L 2/208* (2013.01); *B01J 19/004* (2013.01); *B01L 13/00* (2019.08); *C12M 23/44* (2013.01); *C12M 23/50* (2013.01); *C12M 41/48* (2013.01); *C12N 5/00* (2013.01); *C12N 5/0081* (2013.01); *A61L 2/08* (2013.01); *A61L 2202/11* (2013.01); *A61L 2202/122* (2013.01); *A61L 2202/123* (2013.01); *A61L 2202/14* (2013.01); *B01J 2219/0002* (2013.01); *B01J 2219/0074* (2013.01); *B01L 2200/027* (2013.01); *B01L 2300/049* (2013.01)

(58) Field of Classification Search

CPC ............. A61L 2/04; A61L 2/20; A61L 2/206; A61L 2/208; A61L 2/08; A61L 2202/11; A61L 2202/122; A61L 2202/123; A61L 2202/14; B01J 19/004; B01J 2219/0002; B01J 2219/0074; C12M 23/44; C12M 23/50; C12M 41/48; C12M 23/10; C12M 23/24; C12M 23/34; C12M 23/42; C12M 29/04; C12M 33/10; C12M 35/02; C12M 35/06; C12M 37/00; C12M 47/02; C12N 5/00; C12N 5/0081; B04B 2005/0471

See application file for complete search history.

(56) References Cited

U.S. PATENT DOCUMENTS

| | | | |
|---|---|---|---|
| D252,282 | S | 7/1979 | Wettermann et al. |
| 4,234,023 | A | 11/1980 | Sogi et al. |
| 4,673,334 | A | 6/1987 | Allington et al. |
| 4,696,902 | A | 9/1987 | Bisconte |
| 4,751,184 | A | 6/1988 | Higo et al. |
| D301,926 | S | 6/1989 | Weissman |
| 4,839,292 | A | 6/1989 | Cremonese |
| 4,911,833 | A | 3/1990 | Schoendorfer et al. |
| 5,058,619 | A | 10/1991 | Zheng |
| 5,656,491 | A | 8/1997 | Cassani et al. |
| 6,102,678 | A | 8/2000 | Peclat |
| 6,267,559 | B1 | 7/2001 | Mossman et al. |
| 6,374,684 | B1 | 4/2002 | Dority |
| 6,649,419 | B1 | 11/2003 | Anderson |
| D486,580 | S | 2/2004 | Abdel-Model |
| 6,773,669 | B1 | 8/2004 | Holaday et al. |
| D503,479 | S | 3/2005 | Ina et al. |
| 6,891,182 | B2 | 5/2005 | Watari et al. |
| D555,527 | S | 11/2007 | Lesage |
| D565,178 | S | 3/2008 | Tanaka |
| 7,422,850 | B2 | 9/2008 | Marshall et al. |
| D581,823 | S | 12/2008 | Mori et al. |
| 7,521,224 | B2 | 4/2009 | Johnson et al. |
| 7,550,287 | B2 | 6/2009 | Hibino et al. |
| 7,745,209 | B2 | 6/2010 | Martin et al. |
| D626,224 | S | 10/2010 | Amano et al. |
| 7,816,128 | B2 | 10/2010 | Nakashima et al. |
| D657,068 | S | 4/2012 | Shibata |
| 8,158,426 | B2 | 4/2012 | Wilson et al. |
| 8,158,427 | B2 | 4/2012 | Wilson et al. |
| D660,453 | S | 5/2012 | Jani et al. |
| 8,168,432 | B2 | 5/2012 | Wilson et al. |
| D664,459 | S | 7/2012 | Rha |
| 8,273,572 | B2 | 9/2012 | Martin et al. |
| 8,415,144 | B2 | 4/2013 | Wilson et al. |
| 8,440,458 | B2 | 5/2013 | Zijlstra et al. |
| 8,470,589 | B2 | 6/2013 | Martin et al. |
| D686,335 | S | 7/2013 | Feuerabend et al. |
| 8,492,140 | B2 | 7/2013 | Smith et al. |
| 8,546,142 | B2 | 10/2013 | Martin et al. |
| D693,712 | S | 11/2013 | Noda et al. |
| D693,714 | S | 11/2013 | Noda et al. |
| D699,609 | S | 2/2014 | Noda et al. |
| 8,671,964 | B2 | 3/2014 | Py |
| 8,697,443 | B2 | 4/2014 | Wilson et al. |
| D705,943 | S | 5/2014 | Chang et al. |
| 8,727,132 | B2 | 5/2014 | Miltenyi et al. |
| 8,809,044 | B2 | 8/2014 | Wilson |
| 8,846,399 | B2 | 9/2014 | Martin et al. |
| D717,460 | S | 11/2014 | Manian |
| D719,667 | S | 12/2014 | Manian |
| 8,956,860 | B2 | 2/2015 | Vera et al. |
| 9,040,290 | B2 | 5/2015 | Martin et al. |
| 9,045,721 | B2 | 6/2015 | Martin et al. |
| 9,080,149 | B2 | 7/2015 | Bosio et al. |
| D745,185 | S | 12/2015 | Kimura et al. |
| 9,255,243 | B2 | 2/2016 | Wilson et al. |
| 9,279,099 | B2 | 3/2016 | Okano et al. |
| 9,290,730 | B2 | 3/2016 | Martin et al. |
| 9,410,114 | B2 | 8/2016 | Wilson et al. |
| 9,441,192 | B2 | 9/2016 | Wilson et al. |
| 9,499,780 | B2 | 11/2016 | Smith et al. |
| 9,534,195 | B2 | 1/2017 | Smith et al. |
| 9,556,485 | B2 | 1/2017 | Lin et al. |
| 9,567,565 | B2 | 2/2017 | Vera et al. |
| 9,597,355 | B2 | 3/2017 | Magnant |
| 9,625,463 | B2 | 4/2017 | Miltenyi et al. |
| 9,701,932 | B2 | 7/2017 | Smith et al. |
| D794,822 | S | 8/2017 | Choudhary |
| 9,726,314 | B2 | 8/2017 | Py |
| 9,732,317 | B2 | 8/2017 | Wilson |
| 9,783,768 | B2 | 10/2017 | Larcher et al. |
| D802,156 | S | 11/2017 | Barton et al. |
| 9,845,451 | B2 | 12/2017 | Martin et al. |
| D809,948 | S | 2/2018 | Hirche et al. |
| 10,047,342 | B2 | 8/2018 | Eibl et al. |
| 10,053,663 | B2 | 8/2018 | Kabaha et al. |
| 10,119,970 | B2 | 11/2018 | Miltenyi et al. |
| 10,131,876 | B2 | 11/2018 | Kaiser et al. |
| D846,745 | S | 4/2019 | Clifford et al. |
| 10,253,316 | B2 | 4/2019 | Masquelier et al. |
| 10,294,658 | B2 | 5/2019 | Scannon et al. |
| 10,323,258 | B2 | 6/2019 | Bernate et al. |
| 10,329,559 | B1 | 6/2019 | Masquelier et al. |
| 10,385,307 | B2 | 8/2019 | Rowley et al. |
| 10,421,959 | B1 | 9/2019 | Masquelier et al. |
| D870,576 | S | 12/2019 | Kang |
| D870,911 | S | 12/2019 | Kang |
| D870,917 | S | 12/2019 | Kang |
| 10,508,288 | B1 | 12/2019 | Bernate et al. |
| 10,519,437 | B1 | 12/2019 | Masquelier et al. |
| 10,533,156 | B2 | 1/2020 | Vera et al. |
| 10,584,333 | B1 | 3/2020 | Masquelier et al. |
| 10,584,334 | B1 | 3/2020 | Masquelier et al. |
| 10,588,994 | B2 | 3/2020 | Kawamura et al. |
| 10,620,212 | B2 | 4/2020 | Miltenyi et al. |
| D883,510 | S | 5/2020 | Neuman |
| D885,216 | S | 5/2020 | Hu et al. |

(56) References Cited

U.S. PATENT DOCUMENTS

| | | | |
|---|---|---|---|
| D886,653 | S | 6/2020 | Sugie |
| 10,689,669 | B1 | 6/2020 | Feldman et al. |
| 10,705,090 | B2 | 7/2020 | Miltenyi et al. |
| 10,705,091 | B2 | 7/2020 | Miltenyi et al. |
| 10,723,986 | B2 | 7/2020 | Smith et al. |
| 10,724,043 | B2 | 7/2020 | Sixto et al. |
| 10,844,338 | B1 | 11/2020 | Smith et al. |
| D927,725 | S | 8/2021 | Irle et al. |
| D932,929 | S | 10/2021 | Stone et al. |
| D933,848 | S | 10/2021 | Shapiro et al. |
| 11,161,111 | B2 | 11/2021 | Kabaha et al. |
| 11,198,845 | B2 | 12/2021 | Parietti et al. |
| D941,488 | S | 1/2022 | Fang et al. |
| 11,371,018 | B2 | 6/2022 | Shi et al. |
| 11,376,587 | B2 | 7/2022 | Thakkar et al. |
| 11,447,745 | B2 | 9/2022 | Shi et al. |
| D990,346 | S | 6/2023 | Stone et al. |
| 11,701,654 | B2 | 7/2023 | Azersky et al. |
| 11,786,896 | B2 | 10/2023 | Thakkar et al. |
| 11,826,756 | B2 | 11/2023 | Azersky et al. |
| 11,872,557 | B2 | 1/2024 | Biz et al. |
| D1,020,502 | S | 4/2024 | Kang |
| D1,035,041 | S | 7/2024 | Saiz et al. |
| 12,157,119 | B2 | 12/2024 | Gerlinghaus et al. |
| 12,180,453 | B2 | 12/2024 | Chang et al. |
| D1,067,457 | S | 3/2025 | Fontova et al. |
| D1,071,761 | S | 4/2025 | Nguyen et al. |
| 12,305,156 | B2 | 5/2025 | Burkeen et al. |
| D1,080,914 | S | 6/2025 | Chang et al. |
| 12,337,321 | B2 | 6/2025 | Malleo et al. |
| 12,350,664 | B2 | 7/2025 | Pesch et al. |
| 12,350,667 | B2 | 7/2025 | Azersky et al. |
| 12,350,668 | B2 | 7/2025 | Azersky et al. |
| 12,399,193 | B2 | 8/2025 | Tian et al. |
| D1,094,762 | S | 9/2025 | Fontova et al. |
| D1,094,763 | S | 9/2025 | Fontova et al. |
| 12,403,468 | B2 | 9/2025 | Azersky et al. |
| 12,491,512 | B2 | 12/2025 | Biz et al. |
| 12,492,368 | B2 | 12/2025 | Carmichael et al. |
| 12,497,587 | B2 | 12/2025 | Grout et al. |
| D1,109,359 | S | 1/2026 | Shimizu et al. |
| D1,109,621 | S | 1/2026 | Cesarek et al. |
| 12,551,887 | B2 | 2/2026 | Biz et al. |
| 12,559,710 | B2 | 2/2026 | Azersky et al. |
| D1,115,568 | S | 3/2026 | Henssler et al. |
| D1,116,881 | S | 3/2026 | Furukawa et al. |
| D1,116,882 | S | 3/2026 | Blake et al. |
| 12,570,948 | B2 | 3/2026 | Thakkar et al. |
| 2002/0146817 | A1 | 10/2002 | Cannon et al. |
| 2003/0030272 | A1 | 2/2003 | Johnson et al. |
| 2003/0031542 | A1 | 2/2003 | Hamel et al. |
| 2004/0121454 | A1 | 6/2004 | Jury et al. |
| 2004/0266015 | A1 | 12/2004 | Favuzzi et al. |
| 2005/0053502 | A1 | 3/2005 | Souza |
| 2005/0070018 | A1 | 3/2005 | Johnson et al. |
| 2005/0186671 | A1 | 8/2005 | Cannon et al. |
| 2005/0221470 | A1 | 10/2005 | Matsumoto et al. |
| 2005/0260743 | A1 | 11/2005 | Drake et al. |
| 2006/0194193 | A1 | 8/2006 | Tsuruta et al. |
| 2006/0257999 | A1* | 11/2006 | Chang .................... C40B 60/06 435/289.1 |
| 2007/0185472 | A1 | 8/2007 | Baumfalk et al. |
| 2008/0057568 | A1 | 3/2008 | Kan et al. |
| 2008/0176318 | A1 | 7/2008 | Wilson et al. |
| 2009/0042281 | A1 | 2/2009 | Chang et al. |
| 2009/0053799 | A1 | 2/2009 | Chang-Yen et al. |
| 2009/0130745 | A1 | 5/2009 | Williams et al. |
| 2009/0247417 | A1 | 10/2009 | Haas et al. |
| 2010/0120129 | A1 | 5/2010 | Amshey et al. |
| 2010/0130732 | A1 | 5/2010 | Chung et al. |
| 2010/0151571 | A1 | 6/2010 | Vukasinovic et al. |
| 2010/0172045 | A1 | 7/2010 | Goodman et al. |
| 2010/0301071 | A1 | 12/2010 | Alstad et al. |
| 2011/0003380 | A1 | 1/2011 | Miltenyi et al. |
| 2011/0079071 | A1 | 4/2011 | Schultz et al. |
| 2011/0223064 | A1 | 9/2011 | Katsumi et al. |
| 2011/0229927 | A1 | 9/2011 | Larsen et al. |
| 2011/0262896 | A1 | 10/2011 | Blecka et al. |
| 2012/0138156 | A1 | 6/2012 | Hofman et al. |
| 2012/0148415 | A1 | 6/2012 | Brueckner |
| 2012/0174687 | A1 | 7/2012 | Ohga et al. |
| 2012/0283867 | A1 | 11/2012 | Gelbman et al. |
| 2012/0293338 | A1 | 11/2012 | Chaffey et al. |
| 2013/0078624 | A1 | 3/2013 | Holmes et al. |
| 2013/0115617 | A1 | 5/2013 | Wilson |
| 2013/0132006 | A1 | 5/2013 | Gwynn et al. |
| 2013/0189120 | A1 | 7/2013 | Nelson et al. |
| 2014/0309795 | A1 | 10/2014 | Norton et al. |
| 2015/0158907 | A1 | 6/2015 | Zhou et al. |
| 2015/0307829 | A1 | 10/2015 | Dedry et al. |
| 2015/0336096 | A1 | 11/2015 | Smith et al. |
| 2016/0060680 | A1 | 3/2016 | Buse et al. |
| 2016/0161516 | A1 | 6/2016 | Fritchie et al. |
| 2016/0208216 | A1 | 7/2016 | Vera et al. |
| 2016/0244714 | A1 | 8/2016 | Spuhler et al. |
| 2016/0303563 | A1 | 10/2016 | Granier et al. |
| 2016/0320381 | A1* | 11/2016 | Holmes .................. G01N 35/10 |
| 2016/0320422 | A1 | 11/2016 | Fritchie et al. |
| 2017/0014149 | A1 | 1/2017 | Nakayashiki et al. |
| 2017/0058257 | A1 | 3/2017 | Levner et al. |
| 2017/0058527 | A1 | 3/2017 | Williams et al. |
| 2017/0239420 | A1 | 8/2017 | Wells |
| 2017/0248697 | A1 | 8/2017 | Lo |
| 2017/0307502 | A1 | 10/2017 | Mason et al. |
| 2017/0313977 | A1 | 11/2017 | Wilson |
| 2017/0321226 | A1 | 11/2017 | Gill et al. |
| 2017/0348525 | A1 | 12/2017 | Sano et al. |
| 2017/0362554 | A1 | 12/2017 | Martin et al. |
| 2018/0031592 | A1 | 2/2018 | Dority |
| 2018/0051243 | A1 | 2/2018 | Hogan et al. |
| 2018/0078935 | A1 | 3/2018 | Hung et al. |
| 2018/0185849 | A1 | 7/2018 | Kaplan et al. |
| 2018/0196918 | A1 | 7/2018 | Sadowski et al. |
| 2019/0002874 | A1* | 1/2019 | Belgrader ............ C12Q 1/6865 |
| 2019/0151852 | A1 | 5/2019 | Wiederin et al. |
| 2019/0212233 | A1 | 7/2019 | Jovanovich et al. |
| 2019/0275519 | A1 | 9/2019 | Castillo et al. |
| 2019/0292510 | A1 | 9/2019 | Tandon et al. |
| 2019/0293673 | A1 | 9/2019 | Wescott et al. |
| 2019/0316120 | A1 | 10/2019 | Masquelier et al. |
| 2019/0330579 | A1 | 10/2019 | Guenat et al. |
| 2020/0009557 | A1 | 1/2020 | Frigard et al. |
| 2020/0017901 | A1 | 1/2020 | Collins et al. |
| 2020/0025782 | A1 | 1/2020 | Ahlfors |
| 2020/0033372 | A1 | 1/2020 | Tajima |
| 2020/0048599 | A1 | 2/2020 | Firouzi et al. |
| 2020/0095550 | A1 | 3/2020 | Vera et al. |
| 2020/0132534 | A1 | 4/2020 | Luedemann |
| 2020/0159198 | A1 | 5/2020 | Kapre et al. |
| 2020/0224147 | A1 | 7/2020 | Rogers et al. |
| 2020/0283713 | A1 | 9/2020 | Ball et al. |
| 2020/0292552 | A1 | 9/2020 | Miltenyi et al. |
| 2020/0353004 | A1 | 11/2020 | Nowak et al. |
| 2020/0368411 | A1 | 11/2020 | Camisani et al. |
| 2020/0399578 | A1 | 12/2020 | Corso et al. |
| 2020/0406221 | A1 | 12/2020 | Dabrowski et al. |
| 2021/0001339 | A1 | 1/2021 | Liu et al. |
| 2021/0032583 | A1 | 2/2021 | Smith et al. |
| 2021/0035655 | A1 | 2/2021 | Tanouchi et al. |
| 2021/0040472 | A1 | 2/2021 | Deutsch et al. |
| 2021/0047668 | A1 | 2/2021 | Dabrowski et al. |
| 2021/0079344 | A1 | 3/2021 | Bosio et al. |
| 2021/0147807 | A1 | 5/2021 | Lickert et al. |
| 2021/0244255 | A1 | 8/2021 | Haegermarck et al. |
| 2021/0253997 | A1 | 8/2021 | Wilson |
| 2021/0269755 | A1 | 9/2021 | Smith et al. |
| 2021/0283565 | A1 | 9/2021 | Gerlinghaus et al. |
| 2021/0284948 | A1 | 9/2021 | Hauwaerts et al. |
| 2021/0301239 | A1 | 9/2021 | Natsume et al. |
| 2021/0324318 | A1 | 10/2021 | Parietti et al. |
| 2021/0354104 | A1 | 11/2021 | Pesch et al. |
| 2022/0002652 | A1 | 1/2022 | Patrick et al. |
| 2022/0003796 | A1 | 1/2022 | Ahlfors |
| 2022/0047862 | A1 | 2/2022 | Chang et al. |

(56) References Cited

U.S. PATENT DOCUMENTS

| | | | |
|---|---|---|---|
| 2022/0118442 | A1 | 4/2022 | Handique et al. |
| 2022/0121181 | A1 | 4/2022 | Sobalvarro et al. |
| 2022/0127558 | A1 | 4/2022 | Sowwan et al. |
| 2022/0134338 | A1 | 5/2022 | Chang et al. |
| 2022/0143610 | A1 | 5/2022 | Biz et al. |
| 2022/0150650 | A1 | 5/2022 | Rucker |
| 2022/0163438 | A1 | 5/2022 | Klas et al. |
| 2022/0170951 | A1 | 6/2022 | Holmes et al. |
| 2022/0259546 | A1 | 8/2022 | Blanchard |
| 2022/0282199 | A1 | 9/2022 | Vann |
| 2022/0284574 | A1 | 9/2022 | Wagner et al. |
| 2022/0325219 | A1 | 10/2022 | Parietti et al. |
| 2022/0325240 | A1 | 10/2022 | McFarland et al. |
| 2022/0347683 | A1 | 11/2022 | Thakkar et al. |
| 2023/0044320 | A1 | 2/2023 | Chalony et al. |
| 2023/0051840 | A1 | 2/2023 | Kelso et al. |
| 2023/0149922 | A1 | 5/2023 | Thakkar et al. |
| 2023/0159917 | A1 | 5/2023 | Handique et al. |
| 2023/0321650 | A1 | 10/2023 | Azersky et al. |
| 2023/0415154 | A1 | 12/2023 | Pesch et al. |
| 2023/0415155 | A1 | 12/2023 | Biz et al. |
| 2024/0018955 | A1 | 1/2024 | Hannah et al. |
| 2024/0142485 | A1 | 5/2024 | Meng et al. |
| 2024/0165613 | A1 | 5/2024 | Azersky et al. |
| 2024/0167466 | A1 | 5/2024 | Paraluppi |
| 2024/0240764 | A1 | 7/2024 | Gabrielli et al. |
| 2024/0254426 | A1 | 8/2024 | Elpel et al. |
| 2024/0255537 | A1 | 8/2024 | Malleo et al. |
| 2024/0279585 | A1 | 8/2024 | Griffin et al. |
| 2024/0279588 | A1 | 8/2024 | Malleo et al. |
| 2024/0318116 | A1 | 9/2024 | Chang et al. |
| 2024/0326043 | A1 | 10/2024 | Gerlinghaus et al. |
| 2024/0369586 | A1 | 11/2024 | Tian et al. |
| 2024/0377420 | A1 | 11/2024 | Cesarek |
| 2024/0390897 | A1 | 11/2024 | Azersky et al. |
| 2024/0390898 | A1 | 11/2024 | Azersky et al. |
| 2024/0399365 | A1 | 12/2024 | Biz et al. |
| 2024/0402206 | A1 | 12/2024 | Boppart et al. |
| 2024/0426292 | A1 | 12/2024 | Barrett et al. |
| 2025/0002837 | A1 | 1/2025 | Thakkar et al. |
| 2025/0059492 | A1 | 2/2025 | Beban et al. |
| 2025/0065331 | A1 | 2/2025 | Malleo et al. |
| 2025/0066708 | A1 | 2/2025 | Burkeen et al. |
| 2025/0066709 | A1 | 2/2025 | Grout et al. |
| 2025/0129321 | A1 | 4/2025 | Malleo et al. |
| 2025/0207076 | A1 | 6/2025 | Marchiando et al. |
| 2025/0236832 | A1 | 7/2025 | Chang et al. |
| 2025/0283026 | A1 | 9/2025 | Carmichael et al. |
| 2025/0304904 | A1 | 10/2025 | Azersky et al. |
| 2025/0360504 | A1 | 11/2025 | Azersky et al. |
| 2025/0368943 | A1 | 12/2025 | Burkeen et al. |
| 2025/0375767 | A1 | 12/2025 | Malleo et al. |
| 2026/0029422 | A1 | 1/2026 | Malleo et al. |
| 2026/0056220 | A1 | 2/2026 | Tian et al. |

FOREIGN PATENT DOCUMENTS

| | | | |
|---|---|---|---|
| DE | 69700070 | T2 | 5/1999 |
| EP | 0246912 | A2 | 11/1987 |
| EP | 0991389 | A1 | 4/2000 |
| EP | 0824380 | B1 | 1/2002 |
| EP | 3134512 | B1 | 1/2019 |
| EP | 2809449 | B1 | 10/2019 |
| EP | 3359294 | B1 | 5/2020 |
| EP | 3928867 | A1 | 12/2021 |
| GB | 2268187 | A | 1/1994 |
| JP | 2007325586 | A | 12/2007 |
| KR | 20130018286 | A | 2/2013 |
| KR | 20130065210 | A | 6/2013 |
| KR | 20220131302 | A | 9/2022 |
| WO | WO-9320440 | A1 | 10/1993 |
| WO | WO-2006102416 | A2 | 9/2006 |
| WO | WO-2006112870 | A1 | 10/2006 |
| WO | WO-2006118282 | A1 | 11/2006 |
| WO | WO-2007139742 | A1 | 12/2007 |
| WO | WO-2009072003 | A2 | 6/2009 |
| WO | WO-2017041051 | A1 | 3/2017 |
| WO | WO-2017123663 | A1 | 7/2017 |
| WO | WO-2017190790 | A1 | 11/2017 |
| WO | WO-2018015561 | A1 | 1/2018 |
| WO | WO-2018102471 | A1 | 6/2018 |
| WO | WO-2019232504 | A2 | 12/2019 |
| WO | WO-2020009700 | A1 | 1/2020 |
| WO | WO-2020014264 | A1 | 1/2020 |
| WO | WO-2021168368 | A1 | 8/2021 |
| WO | WO-2021183687 | A2 | 9/2021 |
| WO | WO-2021212124 | A1 | 10/2021 |
| WO | WO-2022137061 | A1 | 6/2022 |
| WO | WO-2023055543 | A1 | 4/2023 |
| WO | WO-2023064187 | A1 | 4/2023 |
| WO | WO-2024044161 | A1 | 2/2024 |
| WO | WO-2024102996 | A1 | 5/2024 |
| WO | WO-2024112702 | A1 | 5/2024 |
| WO | WO-2024152008 | A1 | 7/2024 |
| WO | WO-2024197093 | A2 | 9/2024 |
| WO | WO-2024206703 | A1 | 10/2024 |
| WO | WO-2024233080 | A1 | 11/2024 |
| WO | WO-2024249904 | A1 | 12/2024 |
| WO | WO-2025007051 | A2 | 1/2025 |
| WO | WO-2025038974 | A1 | 2/2025 |
| WO | WO-2025041046 | A1 | 2/2025 |
| WO | WO-2025041047 | A1 | 2/2025 |
| WO | WO-2025041064 | A2 | 2/2025 |
| WO | WO-2025202944 | A2 | 10/2025 |
| WO | WO-2026003813 | A2 | 1/2026 |
| WO | WO-2026024910 | A2 | 1/2026 |

OTHER PUBLICATIONS

CPC (2014). "6 traits of non-spill: How quick disconnect couplings evolved for low-pressure fluid handling," White Paper 8004, 4 total pages.

CPC (2014). "How single-use connections advance aseptic processing: Increased process flexibility and reliability, reduced costs," White Paper 7004, 6 total pages.

CPC (2018). Comparison Guide: Tube Welders and Aseptic Connectors, Technical Guide 7009, 3 total pages.

EMD Millipore (2015). "Lynx® S2S Connector—Low temperature compatibility (−80ΔC)," 4 total pages.

Final Office Action for U.S. Appl. No. 17/331,554 mailed Aug. 29, 2024, 18 pages.

Final Office Action for U.S. Appl. No. 18/244,051 mailed Apr. 4, 2025, 11 pages.

Final Office Action for U.S. Appl. No. 18/652,602 mailed Nov. 1, 2024, 29 pages.

Final Office Action for U.S. Appl. No. 18/731,095 mailed Aug. 7, 2025, 35 pages.

Final Office Action for U.S. Appl. No. 18/731,095 mailed Nov. 26, 2024, 31 pages.

Final Office Action for U.S. Appl. No. 18/759,602 mailed on May 28, 2025, 12 pages.

Final Office Action for U.S. Appl. No. 18/799,963 mailed Jan. 30, 2025, 10 pages.

Final Office Action for U.S. Appl. No. 18/807,699 mailed on Aug. 20, 2025, 22 pages.

Final Office Action for U.S. Appl. No. 18/810,386 mailed on Mar. 28, 2025, 8 pages.

Final Office Action for U.S. Appl. No. 18/920,607 mailed Jun. 4, 2025, 10 pages.

Final Office Action for U.S. Appl. No. 18/988,628 mailed Jun. 12, 2025, 16 pages.

Final Office Action mailed on Apr. 28, 2022, for U.S. Appl. No. 17/198,134, filed Mar. 10, 2021, 11 pages.

Final Office Action mailed on Apr. 28, 2022, for U.S. Appl. No. 17/331,554, filed May 26, 2021, 16 pages.

Final Office Action mailed on Jul. 31, 2023, for U.S. Appl. No. 17/331,554, filed May 26, 2021, 19 pages.

Final Office Action mailed on Mar. 31, 2023, for U.S. Appl. No. 17/579,478, filed Jan. 19, 2022, 8 pages.

(56) References Cited

OTHER PUBLICATIONS

Garcia et al., "Microfluidic Screening of Electric Fields for Electroporation" Sci Rep. Feb. 19, 2016; 6:21238. pp. 1-11.
Genetic Engineering & Biotechnology News (2006). "Thermal welding for sterile connections," located at https://www.genengnews.com/magazine/47/thermal-welding-for-sterile-connections/, 5 total pages.
International Search Report and Written Opinion for Application No. PCT/US2024/025064 mailed Sep. 6, 2024, 17 pages.
International Search Report and Written Opinion for International Application No. PCT/IB2024/058106 mailed Jan. 21, 2025, 13 pages.
International Search Report and Written Opinion for International Application No. PCT/IB2024/058148 mailed Mar. 3, 2025, 21 pages.
International Search Report and Written Opinion for International Application No. PCT/US2023/080593 dated Mar. 21, 2024, 12 pages.
International Search Report and Written Opinion for PCT Application No. PCT/IB2024/058105 mailed Dec. 16, 2024, 12 pages.
International Search Report and Written Opinion for PCT Application No. PCT/US2024/011486 dated May 24, 2024, 12 pages.
International Search Report and Written Opinion for PCT Application No. PCT/US2024/020809 mailed Mar. 24, 2025, 19 pages.
International Search Report and Written Opinion for PCT Application No. PCT/US2024/032062 mailed Sep. 6, 2024, 15 pages.
International Search Report and Written Opinion for PCT Application No. PCT/US2024/036245 mailed Jun. 11, 2025, 13 pages.
International Search Report and Written Opinion for PCT Application No. PCT/US2024/042795 mailed Dec. 16, 2024, 11 pages.
International Search Report mailed on Oct. 13, 2021, for PCT Application No. PCT/US2021/021773, filed on Mar. 10, 2021, 13 pages.
Invitation to Pay Additional fees for International Application No. PCT/IB2024/058148, mailed Jan. 2, 2025, 13 pages.
Invitation to Pay Additional fees for International Application No. PCT/US2024/020809, mailed Jan. 27, 2025, 17 pages.
Invitation to Pay Additional Fees for International Application No. PCT/US2024/022079 dated Jul. 17, 2024, 19 pages.
Invitation to Pay Additional fees for International Application No. PCT/US2024/025064, mailed Jul. 16, 2024, 12 pages.
Jain, S. et al. (2011). "The complete automation of cell culture: improvements for high-throughput and high-content screening," J. Biomol. Screen 16:932-939.
Kato, R. et al. (2010). "A Compact, Automated Cell Culture System for Clinical Scale Cell Expansion from Primary Tissues," Tissue Engineering: Part C 16:947-956.
Kempner, M.E. and Felder, R.A., "A review of cell culture automation". JALA: Journal of the Association for Laboratory Automation (Apr. 2002); 7(2): 56-62.
Kino-Oka, M. et al. (2005). "Bioreactor Design for Successive Culture of Anchorage-Dependent Cells Operated in an Automated Manner," Tissue Engineering 11:535-545.
Knoll, A. et al. (2004). "Flexible automation of cell culture and tissue engineering tasks," Biotechnol. Prog. 20:1825-1835.
Lutkemeyer, D. et al. (2000). "First steps in robot automation of sampling and sample management during cultivation of mammalian cells in pilot scale," Biotechnol. Prog. 16:822-828.
MEDInstill (2021). Intact™ Connectors, located at https://www.medinstill.com/intactconnectors.php, 1 total page.
Millipore® (2020). "Technical Brief—Choosing the right sterile connector based on design and sterility test results," 4 total pages.
Millipore Sigma (2020). "Lynx® CDR Connectors," Datasheet, 4 total pages.
Millipore Sigma (2021). Lynx® CDR Connectors, located at https://www.emdmillipore.com/US/en/product/Lynx-CDR-Connectors,MM_NF-C188801, 2 total pages.
Non-Final Office Action for U.S. Appl. No. 18/244,051 mailed Oct. 9, 2024, 10 pages.
Non-Final Office Action for U.S. Appl. No. 18/652,602 mailed Jul. 17, 2024, 30 pages.
Non-Final Office Action for U.S. Appl. No. 18/731,095 mailed Aug. 8, 2024, 24 pages.
Non-Final Office Action for U.S. Appl. No. 18/731,095 mailed Mar. 6, 2025, 34 pages.
Non-Final Office Action for U.S. Appl. No. 18/759,602 mailed Feb. 20, 2025, 15 pages.
Non-Final Office Action for U.S. Appl. No. 18/759,602 mailed Nov. 8, 2024, 10 pages.
Non-Final Office Action for U.S. Appl. No. 18/792,358 mailed on Nov. 6, 2024, 5 pages.
Non-Final Office Action for U.S. Appl. No. 18/799,963 mailed Sep. 30, 2024, 9 pages.
Non-Final Office Action for U.S. Appl. No. 18/807,699 mailed Apr. 29, 2025, 19 pages.
Non-Final Office Action for U.S. Appl. No. 18/810,386 mailed Nov. 18, 2024, 8 pages.
Non-Final Office action for U.S. Appl. No. 18/920,607 mailed Feb. 28, 2025, 10 pages.
Non-Final Office Action for U.S. Appl. No. 18/988,628 mailed Mar. 3, 2025, 19 pages.
Non-Final Office Action for U.S. Appl. No. 19/091,700 mailed Jul. 7, 2025, 13 pages.
Non-Final Office Action mailed on Apr. 24, 2024, for U.S. Appl. No. 17/331,554, filed May 26, 2021, 17 pages.
Non-Final Office Action mailed on Dec. 22, 2022, for U.S. Appl. No. 17/579,478, filed Jan. 19, 2022, 8 pages.
Non-Final Office Action mailed on Dec. 3, 2021, for U.S. Appl. No. 17/331,556, filed May 26, 2021, 9 pages.
Non-Final Office Action mailed on Feb. 3, 2022, for U.S. Appl. No. 17/198,134, filed Mar. 10, 2021, 5 pages.
Non-Final Office Action mailed on Jun. 26, 2023, for U.S. Appl. No. 17/198,134, filed Mar. 10, 2021, 15 pages.
Non-Final Office Action mailed on Mar. 16, 2023, for U.S. Appl. No. 17/331,554, filed May 26, 2021, 16 pages.
Non-Final Office Action mailed on May 14, 2024, for U.S. Appl. No. 18/611,632, filed Mar. 20, 2024, 13 pages.
Non-Final Office Action mailed on Oct. 28, 2021, for U.S. Appl. No. 17/331,554, filed May 26, 2021, 11 pages.
Non-Final Office Action mailed on Oct. 6, 2021, for U.S. Appl. No. 17/198,134, filed Mar. 10, 2021, 7 pages.
Non-Final Office Action mailed on Sep. 13, 2023, for U.S. Appl. No. 18/141,329, filed Apr. 28, 2023, 7 pages.
Notice of Allowance (Corrected) mailed on Sep. 5, 2024, for U.S. Appl. No. 18/611,632, filed Mar. 20, 2024, 6 pages.
Notice of Allowance for U.S. Appl. No. 17/331,554 mailed Apr. 10, 2025, 6 pages.
Notice of Allowance for U.S. Appl. No. 17/331,554 mailed Mar. 5, 2025, 8 pages.
Notice of Allowance for U.S. Appl. No. 18/487,884 mailed Feb. 26, 2025, 8 pages.
Notice of Allowance for U.S. Appl. No. 18/487,884 mailed on Apr. 3, 2025, 8 pages.
Notice of Allowance for U.S. Appl. No. 18/611,632 mailed Aug. 26, 2024, 9 pages.
Notice of Allowance for U.S. Appl. No. 18/652,602 mailed May 2, 2025, 14 pages.
Notice of Allowance for U.S. Appl. No. 18/792,358 mailed on Mar. 3, 2025, 8 pages.
Notice of Allowance for U.S. Appl. No. 18/792,360 mailed Mar. 4, 2025, 9 pages.
Notice of Allowance for U.S. Appl. No. 18/792,360 mailed on Jan. 29, 2025, 9 pages.
Notice of Allowance for U.S. Appl. No. 18/799,963 mailed Jul. 1, 2025, 7 pages.
Notice of Allowance for U.S. Appl. No. 18/810,386 mailed Aug. 18, 2025, 10 pages.
Notice of Allowance for U.S. Appl. No. 18/810,388 mailed Apr. 30, 2025, 5 pages.
Notice of Allowance for U.S. Appl. No. 18/810,388 mailed Jan. 21, 2025, 8 pages.

(56) References Cited

OTHER PUBLICATIONS

Notice of Allowance for U.S. Appl. No. 18/810,388 mailed on Oct. 9, 2024, 9 pages.
Notice of Allowance for U.S. Appl. No. 18/811,490 mailed Feb. 26, 2025, 8 pages.
Notice of Allowance for U.S. Appl. No. 18/811,490 mailed on Dec. 12, 2024, 8 pages.
Notice of Allowance for U.S. Appl. No. 19/075,709 mailed Jul. 29, 2025, 10 pages.
Notice of Allowance mailed on Apr. 11, 2024, for U.S. Appl. No. 17/198,134, filed Mar. 10, 2021, 9 pages.
Notice of Allowance mailed on Jul. 18, 2023, for U.S. Appl. No. 17/849,422, filed Jun. 24, 2022, 8 pages.
Notice of Allowance mailed on Jul. 25, 2023, for U.S. Appl. No. 17/579,478, filed Jan. 19, 2022, 8 pages.
Notice of Allowance mailed on Jun. 8, 2023, for U.S. Appl. No. 17/849,422, filed Jun. 24, 2022, 8 pages.
Notice of Allowance mailed on Mar. 1, 2022, for U.S. Appl. No. 17/331,556, filed May 26, 2021, 8 pages.
Notice of Allowance mailed on Mar. 22, 2023, for U.S. Appl. No. 17/992,784, filed Nov. 22, 2022, 8 pages.
Notice of Allowance mailed on Oct. 4, 2023, for U.S. Appl. No. 18/141,329, filed Apr. 28, 2023, 8 pages.
Pharma Japan, "Astellas Set to Cut Development Time with Cell Culture Robot, Eyes 4 Billion Yen Profit per Product" Aug. 9, 2023, 3 pages.
Qu, B. et al., "Droplet Electroporation in Microfluidics for Efficient Cell Transformation with or without Cell Wall Removal," Lab Chip (2012) 12:4483-4488.
Saint Gobain (2017). "Pure-Fit® SC—Secure aseptic connections," Brochure, 5 total pages.
Sartorius Stedim Biotech (2011). "Opta® SFT," 4 total pages.
Schwartz C., "Optimizing Cell Separation with Beckman Coulter's Centrifugal Elutriation System," Beckmann Coulter Life Sciences (2014) 6 total pages.
SeriesLock™ (2021). Features and Specifications, located at https://serieslock.com/, 5 total pages.
Shabalina et al., "ARTag, AprilTag and CALTag Fiducial Systems Comparison in a Presence of Partial Rotation: Manual and Automated Approaches" in ICINCO (2017) LNEE 495:536-558.
Shi, Y. et al. (1992). "Performance of Mammalian Cell Culture Bioreactor with a New Impeller Design," Biotechnology and Bioengineering 40:260-270.
Steris (2018). "A compilation of material compatibilities with vaporized hydrogen peroxide," 2 total pages.
Steris (2018). "Sterility assurance levels (SALS): Irradiation," 3 total pages.
Steris (2020). "Overview of sterilization technology comparison," 1 total page.
Strahlendorf, K.A. et al. (2009). "Bio Pharm International—A review of sterile connectors," vol. 2009 Supplement, Issue 8, located at https://www.biopharminternational.com/view/review-sterile-connectors, 9 total pages.
U.S. Appl. No. 29/898,923, filed Aug. 2, 2023, by Gerlinghaus et al.
Written Opinion of the International Searching Authority mailed on Oct. 13, 2021, for PCT Application No. PCT/US2021/021773, filed on Mar. 10, 2021, 20 pages.
PCT Application No. PCT/IB2025/053219, International Search Report and Written Opinion mailed Jan. 23, 2026, Applicant Cellares Corporation; 17 pages.
PCT Application No. PCT/IB2025/053219, Invitation to Pay Additional Fees mailed Nov. 25, 2025; Applicant Cellares Corporation; 13 pages.
PCT Application No. PCT/IB2025/060633, International Search Report and Written Opinion mailed Dec. 15, 2025, Applicant Cellares Corporation.; 13 pages.
PCT Application No. PCT/US2025/038972, International Search Report and Written Opinion mailed Nov. 14, 2025; Applicant Cellares Corporation; 17 pages.
U.S. Appl. No. 18/244,051, Notice of Allowance mailed Oct. 15, 2025; Inventor Biz, Tony et al.; 5 pages.
U.S. Appl. No. 18/731,095, Non-Final Office Action mailed Jan. 27, 2026; Inventor Boppart, Andrew et al.; 39 pages.
U.S. Appl. No. 18/759,602, Notice of Allowance mailed Nov. 10, 2025; Inventor Thakkar, Bharat S. et al.; 9 pages.
U.S. Appl. No. 18/920,607, Non-Final Office Action mailed Jan. 28, 2026; Inventor Malleo, Daniele et al.; 9 pages.
U.S. Appl. No. 18/988,628, Non-final Office Action mailed Feb. 9, 2026; Inventor Marchiando, Amanda M. et al.; 12 pages.
U.S. Appl. No. 19/091,700, Notice of Allowance mailed Oct. 22, 2025; Inventor Azersky, Vladimir et al.; 9 pages.
U.S. Appl. No. 19/278,669, Non-Final Office Action mailed Jan. 14, 2026; Inventor Beban; Marc A. et al.; 11 pages.
U.S. Appl. No. 19/278,672, Final Office Action mailed Mar. 10, 2026; Inventor Malleo, Daniele.; 24 pages.
U.S. Appl. No. 19/278,672, Non-Final Office Action mailed Nov. 5, 2025; Inventor Malleo, Daniele et al.; 23 pages.
U.S. Appl. No. 19/392,013, filed Nov. 17, 2025; Inventor Grout, Wayne E et al.
U.S. Appl. No. 19/534,547, filed Feb. 9, 2026; Inventor Thakkar, Bharat S et al.
U.S. Appl. No. 29/937,490, Notice of Allowance mailed Sep. 10, 2025; Inventor Cesarek, John et al.; 7 pages.

* cited by examiner 1600
1640
1622
1620
1628
1624
1627
1626
1617
1616
1614
1618
1610
1650
1612
1630

1617
1616
1614
1615
1618
1652
1654
2702
1610
1612
1630

Process Design Home Page

Create a Process

Empty Process Setup

Add Reagant and Consumable Container

Process Parameter

Patient Weight Process Parameter

Preprocess Analytic

White Blood Cell Count Preprocess Analytic

FIG. 45
4500
4510
Add Process Parameter
Parameter Info
Calculation Example
calculation-example
Using other parameters in a calculation
Float
Calculation Builder
patient-weight
[cbc-white-blood-cell-count] * 1.618/[patient-weight]
Clear Calculation
Cancel
Add

Process Parameter Calculation

Process Setup

Process Operations Activation Settings

Process Operations Activation Settings

Process Operations

Process Operations Dragging

Process Operations Dragging

Process Operations Filled

Product Monitoring

Product Monitoring

6300

6310

6320

6330

6340

- Vps = voltage set at electroporator output
- Rs = parasitic resistance through the connection
- Ri = interface resistance between fluid and electrode
- Rb = resistance of fluid
- Rchip = Ri + Rb
- Vchip = actual voltage load on chip
- Actual E field = Vchip / electrode gap
- I = current flow through the chip.

Example of feedback-enabled cell-bed forming process

Example of feedback-enabled elutriation process

Example of feedback-enabled harvest process

Preparing BRS for CC 8200

Loading CC into BRS 8210

APPARATUS AND METHOD FOR CONTROL OF CELL PROCESSING SYSTEM

CROSS-REFERENCE TO RELATED APPLICATIONS

This application is a continuation of U.S. patent application Ser. No. 18/799,963, filed Aug. 9, 2024, which is a continuation of U.S. patent application Ser. No. 18/244,051, filed Sep. 8, 2023, which is a divisional of U.S. patent application Ser. No. 17/579,478, filed Jan. 19, 2022, now U.S. Pat. No. 11,872,557, which is a continuation of U.S. patent application Ser. No. 17/198,134, filed Mar. 10, 2021, now U.S. Pat. No. 12,157,119, which claims the benefit of U.S. Provisional Application No. 62/987,745, filed Mar. 10, 2020, and U.S. Provisional Application No. 63/093,038, filed Oct. 16, 2020, the content of each of which is hereby incorporated by reference in its entirety.

TECHNICAL FIELD

Devices, systems, and methods herein relate to manufacturing cell products for biomedical applications using automated systems.

BACKGROUND

Cellular therapies based on hematopoietic stem cells (HSCs), chimeric antigen receptor (CAR) T cells, NK cells, tumor infiltrating lymphocytes (TILs), T-cell receptors (TCRs), regulatory T cells (T regs), gamma delta (γδ) T cells, and others rely on manufacturing of cell products. Manufacturing of such cell products typically involves multiple cell processing steps. Conventional solutions for manufacture of cell products rely on cumbersome manual operations performed in expensive biosafety cabinets and/or clean rooms. Skilled laboratory technicians, adequate sterile enclosures such as cleanroom facilities, and associated protocols and procedures for regulated (GMP) manufacturing are expensive. Many current manufacturing processes employ numerous manual reagent preparation and instrument manipulation steps during a manufacturing protocol, and the processes may require several days or even weeks. Even platforms described as automated cell processing in a closed system generally rely on pre-configured instrumentation and tubing sets that limit operational flexibility and do not reliably prevent process failure due to accidental operator/human error.

Most efforts to automate cell product manufacturing have been directed to automating individual processing steps of a cell therapy manufacturing workflow. Even systems that automate several steps lack end-to-end process flexibility, process robustness, and process scalability. These and other limitations of the previous attempts at automation of cell processing are addressed in various embodiments disclosed here.

SUMMARY

The present disclosure relates generally to methods and systems for processing cell products. By processing a cell product in a cartridge moved between instruments, some variations may achieve one or more advantages over prior cell manufacturing systems, including, for example, improved sterility, automation, lower cost of goods, lower labor costs, higher repeatability, higher reliability, lower risk of operator error, lower risk of contamination, higher process flexibility, higher capacity, higher instrument throughput, higher degree of process scalability, and shorter process duration. Variations of the disclosure may comprise a sterile enclosure, thereby reducing the costs of providing a clean room environment, and/or utilize a workcell having a smaller footprint than current manufacturing facilities. Furthermore, variations of the methods disclosed herein may, in some cases, be performed more quickly and with less risk of cell product loss.

In some variations, the disclosure provides a system for cell processing, comprising a plurality of instruments each independently configured to perform one or more cell processing operation upon a cartridge, and a robot capable of moving the cartridge between each of the plurality of instruments.

In some variations, the system may be enclosed in a workcell. In some variations, the workcell may be automated. In some variations, the plurality of instruments may be configured to interface with the cartridge to perform cell processing operations upon the cartridge. In some variations, the system may comprise a processor. The processor may be configured to control the robot and the plurality of instruments.

In some variations, the system may be configured to receive two or more cartridges. In some variations, the system may comprise the cartridge. In some variations, the cartridge may comprise a plurality of modules. In some variations, the cartridge may comprise a bioreactor module. In some variations, the cartridge may comprise a cell selection module. In some variations, the cell selection module may comprise a magnetic-activated cell selection module. In some variations, the cartridge may comprise a sorting module. In some variations, the sorting module may comprise a fluorescence activated cell sorting (FACS) module. In some variations, the cartridge may comprise an electroporation module. In some variations, the cartridge may comprise a counterflow centrifugal elutriation (CCE) module.

In some variations, the cartridge may comprise one or more sterile liquid transfer ports. In some variations, the cartridge may comprise a liquid transfer bus fluidically coupled to each module. In some variations, the cartridge may comprise a pump fluidically coupled to the liquid transfer bus.

In some variations, the system may comprise a pump actuator configured to interface with the pump. In some variations, the system may comprise a bioreactor instrument. In some variations, the bioreactor instrument may comprise multiple slots for cartridges. In some variations, the system may comprise a cell selection instrument. In some variations, the cell selection instrument may comprise a magnetic-activated cell selection instrument.

In some variations, the system may comprise a sorting instrument. In some variations, the sorting instrument may comprise a fluorescence activated cell sorting (FACS) instrument. In some variations, the system may comprise an electroporation instrument. In some variations, the system may comprise a counterflow centrifugal elutriation (CCE) instrument. In some variations, the system may comprise a reagent vault.

In some variations, the cartridge may comprise a bioreactor module and a selection module. In some variations, the cartridge may comprise a bioreactor module and a CCE module. In some variations, the cartridge may comprise a bioreactor module, selection module, and a CCE module. In some variations, the cartridge may comprise a bioreactor module, selection module, and an electroporation module. In some variations, the cartridge may comprise a bioreactor module, selection module, a CCE module, and an electroporation module. In some variations, the cartridge may comprise a second bioreactor module having an internal volume two or more, five or more, or ten or more times larger than the internal volume of the first bioreactor.

In some variations, the system may comprise an enclosure. In some variations, the enclosure may comprise an ISO7 cleanroom. In some variations, the enclosure may comprise an ISO6 cleanroom. In some variations, the enclosure may comprise an ISO5 cleanroom. In some variations, the enclosure may comprise a feedthrough. In some variations, the system may perform automated manufacturing of cell products.

In some variations, the disclosure provides a cartridge for cell processing, comprising a liquid transfer bus and a plurality of modules, each module fluidically coupled to the liquid transfer bus.

In some variations, the cartridge may comprise one or more sterile liquid transfer ports. In some variations, the cartridge may comprise a bioreactor module. In some variations, the cartridge may comprise a cell selection module. In some variations, the cell selection module may comprise a magnetic-activated cell selection module. In some variations, the cartridge may comprise a sorting module. In some variations, the sorting module may comprise a fluorescence activated cell sorting (FACS) module. In some variations, the cartridge may comprise an electroporation module. In some variations, the cartridge may comprise a counterflow centrifugal elutriation (CCE) module.

In some variations, the cartridge may comprise a mechanoporation module. In some variations, the cartridge may comprise a second bioreactor module having an internal volume two or more, five or more, or ten or more times larger than the internal volume of the first bioreactor. In some variations, the cartridge may comprise a bioreactor module, selection module, and a CCE module. In some variations, the cartridge may comprise a bioreactor module, selection module, and an electroporation module. In some variations, the cartridge may comprise a bioreactor module, selection module, a CCE module, and an electroporation module.

In some variations, the disclosure provides a method for processing cells, comprising moving a cartridge containing a cell product between a plurality of instruments inside an enclosed and automated workcell. The instruments may interface with the cartridge to perform cell processing steps on the cell product.

In some variations, cell processing steps may be performed on the cell product. In some variations, for each cell product, all cell processing steps in the method are performed in a single cartridge.

In some variations, the cell product may be split into a plurality of cell product portions. In some variations, the cell processing steps may be performed on the plurality of cell product portions in parallel. In some variations, at least two cell product portions of the plurality of cell product portions may be combined.

In some variations, the workcell may comprise a robot configured to move cartridges. In some variations, the workcell may comprise a processor. The processor may be configured to control the robot and the plurality of instruments. In some variations, the workcell may be configured to receive two or more cartridges.

In some variations, the cartridge may comprise a plurality of modules. In some variations, the cartridge may comprise a bioreactor module. In some variations, the cartridge may comprise a cell selection module. In some variations, the cell selection module may comprise a magnetic-activated cell selection module.

In some variations, the cartridge may comprise a sorting module. In some variations, the sorting module may comprise a fluorescence activated cell sorting (FACS) module. In some variations, the cartridge may comprise an electroporation module. In some variations, the cartridge may comprise a counterflow centrifugal elutriation (CCE) module. In some variations, the cartridge may comprise one or more sterile liquid transfer ports. In some variations, the cartridge may comprise a liquid transfer bus fluidically coupled to each module. In some variations, the cartridge may comprise a pump fluidically coupled to the liquid transfer bus.

In some variations, the workcell may comprise a pump actuator configured to interface with the pump. In some variations, the workcell may comprise a bioreactor instrument. In some variations, the bioreactor instrument may comprise multiple slots for cartridges. In some variations, the method may comprise performing the cell processing steps on two or more cartridges in parallel.

In some variations, the workcell may comprise a cell selection instrument. In some variations, the cell selection instrument may comprise a magnetic-activated cell selection instrument.

In some variations, the workcell may comprise a sorting instrument. In some variations, the sorting instrument may comprise a fluorescence activated cell sorting (FACS) instrument. In some variations, the workcell may comprise an electroporation instrument. In some variations, the workcell may comprise a counterflow centrifugal elutriation (CCE) instrument. In some variations, the workcell may comprise a reagent vault.

In some variations, the cartridge may comprise a bioreactor module and a selection module. In some variations, the cartridge may comprise a bioreactor module and a CCE module. In some variations, the cartridge may comprise a bioreactor module, selection module, and a CCE module. In some variations, the cartridge may comprise a bioreactor module, selection module, and an electroporation module. In some variations, the cartridge may comprise a bioreactor module, selection module, a CCE module, and an electroporation module.

In some variations, the workcell may comprise an enclosure. In some variations, the enclosure may comprise an ISO7 cleanroom. In some variations, the enclosure may comprise an ISO6 cleanroom. In some variations, the enclosure may comprise an ISO5 cleanroom. In some variations, the enclosure may comprise a feedthrough.

In some variations, the method may perform automated manufacturing of a cell product. In some variations, the cell product may comprise a chimeric antigen receptor (CAR) T cell product. In some variations, the cell product may comprise a natural killer (NK) cell product. In some variations, the cell product may comprise a hematopoietic stem cell (HSC) cell product. In some variations, the cell product may comprise a tumor infiltrating lymphocyte (TIL) cell product. In some variations, the cell product may comprise a regulatory T (Treg) cell product.

In some variations, the disclosure provides a method for processing a solution containing a cell product, performed in an automated system, the method comprising one or more cell processing steps, performed serially in any order, selected from: an enrichment step, a concentration step, a buffer exchange step, a formulation step, a washing step, a selection step, a resting step, an expansion step, a tissue-digestion step, an activation step, a transduction step, a transfection step, and a harvesting step.

In some variations, an enrichment step may comprise enriching a selected population of cells in the solution by conveying the solution to a CCE module of the cartridge via a liquid transfer bus, operating the robot to move the cartridge to a CCE instrument so that the CCE module interfaces with the CCE instrument, and operating the CCE instrument to cause the CCE module to enrich the selected population of cells.

In some variations, a washing step may comprise washing a selected population of cells in the solution by conveying the solution to the CCE module of the cartridge via the liquid transfer bus, operating the robot to move the cartridge to the CCE instrument so that the CCE module interfaces with the CCE instrument, and operating the CCE instrument to cause the CCE module to remove media from the solution, introduce media into the solution, and/or replace media in the solution.

In some variations, a selection step may comprise selecting a selected population of cells in the solution by conveying the solution to a selection module of the cartridge via the liquid transfer bus, operating the robot to move the cartridge to a selection instrument so that the selection module interfaces with the selection instrument, and operating the selection instrument to cause the selection module to select the selected population of cells.

In some variations, a sorting step may comprise sorting a population of cells in the solution by conveying the solution to a sorting module of the cartridge via the liquid transfer bus, operating the robot to move the cartridge to a sorting instrument so that the sorting module interfaces with the sorting instrument, and operating the sorting instrument to cause the sorting module to sort the population of cells.

In some variations, a resting step may comprise conveying the solution to a bioreactor module of the cartridge via the liquid transfer bus, operating the robot to move the cartridge to the bioreactor instrument so that the bioreactor module interfaces with the bioreactor instrument, and operating the bioreactor instrument to cause the bioreactor module to maintain the cells.

In some variations, an expansion step may comprise expanding the cells in the solution by conveying the solution to the bioreactor module of the cartridge via the liquid transfer bus, operating the robot to move the cartridge to the bioreactor instrument so that the bioreactor module interfaces with the bioreactor instrument, and operating the bioreactor instrument to cause the bioreactor module to allow the cells to expand by cellular replication.

In some variations, a tissue-digestion step may comprise conveying an enzyme reagent via the liquid transfer bus to a module containing a solution containing a tissue such that the enzyme reagent causes digestion of the tissue to release a select cell population into the solution.

In some variations, an activating step may comprise activating a selected population of cells in the solution by conveying an activating reagent via the liquid transfer bus to a module containing the solution containing the cell product.

In some variations, an electroporation step may comprise conveying the solution to an electroporation module of the cartridge via the liquid transfer bus, operating the robot to move the cartridge to an electroporation instrument so that the electroporation module interfaces with the electroporation instrument, and operating the electroporation instrument to cause the electroporation module to electroporate the selected population of cells in the presence of the vector.

In some variations, a transduction step may comprise conveying an effective amount of a vector via the liquid transfer bus to a module containing the solution containing the cell product, thereby transducing a selected population of cells in the solution. In some variations, a fill/finishing step may comprise conveying a formulation solution via the liquid transfer bus to a module containing the cell product to generate a finished cell product and conveying the finished cell product to one or more product collection bags.

In some variations, the method may comprise sterilizing, either manually or automatically, the cartridge in a feed-through port. In some variations, the method may comprise introducing, either manually or automatically, one or more of a fluid and the cell product into the cartridge via a sterile liquid transfer port. In some variations, the method may comprise a harvesting step comprising removing, either manually or automatically, the cell product from the cartridge. In some variations, the cell product may comprise an immune cell. In some variations, in order, the enrichment step, the selection step, the activation step, the transduction step, the expansion step, and the harvesting step.

In some variations, the immune cell may comprise a genetically engineered chimeric antigen receptor T cell. In some variations, the immune cell may comprise a genetically engineered T cell receptor (TCR) cell. In some variations, the immune cell may comprise is a natural-killer (NK) cell. In some variations, the cell product may comprise a hematopoietic stem cell (HSC). In some variations, the method may comprise, in order, the enrichment step, the selection step, the resting step, the transduction step, and the harvesting step. In some variations, the cell product may comprise a tumor infiltrating lymphocyte (TIL). In some variations, the method may comprise, in order, the tissue-digestion step, the washing step, the activation step, the expansion step, and the harvesting step.

Also described here is a counterflow centrifugal elutriation (CCE) module, comprising a conical element having an internal surface and an external surface fixedly attached to a distal end of a linear member having an internal surface and an external surface, the proximal end of the linear member rotationally attached to a fulcrum to permit extension, retraction, and rotation of the linear member.

Also described here is a workcell comprising an enclosure, a plurality of instruments each independently configured to perform one or more cell processing operation upon a cartridge, and a robot capable of moving the cartridge between each of the plurality of instruments.

In some variations, the enclosure may comprise an air filtration inlet configured to maintain ISO 7 or better air quality within an interior zone of the workcell. In some variations, the workcell may be automated. In some variations, the instruments may interface with the cartridge to perform cell processing operations upon the cartridge. In some variations, the workcell may comprise a processor. The processor may be configured to control the robot and the plurality of instruments.

In some variations, the workcell may be configured to receive two or more cartridges. In some variations, the workcell may comprise the cartridge. In some variations, the cartridge may comprise a plurality of modules. In some variations, the cartridge may comprise a bioreactor module. In some variations, the cartridge may comprise a cell selection module. In some variations, the cell selection module may comprise a magnetic-activated cell selection module. In some variations, the cartridge may comprise a sorting module.

In some variations, the sorting module may comprise a fluorescence activated cell sorting (FACS) module. In some variations, the cartridge may comprise an electroporation module. In some variations, the cartridge may comprise a counterflow centrifugal elutriation (CCE) module. In some variations, the cartridge may comprise one or more sterile liquid transfer ports. In some variations, the cartridge may comprise a liquid transfer bus fluidically coupled to each module. In some variations, the cartridge may comprise a pump fluidically coupled to the liquid transfer bus.

In some variations, the workcell may comprise a pump actuator configured to interface with the pump. In some variations, the workcell may comprise a bioreactor instrument. In some variations, the bioreactor instrument may comprise multiple slots for cartridges. In some variations, the workcell may comprise a cell selection instrument. In some variations, the cell selection instrument may comprise a magnetic-activated cell selection instrument. In some variations, the workcell may comprise a sorting instrument. In some variations, the sorting instrument may comprise a fluorescence activated cell sorting (FACS) instrument. In some variations, the workcell may comprise an electroporation instrument.

In some variations, the workcell may comprise a counterflow centrifugal elutriation (CCE) instrument. In some variations, the workcell may comprise a reagent vault. In some variations, the cartridge may comprise a bioreactor module and a selection module. In some variations, the cartridge may comprise a bioreactor module and a CCE module. In some variations, the cartridge may comprise a bioreactor module, selection module, and a CCE module. In some variations, the cartridge may comprise a bioreactor module, selection module, and an electroporation module. In some variations, the cartridge may comprise a bioreactor module, selection module, a CCE module, and an electroporation module. In some variations, the cartridge may comprise a second bioreactor module having an internal volume two or more, five or more, or ten or more times larger than the internal volume of the first bioreactor. In some variations, the enclosure may comprise a feedthrough. In some variations, the workcell may perform automated manufacturing of cell products. In some variations, the system may comprise a plurality of bioreactor instruments. Each bioreactor instrument may be configured to receive a single cartridge.

Also described here is a rotor comprising a first side comprising a first fluid conduit, a second side comprising a second fluid conduit, the second side opposite the first side, and a cone coupled between the first fluid conduit and the second fluid conduit.

In some variations, the cone may comprise a bicone. In some variations, the bicone may comprise a first cone including a first base and a second cone including a second base. The first base may face the second base. In some variations, the rotor may comprise a magnetic portion. In some variations, the rotor may define a rotation axis. In some variations, at least a portion of the first fluid conduit and at least a portion of the second fluid conduit may extend parallel to the rotation axis. In some variations, at least a portion of the first fluid conduit and at least a portion of the second fluid conduit may be co-axial.

In some variations, the cone may comprise a volume of between about 10 ml and about 40 ml. In some variations, the cone may comprise a cone angle of between about 30 degrees and about 60 degrees. In some variations, at least a portion of the rotor may be optically transparent. In some variations, the rotor may comprise an asymmetric shape. In some variations, a first portion may comprise the cone and a second portion comprising a paddle shape.

In some variations, a cartridge for cell processing may comprise a liquid transfer bus and a plurality of modules. Each module may be fluidically linked to the liquid transfer bus. The cartridge may comprise a counterflow centrifugal elutriation (CCE) module comprising the rotors described herein.

Also described here is a rotor comprising a first fluid conduit, a first fluid conduit, a first cone coupled to the first fluid conduit. The first cone may comprise a first volume. A second fluid conduit may be coupled to the first cone. A second cone may be coupled to the second conduit. The second cone may comprise a second volume larger than the first volume. A third fluid conduit may be coupled to the second cone.

In some variations, the first cone may comprise a first bicone and the second cone may comprise a second bicone. In some variations, the first bicone may comprise a third cone including a first base and a fourth cone including a second base. The first base may face the second base. The second bicone may comprise a fifth cone including a third base and a sixth cone including a fourth base. The third base may face the fourth base.

In some variations, the rotor may comprise a magnetic portion. In some variations, at least a portion of the rotor may be optically transparent. In some variations, the first fluid conduit may comprise an inlet and the third fluid conduit comprises an outlet.

Also described here is a system for cell processing comprising a cartridge comprising a housing comprising a rotor configured to separate cells from a fluid, and an instrument comprising a magnet configured to interface with the cartridge to magnetically rotate the rotor.

In some variations, the cartridge may be configured to move between a plurality of instruments. In some variations, an air gap may be between the housing and the magnet. In some variations, the housing may enclose the rotor. In some variations, the housing may comprise a consumable component and the magnet comprises a durable component.

In some variations, the magnet may be releasably coupled to the housing. In some variations, the magnet may be configured to be moved relative to the housing. In some variations, the separated cells may comprise a first size and a first density and non-separated cells of the fluid comprise a second size and a second density different from the first size and the first density. Also described here is a cartridge for cell processing, comprising a liquid transfer bus and a plurality of modules. Each module may be fluidically linked to the liquid transfer bus. The cartridge may comprise a counterflow centrifugal elutriation (CCE) module comprising the rotor described here.

Also described here is a method of counterflow centrifugal elutriation (CCE) comprising moving a rotor towards a magnet, the rotor defining a rotational axis, flowing the fluid through the rotor, magnetically rotating the rotor about the rotational axis using the magnet while flowing the fluid through the rotor.

In some variations, image data of one or more of the fluid and particles in the rotor may be generated using an optical sensor. One or more of a rotation rate of the rotor and a flow rate of the fluid may be selected based at least in part on the image data.

In some variations, one or more of the fluid and the cells may be illuminated using an illumination source. In some variations, the method may comprise moving the rotor away from the magnet. In some variations, the method may comprising moving the rotor towards an illumination source and an optical sensor, and moving the rotor away from the illumination source and the optical sensor.

In some variations, moving the rotor comprises advancing and withdrawing the magnet relative to the rotor using a robot. In some variations, rotating the rotor comprises a rotation rate of up to 6,000 RPM. In some variations, flowing the fluid comprises a flow rate of up to about 150 ml/min while rotating the rotor.

Also described here is a method of magnetic-activated cell selection comprising flowing the fluid comprising input cells into a flow cell. A set of the cells may be labeled with magnetic-activated cell selection (MACS) reagent. The set of cells may be magnetically attracted towards a magnet array for a dwell time. The set of cells may flow out of the flow cell after the dwell time.

In some variations, the method may comprise incubating the MACS reagent with the input cells to label the set of cells with the MACS reagent. In some variations, the method may comprise incubating the MACS reagent may comprise a temperature between about 1° C. and about 10° C. In some variations, the method may comprise flowing the set of cells out of the flow cell may comprise flowing a gas through the flow cell. In some variations, the method may comprise flowing the fluid without the set of cells out of the flow cell after the dwell time. In some variations, the dwell time may be at least about one minute. In some variations, the magnet array may be disposed external to the flow cell. In some variations, the method may comprise moving the magnet array relative to the flow cell. In some variations, moving the magnet array may comprise moving the magnet array away from the flow cell to facilitate flowing the set of cells out of the flow cell. In some variations, a longitudinal axis of the flow cell may be perpendicular to ground. In some variations, the flow cell may be absent beads.

Also described here is a magnetic-activated cell selection (MACS) module comprising a flow cell comprising an elongate cavity having a cavity height, a magnet array may comprise a plurality of magnets. Each of the magnets may be spaced apart by a spacing distance. A ratio of the cavity height to the spacing distance may be between about 20:1 and about 1:20.

In some variations, the flow cell may comprise a set of linear channels comprising a first channel parallel to a second channel, and a third channel in fluid communication with each of the first channel and the second channel. In some variations, the first channel may comprise a first cavity height and the second channel may comprise a second cavity height. A ratio of the first cavity height to a second cavity height may be between about 1:1 to about 3:7. In some variations, the third channel may comprise a ratio of a length of the third channel to a diameter of the third channel of between about 2:1 to about 6:1.

In some variations, a first fluid conduit may be coupled to an inlet of the flow cell and an outlet of the flow cell. The first fluid conduit may be configured to receive the set of cells from the flow cell. A second fluid conduit may be coupled to the inlet of the flow cell and the outlet of the flow cell. The second fluid conduit may be configured to receive a fluid without the set of cells from the flow cell.

In some variations, a cartridge for cell processing may comprise a liquid transfer bus and a plurality of modules. Each module may be fluidically linked to the liquid transfer bus. The cartridge may comprise a magnetic-activated cell selection (MACS) module as described herein.

Also described here is a system for cell processing comprising a cartridge comprising a rotor configured for counterflow centrifugal elutriation of cells in a fluid. A first magnet may be configured to magnetically rotate the rotor and separate the cells from the fluid in the rotor. The cartridge may further comprise a flow cell in fluid communication with the rotor and configured to receive the cells from the rotor. A second magnet may be configured to magnetically separate the cells in the flow cell.

In some variations, an illumination source may be configured to illuminate the cells. An optical sensor may be configured to generate image data corresponding to the cells. In some variations, the system may comprise one or more of an oxygen depletion sensor, leak sensor, inertial sensor, pressure sensor, and bubble sensor. In some variations, the system may comprise one or more valves and pumps.

In some variations, the separated cells may comprise a first size and a first density and non-separated cells of the fluid comprise a second size and a second density different from the first size and the first density.

Also described here is an electroporation module comprising a fluid conduit configured to receive a first fluid comprising cells and a second fluid, a set of electrodes coupled to the fluid conduit, a pump coupled to the fluid conduit, and a controller comprising a processor and memory. The controller may be configured to generate a first signal to introduce the first fluid into the fluid conduit using the pump, generate a second signal to introduce the second fluid into the fluid conduit such that the second fluid separates the first fluid from a third fluid, and generate an electroporation signal to electroporate the cells in the fluid conduit using the set of electrodes.

In some variations, the second fluid may comprise a gas or oil. In some variations, the controller may be configured to generate a third signal to introduce the third fluid into the fluid conduit, the third fluid separated from the first fluid by the second fluid.

In some variations, a cartridge for cell processing may comprise a liquid transfer bus and a plurality of modules. Each module may be fluidically linked to the liquid transfer bus. The cartridge may comprise an electroporation module as described here.

Also described here is a method of electroporating cells comprising receiving a first fluid comprising cells in a fluid conduit, receiving a second fluid in the fluid conduit to separate the first fluid from a third fluid, and applying an electroporation signal to the first fluid to electroporate the cells.

In some variations, the method may comprise receiving the third fluid in the fluid conduit separated from the first fluid by the second fluid. In some variations, the first fluid substantially static when applying the electroporation signal.

Also described here is a method of electroporating cells comprising receiving a first fluid comprising cells in a fluid conduit, applying a resistance measurement signal to the first fluid using a set of electrodes, measuring a resistance between the first fluid and the set of electrodes, and applying an electroporation signal to the first fluid based on the measured resistance.

In some variations, the method may comprise receiving a second fluid comprising a gas in the fluid conduit before applying the electroporation signal to the fluid, the first fluid separated from a third fluid by the second fluid.

Also described here is a bioreactor comprising an enclosure comprising a base, a top, and at least one sidewall. A gas-permeable membrane may be coupled to one or more of the base and the sidewall of the enclosure.

In some variations, the enclosure may comprise one or more nested surfaces curved around a longitudinal axis of the enclosure. In some variations, the one more nested surfaces may comprise a set of concentric toroids. In some variations, the enclosure may comprise a toroid shape. In some variations, the enclosure may comprise a first chamber having a first volume and a second chamber having a second volume, the first chamber separated from the second chamber, and the first volume smaller than the second volume. In some variations, the enclosure may comprise a column extending along a longitudinal axis of the enclosure. In some variations, a cavity may be between the enclosure and the gas-permeable membrane. In some variations, the gas-permeable membrane may extend along the base and the sidewall of the enclosure. In some variations, an outer surface of the gas-permeable membrane may comprise one or more projections.

In some variations, a base of the gas-permeable membrane may comprise an angle between about 3 degrees and about 10 degrees relative to the base of the enclosure. In some variations, the gas-permeable membrane may comprise a curved surface. In some variations, the gas-permeable membrane may comprise a set of patterned curved surfaces. In some variations, the set of patterned curved surfaces may comprise a radius of curvature of between about 50 mm and about 500 mm.

In some variations, a cartridge for cell processing may comprise a liquid transfer bus and a plurality of modules. Each module may be fluidically linked to the liquid transfer bus. The cartridge may comprise a bioreactor module as described here. In some variations, a system for cell processing may comprising the cartridge described here and may further comprise a bioreactor instrument configured to interface with the cartridge. The bioreactor instrument may comprise an agitator configured to couple to the bioreactor. The agitator may be configured to agitate cell culture media comprising cells. In some variations, a fluid connector may be configured to couple the bioreactor to a liquid transfer bus. The fluid connector may comprise foldable sidewalls. In some variations, the system may comprise a temperature regulator coupled to the bioreactor. In some variations, the system may comprise a gas regulator coupled to the bioreactor.

Also described here is a fluid connector comprising a first connector comprising a first proximal end configured to couple to a first fluid device, and a first distal end comprising a first port. A second connector may comprise a second proximal end configured to couple to a second fluid device, and a second distal end comprising a second port configured to couple to the first port. The first distal end may comprise a first lumen and the second distal end may comprise a second lumen. One of the first valve and the second valve may be configured to translate within the first lumen and the second lumen.

In some variations, the first valve and the second valve may be configured to transition from a closed configuration to an open configuration only when the first valve couples to the second valve. In some variations, the first port and the second port may be configured to transition between an open configuration and a closed configuration. In some variations, the first connector may comprise a first port actuator and/or the second connector comprises a second port actuator. In some variations, the second port may be coupled to the first port defines a chamber.

In some variations, one or more of the first connector and the second connector may comprise a sterilant port configured to couple to a sterilant source. The sterilant port may be configured to be in fluid communication with the first distal end and the second distal end when the second port is coupled to the first port.

In some variations, the chamber may be configured to receive one or more of a fluid and a sterilant from the sterilant port. In some variations, the sterilant port may be configured to receive a sterilant such that the sterilant sterilizes the first connector and the second connector.

In some variations, the first connector may comprise a first valve, and the second connector may comprise a second valve configured to couple to the first valve. In some variations, a first seal may comprise the first port coupled to the second port, and a second seal may comprise the first valve coupled to the second valve. In some variations, the sterilant may comprise one or more of vaporized hydrogen peroxide and ethylene oxide.

In some variations, the fluid connector may comprise one or more robot engagement features. In some variations, the first connector may comprise a first alignment feature and the second connector may comprise a second alignment feature configured to couple to the first alignment feature in a predetermined axial and rotational configuration. In some variations, one or more of the first fluid device and the second fluid device may comprise an instrument.

In some variations, a system may further comprise a robot configured to operate the fluid connector, and a controller comprising a memory and processor. The controller may be coupled to the robot. The controller may be configured to generate a first port signal to couple the first port to the second port using the robotic arm. In some variations, the controller may be configured to generate a first valve signal to translate the first valve relative to the second valve using the robotic arm, and generate a second valve signal to transition the first valve and the second valve to the open configuration. In some variations, the controller may be configured to generate a second port signal to decouple the first port from the second port. A sterility of the fluid connector may be maintained before coupling the first port to the second port and after decoupling the first port from the second port.

In some variations, a fluid pump may be coupled to the sterilant source. The controller may be configured to generate a first fluid pump signal to circulate a fluid into the chamber through the sterilant port. In some variations, the controller may be configured to generate a second fluid pump signal to circulate the sterilant into the chamber through the sterilant port to sterilize at least the chamber.

In some variations, the controller may be configured to generate a third fluid pump signal to remove the sterilant from the chamber. In some variations, the controller may be configured to generate a thermal sterilization signal to thermally sterilize the fluid connector. In some variations, the controller may be configured to generate a radiation sterilization signal to sterilize the fluid connector using radiation. In some variations, the robot may be configured to couple a fluid connector between at least two of the plurality of instruments and the cartridge.

In some variations, the fluid connector may further comprise a controller comprising a memory and processor, the controller coupled to the robot. The controller may be configured to generate a port signal to couple the first port to the second port using the robotic arm, generate a first valve signal to translate the first valve relative to the second valve using the robotic arm, and generate a second valve signal to transition the first valve and the second valve to the open configuration.

Also described here is a non-transitory computer-readable medium for transforming user-defined cell processing operations into cell processing steps to be executed by an automated cell processing system. The non-transitory computer-readable medium may comprise instructions stored thereon that when executed on a processor perform the steps of receiving an ordered input list of cell processing operations, and executing a transformation model on the ordered input list to create an ordered output list of cell processing steps capable of being performed by the system.

In some variations, the ordered output list may be capable of being performed by the system to control a robot to move one or more cartridges each containing a cell product between the instruments, and control the instruments to perform cell processing steps on each cell product.

In some variations, the method may comprise receiving one or more sets of cell processing parameters, each set associated with one of the cell processing operations, and each set of cell processing parameters specifying characteristics of the cell processing step to be performed by the instrument at that cell processing step. In some variations, the transformation model may comprise constraints on the ordered output list determined by configuration of the automated cell processing system. In some variations, the constraints may comprise information on the configuration of the automated cell processing system. In some variations, the constraints may comprise one or more of a type and/or a number of instruments, a type and/or a number of modules on the cartridge, a type and a number of reservoirs on the cartridge, a type and/or a number of sterile liquid transfer ports on the cartridge, and a number and a position of fluid paths between the modules, reservoirs, and sterile liquid transfer ports on the cartridge.

In some variations, the steps may further comprise receiving a set of more than one ordered input lists of cell processing operations to be performed on more than one cartridge on the automated cell processing system, and executing the transformation model on the sets of ordered input lists to create the ordered output list of cell processing steps. The ordered output list may be capable of being executed by the system to control the robot to move the more than one cartridges, each comprising its cell product, between the instruments, and control the instruments to perform cell processing steps on each cell product of each cartridge.

In some variations, an automated cell processing system may comprise the non-transitory computer-readable medium of any preceding claim.

In some variations, a computer-implemented method for transforming user-defined cell processing operations into cell processing steps to be executed by a processor of an automated cell processing system may comprise receiving an ordered input list of cell processing operations, and executing a transformation model on the ordered input list to create an ordered output list of cell processing steps capable of being performed by the system.

In some variations, the method may include controlling a robot to move one or more cartridges each containing a cell product between the instruments, and controlling the instruments to perform cell processing steps on each cell product.

In some variations, the method may comprise receiving one or more sets of cell processing parameters, each set associated with one of the cell processing operations, and each set of cell processing parameters specifying characteristics of the cell processing step to be performed by the instrument at that cell processing step. In some variations, the transformation model may comprise constraints on the ordered output list determined by configuration of the automated cell processing system. In some variations, the constraints may comprise information on the configuration of the automated cell processing system.

In some variations, the constraints may comprise one or more of a type and/or number of instruments, a type and/or number of modules on the cartridge, a type and number of reservoirs on the cartridge, a type and/or number of sterile liquid transfer ports on the cartridge, and a number and position of fluid paths between the modules, reservoirs, and sterile liquid transfer ports on the cartridge.

In some variations, the method may comprise receiving a set of more than one ordered input lists of cell processing operations to be performed on more than one cartridge on the automated cell processing system, executing the transformation model on the sets of ordered input lists to create the ordered output list of cell processing steps, controlling the robot to move the more than one cartridges, each comprising its cell product, between the instruments, and controlling the instruments to perform cell processing steps on each cell product of each cartridge.

Additional variations, features, and advantages of the invention will be apparent from the following detailed description and through practice of the invention.

DETAILED DESCRIPTION

Figure 1A:
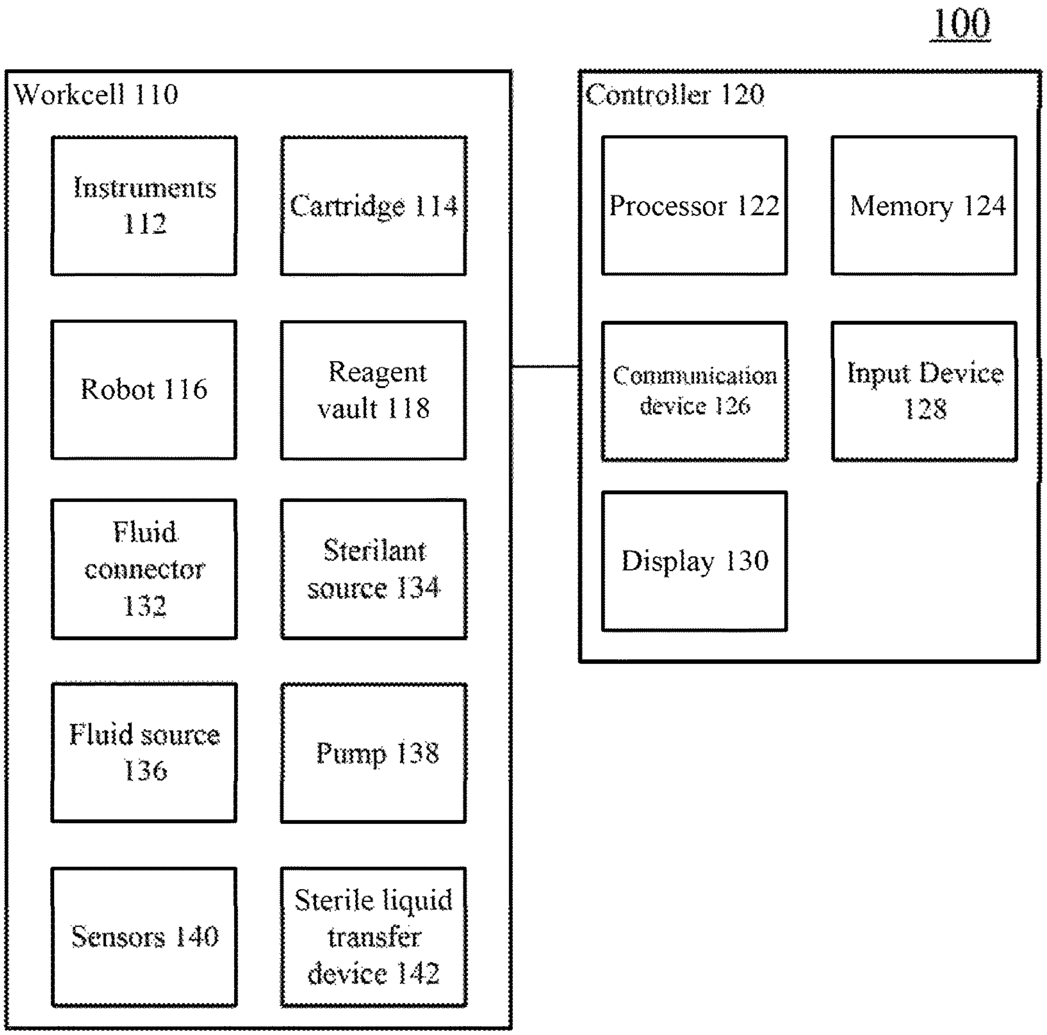
FIG. 1A is a block diagram of an illustrative variation of a cell processing system.

Systems and methods for processing and manufacturing cell products for biomedical applications are described herein. Cell processing methods and systems may comprise moving a cartridge containing a cell product between a plurality of instruments inside a workcell. One or more instruments may be configured to interface with the cartridge to perform cell processing steps on the cell product, such that the system (e.g., workcell) performs cell processing steps on the cell product. In some variations, a plurality of cell processing steps may be performed within a single cartridge. For example, a robotic arm may be configured to move a cartridge between instruments for different cell processing steps. The cartridge may comprise a plurality of cell processing devices (e.g., modules) such as a bioreactor, a counterflow centrifugal elutriation (CCE) module, a magnetic cell sorter (e.g., magnetic-activated cell selection module), an electroporation device (e.g., electroporation module), a sorting module (e.g. fluorescence activated cell sorting (FACS) module), an acoustic flowcell module, a centrifugation module, a microfluidic enrichment module, combinations thereof, and the like. In some variations, the system may process two or more cartridges in parallel. For example, the bioreactor may comprise a plurality of slots configured to interface with a plurality of cartridges concurrently, as one process step (e.g., cell culturing in a bioreactor) may typically be the rate limiting step for the operation of the cell processing system. The cell processing systems described herein may reduce operator intervention and increase throughput by automating cartridge (and cell product) movement between instruments using a robot. However, in some variations, the cartridge may be moved between instruments manually. Furthermore, throughput of the system may be increased by using a plurality of bioreactors, thereby allowing the system to simultaneously process a plurality of cartridges for a plurality of patients. Moreover, the automated cell processing system may facilitate sterile liquid transfers between the cartridge and instruments or other components of the system such as a fluid connector (e.g., sterile liquid transfer port), reagent vault, a second cartridge, a sampling vessel (e.g., sterile liquid transfer device, combinations thereof, and the like.

Workcell

In some variations, a system for cell processing (e.g., workcell) may comprise a plurality of instruments each independently configured to perform one or more cell processing operations upon a cartridge. A robot may be configured to move the cartridge between each of the plurality of instruments. The instruments may comprise one or more of a bioreactor instrument, a cell selection instrument (e.g., a magnetic-activated cell selection instrument), a sorting instrument (e.g., a fluorescence activated cell sorting (FACS) instrument), an electroporation instrument, a counterflow centrifugal elutriation (CCE) instrument, a reagent vault, and the like. The system may perform automated manufacturing of cell products.

A cartridge may be configured to be portable and facilitate automated and sterile cell processing using a workcell and robot. For example, the cartridge may be configured to move relative to one or more instruments of the workcell to perform different cell processing steps. In some variations, an instrument may be configured to move relative to a cartridge. In some variations, the cartridge may comprise a plurality of modules including one or more of a bioreactor module, a cell selection module (e.g., magnetic-activated cell selection module), a sorting module (e.g., fluorescence activated cell sorting (FACS) module), an electroporation module, and a counterflow centrifugal elutriation (CCE) module. The cartridge may further comprise one or more of a sterile liquid transfer port, a liquid transfer bus fluidically coupled to each module, and a pump fluidically coupled to the liquid transfer bus.

In some variations, a method of processing a solution containing a cell product may include the cell processing steps of digesting tissue using an enzyme reagent to release a select cell population into solution, enriching cells using a CCE instrument, washing cells using the CCE instrument, selecting cells in the solution using a selection instrument, sorting cells in the solution using a sorting instrument, differentiating or expanding the cells in a bioreactor, activating cells using an activating reagent, electroporating cells, transducing cells using a vector, and finishing a cell product.

Cell Selection System

The cell processing systems described herein may comprise a cell selection system configured to separate cells based on predetermined criteria. For example, cells may be separated based on physical characteristics such as size and/or density using, for example, a counterflow centrifugation elutriation instrument. Cells may also be separated based on the presence of predetermined antigens of a cell using, for example, a magnetic-activated cell selection instrument. In some variations, a cell selection system comprising modules for these separation methods may facilitate one or more cell processing steps including, but not limited to, cell concentration, cell dilution, cell washing, buffer replacement, and magnetic separation. The cell selection systems described herein may increase throughput and cell yields output, in a compact and portable structure. For example, prior to magnetically separating cells, a suspension of cells may be mixed with magnetic reagents in excess or at a predetermined concentration (e.g., cells/ml). Likewise, after magnetically separating cells, the cells may be washed in a solution (e.g., suitable buffered solution).

In some variations, a cell separation system may comprise a rotor configured for counterflow centrifugation elutriation of cells in a fluid, a first magnet configured to magnetically rotate the rotor and separate the cells from the fluid in the rotor, a flow cell in fluid communication with the rotor and configured to receive the cells from the rotor, and a second magnet configured to magnetically separate the cells in the flow cell.

In some variations, a CCE module may be integrated into a cartridge to enable a cell processing system to separate cells based on cell size and/or density. In some variations, a cell separation system may comprise a housing comprising a rotor configured to separate cells from a fluid (e.g., separate cells of different size and/or density from cells that remain in the fluid), and a magnet configured to magnetically rotate the rotor. The housing may be configured to move relative to the magnet or vice versa (e.g., move the magnet relative to the housing). The CCE modules described herein may provide cell separation within a compact and portable housing where the magnet may be disposed external to the housing (e.g., magnet disposed within a CCE instrument).

In some variations, a compact rotor that may aid cartridge integration may comprise input and output fluid conduits extending from the rotor towards opposing sides of a rotor housing. For example, a rotor may comprise a first side comprising a first fluid conduit and a second side comprising a second fluid conduit where the second side is opposite the first side. An elutriation chamber (e.g., cone) may be coupled between the first fluid conduit and the second fluid conduit.

In some variations, a method of separating cells from a fluid may comprise moving a rotor towards a magnet, the rotor defining a rotational axis, flowing the fluid through the rotor, rotating the rotor (e.g., magnetically) about the rotational axis using the magnet while flowing the fluid through the rotor, and moving the rotor away from the magnet.

In some variations, a method of separating cells from a fluid may comprise flowing the fluid comprising the cells into a flow cell. A set of the cells may be labeled with magnetic particles. The set of cells may be magnetically attracted towards a magnet array for a dwell time, and the set of cells may flow out of the flow cell after the dwell time.

In some variations, a flow cell may comprise an elongate cavity having a cavity height and a magnet array comprising a plurality of magnets, each of the magnets spaced apart by a spacing distance. A predetermined ratio between the cavity height to the spacing distance may optimize magnetic separation of the cells in the flow cell.

Electroporation

In some variations, an electroporation module as described herein may be configured to facilitate one or more of transduction and transfection of cells. As described in more detail herein, a volume of fluid (e.g., first batch) comprising cells may be physically separated from a subsequent volume of fluid (e.g., second batch, third batch) comprising cells by a gas (e.g., air gap). Applying an electroporation signal (e.g., voltage pulse, waveform) separately to each discrete batch of fluid may improve electroporation efficiency and thus increase throughput. In some variations, active electric field compensation may similarly improve electroporation efficiency and throughput.

In some variations, a cell processor may comprise a fluid conduit configured to receive a first fluid comprising cells and a second fluid (e.g., gas, oil), a set of electrodes coupled to the fluid conduit, a pump coupled to the fluid conduit, and a controller comprising a processor and memory. The controller may be configured to generate a first signal to introduce the first fluid into the fluid conduit using the pump, generate a second signal to introduce the second fluid into the fluid conduit such that the second fluid separates the first fluid from a third fluid, and generate an electroporation signal to electroporate the cells in the fluid conduit using the set of electrodes.

In some variations, a method of electroporating cells may comprise receiving a first fluid comprising cells in a fluid conduit, receiving a second fluid comprising a gas in the fluid conduit to separate the first fluid from a third fluid, and applying an electroporation signal to the first fluid to electroporate the cells.

In some variations, a method of electroporating cells may comprise receiving a first fluid comprising cells in a fluid conduit, applying a resistance measurement signal to the first fluid using a set of electrodes, measuring a resistance between the first fluid and the set of electrodes, and applying an electroporation signal to the first fluid based on the measured resistance.

Bioreactor

In some variations, a bioreactor may comprise an enclosure comprising a base and a sidewall, and a gas-permeable membrane coupled to one or more of the base and the sidewall of the enclosure. The gas-permeable membrane may aid cell culture. In some variations, a cell processing system may comprise the bioreactor and an agitator coupled to the bioreactor. The agitator may be configured to agitate the bioreactor based on orbital motion.

Fluid Connector

Currently, there is no automated, multi-use sterile fluid connector solution for cell therapy production where a set of sterile fluid connectors are capable of multiple connection and disconnection cycles with a system. For example, conventional sterile fluid connectors are typically single-use devices and are thus expensive and labor intensive. Generally, the fluid connectors described herein include a plurality of sealed enclosures between a sterile portion (e.g., fluid connector lumen or cavity) and an external (e.g., non-sterile) ambient environment, thereby facilitating aseptic control of a fluid connector and devices coupled thereto. The fluid connectors described herein may be a durable component that may be reused for multiple cycles while maintaining sterility and/or bioburden control. For example, the fluid connector may be sterilized using a sterilant without harming the cell product or other biological material.

In some variations, a sterile manufacturing system as described herein may utilize one or more sterile fluid connectors and have a configuration suitable to be manipulated by a robot such as a robotic arm. The sterile fluid connectors described herein enable the transfer of fluids in an automated, sterile, and metered manner for automating cell therapy manufacturing. Automating cell therapy manufacturing may in turn provide lower per patient manufacturing costs, a lower risk of process failure, and the ability to meet commercial scale patient demand for cell therapies. In some variations, sterile fluid connectors may increase one or more of sterility, efficiency, and speed by removing a human operator from the manufacturing process. An automated and integrated sterilization process as described herein may be applied to the fluid connector to maintain sterility of the system. For example, the fluid connector may maintain sterility through multiple connection/disconnection cycles between separate sterile closed volume fluid devices (e.g., enclosure, container, vessel, cartridge, instrument, bioreactor, enclosed vessel, sealed chamber). Accordingly, the systems, devices, and methods described herein may reduce the complexity of a sterilization process, reduce energy usage, and increase sterilization efficiency.

In some variations, a fluid connector may comprise a first connector configured to mate with a second connector (e.g., male connector and female connector). Respective proximal ends of the connectors may be configured to connect (e.g., be in fluid communication, form a fluid pathway) with respective fluid devices in order to transfer one or more of fluid (e.g., liquid and/or gas) and biological material (e.g., cell product) between the fluid devices. The distal ends of the connectors may comprise ports configured to mate with each other. The fluid connector may also comprise a sterilant port configured to facilitate sterilization of a chamber within the distal ends of the first and second connectors. The fluid connector may be sterilized before or after connection as desired to ensure sterility. In this manner, the fluid connector may be reused for multiple connection and disconnection cycles.

In some variations, a system (e.g., workcell) utilizing the fluid connectors described herein may comprise a robot configured to operate the fluid connector and a controller configured to control the robot to manipulate (e.g., move, connect, open, close, disconnect) the first and second connectors together (without human interaction) while maintaining sterility of the fluid connector and a plurality of fluid devices, thereby further reducing the risk of contamination. The fluid devices may be one or more of an instrument, cartridge, and the like.

Cell Processing Control

Systems and methods for manufacturing cell products for biomedical applications using automated systems are described herein. Conventional semi-automated solutions for cell processing do not allow users to define biological processes. Instead, users select from a limited set of predefined machine processes and process-control parameters. Currently, there is no scalable manufacturing solution for cell therapy production. For example, cell therapy manufacturing is conventionally executed batchwise (i.e. one product will be manufactured in a single room/suite, with required processing tools located inside). This can either be guided by a technician following a standard operating procedure (SOP), or in some cases, processing tools (e.g., Miltenyi Prodigy, Lonza Cocoon) can carry out a series of processing steps for a single patient product on a single multi-functional processing tool. However, existing solutions (e.g., Miltenyi Prodigy) do not allow users to define biological processes. Furthermore, the manual labor required of conventional solutions increases the risk of product contamination and human error.

In some variations, a set of cell therapy biological manufacturing processes may be transformed into a set of machine instructions suitable for automated execution using the systems described herein. For example, a method of transforming user-defined cell processing operations into cell processing steps to be executed by a processor of an automated cell processing system may comprise receiving an ordered input list of cell processing operations, and executing a transformation model on the ordered input list to create an ordered output list of cell processing steps capable of being performed by the system. As used herein, a transform model may refer to an algorithm, process, or transformation configured to translate a set of cell processing steps into a set of machine or hardware instructions for the system. In some variations, a robot may be controlled to move one or more cartridges each containing a cell product between the instruments, and the instruments may be controlled to perform cell processing steps on each cell product. In this manner, the systems and methods enable biologists to define manufacturing processes in biological terms and have the system transform this biological model (e.g., process definition) into a set of machine-executed instructions.

The end-to-end closed system automation described herein may reduce process failure rates and cost. For example, end-to-end automation may reduce manufacturing time (e.g., dwell times) and increase throughput as compared to conventional manual methods. For example, a plurality of processes (e.g., 10 or more) may be executed simultaneously. The methods described herein may further reduce opportunities for contamination and user error. Thus, the systems, apparatuses, and methods described herein may increase one or more of cell processing automation, repeatability, reliability, process flexibility, instrument throughput, process scalability, and reduce one or more of labor costs, and process duration.

I. System

Described here are systems and apparatuses configured to perform cell processing steps to manufacture a cell product (e.g., cell therapy product). In some variations, a cell processing system may comprise a plurality of instruments each independently configured to perform one or more cell processing operations upon a cartridge (e.g., fluid device), and a robot capable of moving the cartridge between each of the plurality of instruments. The use of a robot and controller may facilitate one or more of automation, efficiency, and sterility of a cell processing system.

In some variations, a system for cell processing may comprise a plurality of instruments each independently configured to perform one or more cell processing operation upon a cartridge. A robot may be capable of moving the cartridge between each of the plurality of instruments. In some variations, the system may be a workcell comprising an enclosure.

FIG. 1A is a block diagram of a cell processing system 100 comprising a workcell 110 and controller 120. In some variations, the workcell 110 may comprise one or more of an instrument 112, a cartridge 114 (e.g., consumable, fluid device), a robot 116 (e.g., robotic arm), a reagent vault 118, a fluid connector 132, a sterilant source 134, a fluid source 136, a pump 138, a sensor 140, and a sterile liquid transfer device 142. In some variations, the controller 120 may comprise one or more of a processor 122, a memory 124, a communication device 126, an input device 128, and a display 130.

In some variations, a workcell may comprise a fully, or at least partially, enclosed housing inside which one or more cell processing steps are performed in a fully, or at least partially, automated process. In some variations, the workcell may be an open system lacking an enclosure, which may be configured for use in clean room, biosafety cabinet, or other sterile location. In some variations, the cartridge 114 may be moved using the robot 116 to reduce manual labor in the cell processing steps. In some variations, the workcell may be configured to perform sterile liquid transfers into and out of the cartridge in a fully or partially automated process. For example, one or more fluids may be stored in a sterile liquid transfer device 142. In some variations, the sterile liquid transfer device may be a portable consumable that may be moved within the system 100. The sterile liquid transfer devices and fluid connectors described herein enable the transfer of fluids in an automated, sterile, and metered manner for automating cell therapy manufacturing. In some variations, the enclosure of the workcell may be configured to meet International Organization for Standardization (ISO) standard ISO7 or better (e.g., ISO6 or ISO5). An advantage of meeting ISO7 or better standards is that the system may be used in a facility that does not meet ISO7 standards (i.e. that lack a clean room or other sufficiently filtered air space). Optionally, the facility may be an ISO8 or ISO9 facility. In some variations, a workcell may comprise a volume of less than about 800 $m^3$, less than about 700 $m^3$, less than about 600 $m^3$, less than about 500 $m^3$, less than about 300 $m^3$, less than about 250 $m^3$, less than about 200 $m^3$, less than about 150 $m^3$, less than about 100 $m^3$, less than about 50 $m^3$, less than about 25 $m^3$, less than about 10 $m^3$, and less than about 5 $m^3$, including all ranges and sub-values in-between.

In some variations, a robot 116 may be configured to manipulate consumable cartridges 114 and fluid connectors 132 between different instruments to perform a predetermined sequence of cell processing steps. In some variations, the same consumable cartridge 114 may be received by different instruments 112 and/or multiple cartridges 114 may be processed in parallel.

In some variations, a cartridge 114 may contain cell product from different donors or contain cell product intended for different recipients. The cell product from a single donor may be split between multiple cartridges 114 if necessary to generate enough product for therapeutic use, or when a donor is providing product for several recipients (e.g., for allogeneic transplant). The cell product for a single recipient may be split between multiple cartridges 114 if necessary to generate enough product for therapeutic use in that recipient. The cell product for a single recipient may be split between multiple cartridges 114 if necessary to generate several cell products with unique genetic modifications, and then optionally recombined in certain ratios for therapeutic use in that recipient. For example, a fluid connector 132 may be coupled between two or more cartridges 114 to transfer a cell product and/or fluid between the cartridges 114. Furthermore, a fluid connector 132 may be coupled between any set of fluid-carrying components of the system 100 (e.g., cartridge 114, reagent vault 118, fluid source 136, sterile liquid transfer device 142, fluid conduit, container, vessel, etc.). For example, a first fluid connector may be coupled between a first cartridge and a sterile liquid transfer device, and a second fluid connector may be coupled between the sterile liquid transfer device and a second cartridge.

Figure 1B:
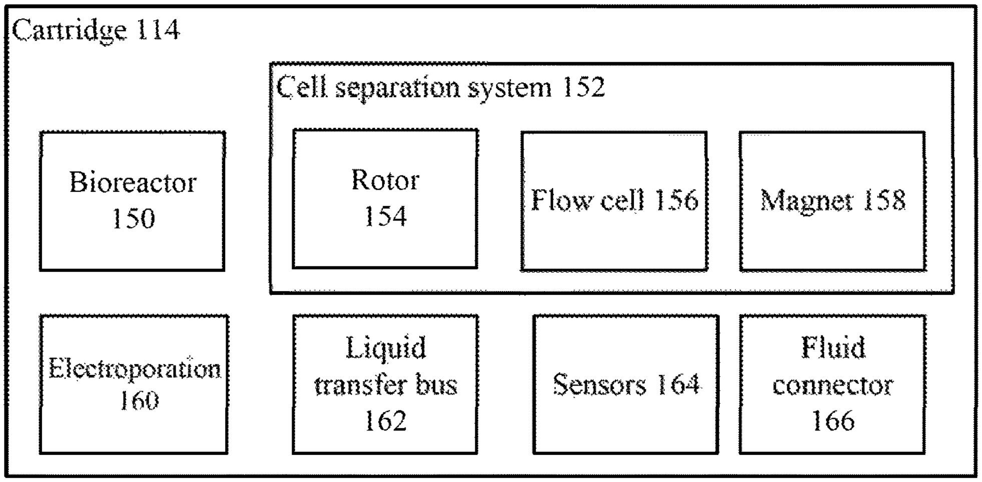
FIG. 1B is a block diagram of an illustrative variation of a cartridge.

As illustrated in FIG. 1B, a cartridge 114 may comprise one or more of a bioreactor 150, cell separation system 152, electroporation module 160, liquid transfer bus 162, sensor 164, and fluid connector 166, as described in more detail herein. A cell separation system 152 may comprise one or more of a rotor 154, flow cell 156, and magnet 158. In some variations, the magnet 158 may comprise one or more magnets and/or magnet arrays. For example, the cell separation system 152 may comprise a first magnet configured to magnetically rotate a rotor 154 and a second magnet (e.g., magnet array) configured to magnetically separate cells in flow cell 156.

Workcell

In some variations, a workcell 110 may comprise at least a partially enclosed enclosure (e.g., housing) in which one or more automated cell processing steps are performed. For example, the workcell 110 may be configured to transfer sterile liquid into and out of a cartridge 114 in a fully or partially automated process. In some variations, a workcell 110 may not have an enclosure and be configured for use in a clean room, a biosafety cabinet, or other suitably clean or sterile location. In some variations, the workcell 100 may comprise a feedthrough access biosafety cabinet, quality control instrumentation, pump, consumable (e.g., fluid device), fluid connector, consumable feedthrough, and sterilization system (e.g., sterilant source and/or generator, fluid source, heater/dessicator, aerator).

Figure 2A:
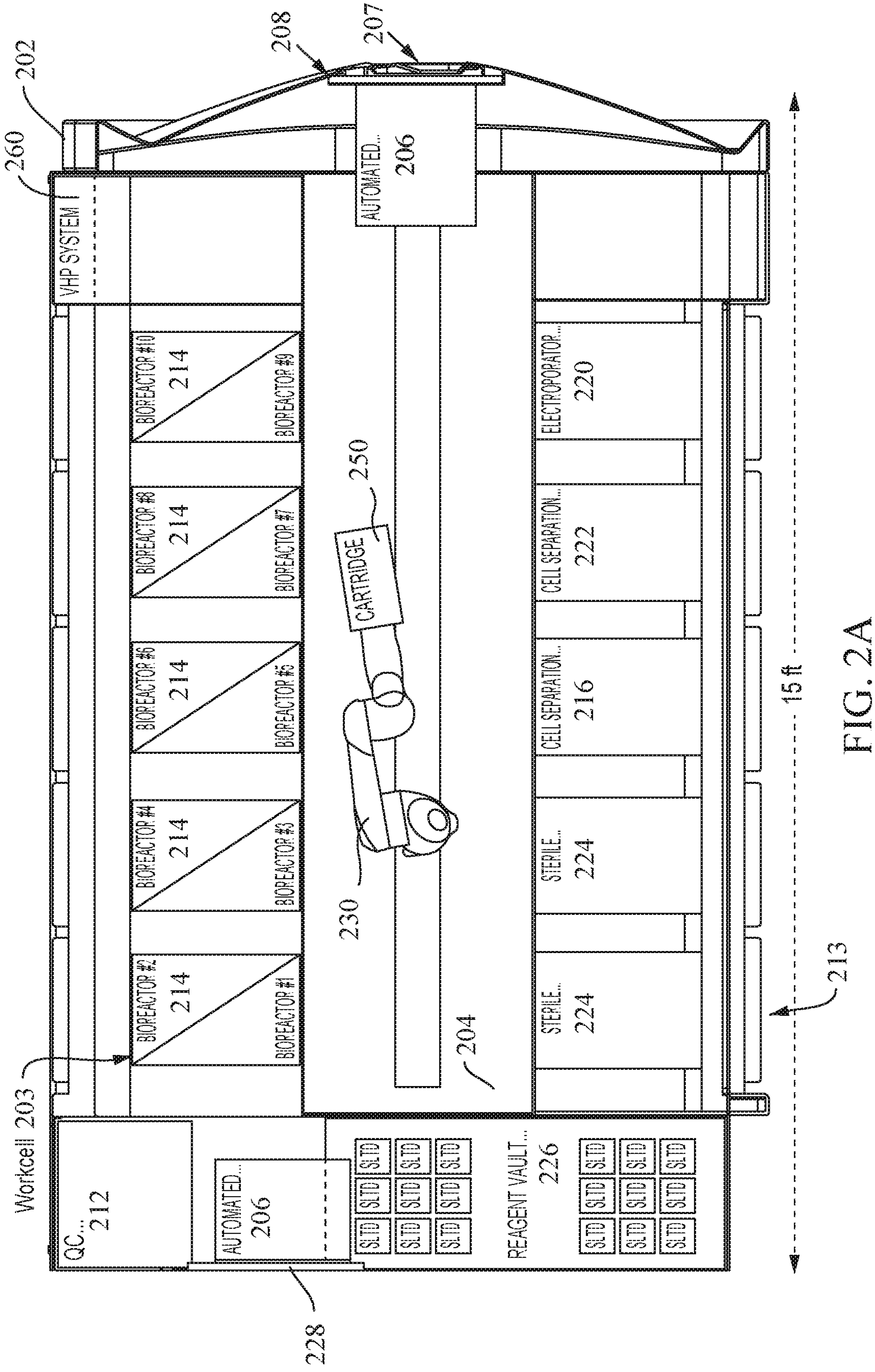
FIG. 2A is a block diagram of an illustrative variation of a cell processing system.

FIG. 2A is a block diagram of a cell processing system including a workcell 203. Workcell 203 may comprise an enclosure 202 having four walls, a base, and a roof. The workcell may be divided into an interior zone 204 with a feedthrough 206 access, and quality control (QC) instrumentation 212. An air filtration inlet (not shown) may provide high-efficiency particulate air (HEPA) filtration to provide ISO7 or better air quality in the interior zone 204.

This air filtration may maintain sterile cell processing in an ISO8 or ISO9 manufacturing environment. The workcell 203 may also have an air filter on the air outlet to preserve the ISO rating of the room. In some variations, the workcell 203 may further comprise, inside the interior zone 104, a bioreactor instrument 214, a cell selection instrument 216 (e.g., MACS), an electroporation instrument (EP) 220, a counterflow centrifugation elutriation (CCE) instrument 222, a sterile liquid transfer instrument 224 (e.g., fluid connector), a reagent vault 226, and a sterilization system 260. The reagent vault 226 may be accessible by a user through a sample pickup port 228. A robot 230 (e.g., support arm, robotic arm) may be configured to move one or more cartridges 250 (e.g., consumables) from any instrument to any other instrument and/or move one or more cartridges 250 to and from a reagent vault. In some variations, the workcell 203 may comprise one or more moveable barrier 213 (e.g., access, door) configured to facilitate access to one or more of the instruments in the workcell 203.

In some variations of methods according to the disclosure, a human operator may load one or more empty cartridges 250 into the feedthrough 206 via cartridge port 207. The cartridges 250 may be pre-sterilized, or the feedthrough 206 may sterilize the cartridge 250 using ultraviolet radiation (UV), or chemical sterilizing agents provided as a vapor, spray, or wash. The feedthrough 206 chamber may optionally be configured to automatically spray, wash, irradiate, or otherwise treat cartridges (e.g. with ethanol and/or isopropyl alcohol solutions, vaporized hydrogen peroxide (VHP)) to maintain sterility of the interior zone 204 (e.g., ISO 7 or better). The cartridge 250 may be passed to the biosafety cabinet 206, where input cell product is provided and loaded to the cartridge through a sterile liquid transfer port into the cartridge 250. The user (via robot 230) may then move the cartridge 250 back to the feedthrough 206 and initiate automated processing using a computer processor in the computer server rack (e.g., controller 120). The robot 230 may be configured to move the cartridge 250 in a predefined sequence to a plurality of instruments and stations, with the components of the workcell 200. At the end of cell processing, the cartridge 250, now containing the processed cell product, may be returned to the feedthrough 206 for retrieval by the user. In some variations, an outer surface of the enclosure 202 may comprise an input/output device 208 (e.g., display, touchscreen).

Figure 2B:
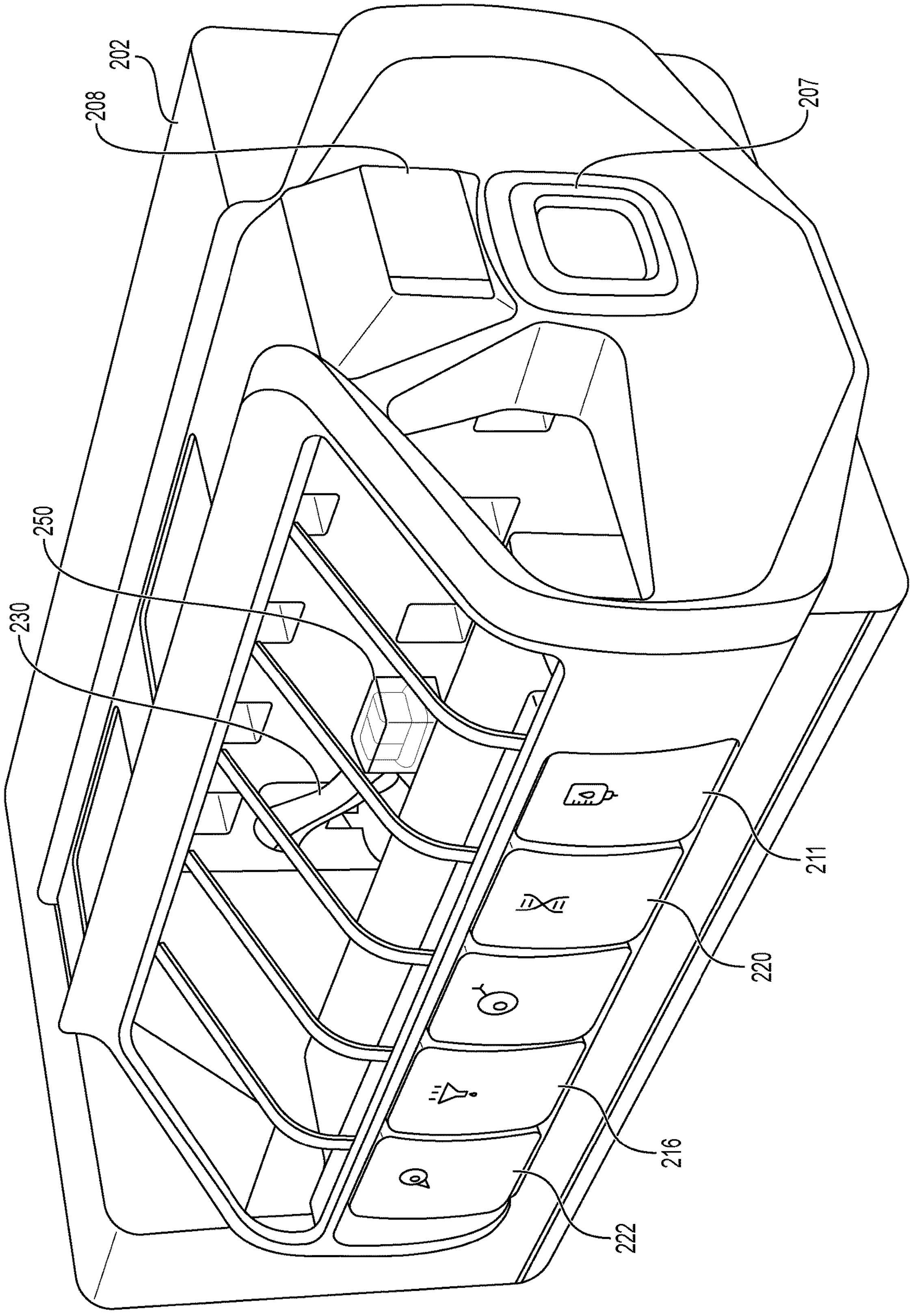
FIG. 2B is a perspective view of an illustrative variation of a workcell of a cell processing system.
Figure 2C:
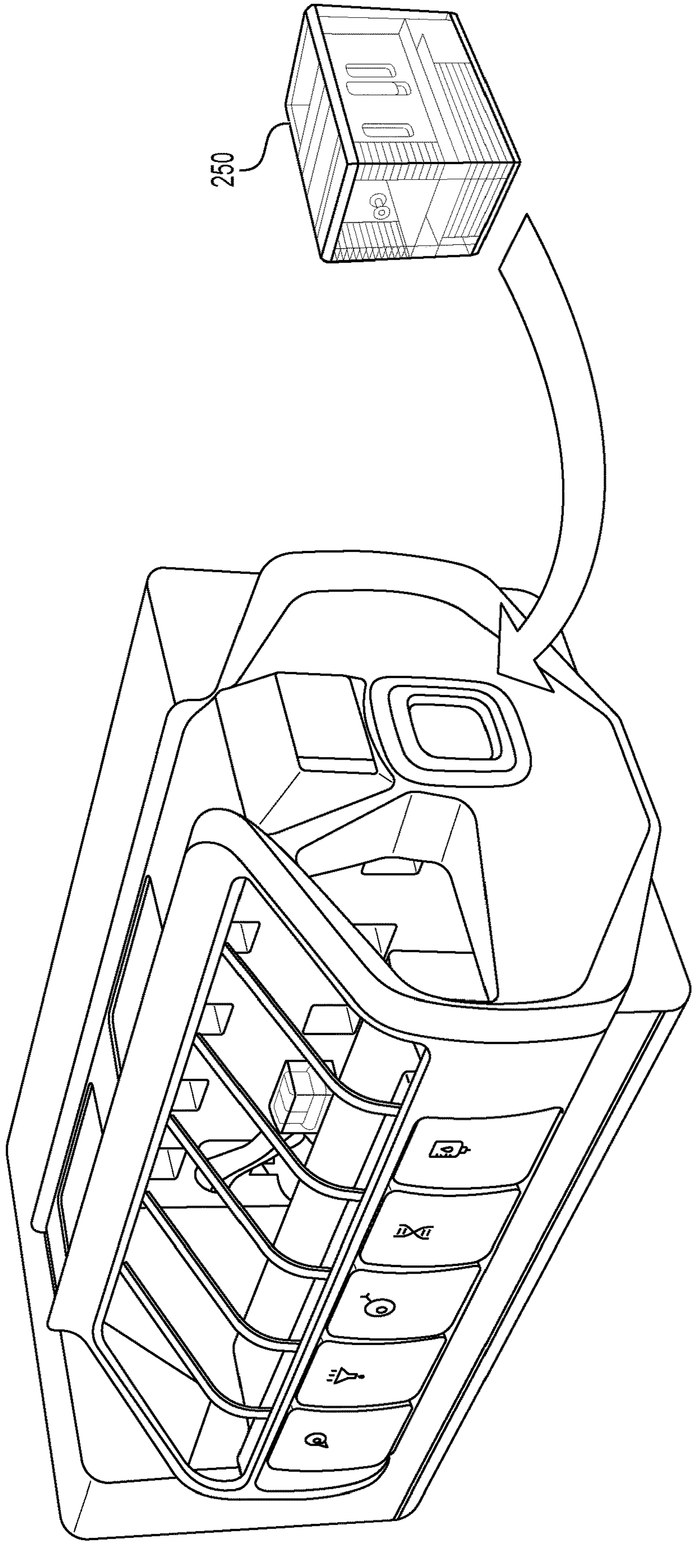
FIG. 2C is a perspective view of an illustrative variation of a workcell and cartridge of a cell processing system.

FIG. 2B is a perspective view of a workcell 205 of a cell processing system. FIG. 2C is a perspective view of a cell processing system depicting a cartridge 250 (e.g., any of the cartridges described herein) introduced into a workcell 205 (e.g., any of the workcells described herein). A plurality of cartridges may be inserted into the workcell 205 simultaneously and undergo one or more cell processing operations in parallel.

In some variations, the workcell 205 may comprise a height of more than about a meter, between about 1 m and about 3 m, between about 1 m and about 5 m, between about 3, and about 10 m, between about 5 m and about 20 m, between about 10 m and about 30 m, between about 20 m and 100 m, and more than about 100 m, including all values and ranges in-between. In some variations, the workcell 205 may comprise one or more of a length and width of more than about 1 meter, between about 1 m and about 5 m, between about 3, and about 10 m, between about 5 m and about 20 m, between about 10 m and about 30 m, between about 20 m and 100 m, and more than about 100 m, including all values and ranges in-between.

Figure 2D:
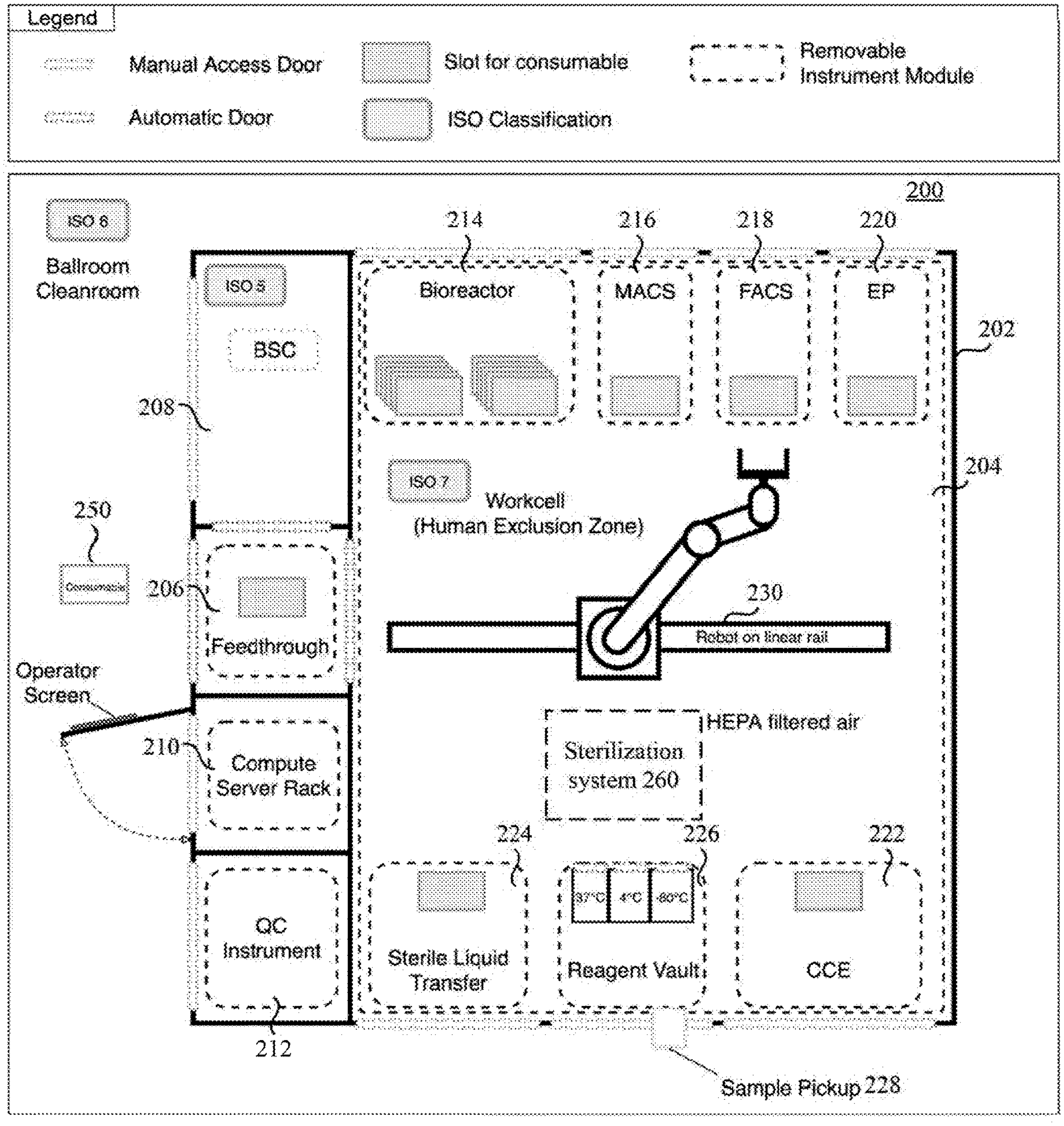
FIG. 2D is a block diagram of an illustrative variation of a cell processing system.

FIG. 2D is a schematic illustration of a variation of a workcell 200. Workcell 200 may comprise an enclosure 202 having four walls, a base, and a roof. The workcell may be divided into an interior zone 204 with a feedthrough 206 access, a biosafety cabinet (BSC) 208, compute server rack 210 (e.g., controller 120), and quality control (QC) instrumentation 212. An air filtration inlet (not shown) may provide high-efficiency particulate air (HEPA) filtration to provide ISO7 or better air quality in the interior zone 204. This air filtration may maintain sterile cell processing in an ISO8 or ISO9 manufacturing environment. The workcell may also have an air filter on the air outlet to preserve the ISO rating of the room. In some variations, the workcell 200 may further comprise, inside the interior zone 204, an instrument 211 (e.g., disposed in a universal instrument bay), a bioreactor instrument 214, a cell selection instrument 216 (e.g., MACS, cell selection system), a cell sorting instrument 218 (e.g., FACS), an electroporation instrument (EP) 220, and a counterflow centrifugation elutriation (CCE) instrument 222, a sterile liquid transfer instrument 224 (e.g., fluid connector), a reagent vault 226, and a sterilization system 260 comprising one or more of a sterilant source, fluid source, and a pump. The reagent vault 226 may be accessible by a user through a sample pickup port 228. A robot 230 (e.g., support arm, robotic arm) may be configured to move one or more cartridges 250 (e.g., consumables) from any instrument to any other instrument or reagent vault.

In some variations, a human operator may load one or more cartridges 250 into the feedthrough 206. The cartridges 250 may be pre-sterilized, or the feedthrough 206 may sterilize the cartridge 250 using ultraviolet radiation (UV), or chemical sterilizing agents provided as a spray or wash. The feedthrough 206 chamber may optionally be configured to automatically spray, wash, irradiate, or otherwise treat cartridges (e.g. with ethanol and/or isopropyl alcohol solutions) to maintain sterility of the interior zone 204 (e.g., ISO 7 or better) or the biosafety cabinet 208 (e.g., ISO 5 or better). The cartridge 250 may be passed to the biosafety cabinet 206, where input cell product is provided and loaded to the cartridge using a sterile liquid transfer instrument 224 (e.g., fluid connector) into the cartridge 250. The user may then move the cartridge 250 back to the feedthrough 206 and initiate automated processing using a computer processor in the computer server rack 210 (e.g., controller 120). The robot 230 may be configured to move the cartridge 250 in a predefined sequence to a plurality of instruments and stations, with the components of the workcell 200 being controlled by the computer processor of the computer server rack 210. Additionally or alternatively, the sequence that the cartridge 250 moves within the workcell 200 may not be predefined. For example, cartridge 250 movement may not be dependent on one or more of the result of a previous step, sensor value, predetermined threshold (e.g., based on a quality control system), and the like. At the end of cell processing, the cartridge 250, now containing the processed cell product, may be returned to the feedthrough 206 for retrieval by the user. Additionally or alternatively, the cell product 250 containing the processed cell product may be transferred (via a fluid connector) to a second cartridge (e.g., single-use cartridge) and stored in the reagent vault 226 for retrieval by the user.

In some variations, cells from a patient and starting reagents may be loaded into a cartridge (e.g., single-use cartridge) by a human operator in a biosafety cabinet located separate from the workcell or integrated into the workcell. In some variations, the cartridges described herein comprising a cell product and reagent may move through a non-sterile field without contamination since the cartridge is closed. The cartridge may further undergo an automated decontamination routine. For example, the cartridge may be placed within a feedthrough capable of facilitating decontamination of the cartridge before entering the ISO 7 environment in the workcell.

Figure 2E:
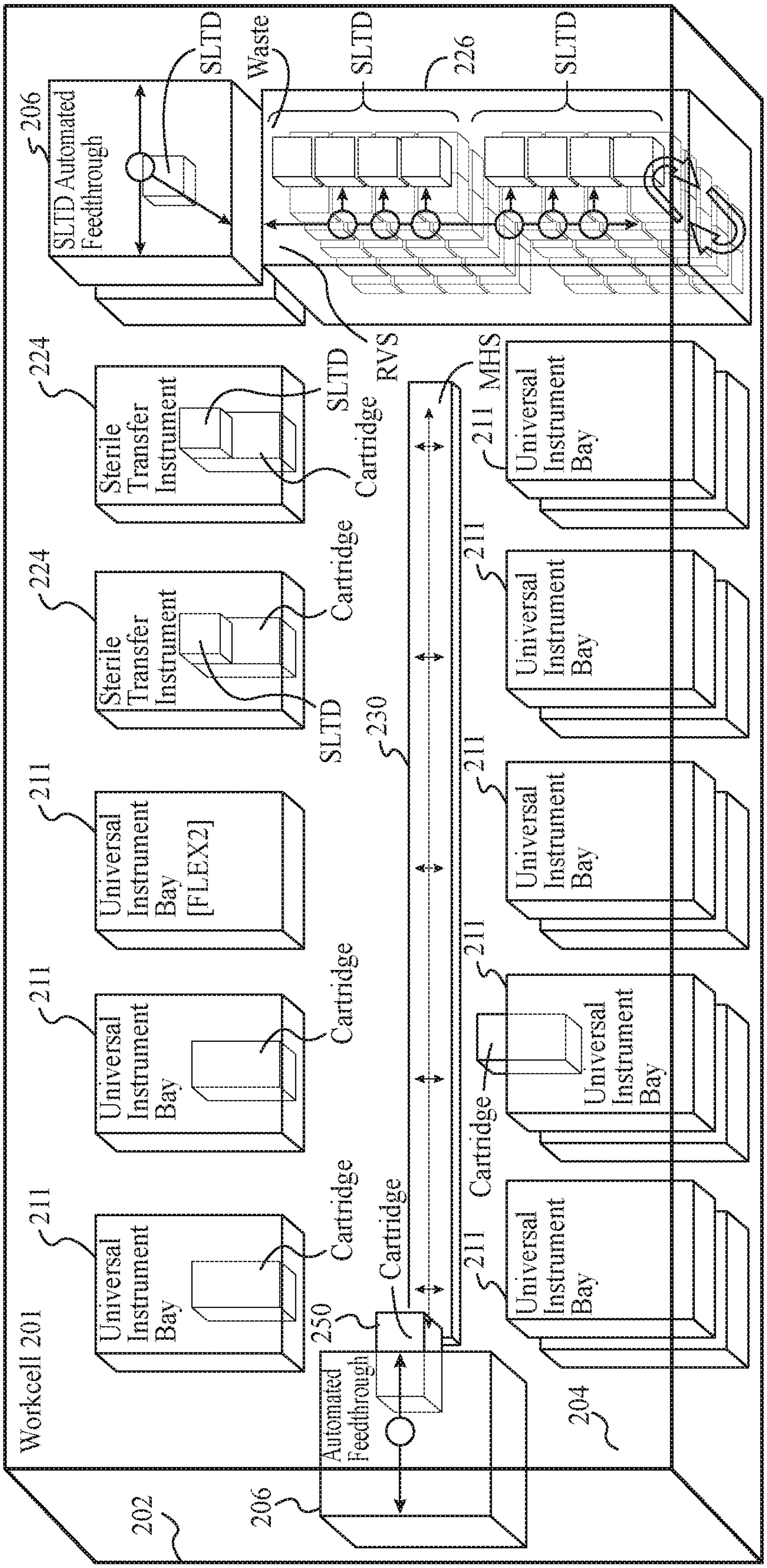
FIG. 2E is a block diagram of another illustrative variation of a cell processing system.

FIG. 2E is a plan schematic illustration of another variation of a workcell 201. Workcells 200, 201, and 203 may comprise an enclosure 202 having four walls, a base, and a roof. The workcell may be divided into an interior zone 204 with a feedthrough 206 access, a biosafety cabinet (BSC) 208, compute server rack 210 (e.g., controller 120), and quality control (QC) instrumentation 212. An air filtration inlet (not shown) may provide high-efficiency particulate air (HEPA) filtration to provide ISO7 or better air quality in the interior zone 204. This air filtration may maintain sterile cell processing in an ISO8 or ISO9 manufacturing environment. The workcell may also have an air filter on the air outlet to preserve the ISO rating of the room. In some variations, the workcell 200 may further comprise, inside the interior zone 104, an instrument 211 (e.g., disposed in a universal instrument bay), a bioreactor instrument 214, a cell selection instrument 216 (e.g., MACS), a cell sorting instrument 218 (e.g., FACS), an electroporation instrument (EP) 220, and a counterflow centrifugation elutriation (CCE) instrument 222, a sterile liquid transfer instrument 224, and a reagent vault 226. The reagent vault 226 may be accessible by a user through a sample pickup port 228 (e.g., a door which may facilitate bulk loading of sterile liquid transfer instruments 224). A robot 230 (e.g., support arm, robotic arm) may be configured to move one or more cartridges 250 (e.g., consumables) from any instrument to any other instrument or reagent vault.

In some variations of methods according to the disclosure, a human operator may load one or more empty cartridges 250 into the feedthrough 206. Additionally or alternatively, pre-filled cartridges may be loaded into the feedthrough 206. The cartridges 250 may be pre-sterilized, or the feedthrough 206 may sterilize the cartridge 250 using ultraviolet radiation (UV), or chemical sterilizing agents provided as a spray or wash. The feedthrough 206 chamber may optionally be configured to automatically spray, wash, irradiate, or otherwise treat cartridges (e.g. with ethanol and/or isopropyl alcohol solutions) to maintain sterility of the interior zone 204 (e.g., ISO 7 or better) or the biosafety cabinet 208 (e.g., ISO 5 or better). The cartridge 250 may be passed to the biosafety cabinet 106, where input cell product is provided and loaded to the cartridge through a sterile liquid transfer port into the cartridge 250. The user may then move the cartridge 250 back to the feedthrough 206 and initiate automated processing using a computer processor in the computer server rack 210 (e.g., controller 120). The robot 230 may be configured to move the cartridge 250 in a predefined sequence to a plurality of instruments and stations, with the components of the workcell 200 being controlled by the computer processor of the computer server rack 210. At the end of cell processing, the cartridge 250, now containing the processed cell product, may be returned to the feedthrough 206 for retrieval by the user.

Figure 3:
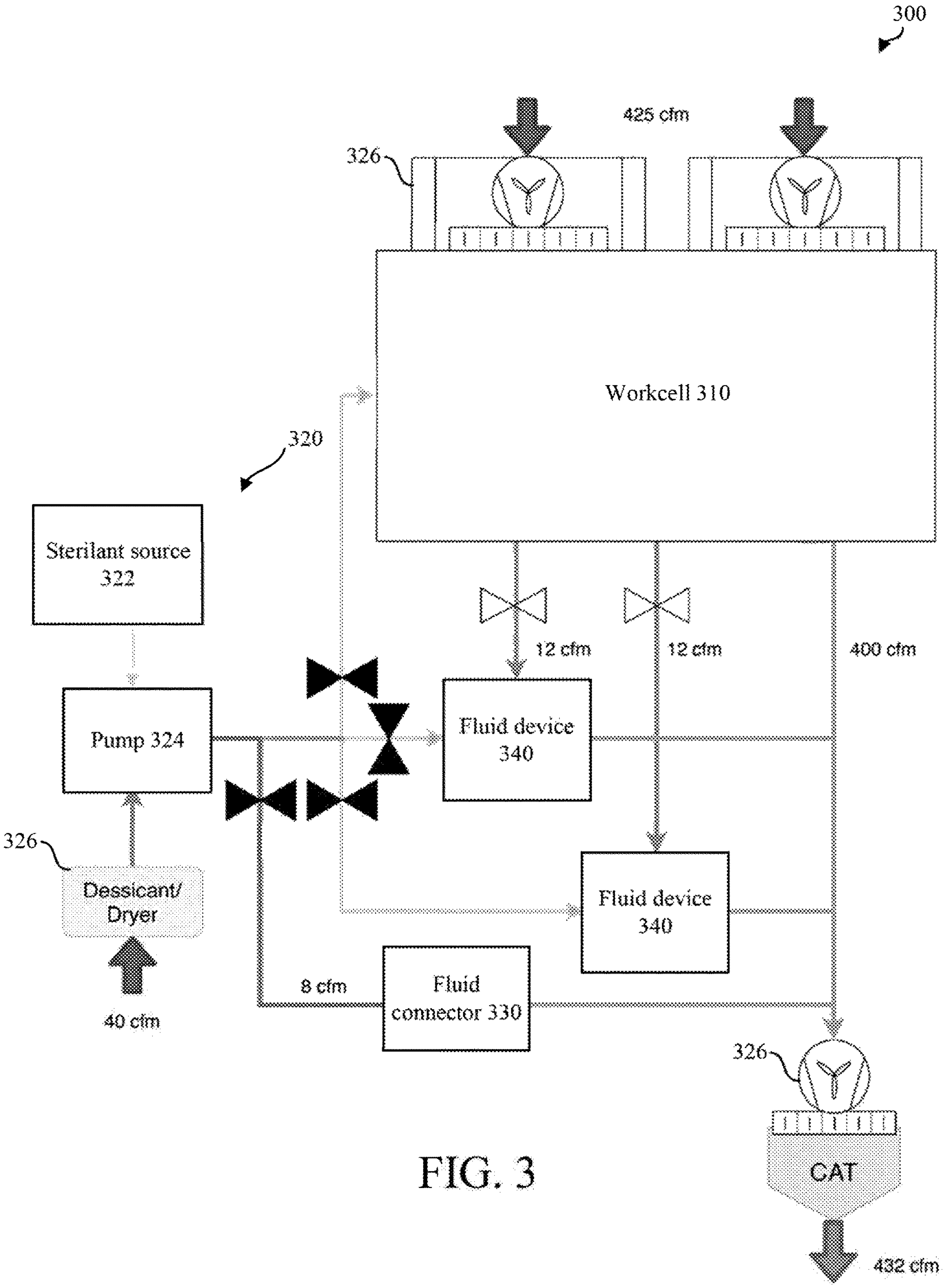
FIG. 3 is a block diagram of another illustrative variation of a cell processing system.

In some variations, one or more components of a sterilization system (e.g., sterilant source, pump) may be coupled to a workcell. For example, FIG. 3 is a block diagram of a cell processing system 300 comprising a workcell 310, sterilization system 320, fluid connector 330 and fluid devices 340. In some variations, the fluid devices 340 may comprise a main (e.g., consumable) feedthrough and a fluid device (e.g., reagent) feedthrough. The sterilization system 320 may comprise a sterilant source 322, pump 324, and heater (e.g., desiccant/dryer) 326. For example, the heater 326 may be configured to aerate at a predetermined set of conditions. The sterilization system 320 may be coupled and in fluid communication with one or more of the workcell 310, fluid connector 330, and fluid device 340. In some variations, a robot (not shown) may be configured to manipulate and operate the cell processing system 300. For example, the fluid connector 330 may be coupled to one or more of the fluid devices 340 and instruments (not shown). One or more of the workcell 310, fluid connector 330, and fluid devices 340 may be sterilized and/or aerated by circulating one or more of a sterilant and fluid (e.g., heated air, vaporized hydrogen peroxide (VHP)) using the sterilization system 320. In some variations, the sterilization system 320 may comprise one or more of vaporized hydrogen peroxide (VHP), electron-beam (e-beam) sterilization, dry thermal decontamination, and steam-in-place. In some variations, the sterilization system 320 may provide a sterility assurance level (SAL) of at least 10-3 SAL.

Figure 4A:
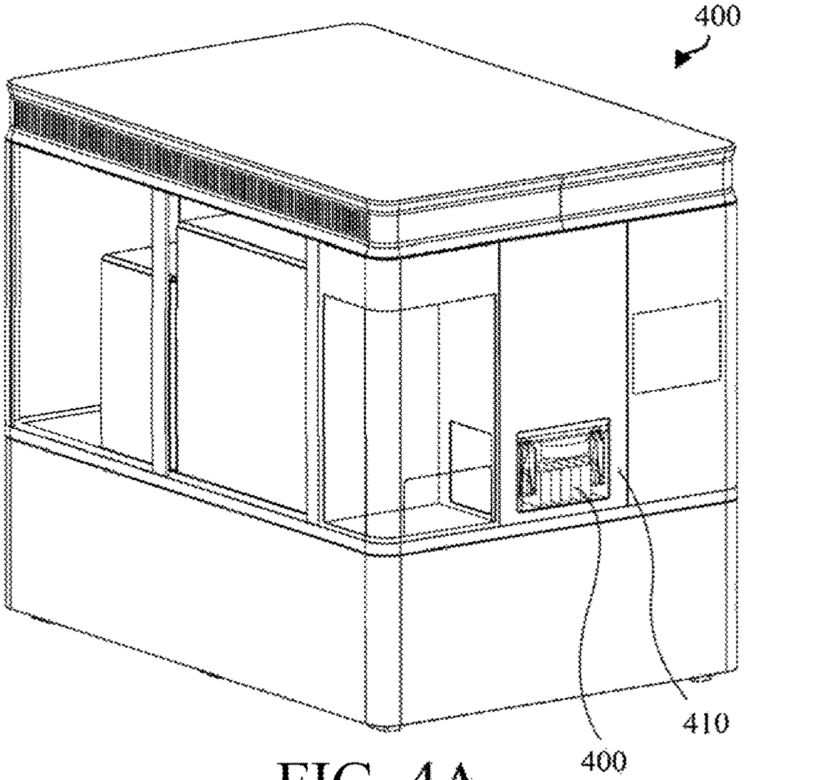
FIG. 4A is a perspective view of another illustrative variation of a cell processing system.
Figure 4B:
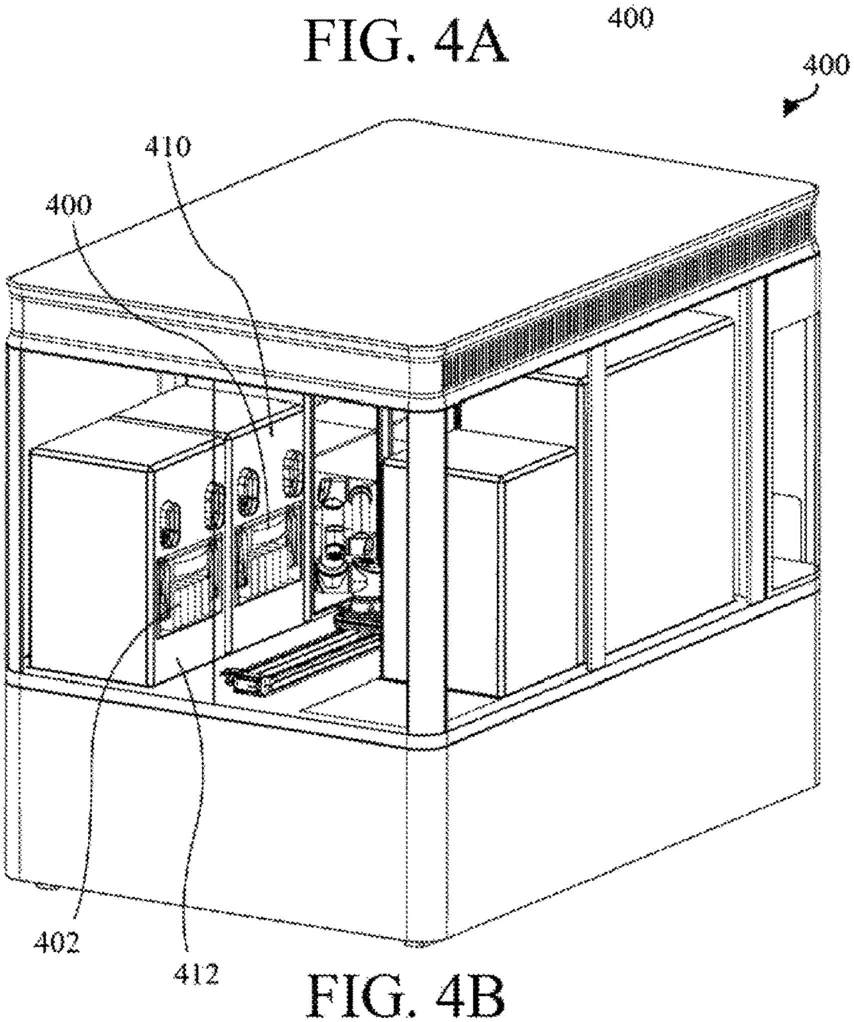
FIG. 4B is another perspective view of another illustrative variation of a cell processing system.

FIGS. 4A and 4B illustrate perspective views of a cell processing system 400 comprising a cartridge 400, 402, feedthrough 410, 412, and fluid connector 420, 422 (e.g., sterile liquid transfer instrument). For example, cartridge 400 is shown in the feedthrough 410 in FIG. 16A while a robot (not shown) has moved cartridge 400 to fluid connector 420.

Robot

Generally, a robot may comprise any mechanical device capable of moving a cartridge from one location to another location. For example, the robot may comprise a mechanical manipulator (e.g., an arm) in a fixed location, or attached to a linear rail, or a 2- or 3-dimensional rail system. In a variation, the robot comprises a robotic shuffle system. In a further variation, the robot comprises a wheeled device. In some variations, the system comprises two or more robots of the same or different type (e.g., two robotic arms each independently configured for moving cartridges between instruments). The robot may also comprise an end effector for precise handling of different cartridges or barcode scanning or radio-frequency identification tag (RFID) reading.

Figure 5:
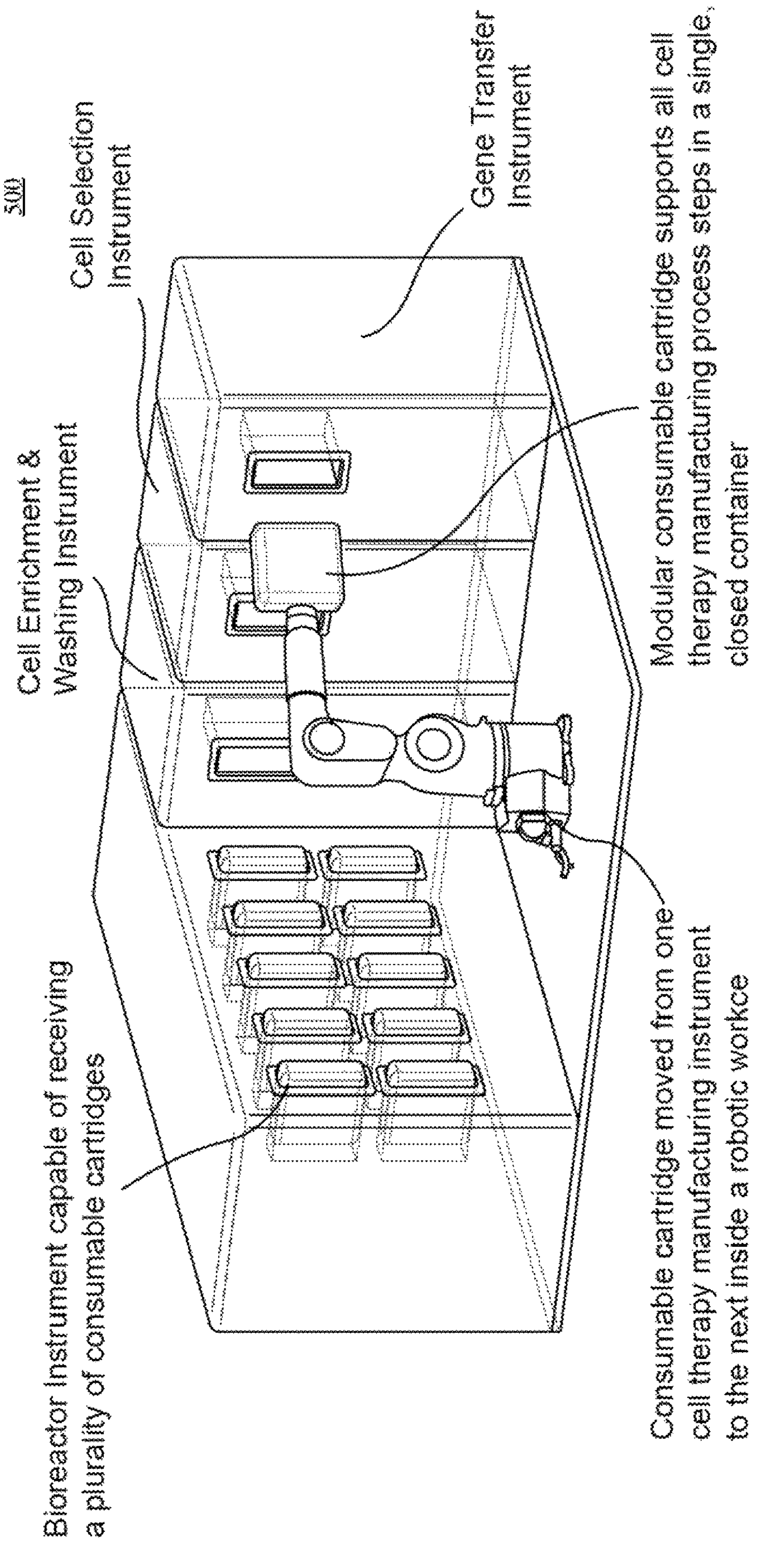
FIG. 5 is a perspective view of another illustrative variation of a cell processing system.

FIG. 5 is a perspective view of a cell processing system 500 in which a robot arm moves consumable cartridges between slots in various instruments each configured to perform a different cell processing step. In some variations, the same consumable cartridge can be received by different instruments. The system 500 may comprise a modular design to accommodate different instrument configurations. In some variations, a plurality of cartridges may be processed in parallel. Each cartridge may contain a cell product from different donors or contain a cell product intended for different recipients. For example, a cell product from a single donor may be split between a plurality of cartridges to generate a predetermined quantity of cell product for therapeutic use such as when a donor is providing product for several recipients (e.g., for allogeneic transplant). In some variations, the cell product for a single recipient may be split between a plurality of cartridges to generate a predetermined quantity of product for therapeutic use in that recipient. In some variations, the cell product for a single recipient may be split between a plurality of cartridges to generate a predetermined quantity of several cell products with unique genetic modifications, which may be recombined in certain ratios for therapeutic use in that recipient.

Cartridge

Generally, the cell processing systems described herein may comprise one or more cartridges including one or more modules configured to interface with an instrument or instruments. A robot (e.g., robotic arm) may be configured to move a cartridge and/or instrument to perform one or more cell processing steps. For example, a cartridge may comprise a bioreactor module and/or fluid connector (e.g., sterile liquid transfer port) coupled by the robot to a bioreactor instrument of a workcell. Once a predetermined processing step has been completed, the cartridge may be moved by the robot to another instrument of the workcell, and another cartridge may be coupled to the bioreactor instrument. Thus, a portable cartridge and shareable instruments may increase the efficiency, throughput, and flexibility of a cell manufacturing process.

In some variations, the cartridge may optionally provide a self-contained device capable of performing one or more cell processing steps. The modules may be integrated into a fixed configuration within the cartridge. Additionally or alternatively, the modules may be configurable or moveable within the cartridge, permitting various cartridges to be assembled from shared modules. Similarly stated, the cartridge can be a single, closed unit with fixed components for each module; or the cartridge may contain configurable modules coupled by configurable fluidic, mechanical, optical, and electrical connections. In some variations, one or more sub-cartridges, each containing a set of modules, may be configured to be assembled to perform various cell processing workflows. The modules may each be provided in a distinct housing or may be integrated into a cartridge or sub-cartridge with other modules. The disclosure generally shows modules as distinct groups of components for the sake of simplicity, but may be arranged in any suitable configuration. For example, the components for different modules may be interspersed with each other such that each module is defined by the set of connected components that collectively perform a predetermined function. However, the components of each module may or may not be physically grouped within the cartridge. In some variations, multiple cartridges may be used to process a single cell product through transfer of the cell product from one cartridge to another cartridge of the same or different type and/or by splitting cell product into more cartridges and/or pooling multiple cell products into fewer cartridges.

Generally, each of the instruments of the system interfaces with its respective module or modules on the cartridge e.g., an electroporation module on the cartridge (if present) is moved by the system to an electroporation instrument and interfaces with the electroporation instrument to perform an electroporation step on the cell product—and may also interface with common components, such as components of a fluidic bus line (e.g., pumps, valves, sensors, etc.). An advantage of such split module/instrument designs is that expensive components (e.g., motors, sensors, heaters, lasers, etc.) may be retained in the instruments of the system while multiple cartridges are processed. The use of disposable cartridges may eliminate the need, in such variations, to sterilize cartridges between use. Furthermore, the utilization of shared instruments (e.g. electroporation instrument, CCE instrument, MACS instrument, sterile liquid transfer instrument, FACS instrument, and the like) may be increased since a plurality of the instruments may be utilized simultaneously in parallel by a plurality of cell manufacturing processes. In contrast, conventional semi-automated instruments (e.g., Miltenyi Prodigy) have instrument components that sit idle and are incapable of simultaneous parallel use.

Figure 6:
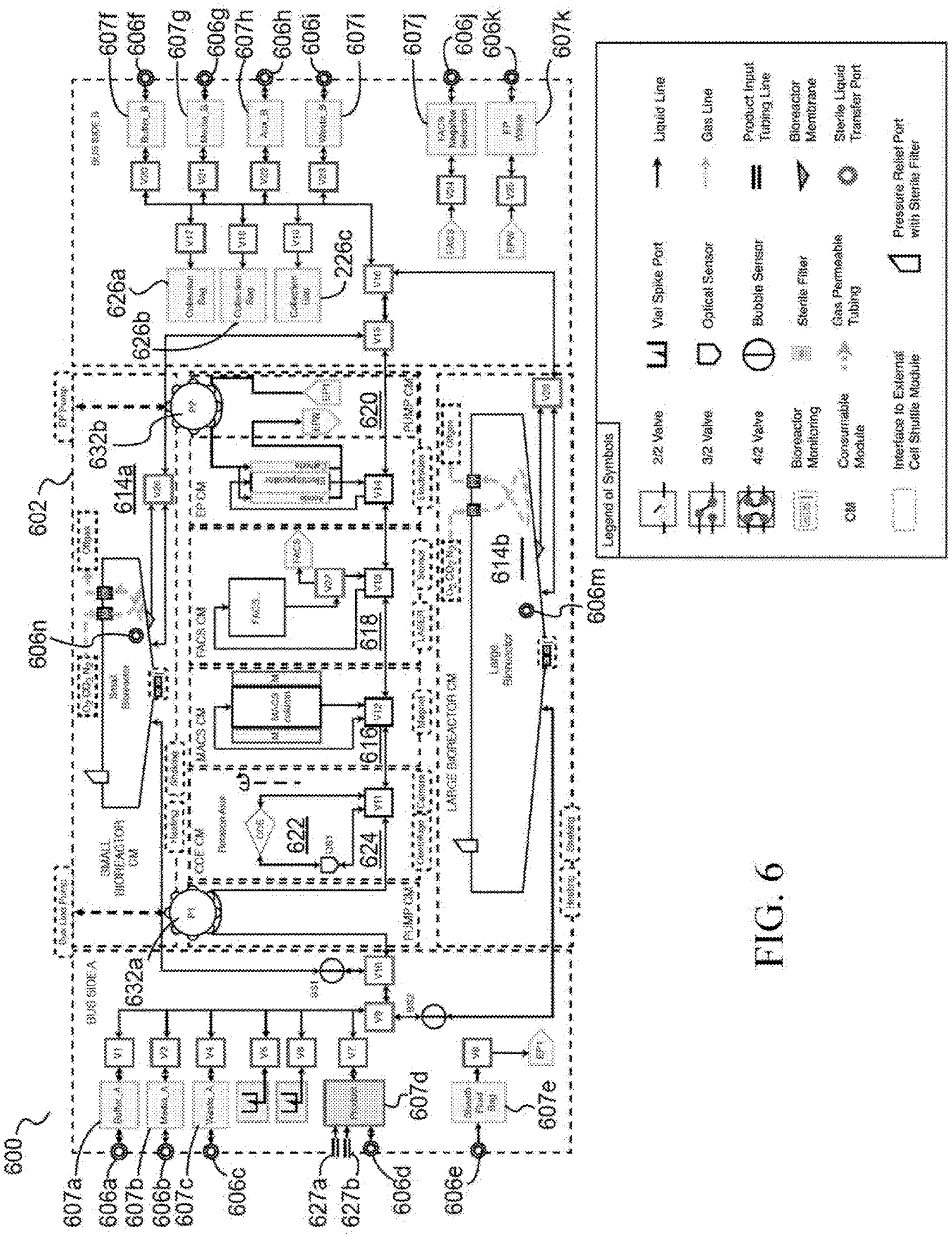
FIG. 6 is a schematic diagram of an illustrative variation of a cartridge.

FIG. 6 is a schematic illustration of a cartridge 600 that may be a consumable produced from materials at a cost that make recycling or limited use practical. The cartridge 600 may comprise a liquid transfer bus 624 fluidically coupled to a small bioreactor module 614*a*, a large bioreactor module 614*b*, a cell selection module 616, a cell sorting module 618, an electroporation module 620, and a counterflow centrifugation elutriation (CCE) module 622. In some variations, the cell selection module 616 may be a magnetic-activated cell selection (MACS) module. The cell sorting module 618 may comprise a fluorescence activated cell sorting (FACS) module. The cartridge 600 may comprise a housing 602 that renders the cartridge self-contained, and optionally protects the contents from contamination. Sterile liquid transfer ports (SLTPs) 606*a*-606*k* may be fluidically coupled to reservoirs 607*a*-607*k*, and each independently be a flexible bag or a rigid container. In some variations, flexible bags may be configured to hold large volumes and to permit transfer of fluid without replacing transferred fluid with liquid or gas to maintain the pressure in the reservoir, as the bag may collapse when fluid is transferred out and expand when fluid is transferred in.

In some variations, the liquid transfer bus 624 may comprise valves V1 to V28 and corresponding tubing that fluidically links the valves to one another and to each of the modules. Valves shown coupled to four fluidic lines are 4/2 (4 port 2 position) valves and valves shown coupled to three fluidic lines are 3/2 (3 port 2 position) valves. Internal flow paths of the valves are indicated in the legend. The cartridge may further comprise a first pump 632*a* and a second pump 632*b*, each of which expose tubing on the exterior of the housing 602 to permit each pump to interface with pump actuators (e.g., rotors) in some instruments in the system (e.g., workcell). The liquid transfer bus 624 may be fluidically coupled to reservoir 607*d* and a product bag which is fluidically coupled to STLP 606*d* and to product input tubing lines 627*a*-627*b*. An operator may input a cell product into reservoir 607*d* by connecting product input tubing line 627*a* or 627*b* to an external source of cells (e.g., a bag of cells collected from a donor). SLTP 606*d* may be configured to permit a system according to the disclosure (e.g., workcell 110) to add fluid to the reservoir 607*d* in an automated fashion. For example, one or more fluid-carrying containers such as reservoirs 607*a*-607*k*, bags, etc. may receive fluid using an SLTP. Additionally or alternatively, the SLTP may be configured to periodically sample one or more of the fluid-carrying containers. The cartridge may further comprise collection bags 626*a*-626*c*, fluidically coupled to the liquid transfer bus 624 via valves V17-V19. The cartridge 600 may be configured to permit an operator to remove the collection bags 626*a*-626*c* after completion of cell processing by the system.

Figure 7:
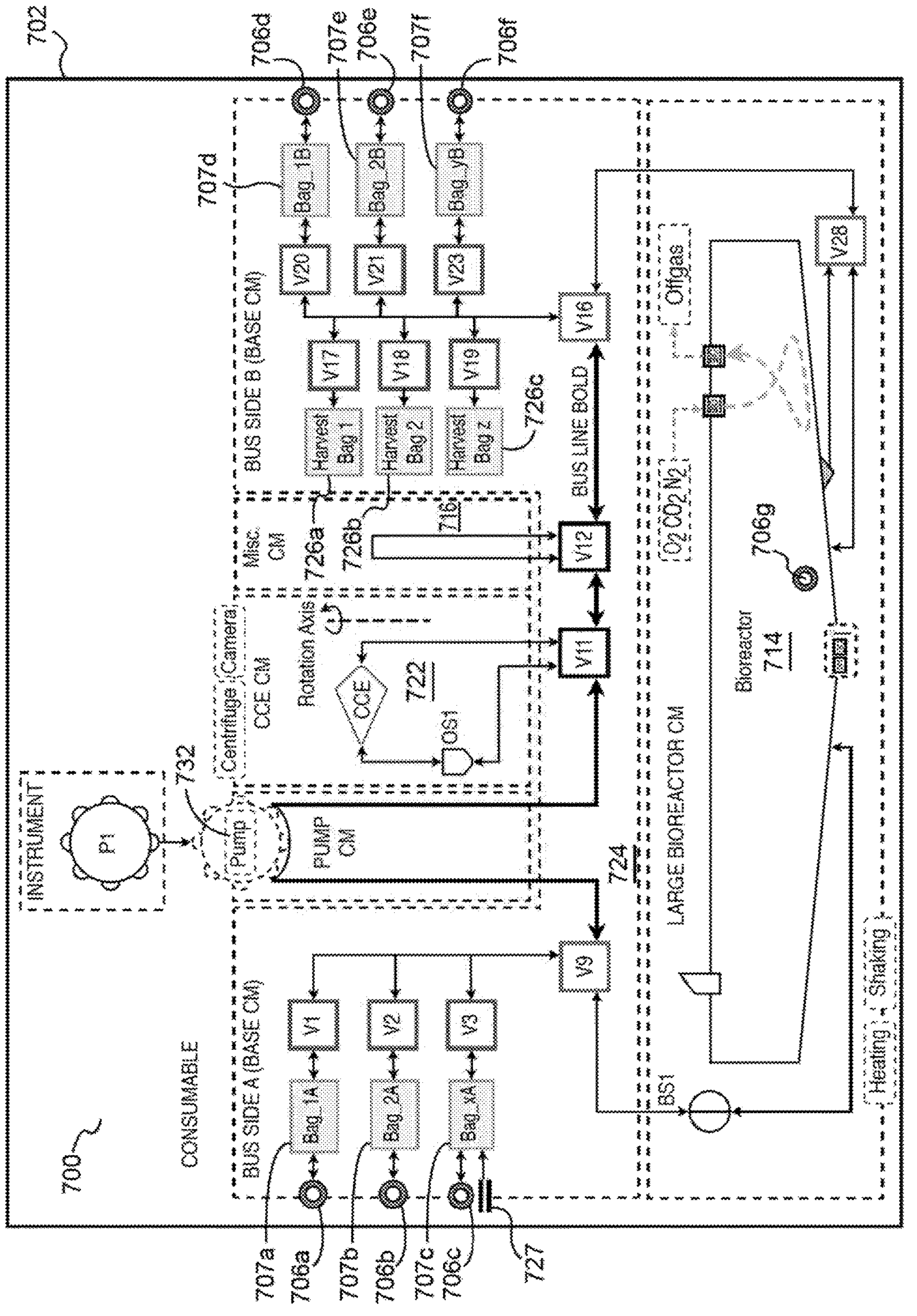
FIG. 7 is a schematic diagram of another illustrative variation of a cartridge.

FIG. 7 is a schematic diagram of another variation of a cartridge 700. For example, cartridge 700 may comprise a reduced feature set compared to cartridge 600. The cartridge 700 may comprise a liquid transfer bus 724 fluidically coupled to a bioreactor module 714, a counterflow centrifugation elutriation (CCE) module 722, and a module 716 selected from cell selection module, a cell sorting module, an electroporation module, or any other cell processing module. The cartridge 700 may comprise a housing 702 and sterile liquid transfer ports (SLTPs) 706*a*-706*f* (e.g., fluid connector) fluidically coupled to reservoirs 707*a*-707*f*, which may be each independently be a flexible bag or a rigid container. SLTP 706*g* is fluidically coupled to the bioreactor module 714 to permit direct access by a system or an operator to the bioreactor. Reservoir 707*c* may be fluidically coupled to SLTP 707*c* and product input tubing line 727. In some variations, the liquid transfer bus 724 may comprise 14 valves V1-V3, V9, V11-V12, V17-V23 and V28 and tubing that fluidically couples the values to one another and/or each of the modules. The cartridge may further comprise collection bags 726*a*-726*c* fluidically coupled to the liquid transfer bus 724 via valves V17-V19. The cartridge may further comprise a pump 732 which exposes the tubing on the exterior of the housing 702 to permit each pump to interface with a pump actuator in the system (e.g., workcell).

Figure 8A:
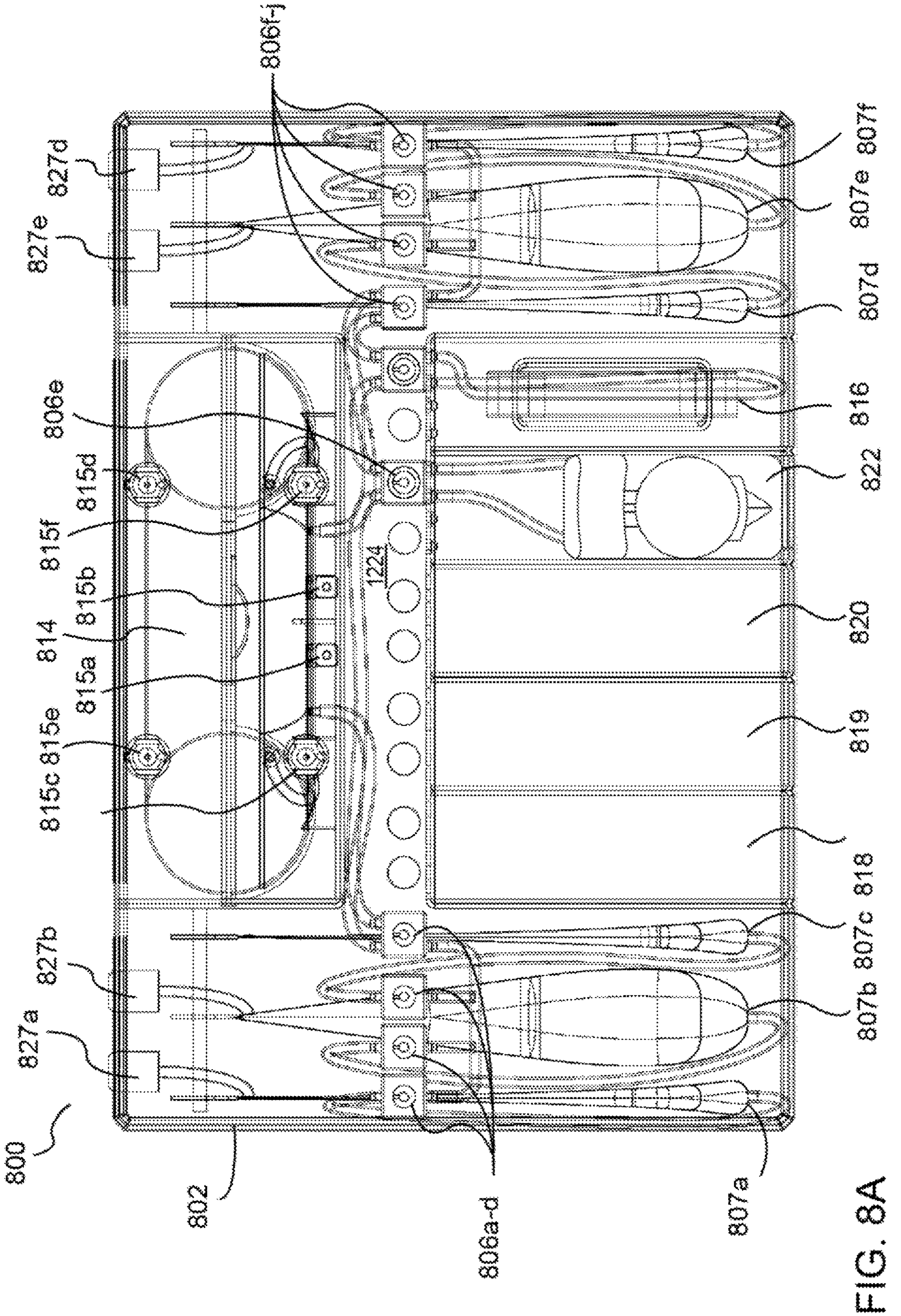
FIG. 8A is a side view of an illustrative variation of a cartridge.
Figure 8B:
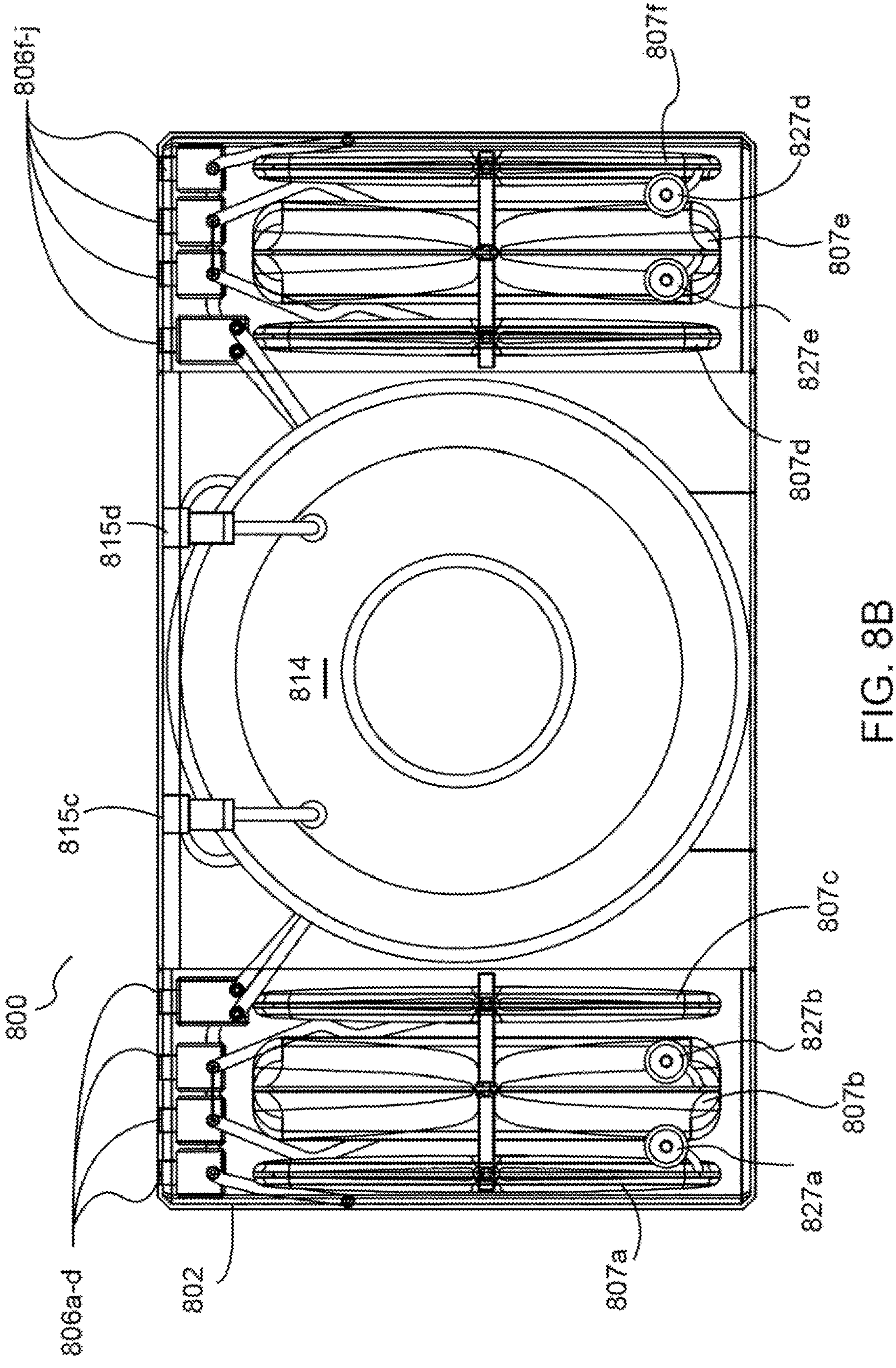
FIG. 8B is a top view of an illustrative variation of a cartridge.

A side and top view of another variation of a cartridge is shown in respective FIGS. 8A and 8B. In some variations, a cartridge 800 may comprise a bioreactor 814, a pump 816, and a counterflow centrifugation elutriation (CCE) module 822. The cartridge 800 may comprise blanks 818, 819, and 820 configured to house additional module(s) such as a cell selection module, cell sorting module, an electroporation module, a small bioreactor module, and the like. In some variations, a blank may define an empty volume of the cartridge reserved to house a module at another time. In some variations, the cartridge 800 may comprise two or more additional bioreactors and/or reservoirs in blanks 818, 819, 820. Along the near surface of the cartridge 800 may be fluid connectors 806*a*-806*j* (e.g., SLTP) fluidically connected to reservoirs 807*a*-807*f*. Reservoirs 807*b* and 807*e* may comprise fluid (e.g., buffer or media). Along the top surface are product input tubing lines 827*a*-827*d*, which may be fluidically connected to reservoirs 807*a*, 807*b*, 807*e*, and 807*f*, respectively. A liquid transfer bus 824 may fluidically connect the STLPs, reservoirs, and product input tubing lines to the modules via tubing.

In some variations, the housing 802 may have external dimensions of about 225 mm×about 280 mm×385 mm, about 225 mm×about 295 mm×385 mm, and about 450 mm×about 300 mm×about 250 mm, including all values and sub-ranges in-between. In some variations, the cartridge 800 may be about 10%, about 20%, about 30% or more smaller in volume, including all ranges and sub-values in-between. In some variations, the cartridge 800 may be about 10%, about 20%, about 30%, about 50%, about 100%, about 200%, or more in volume, including all ranges and sub-values in-between.

Figure 8C:
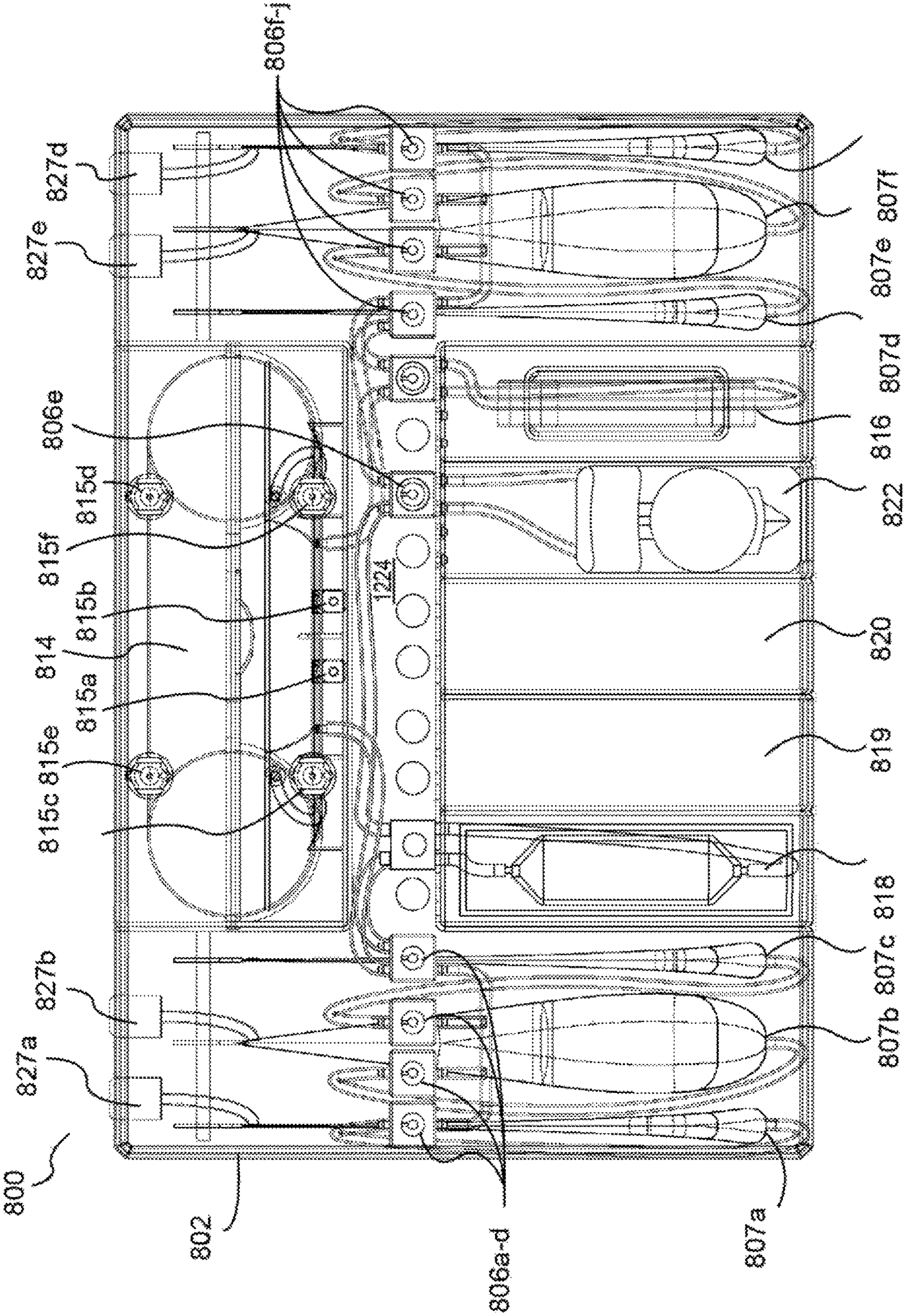
FIG. 8C is a side view of an illustrative variation of a cartridge.
Figure 8D:
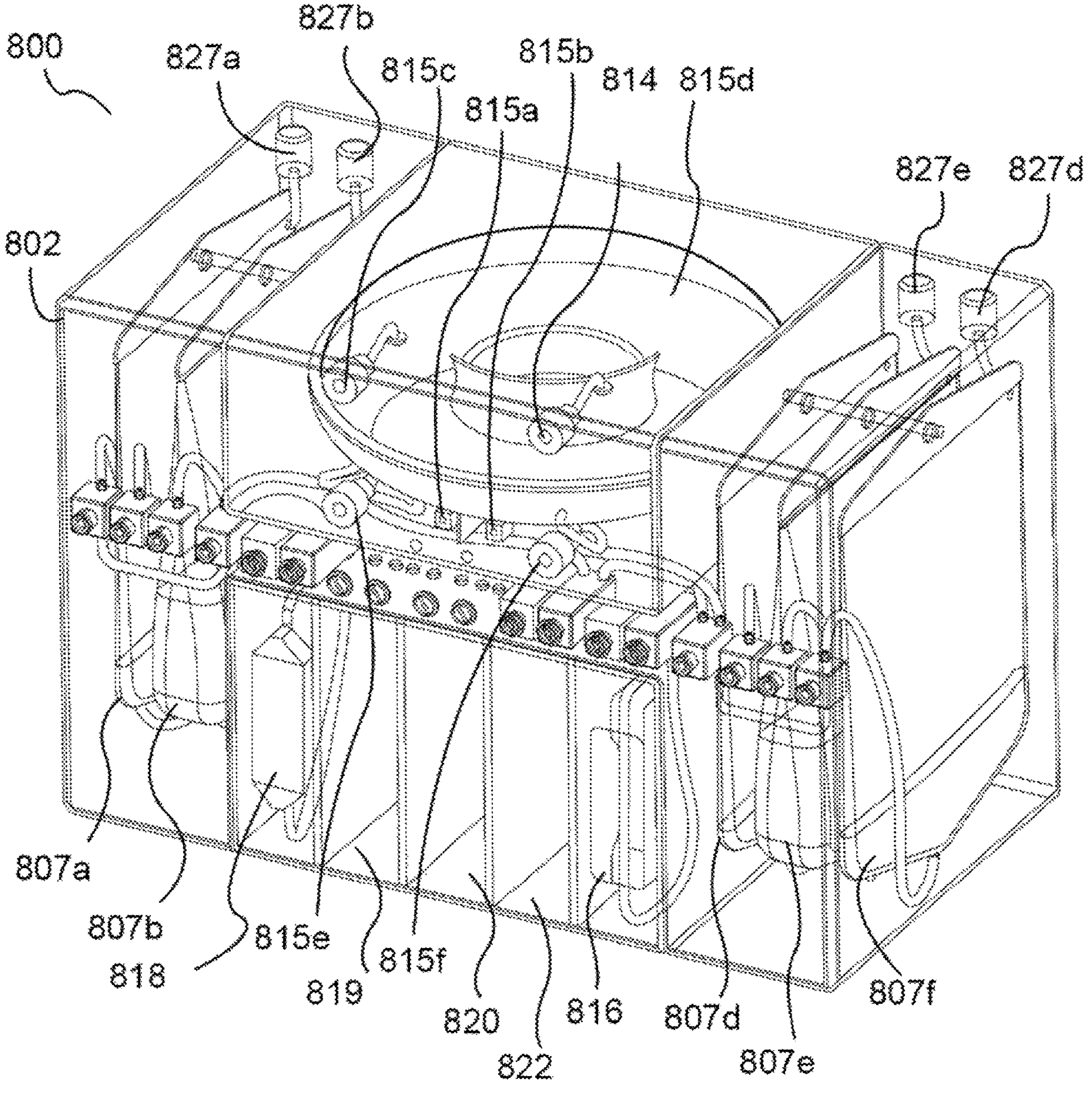
FIG. 8D is a perspective view of an illustrative variation of a cartridge.

In some variations, a cartridge 800 as shown in the side view of FIG. 8C and perspective view of FIG. 8D may comprise a MACS module 818. For example, the bioreactor module 814 may comprise ports 815*a*-815*f* including a pH and dissolved oxygen (DO) sensors (ports 815*a* and 815*b*), a gas input line 815*c*, an output line 815*d* each having a sterile filter behind the connector, and a coolant input line 815*e* and output line 815*f* from the bioreactor instrument interface when it interfaces with bioreactor module 814 (for heat exchange). For example, the gas input line 815*c* may be configured for gas transfer into a fluid (e.g., through head-space gas control or a gas-permeable membrane).

Figure 9:
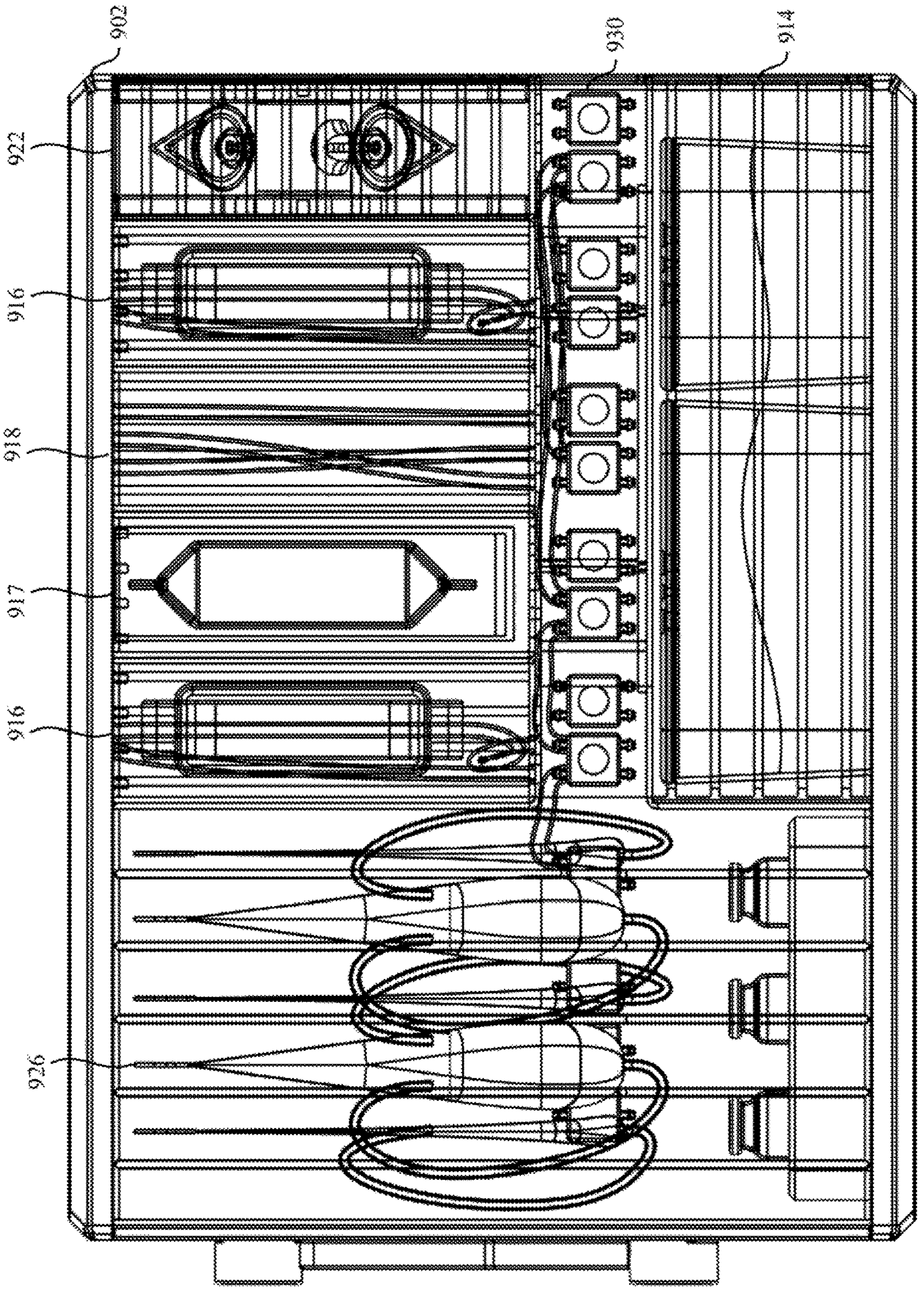
FIG. 9 shows a cross-sectional side view of an illustrative variation of a cartridge.

FIG. 9 shows a cross-sectional side view of a cartridge 900. In some variations, a cartridge 900 may comprise an enclosure (e.g., housing), a bioreactor 914, one or more pumps 916, valve 930, cell selection module 917, and a counterflow centrifugation elutriation (CCE) module 922. In some variations, the cell selection module 616 may be a magnetic-activated cell selection (MACS) module 917. The cartridge may further comprise collection bags 926. The cartridge 900 may optionally comprise blanks configured to house additional module(s) such as a cell selection module, a cell sorting module, an electroporation module 918, and the like. In some variations, the cartridge 900 may comprise one or more bioreactors and/or reservoirs in the blanks.

Figure 10A:
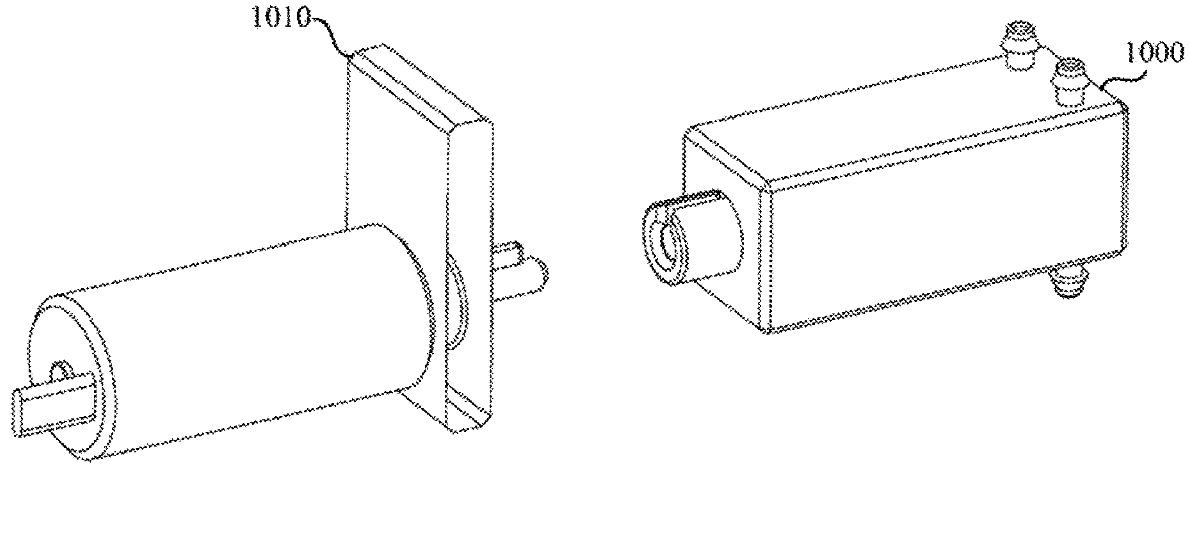
FIG. 10A shows an illustrative variation of a rotary valve and an actuator.
Figure 10B:
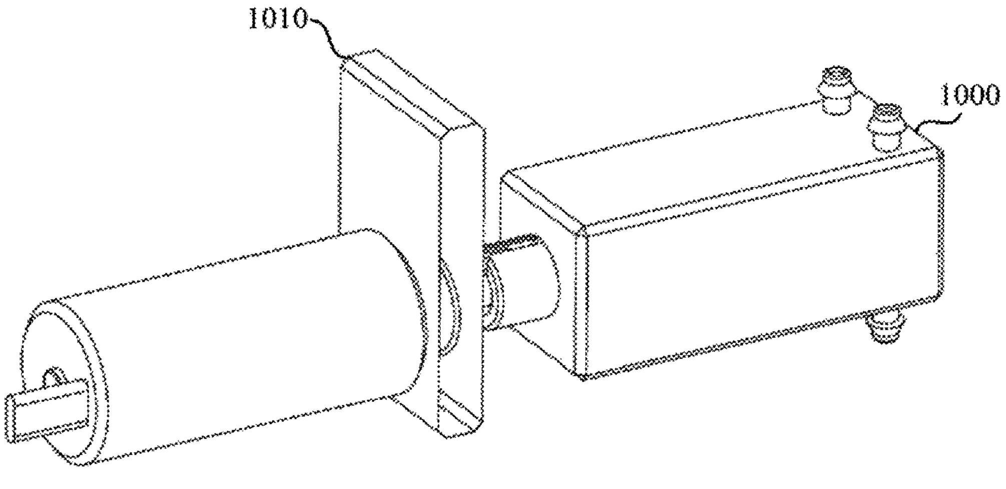
FIG. 10B shows an illustrative variation of a rotary valve docked with an actuator.

In some variations, a cartridge may comprise one or more valves. In some variations, the valve 1000 on the cartridge may be configured to receive an actuator 1010 provided by an instrument (as shown in FIG. 10A). As the cartridge is inserted into the instrument, the valve 1000 may be configured to dock with the actuator 1010 (as shown in FIG. 10B), such that rotation of the actuator 1010 may cause switching of the valve 1000 from one position to another position. In some variations, the valves may be constructed to pinch a section of soft tubing. The pinch valves may comprise a closed configuration, and an external actuator may be configured to interface with the pinch valve (e.g., utilizing a solenoid with linear motion) to open or close the valve. The valves themselves may be configured to be disposable whereas the actuators may be integrated into an instrument configured to process cartridges repeatedly.

Reagent Vault

In some variations, the system comprises a reagent vault (or reagent vaults) where reagents are stored including but not limited to cell culture media, buffer, cytokines, proteins, enzymes, polynucleotides, transfection reagents, non-viral vectors, viral vectors, antibiotics, nutrients, cryoprotectants, solvents, cellular materials, and pharmaceutically acceptable excipients. Additionally or alternatively, waste may be stored in the reagent vault. In some variations, in-process samples extracted from one or more cartridges may be stored in the reagent vault. The reagent vault may comprise one or more controlled temperature compartments (e.g., freezers, coolers, water baths, warming chambers, or others, at e.g. about −80° C., about −20° C., about 4° C., about 25° C., about 30° C., about 37° C., and about 42° C.). Temperatures in these compartments may be varied during the cell manufacturing process to heat or cool reagents. In variations of the methods of the disclosure, a cartridge may be moved by the robot (or manually by an operator) to the reagent vault. The reagent vault interfaces with one or more sterile liquid transfer ports on the cartridge, and the reagent or material is dispensed into the cartridge. Optionally, fluid is added or removed from the cartridge before, during, or after reagent addition or removal. In some variations, the system comprises a sterile liquid transfer instrument, similarly configured to transfer fluid into or out of the cartridge in an automated, manual, or semi-automated fashion. An operator may stock the sterile liquid transfer station with reagents manually, or they may be supplied by a robot (e.g. from a feedthrough or other location). In some cases, a robot moves a reagent or reagents from the reagent vault to the sterile liquid transfer station. The reagent vault may have automated doors to permit access by the robot for sterile liquid transfer devices and/or other reagent vessels, optionally each under independent closed loop temperature control. The devices and vessels may be configured for pick-and-place movement by the robot. In some variations, the reagent vault may comprise one or more sample pickup areas. For example, a robot may be configured to move one or more reagents to and from one or more of the sample pickup areas.

Various materials can be used to construct the cartridge and the cartridge housing, including metal, plastic, rubber, and/or glass, or combinations thereof. The cartridge, its components, and its housing may be molded, machined, extruded, 3D printed, or any combination thereof. The cartridge may contain components that are commercially available (e.g., tubing, valves, fittings); these components may be attached or integrated with custom components or devices. The housing of the cartridge may constitute an additional layer of enclosure that further protects the sterility of the cell product. The operator may perform loading or unloading of the cartridge in an ISO 5 or better environment, utilizing aseptic technique to ensure that sterility of the contents of the cartridge is maintained when the cartridge is opened. In some variations, the operator may perform loading or unloading of the cartridge using manual aseptic connections (e.g., sterile tube welding). The robotic system may also perform sterile loading or unloading of liquids into and out of the cartridge through the use of the sterile liquid transfer instrument and sterile liquid transfer ports on the cartridge.

Counterflow Centrifugal Elutriation

Counterflow centrifugal elutriation (CCE) is a technique used to separate cells based on characteristics such as size and/or density. Counterflow centrifugal elutriation combines centrifugation with counterflow elutriation where centrifugation corresponds to the process of sedimentation under the influence of a centrifugal force field and counterflow elutriation corresponds to the process of separation by washing. Separation takes place in a cone (e.g., bicone, funnel) shaped elutriation chamber. Particles (e.g., cells) conveyed in a fluid into the elutriation chamber are acted upon by two opposing forces: centrifugal force driving the fluid away from an axis of rotation; and fluid velocity driving the fluid towards the axis of rotation (e.g., counterflow). By varying the flow rate and the centrifugal force, the separation of particles (e.g., cells) may be achieved. For example, as described in more detail herein, particles may be separated based on properties such as size and density.

Counterflow centrifugal elutriation may perform multiple operations useful for cell therapy manufacturing workflows including, but not limited to, cell washing, cell concentration, media/buffer replacement, transduction, and separation of white blood cells from other blood components (e.g., platelets, and red blood cells). In some variations, a fluid source (e.g., apheresis bag) for a cell separation process may comprise a suspension of white blood cells, red blood cells, platelets, and plasma. In order to separate immune cells of interest, white blood cells may be isolated and subsequently magnetically tagged for magnetic separation. A white blood cell separation step may be performed in a CCE module to separate cells based on size and density, while magnetic separation may be performed in a MACS module. In some variations, a CCE module may be integrated into a cartridge to enable a cell processing system to separate cells based on one or more of a progression through a cell cycle (e.g., $G_1$/M phase cells being larger than $G_0$, S, or G2 phase cells) and cell type (e.g., white blood cells from red blood cells and/or platelets).

Generally, a rotor configured to spin may comprise an elutriation chamber (e.g., cone, bicone). A fluid comprising a suspension of cells may be pumped under continuous flow into the rotor. As cells are introduced into the cone (e.g., bicone), the cells migrate according to their sedimentation rates to positions in the gradient where the effects of the two forces upon them are balanced. Smaller cells having low sedimentation rates (e.g., platelets) may be quickly washed toward the axis of rotation with increased flow velocity. Such smaller cells may be output (e.g., washed out) of the cone. Relatively larger (or denser) cells (e.g., red blood cells) flow through the cone relatively more slowly and reach equilibrium at an elutriation boundary where the centrifugal force and the drag force are in balance, and the fluid velocity is relatively low because the cone has widened. The largest or densest cells (e.g., white blood cells) remain near the inlet to the chamber where centrifugal force and fluid velocity are high. By increasing the flow rate in gradual steps, successive fractions of increasingly large or dense cells (e.g., platelets→red blood cells→white blood cells) may be output from the rotor. Continued incremental increases in fluid flow rate will eventually elutriate all cells from the cone.

Figure 56:
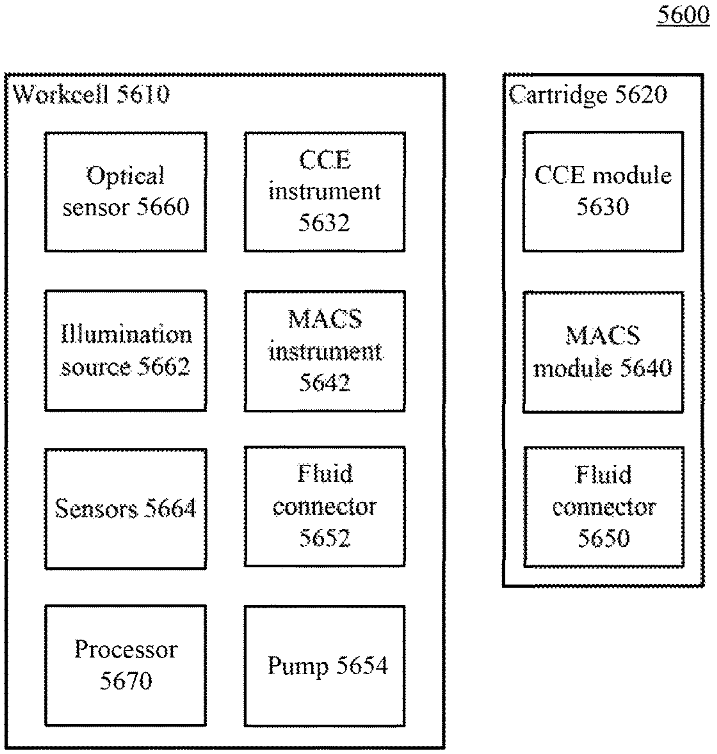
FIG. 56 is a block diagram of an illustrative variation of a cell separation system.

FIG. 56 is a block diagram of a cell separation system 5600 comprising a workcell 5610 and at least one cartridge 5620. In some variations, the workcell 5610 may comprise one or more of a counterflow centrifugal elutriation (CCE) instrument 5632 (e.g., first magnet), a magnetic-activated cell selection (MACS) instrument 5642 (e.g., magnet array, second magnet), a fluid connector 5652, a pump 5654, an imaging system comprising an optical sensor 5660 and an illumination source 5662, a sensor 5664, and a processor 5670. In some variations, the cartridge 5620 may comprise one or more of a CCE module 5630 (e.g., rotor), a MACS module 5640 (e.g., flow cell), and a fluid connector 5650 (e.g., sterile liquid transfer port, liquid transfer bus). For example, a cartridge for cell processing may comprise a liquid transfer bus and a plurality of modules, each module fluidically linked to the liquid transfer bus. The modules may include any of the CCE modules or MACS modules described herein. In some variations, a robot (not shown) may be configured to move the cartridge 5620 between different locations within the workcell 5610 to perform different cell processing steps.

In some variations, the imaging system (e.g., optical sensor 5660, illumination source 5622) may be configured to generate image data corresponding to one or more of the CCE module 5630 and MACS module 5640. For example, image data of fluid flow through a rotor of a CCE module 5630 may be analyzed and used to control a flow rate of fluid and/or rotation rate of the rotor, as described in more detail herein. In some variations, the optical sensor 5660 may be a CMOS/CCD sensor having, for example a resolution of about 100 μm, a working distance of between about 40 mm and about 100 mm, and a focal length of less than about 8 mm. The optical sensor 5660 may be configured to operate synchronously with the illumination source 5662. In some variations, the optical sensor 5660 may comprise one or more of a colorimeter, turbidity sensor, and optical density sensor. In some variations, the illumination source 5662 may operate as a strobe light configured to output light pulses synchronized to a rotation rate of a rotor of the CCE module 5630.

In some variations, the sensor 5664 may comprise one or more of an optical density sensor configured to measure an intensity of fluid, a leak detector configured to detect moisture and/or leaks, an inertial sensor configured to measure vibration, a pressure sensor configured to measure pressure in a fluidic line (e.g., photoelectric sensor), a bubble sensor configured to detect the presence of a bubble in a fluid conduit, colorimetric sensor, vibration sensor, and the like.

In some variations, the fluid connector 5652 may comprise one or more valves, configured to control fluid flow between the workcell and the cartridge 5620. The processor 5670 may correspond to the controller (e.g., processor and memory) described in more detail herein. The processor 5670 may be configured to control one or more of the CCE instrument 5632, the MACS instrument 5642, the pump 5654, fluid connector 5652 (e.g., valves), the optical sensor 5660, the illumination source 5662, and the sensors 5664.

In some variations, a system 5600 for cell processing may comprise a cartridge 5600 comprising a rotor of a CCE module 5630 configured for counterflow centrifugation elutriation of cells in a fluid. A first magnet of a CCE instrument 5632 may be configured to magnetically rotate the rotor and separate the cells from the fluid in the rotor. The cartridge may further comprise a flow cell of a MACS module 5640 coupled to the rotor and configured to receive the cells from the rotor. A second magnet of a MACS instrument 5642 may be configured to magnetically separate the cells in the flow cell.

In some variations, an illumination source 5662 may be configured to illuminate the cells. An optical sensor 5660 may be configured to generate image data corresponding to the cells. In some variations, the system 5600 may comprise one or more of an oxygen depletion sensor, leak sensor, inertial sensor, pressure sensor, and bubble sensor. In some variations, the system 5600 may comprise one or more valves and pumps.

Figure 57:
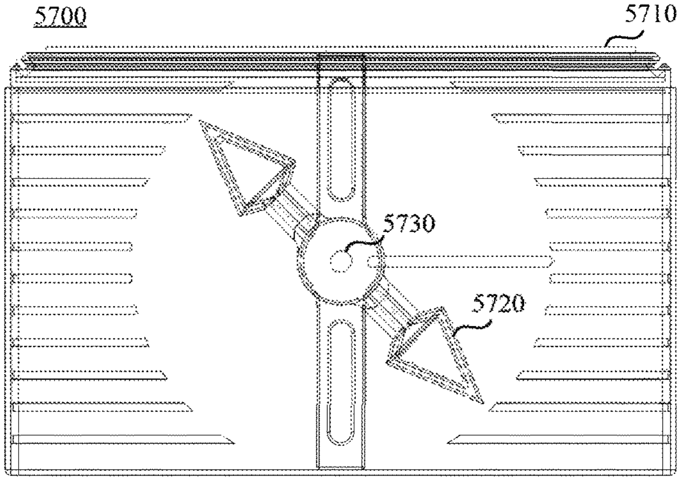
FIG. 57 is a cross-sectional side view of an illustrative variation of a counterflow centrifugal elutriation (CCE) module.

FIG. 57 is a cross-sectional side view of a counterflow centrifugal elutriation (CCE) module 5700 comprising a housing 5710 (e.g., enclosure), a rotor 5720 configured to rotate within and relative to the housing 5710, and one or more fluid ports 5730 (e.g., fluid inlet, fluid outlet). In some variations, the CCE module 5700 may be portable and configured to move within a workcell 5610 and cartridge 5620. For example, a robot may move the CCE module 5700 between different instruments of a workcell 5610.

Figure 58:
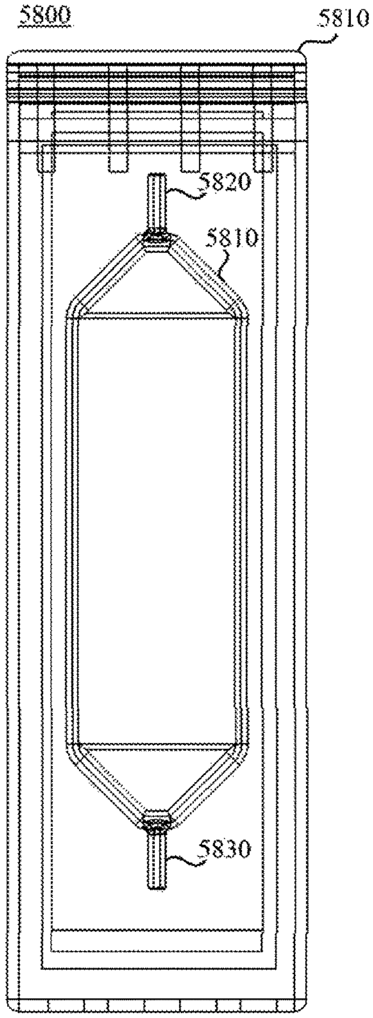
FIG. 58 is a cross-sectional side view of an illustrative variation of a magnetic-activated cell selection (MACS) module.

FIG. 58 is a cross-sectional side view of a magnetic-activated cell selection (MACS) module comprising a housing 5810 (e.g., enclosure), a first fluid port 5820 (e.g., fluid inlet), a second fluid port 5830 (e.g., fluid outlet), and a flow cell 5810 coupled in between the first fluid port 5820 and the second fluid port 5830. As described in more detail herein, the flow cell 5810 may comprise a cavity (e.g., chamber) comprising one or more channels (e.g., linear channels, laminar fluid flow channel). In some variations, the cavity of the flow cell 5810 may be substantially empty. For example, the flow cell 5810 may be absent a mesh, beads, tortuous channels, and the like. In some variations, the flow cell 5810 may have a longitudinal axis aligned perpendicular to ground. That is, the flow cell 5810 may be oriented vertically where the first fluid port 5820 is disposed at a higher elevation than the second fluid port 5830 such that gravity may aid fluid flow through the flow cell 5810. In some variations, the MACS module 5800 may be portable and configured to move within a workcell 5610 and cartridge 5620. For example, a robot may move the MACS module 5630 between different instruments of a workcell 5610.

Figure 59A:
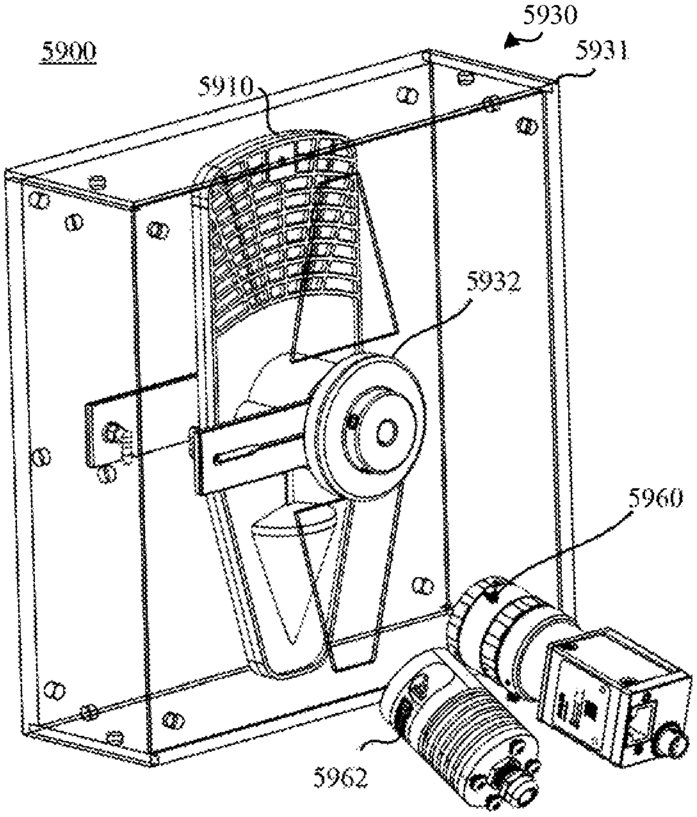
FIGS. 59A-59C are perspective views of an illustrative variation of a CCE system.
Figure 59B:
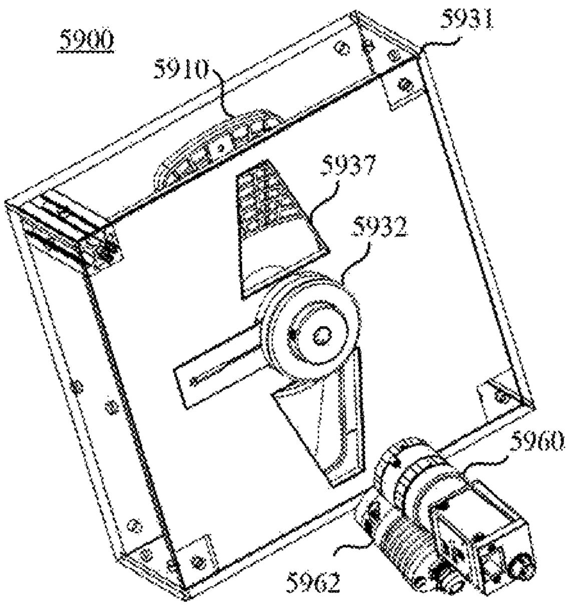

FIGS. 59A and 59B are perspective views of a system 5900 for cell processing (e.g., CCE system) comprising a CCE module 5930 (e.g., cartridge) including a housing 5931 and a rotor 5910, a CCE instrument 5932, an optical sensor 5960, and an illumination source 5962. In some variations, the CCE instrument 5932 may comprise a magnet configured to magnetically rotate the rotor 5910 within the CCE module 5930. One or more portions of the housing 5931 and rotor 5910 may be optically transparent to facilitate illumination by the illumination source 5962 and image data generation by the optical sensor 5960.

Figure 59C:
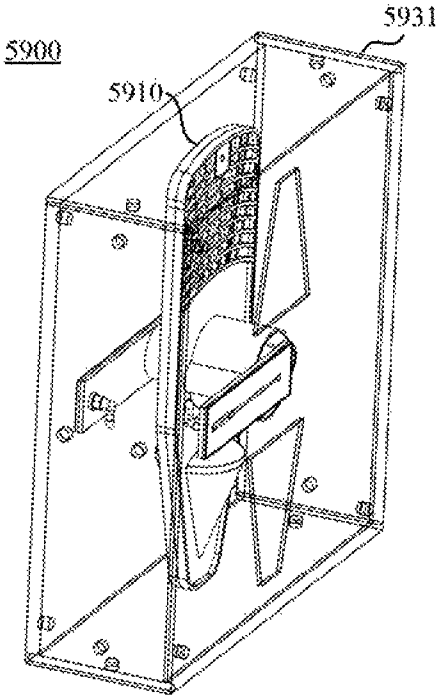

In some variations, the system 5900 for cell processing may comprise a cartridge 5930 comprising a housing 5931 comprising a rotor 5910 configured to separate cells from a fluid. An instrument 5932 comprising a magnet may be configured to interface with the cartridge 5930 to magnetically rotate the rotor 5910. The cartridge 5930 may be configured to move a cell product between a plurality of instruments. In some variations, the housing 5931 may enclose the rotor 5910. In some variations, the housing 5931 may comprise one or more apertures 5937 configured to facilitate visualization (e.g., imaging) of the rotor 5910. FIGS. 59A and 59B depict a magnet 5932 in proximity, but not attached, to housing 5931. FIG. 59C is a perspective view of the rotor 5910 and housing 5931 without the magnet 5932, optical sensor 5960, and illumination source 5962.

In some variations, the cartridge 5930 (e.g., housing 5931, 5910) may comprise a consumable component such as a disposable component, limited use component, single use component, and the like. In some variations, the magnet 5932 may comprise a durable component that may be re-used a plurality of times. In some variations, the magnet 5932 may be releasably coupled to the housing 5931. For example, the housing 5931 may be moved relative to the magnet 5932 to facilitate magnetic coupling between the magnet 5932 and a plurality of cartridges 5930. Additionally or alternatively, the magnet 5932 may be configured to be moved relative to the housing 5931.

Figure 59D:
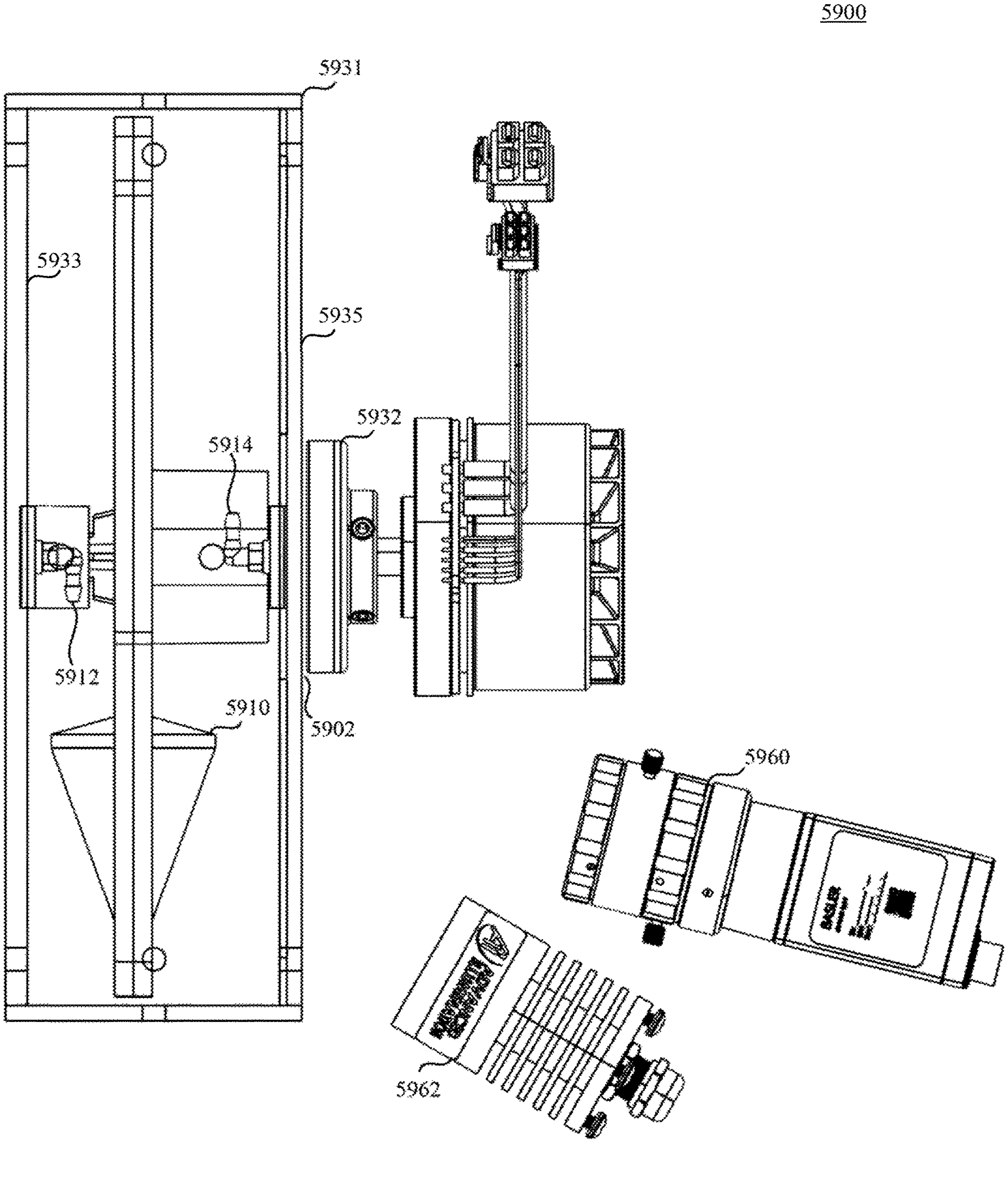
FIG. 59D is a side cross-sectional view of an illustrative variation of a CCE system.

FIG. 59D is a side cross-sectional view of a CCE module 5930. In some variations, the housing 5931 of the rotor 5910 may comprise a first side 5933 comprising the first fluid port 5912 (e.g., first fluid conduit) and a second side 5935 comprising the second fluid port 5914 where the second side 5935 is opposite the first side 5933. The rotor 5910 (including a cone or bicone as described in more detail herein) may be coupled between the first fluid port 5912 and the second fluid port 5914. In some variations, the CCE module 5930 may comprise an air gap 5902 between the housing 5931 and a magnet 5932. That is, the cartridge 5930 and magnet 5932 may couple in a non-contact manner. Consequently, the cartridge need not mechanically couple to the magnet 5932 to perform counterflow centrifugal elutriation. Therefore, the rotor 5910 may have a low alignment sensitivity with the magnet 5932, as well as low vibration between the rotor 5910 and the magnet 5932. Furthermore, the space between the rotor 5910 and magnet 5932 enables the second fluid port 5914 to extend toward the second side 5935 of the housing 5931, thus allowing for fluid to flow on each side of the rotor 5910.

In some variations, counterflow centrifugal elutriation may be performed by the system 5900 by moving a magnet 5932 towards a rotor 5910 (or vice versa). The rotor may define a rotational axis (e.g., coaxial with the first fluid port 5912 and the second fluid port 5914). Fluid may flow through the rotor via the first fluid port 5912 and the second fluid port 5914. The magnet 5932 may magnetically rotate the rotor about the rotational axis while flowing the fluid through the rotor 5910. The rotor may move away from the magnet. For example, moving the rotor 5910 may include advancing and withdrawing the rotor 5910 relative to the magnet 5932 using a robot (not shown).

In some variations, fluid may flow through first fluid port 5912 along the first side 5933 of the rotor 5910 and into the rotor 5910. After counterflow centrifugal elutriation through the rotor 5910, the fluid may flow out of the rotor 5910 through second fluid port 5914 along the second side 5935 of the rotor 5910.

In some variations, counterflow centrifugal elutriation may be visualized by optical sensor 5960 and illumination source 5962 in order to monitor and modify cell separation in real-time based on predetermined criteria in a closed loop manner in order to maximize elutriation efficiency. In some variations, an optical sensor 5960 may be configured to image any portion of the rotor through which fluid flows (e.g., first fluid conduit, second fluid conduit, third fluid conduit, first bicone, second bicone). For example, image data of one or more of the fluid and the cells in the rotor 5910 may be generated using the optical sensor 5960. In some variations, one or more of the fluid and the cells may be illuminated using the illumination source 5962. For example, an output of a cone may be imaged by an optical sensor to identify non-target cells being elutriated.

In some variations, one or more of a rotation rate of the rotor and a flow rate of the fluid may be selected based at least in part on the image data. For example, the rotor may comprise a rotation rate of up to 6,000 RPM. For example, the fluid may comprise a flow rate of up to about 150 ml/min while rotating the rotor. In some variations, the rotor may be moved towards the illumination source 5962 and the optical sensor 5960. Additionally or alternatively, the rotor 5910 may be moved away from the illumination source 5962 and the optical sensor 5960.

Figure 59E:
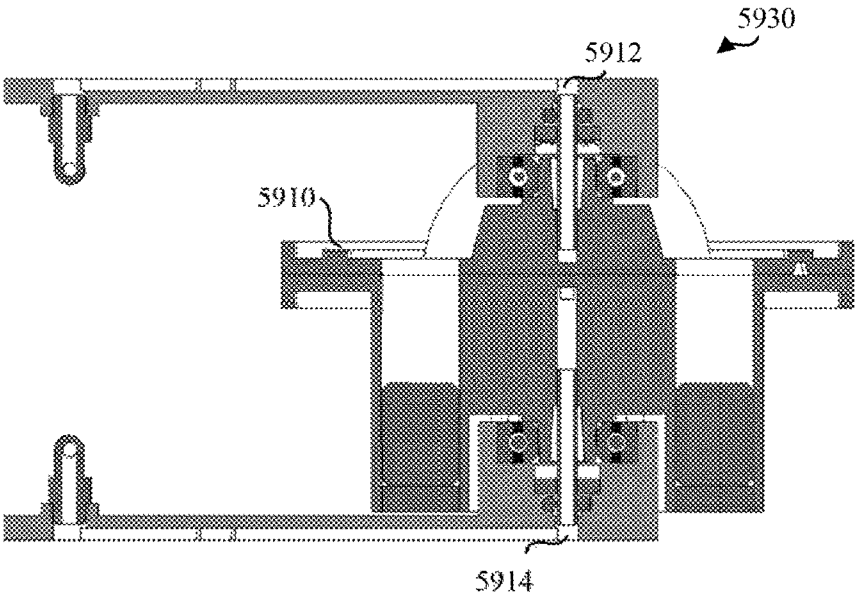
FIGS. 59E-59G are side cross-sectional views of an illustrative variation of a rotor of a CCE module.
Figure 59F:
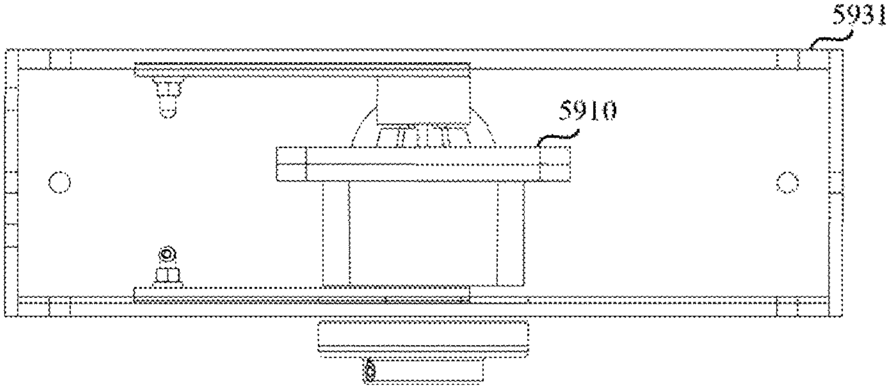
Figure 59G:
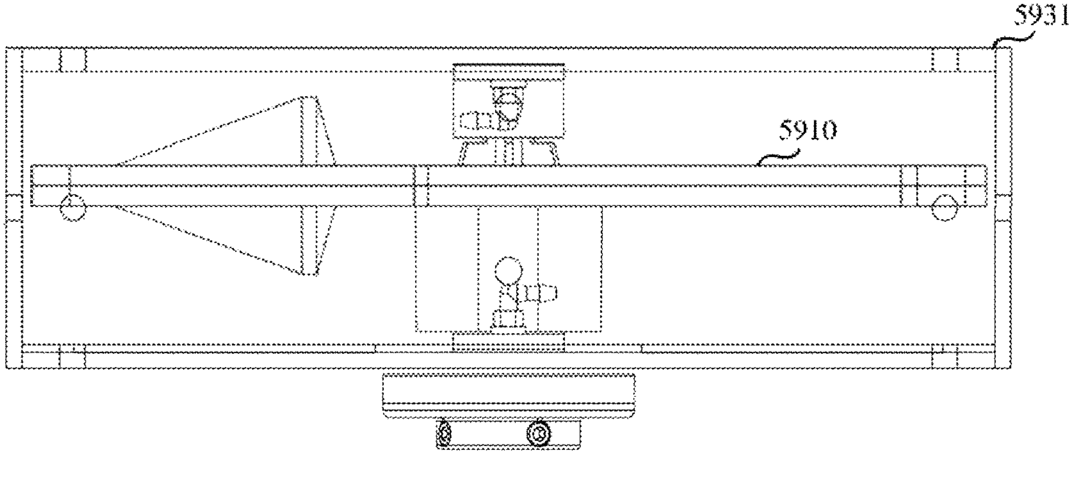

FIG. 59E is a side cross-sectional view of a rotor 5910 including a first fluid port 5912 (e.g., fluid conduit, inlet) and a second fluid port 5914 (e.g., fluid conduit, outlet). In some variations, the first fluid port 5912 and the second fluid port 5914 may extend in parallel with each other and/or a rotational axis of the rotor 5910. In some variations, the first fluid port 5912 and the second fluid port 5914 may be disposed on opposite sides of the rotor 5910, which may simplify fluid routing, cartridge design, and also reduce manufacturing costs. For example, the fluidic seals may be simplified since they contain only a single lumen each. Conventionally, a complicated fluid flow path (including inlet and outlet) is formed on a first side of a rotor due to a fixed mechanical coupling of a drive motor to a second side of the rotor. FIGS. 59F and 59G are cross-sectional side views of a rotor 5910 disposed within housing 5931.

Figure 60A:
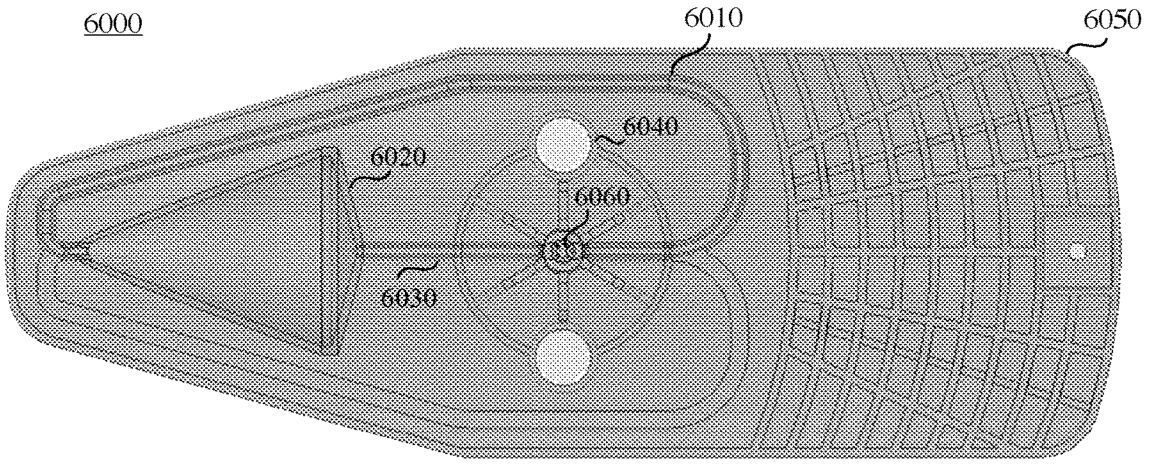
FIG. 60A is a plan view of an illustrative variation of a rotor of a CCE module.

FIG. 60A is a plan view of a rotor 6000 that may be used with any of the CCE systems, CCE modules, cartridges, housings, combinations thereof, and the like described herein. The rotor 6000 may comprise a first fluid conduit 6010, a cone 6020 (e.g., bicone), a second fluid conduit 6030, a magnetic portion 6040 (e.g., magnet), and housing 6050. Fluid may flow sequentially through the first fluid conduit 6010, the cone 6020, and the second fluid conduit 6030. In some variations, the magnetic portion 6040 may comprise one or more magnets. In some variations, the rotor 6000 may define a rotation axis 6060. In some variations, at least a portion of the first fluid conduit 6010 and at least a portion of the second fluid conduit 6030 may extend parallel to the rotation axis (e.g., into and out of the page with respect to FIG. 60A). In some variations, at least a portion of the first fluid conduit 6010 and at least a portion of the second fluid conduit 6030 may be co-axial.

In some variations, the cone 6020 may comprise a bicone having a first cone including a first base and a second cone including a second base such that the first base faces the second base. In some variations, a bicone may comprise a cylinder (or some other shape) between and/or in fluid communication with the first cone and the second cone. For example, one or more cones of a rotor may comprise a generally stepped shape. For example, one or more cones may comprise stacked circular steps. In some variations, a cone of a rotor may comprise a single cone.

In some variations, at least a portion of the rotor may be optically transparent to facilitate visualization and/or imaging of the rotor 6000 and/or fluid (e.g., cells) in the rotor 6000. For example, the cone 6020 may be transparent, as well as portions of the first fluid conduit 6010 and the second fluid conduit 6030.

In some variations, the cone may comprise a volume of between about 10 ml and about 40 ml. In some variations, the cone may comprise a cone angle of between about 40 degrees and about 60 degrees.

In some variations, a cone may comprise a first cone (e.g., distal cone) and a second cone (e.g., proximal cone) where the first cone is larger than the second cone. In some variations, a first cone length may be between about 60 mm and about 90 mm. In some variations, a proximal cone length may be between about 15 mm and about 40 mm. In some variations, a cone diameter (e.g., maximum diameter of the cone) may be between about 15 mm and about 40 mm.

In some variations, the rotor 6000 may comprise an asymmetric shape. In some variations, a first portion (e.g., first end) of the rotor 6000 may comprise the cone 6020 and a second portion (e.g., second end) may comprise a paddle shape.

In some variations, the cone may comprise a length of at least about 4 cm (e.g., between about 9 cm and about 12 cm), a cone diameter of about 5 cm or less (e.g., between about 3 cm and about 5 cm), a fluid flow rate of up to about 100 ml/min (e.g., between about 60 ml/min and about 100 ml/min), and a rotation rate of less than about 3000 RPM. The shape of the first cone and the second cone may be generally linear (as opposed to convex or concave).

Figure 60B:
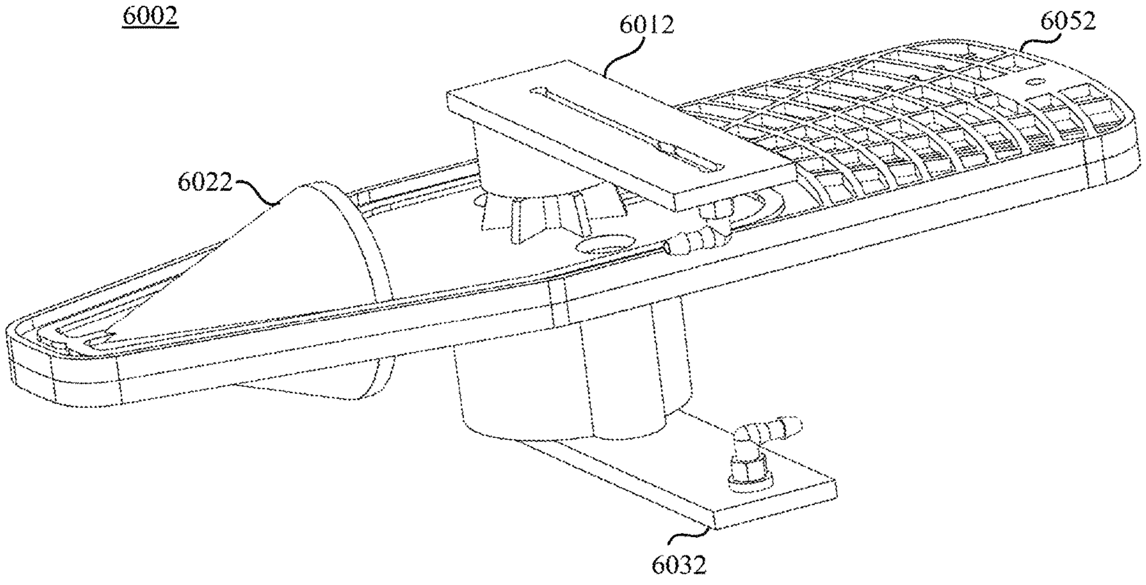
FIGS. 60B and 60C are perspective views of an illustrative variation of a rotor of a CCE module.
Figure 60C:
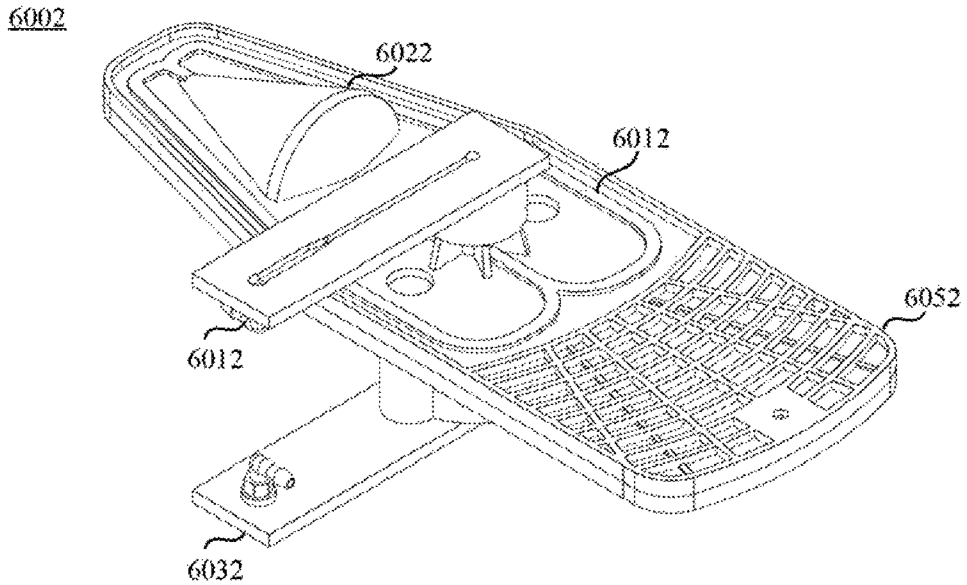
Figure 60D:
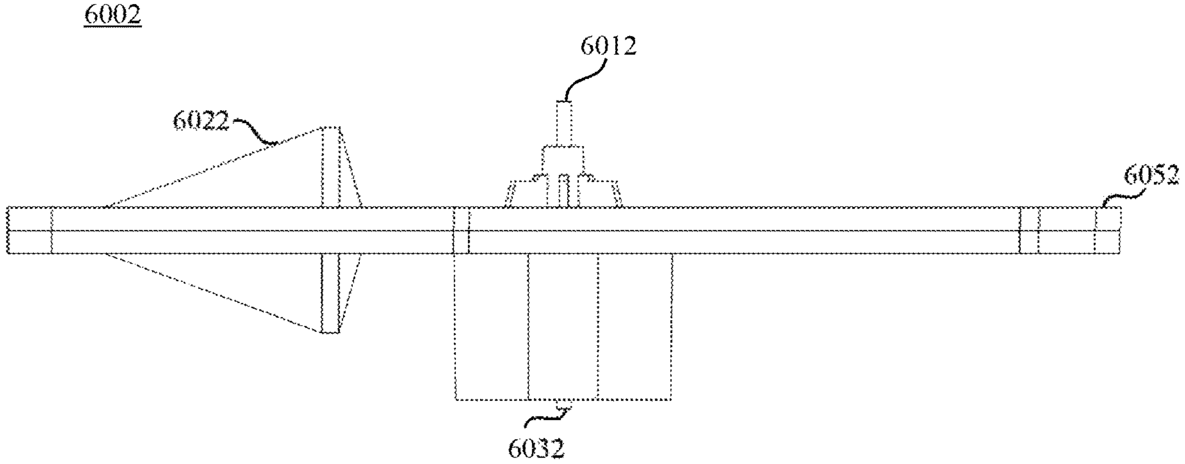
FIG. 60D is a side view of an illustrative variation of a rotor of a CCE module.
Figure 60E:
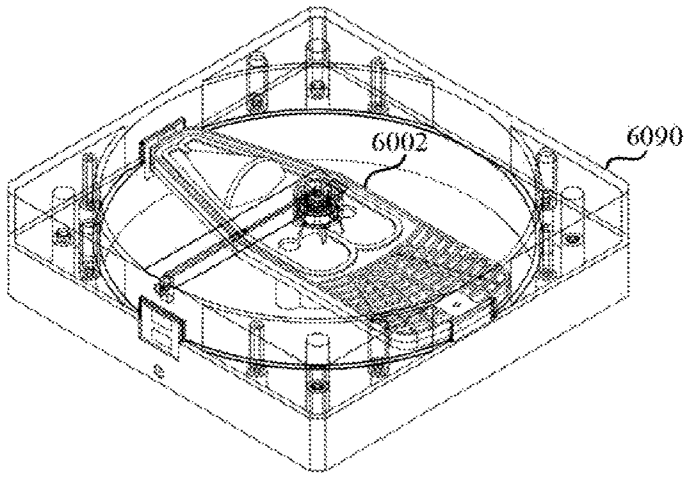
FIG. 60E is a perspective view of an illustrative variation of a rotor in a housing.

FIGS. 60B and 60C are perspective views, and FIG. 60D is a side view of a rotor 6002 comprising a first fluid conduit 6012, a cone 6022, a second fluid conduit 6032, and a housing 6052. FIG. 60E is a perspective view of the rotor 6002 disposed in a housing 6090.

Figure 60F:
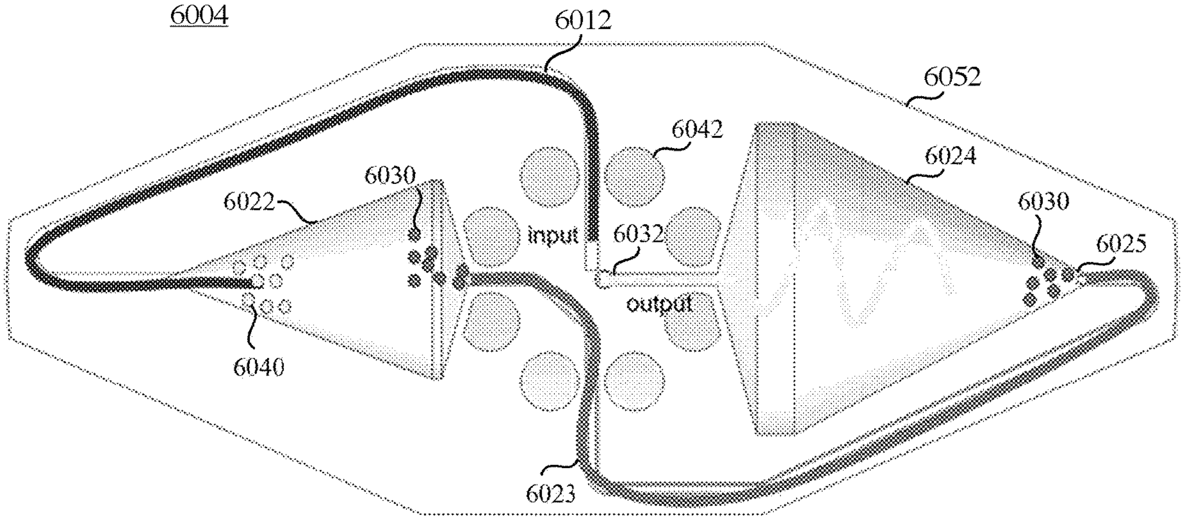
FIGS. 60F and 60G are plan schematic views of illustrative variations of a rotor of a CCE module.

FIG. 60F is a plan view of a rotor 6004 having two cones (e.g., two bicones) configured to elutriate cells (e.g., red blood cells, leukapheresis product) in a second cone in order to recirculate a buffer for reuse. The rotor 6004 may comprise a housing 6052, a first fluid conduit 6012, a first cone 6022 coupled to the first fluid conduit 6012, a second fluid conduit 6023 coupled to the first cone 6022, and a second cone 6024 coupled to the second conduit 6023, and a third fluid conduit 6032 coupled to the second cone 6024. The first cone 6022 may comprise a first volume, and the second cone 6024 may comprise a second volume larger than the first volume. In some variations, a ratio of a second volume to a first volume may be between about 2:1 to about 5:1. Fluid may flow sequentially through the first fluid conduit 6012, the first cone 6022, the second fluid conduit 6023, the second cone 6024, and the third fluid conduit 6032. In some variations, the rotor 6004 may comprise a magnetic portion 6042.

In some variations, the first cone 6022 may comprise a first bicone and the second cone 6024 may comprise a second bicone. In some variations, the first bicone may comprise a third cone including a first base and a fourth cone including a second base such that the first base faces the second base. In some variations, the second bicone may comprise a fifth cone including a third base and a sixth cone including a fourth base such that the third base faces the fourth base.

In some variations, a portion of the rotor 6004 may be optically transparent, such as first cone 6022, second cone 6024, and at least a portion of first fluid conduit 6012, second fluid conduit 6023, and third fluid conduit 6032. In some variations, the first fluid conduit 6012 may comprise an inlet and the third fluid conduit 6032 may comprise an outlet.

In some variations, cells may enter the first cone 6022 and red blood cells (RBCs) 6030 may be elutriated into the second cone 6024. Since the second cone 6024 is further out from an axis of rotation (center of housing 6052), the RBCs 6030 may be concentrated at an inlet 6025 of the second cone 6024 due to centrifugation. The larger volume of the second cone 6024 may further reduce the velocity of fluid (e.g., buffer), thereby reducing the force on RBCs 6030 within the second cone 6024. By recirculating the fluid (e.g., buffer), a higher concentration of RBCs may be elutriated with less fluid (e.g., buffer). In some variations, white blood cells 6040 may be harvested from the first cone 6022. An optical sensor may be configured to image the first cone 6022 to generate imaging data used to identify a boundary between the WBCs 6040 and RBCs 6030. In some variations, the recirculating fluid may be passed through a filter to remove small particles (e.g., platelets) with less fluid (e.g., buffer).

Figure 60G:
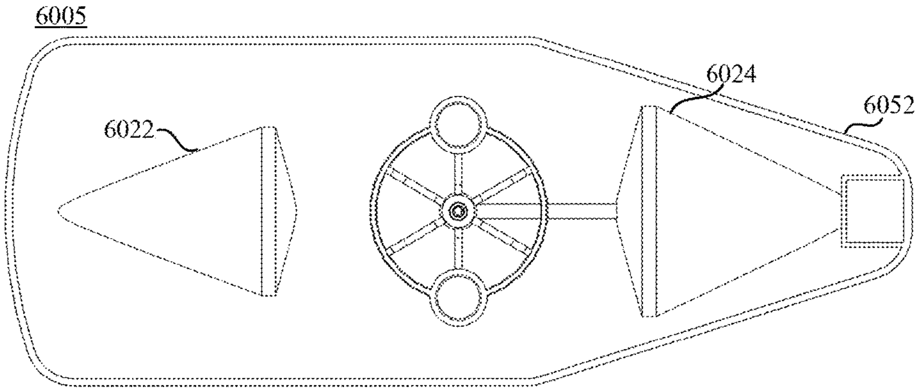
Figure 60H:
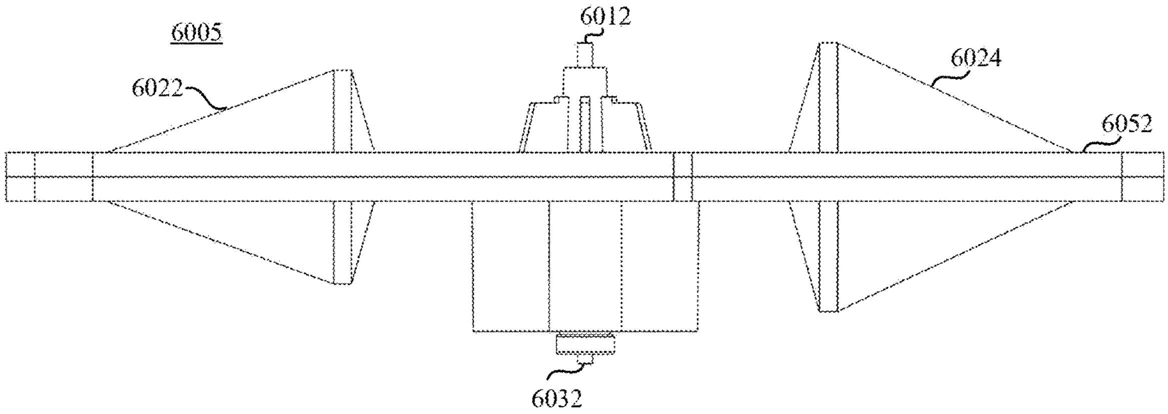
FIG. 60H is a side view of an illustrative variation of a rotor of a CCE module.

FIG. 60G is a plan view and FIG. 60H is a side view of a rotor 6005 having two cones (e.g., two bicones) configured to elutriate cells (e.g., red blood cells) in a second cone. A rotor having two cones may facilitate recirculation of buffer for reuse. The rotor 6006 may comprise a housing 6052, a first fluid conduit 6012, a first cone 6022 coupled to the first fluid conduit 6012, a second cone 6024 coupled to the first cone 6022, and a fluid conduit 6032 (e.g., outlet) coupled to the second cone 6024.

Figure 60I:
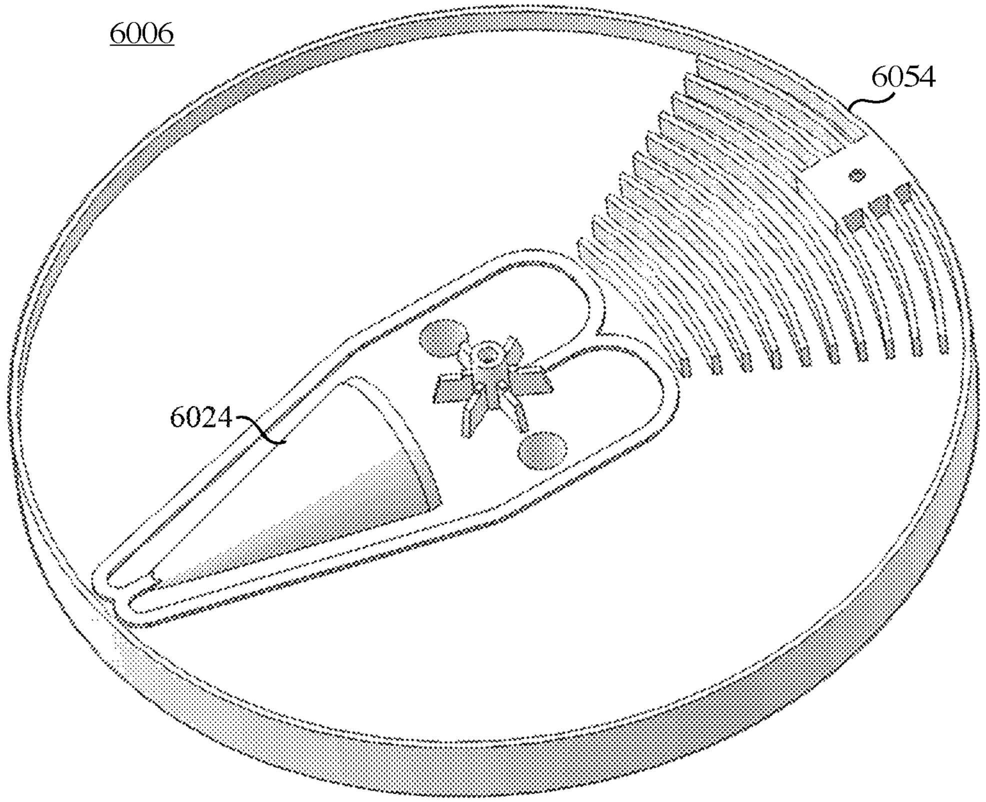
FIG. 60I is a perspective view of another illustrative variation of a rotor of a CCE module.
Figure 60J:
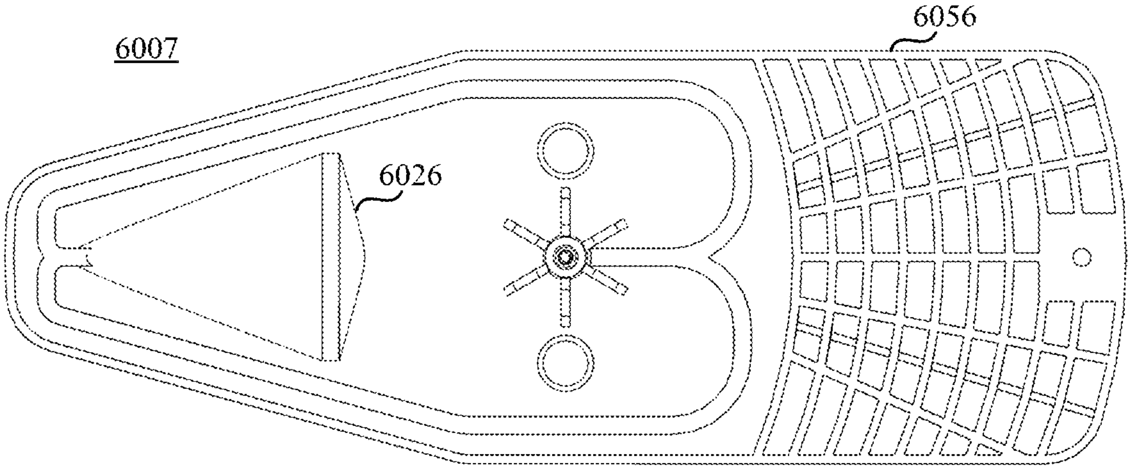
FIG. 60J is a perspective view of yet another illustrative variation of a rotor of a CCE module.
Figure 60K:
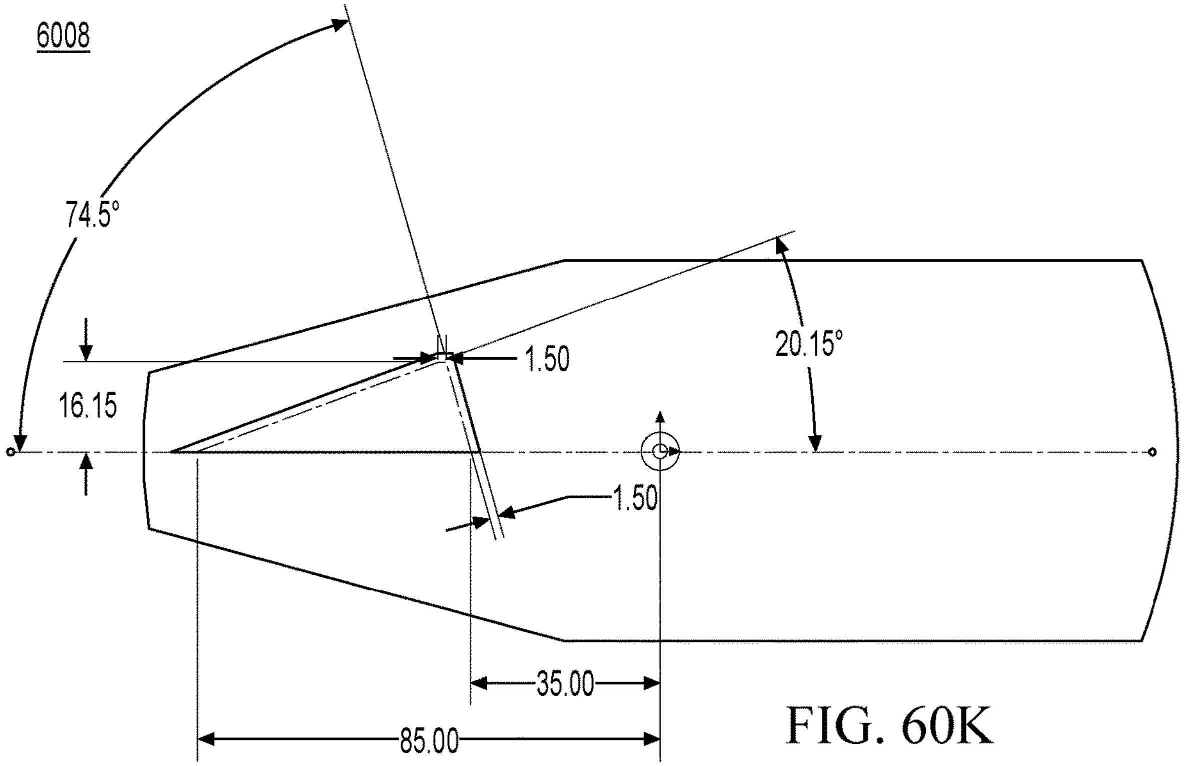
FIG. 60K is a schematic plan view of another illustrative variation of rotor dimensions of a CCE module.
Figure 60L:
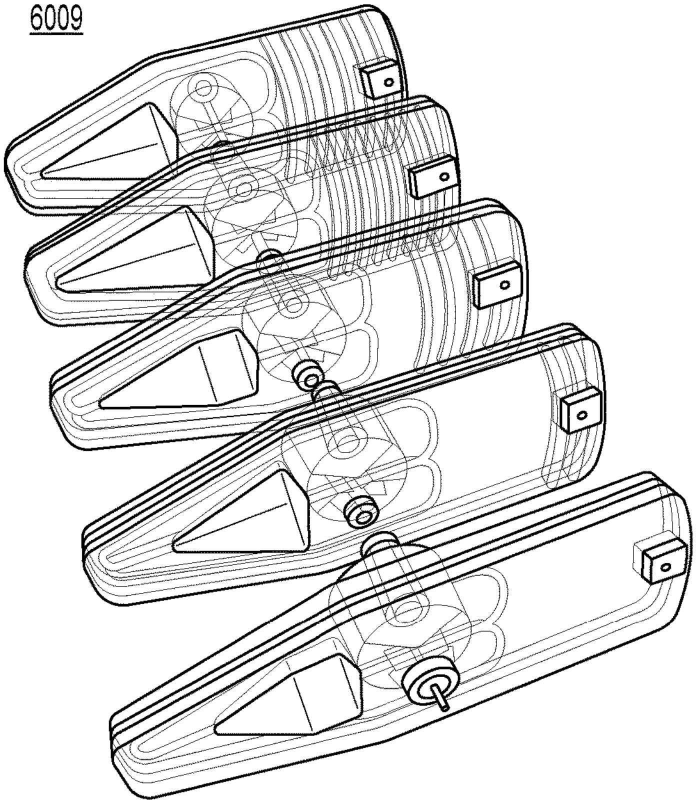
FIG. 60L is an image of a set of illustrative variations of rotors of a CCE module.

FIG. 60I is a perspective view of a rotor 6006 comprising a cone 6024 and housing 6054. FIG. 60J is a perspective view of a rotor 6007 comprising a cone 6026 and housing 6056. FIG. 60K is a schematic plan view of rotor 6008 and corresponding dimensions. FIG. 60L is an image of a set of rotors having varying dimensions.

Figure 11A:
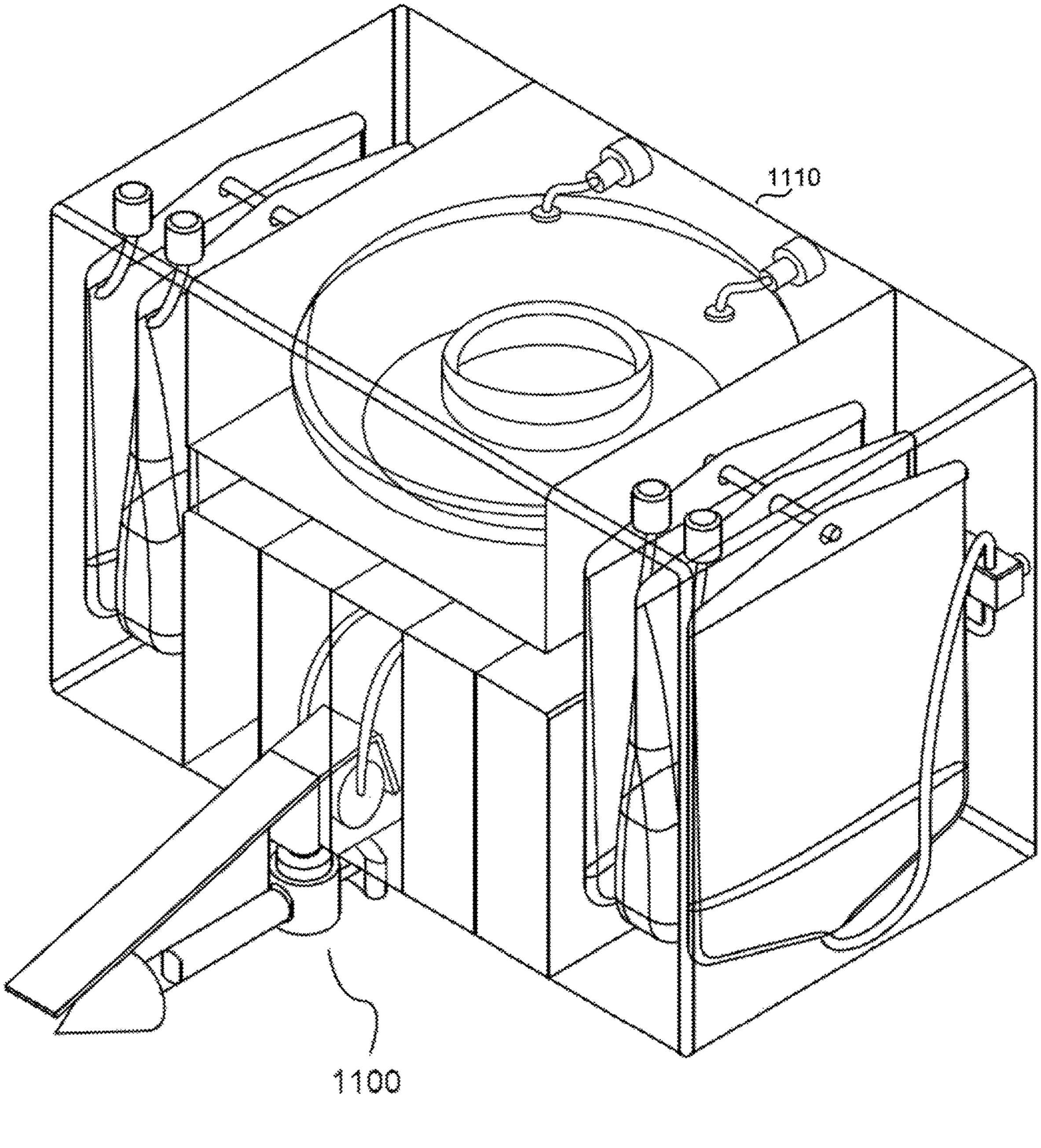
FIG. 11A is a perspective view of an illustrative variation of a cartridge comprising a CCE module in an extended configuration.
Figure 11B:
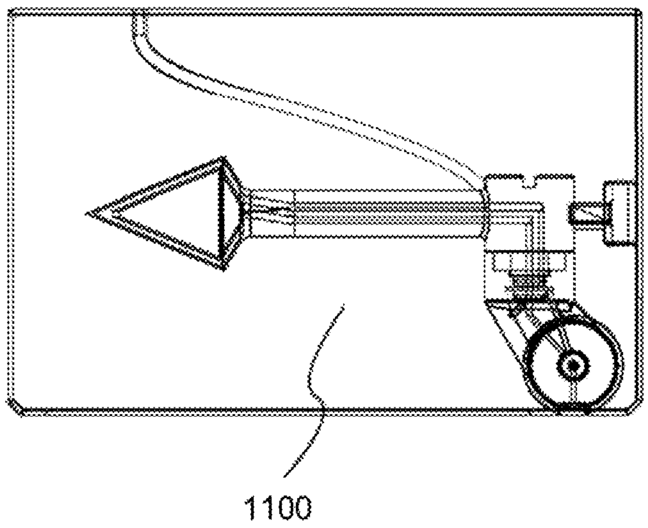
FIG. 11B is a cross-sectional side view of illustrative variation of a CCE module in a retracted configuration.
Figure 11C:
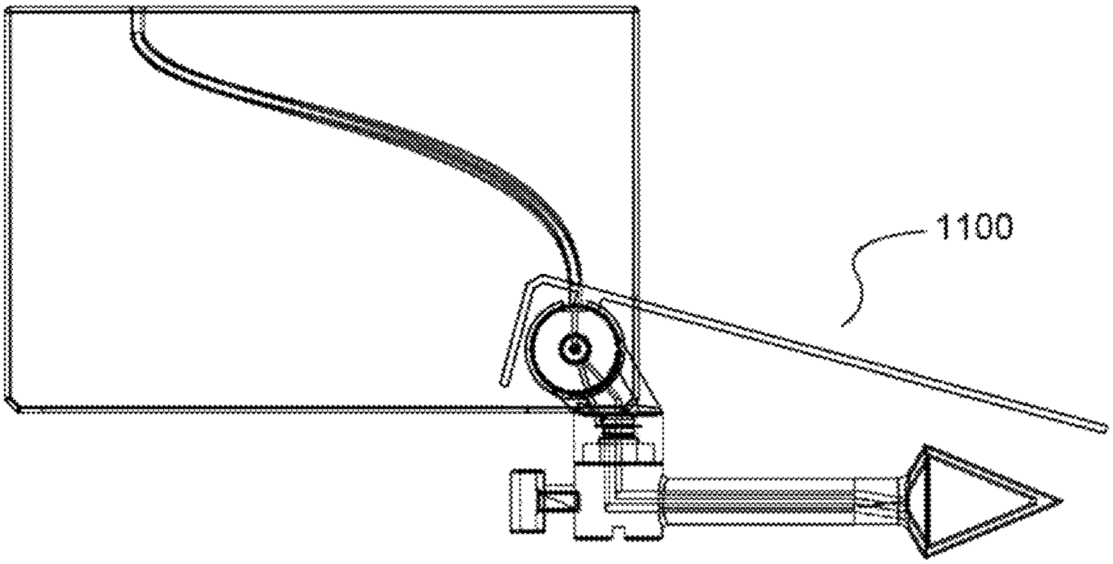
FIG. 11C is a cross-sectional side view of an illustrative variation of a CCE module in an extended configuration.

FIGS. 11A-11C depict another variation of the counter-flow centrifugal elutriation (CCE) module 1100. FIG. 11A is a perspective view of a cartridge 1110 comprising a CCE module 1100 in an extended configuration configured to receive a CCE instrument. FIGS. 11B and 11C are cross-sectional side views of a CCE module 1100 in respective retracted and extended configurations. In some variations, a CCE module may comprise a conical element having an internal surface and an external surface fixedly attached to a distal end of a linear member having an internal surface and an external surface. The proximal end of the linear member may be rotationally attached to a fulcrum in order to enable extension, retraction, and/or rotation of the linear member. For example, FIG. 11C depicts a linear member extended outside the housing of the cartridge and then rotated to generate a centrifugal force. A cell product may be conveyed between the internal surface and external surface of the linear member (optionally in tubing) to the conical element and fed into an opening at the distal end of the internal surface of the conical element, such that the flow of the cell product may run counter to the centrifugal force generated by rotation of the linear member. Cells in the cell product may be separated based on the ratio of their hydrodynamic cross section to their mass, due to the counterflow of the solution and sedimentation of cells subject to centrifugal force. The flow rate may then be increased and/or the rotation of the linear member may be decreased to permit cells to selectively return through the void in the interior surface of the linear member to the proximal end of the linear member. The selected cells may be directed into a tube that returns the selected cells to the cartridge. After an enrichment/washing step is performed, the linear member may be retracted into the housing to the retracted configuration as shown in FIG. 11B.

Magnetic Cell Selection

Generally, the systems and methods described herein may select cells on the basis of magnetically labeled cells corresponding to cells having a predetermined antigen. For example, a cell suspension of interest may be immunologically labeled with magnetic particles (e.g., magnetic beads) configured to selectively bind to the surface of the cells of interest. The labeled cells may generate a large magnetic moment when the cell suspension is flowed through a flow cell. The flow cell may be disposed in proximity to a magnet array (e.g., permanent magnets, electromagnet) generating a magnetic field having a gradient across the flow cell to attract the labeled cells for separation, capture, recovery, and/or purification. The magnet array may be configured to generate non-uniform magnetic fields at the edges and the interfaces of the individual magnets so as to cover the full volume of the flow cell such that a magnetophoretic force equals a drag force exerted by the fluid flowing through the flow cell.

Figures 61A, 61B, 61C:
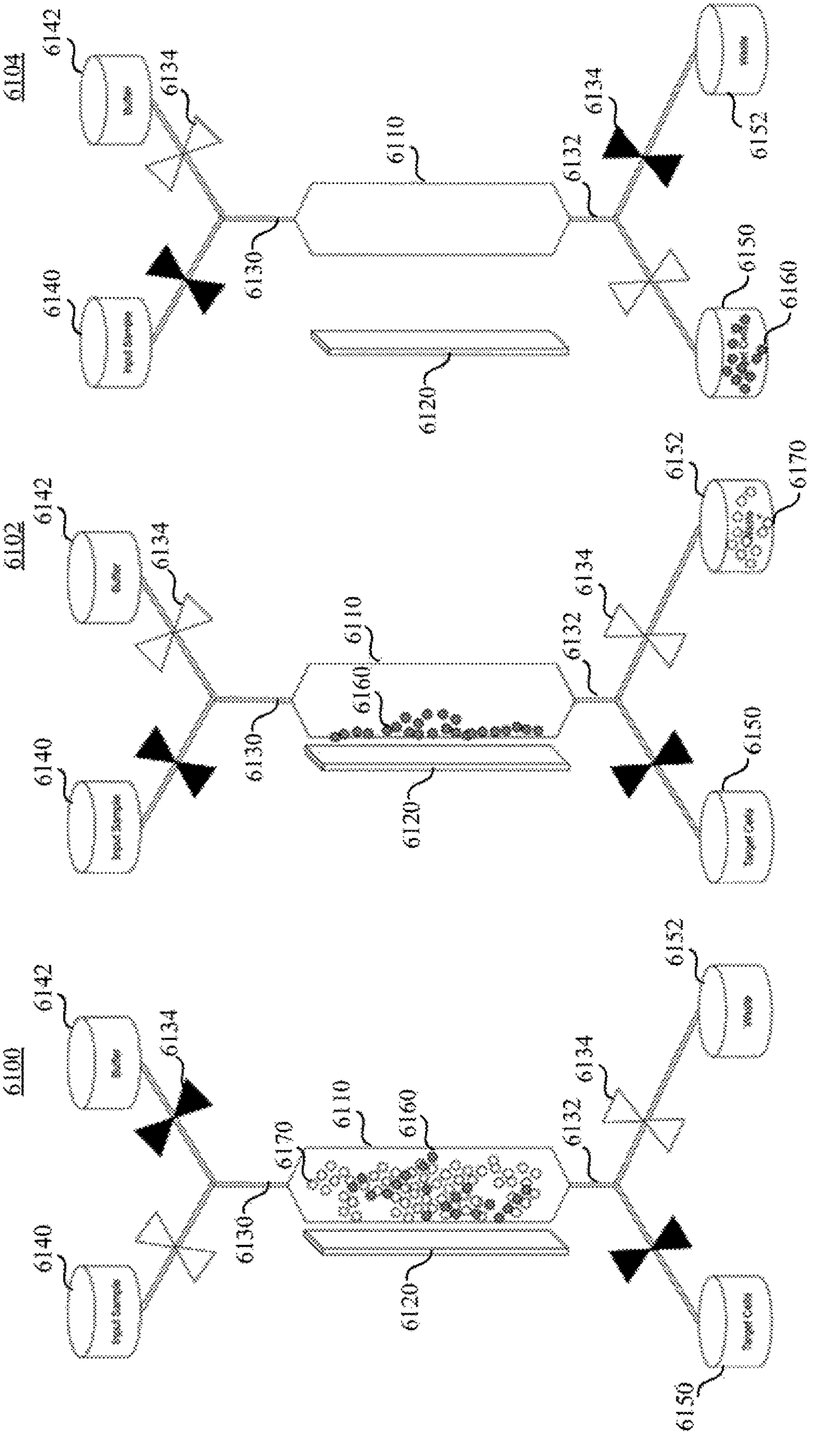
FIGS. 61A-61C are schematic views of an illustrative variation of a cell separation process.

FIG. 61A-61C are schematic views of a magnetic cell separation (e.g., magnetic-activated cell selection) system and process. A magnetic cell separation system may comprise a flow cell 6110 comprising an inlet 6130 and an outlet 6132, a magnet array 6120, a first fluid source 6140 (e.g., input sample source), a second fluid source 6142 (e.g., buffer source), a third fluid source 6150 (e.g., target cell reservoir), a fourth fluid source 6152 (e.g., waste reservoir), and a set of valves 6134. As shown in step 6100, a set of cells 6160, 6170 may comprise labeled cells 6160 (e.g., magnetically labeled cells) and non-labeled cells 6170 may flow into the flow cell 6110. For example, a set of the cells 6160 may be labeled with a magnetic-activated cell selection (MACS) reagent. A MACS reagent may be incubated with the set of cells to label (e.g., attach, couple) the cells to the MACS reagent. As described in more detail herein, the magnet array 6120 may be disposed external to the flow cell 6110 such that the magnet array 6120 may be moveable relative to the flow cell 6110. For example, the magnet array 6120 may move away from the flow cell 6110 to facilitate flowing the set of cells 6160 out of the flow cell 6110. Conventional flow cells comprise tortuous paths including meshes and/or beads to capture cells. However, recovery of labeled cells from conventional flow cell configurations is difficult, By contrast, the flow cells 6110 described herein may lack tortuous paths such as beads, meshes, and the like, and therefore enable serial separations to be performed efficiently using either positive selection or negative selection. In some variations, the flow cells may comprise generally laminar channels as described in more detail herein.

At step 6102, the magnet array 6120 may magnetically attract the set of cells 6160 towards the magnet array 6120 for a predetermined dwell time and/or based on a measured quantity of magnetically separated cells. In some variations, the dwell time may be at least one minute (e.g., at least two minutes, at least three minutes, at least five minutes). The non-labeled cells 6170 are not magnetically attracted to the magnet array 6120 and may flow out of the outlet 6132 of the flow cell 6110 and into the fourth fluid source 6152. In some variations, the fluid (e.g., cells 6160, 6170) within the flow cell may be held statically within the flow cell 6110 for a dwell time before the fluid (e.g., cells 6170) flow from outlet 6132. In some variations, a longitudinal axis of the flow cell 6110 may be oriented substantially perpendicular to ground in order for fluid flow through the flow cell 6110 to be aided by gravity. At step 6104, the magnetic coupling between the magnet array 6120 and the cells 6160 may be released after the dwell time, and the cells 6160 may flow into the third reservoir 6150.

In some variations, stiction may cause cells to remain attached to a surface of a flow cell even after removal of a magnet array 6120. Therefore, a gas may be flowed through the flow cell 6110 to aid cell collection into the third reservoir 6150. Gas flow through the flow cell may provide improved cell recovery over liquid flushing through the flow cell. An interface generated by a gas (e.g., bubble, air gap) may be maintained by gravity, thereby enabling implementation of a relatively wide flowcell that further improves cell recovery relative to a horizontally oriented flow cell. The MACS modules described herein may be configured for positive selection and/or negative selection by modifying the sequence of steps.

Additionally or alternatively, an optical sensor may be configured to image a flow cell to generate imaging data used to identify a quantity of cells magnetically attracted to the magnet array. Fluid containing labeled cells may be flowed out of the flow cell when a predetermined quantity of cells have been measured by the optical sensor.

Figure 62A:
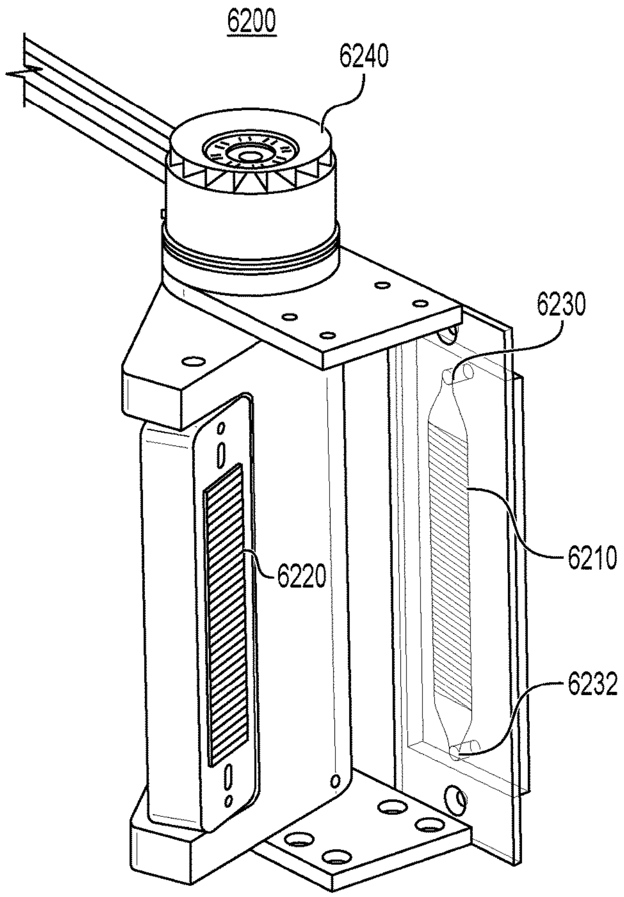
FIG. 62A is a perspective view of an illustrative variation of a MACS system in a first configuration.
Figure 62B:
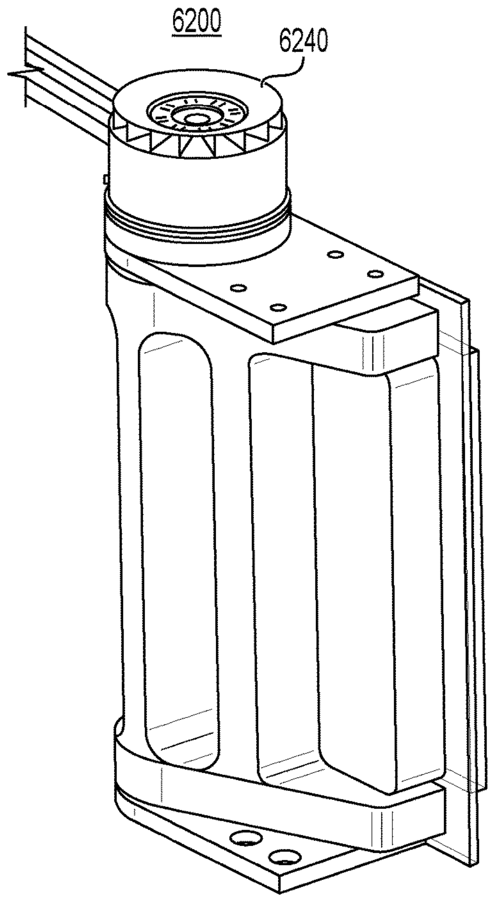
FIG. 62B is a perspective view of an illustrative variation of a MACS system in a second configuration.
Figure 62C:
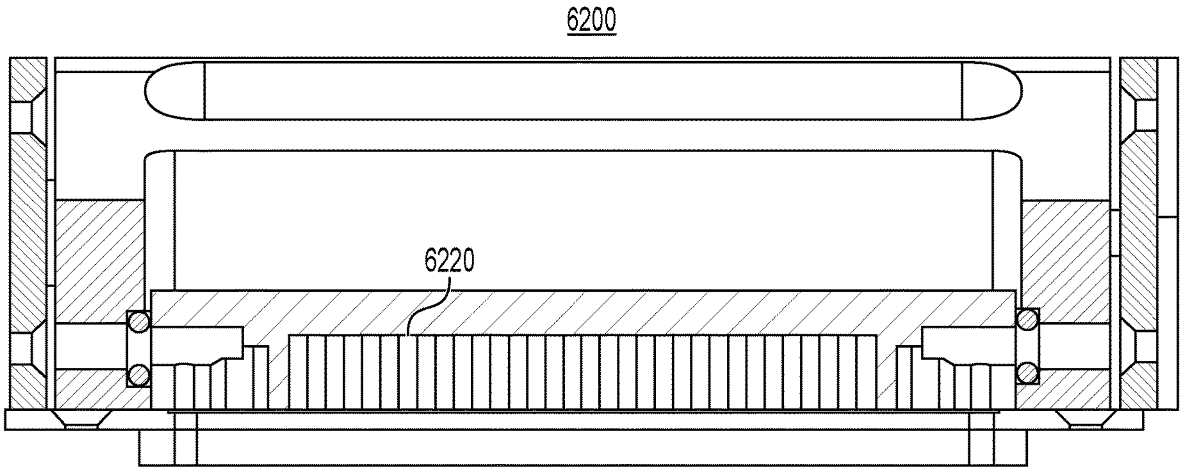
FIG. 62C is a cross-sectional side view of an illustrative variation of a MACS system.
Figures 62D, 62E:
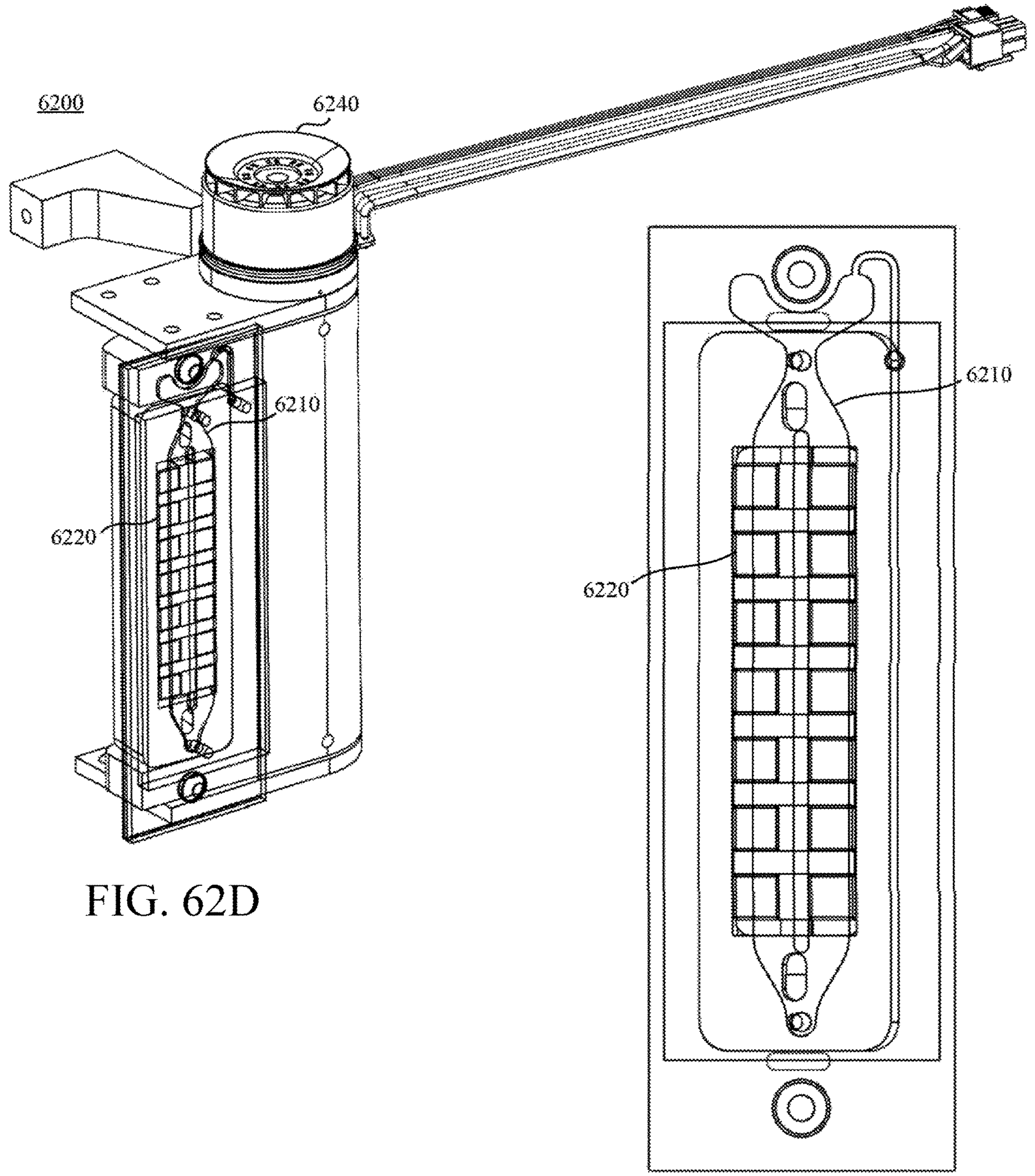
FIG. 62D is a perspective view of an illustrative variation of a MACS system in the second configuration.
FIG. 62E is a plan view of an illustrative variation of a flow cell and magnet array of a MACS system.

FIG. 62A is a perspective view of a MACS module 6200 in a first configuration. The MACS module 6200 (as well as any of the MACS modules described herein) may be a component of any of the cartridges described herein. For example, a cartridge for cell processing may comprise a liquid transfer bus and a plurality of modules with each module fluidically linked to the liquid transfer bus. The MACS module 6200 may comprise a flow cell 6210 comprising an elongate cavity having a cavity height, an inlet 6230, and an outlet 6232. The MACS module 6200 may further comprise a magnet array 6220 comprising a plurality of magnets. Each of the magnets may be spaced apart by a spacing distance, such as illustrated in FIGS. 62G, 63D, and 63E, although FIGS. 62A-62E illustrate a magnet array 6220 with magnets in contact with adjacent magnets.

Figure 62F:
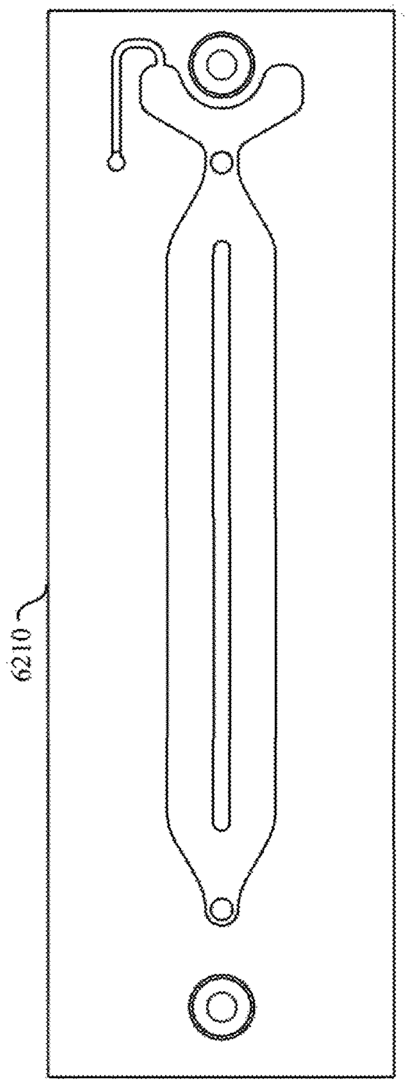
FIG. 62F is a plan view of an illustrative variation of a flow cell of a MACS system.
Figure 62G:
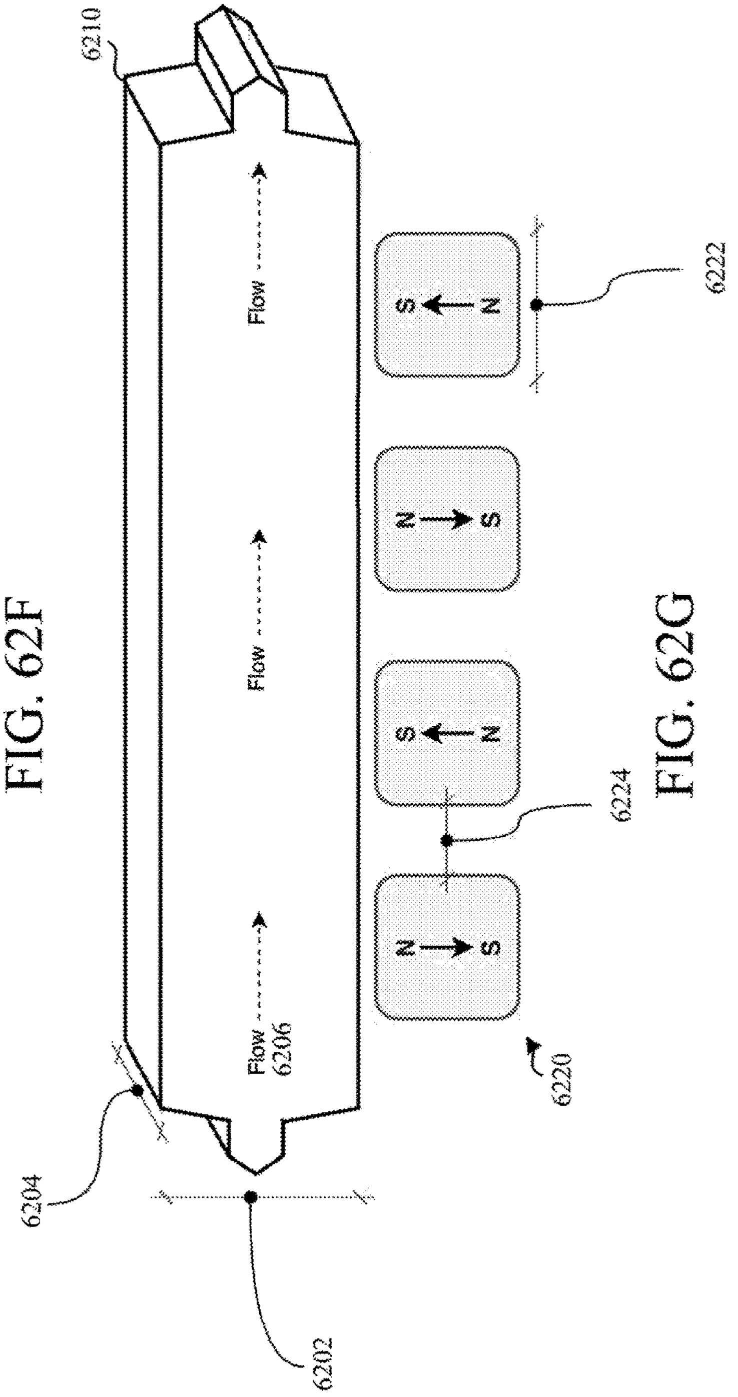
FIG. 62G is a schematic diagram of an illustrative variation of a flow cell and magnet array.
Figure 63A:
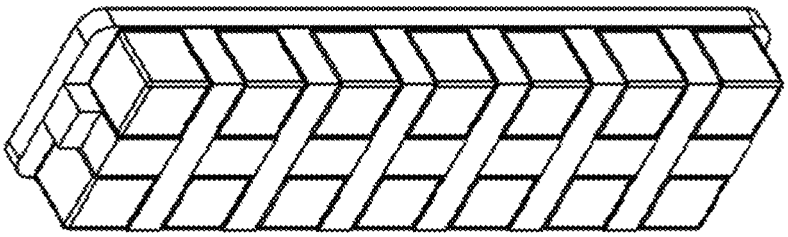
FIGS. 63A-63E are perspective views of illustrative variations of a magnet array.
Figure 63B:
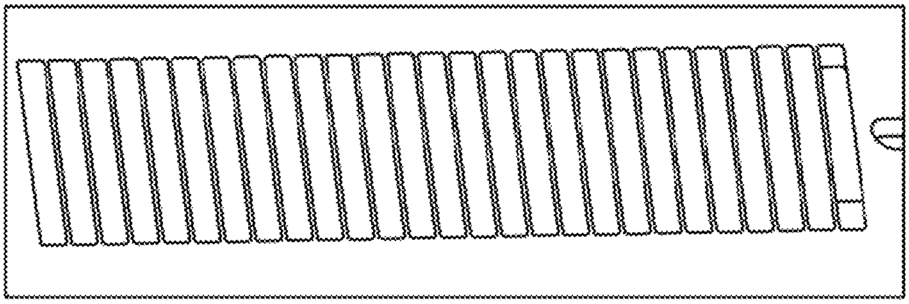
Figure 63C:
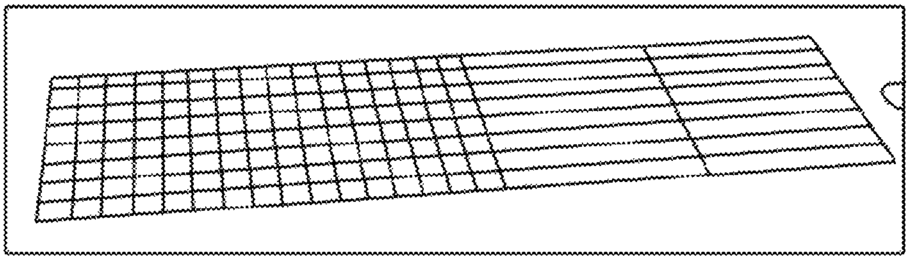
Figure 63D:
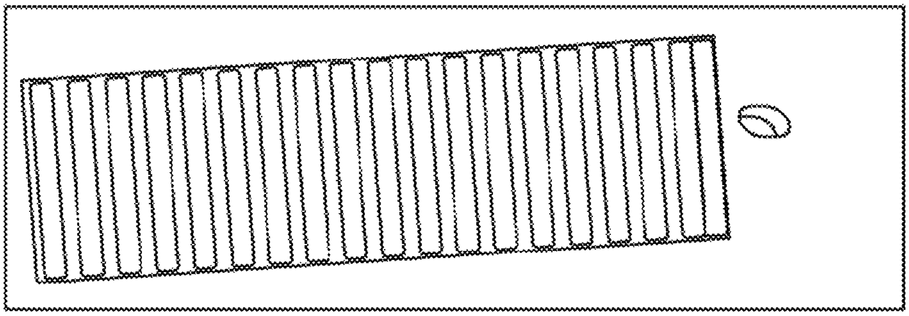
Figure 63E:
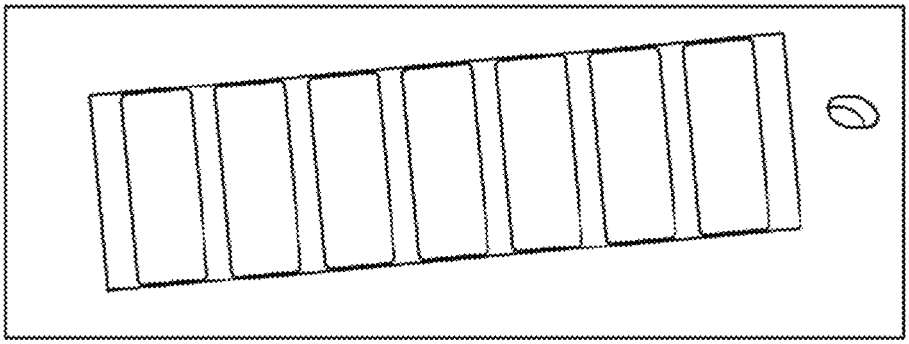

FIG. 62G is a schematic diagram of the flow cell 6210 and magnet array 6220. In some variations, the flow cell 6210 may comprise a cavity height 6202 and a cavity width 6204. Fluid may be configured to flow through the flow cell 6210 in a first direction 6206. The magnet array 6220 may comprise a plurality of magnets with each magnet comprising a respective width 6222. In some variations, adjacent magnets may be separated by a predetermined spacing distance 6224. Each magnet pair may have the same or different spacing distance 6224. As shown in FIG. 62G, an orientation (e.g., poles) of the magnets in the magnet array 6220 may comprise a predetermined pattern.

In some variations, a ratio of the cavity height 6202 to the spacing distance 6224 is between about 20:1 and about 1:20, between about 10:1 and about 1:10, between about 5:1 and about 1:5, and between about 3:1 and about 1:3, including all values and sub-ranges in-between. In some variations, an actuator 6240 (e.g., linear, rotary) may be configured to move the magnet array 6220 relative to the flow cell 6210. In some variations, an orientation (e.g., poles) of the magnets in the magnet array 6220 may comprise a predetermined pattern (e.g., Halbach array).

In some variations, the magnet array 6220 may move relative to the flow cell 6210 or vice versa. FIG. 62A illustrates the MACS module 6200 in an open configuration and FIG. 62B illustrates the MACS module 6200 in a closed configuration. FIG. 62B is a perspective view of the MACS system 6200 in a second configuration where labeled cells may be magnetically attracted towards the magnet array 6220. In the second configuration, the magnetic field lines generated by the magnet array traverse the flow channel exerting a magnetophoretic force on magnetically tagged cells that are injected into the channel. FIG. 62C is a cross-sectional side view of the MACS system 6200 including the magnet array 6220. FIG. 62D is a perspective view of a MACS system 6200 in the second configuration. FIG. 62E is a plan view of a flow cell 6210 and magnet array 6220 of a MACS system. FIG. 62F is a plan view of a flow cell 6210 of a MACS system.

FIG. 63A-63E are perspective views of a set of magnet arrays 6300, 6310, 6320, 6330, 6340. One or more of the size, strength, shape, spacing, and orientation of the magnets in a magnet array may be set to generate a magnetic field to attract magnetically-labeled cells. Additionally or alternatively, a magnet array may comprise a high-magnetic permeability material configured to enhance or reduce the field strength and field gradients within the flow cell. The material may be disposed between a magnet and flowcell. Additionally or alternatively, the material may be disposed within the flowcell and/or on one or more sides of the flowcell.

Figure 64A:
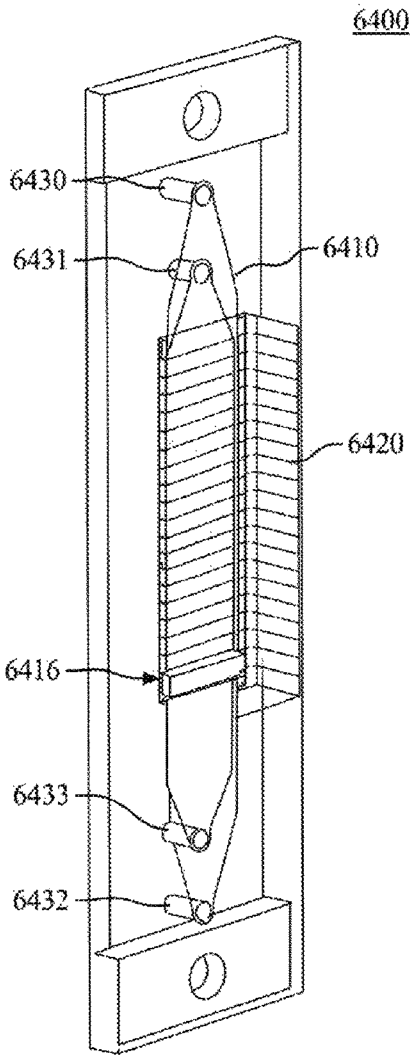
FIG. 64A is a perspective view of an illustrative variation of a flow cell.
Figure 64B:
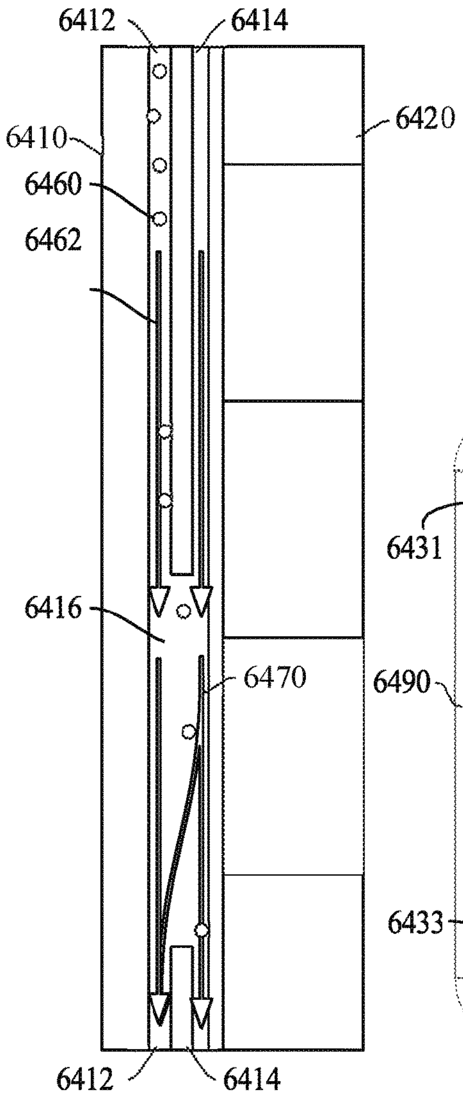
FIG. 64B is a cross-sectional side view of an illustrative variation of a flow cell.

FIGS. 64A and 64B are respective perspective and cross-sectional side views of a MACS module 6400 comprising a flow cell 6410 and a magnet array 6420. The flow cell 6410 may comprise a set of linear channels 6412, 6414, 6416 comprising a first channel 6412 parallel to a second channel 6414, and a third channel 6416 in fluid communication with each of the first channel 6412 and the second channel 6416. As shown in FIG. 64B, the third channel 6416 may be disposed between the first channel 6412 and the second channel 6416 and define a volume where fluid from the first channel 6412 and the second channel 6416 interact (e.g., mix). In some variations, the flow cell 6410 may comprise a first inlet 6430 coupled to the first channel 6412 and configured to receive a first fluid 6460 (e.g., cells). A second inlet 6431 may be coupled to the second channel 6414 and configured to receive a second fluid 6470 (e.g., buffer). The flow cell 6410 may comprise a first outlet 6432 coupled to the first channel 6412 and a second outlet 6433 coupled to the second channel 6414.

The magnet array 6420 may be disposed external to the flow cell 6400 and may be moved relative to the flow cell 6400 as described herein. In some variations, a longitudinal axis of the flow cell 6410 may be perpendicular to ground such that fluid flows in a generally vertical direction.

In some variations, the first channel 6412 may have different dimensions form the second channel 6414. For example, a first cavity height of the first channel 6412 may be larger than a second cavity height of the second channel 6414. For example, a ratio of the first cavity height to a second cavity height may be between about 1:1 to about 3:7, between about 1:1 to about 2:3, and between about 2:3 to about 3:7, including all values and sub-ranges in-between. Fluid flowing through the first channel 6412 may have a slower flow rate relative to the second channel 6414 due to the larger cavity height of the first channel 6412 relative to the second channel 6414. In some variations, the third channel 6416 may comprise a ratio of a length of the third channel 6416 to a diameter of the third channel 6416 of between about 2:1 to about 6:1, between about 2:1 to about 3:1, between about 3:1 to about 4:1, between about 4:1 to about 5:1, between about 5:1 to about 6:1, and between about 3:1 to about 5:1, including all values and sub-ranges in-between.

As shown in FIG. 64B, a first fluid 6462 may flow through the flow cell 6410 generally following a first direction. The magnetically-labeled cells 6416 within the first fluid 6462 may separate from the rest of the first fluid 6462 within the third channel 6416 as the magnetic attractive forces generated by magnet array 6420 pulls the cells 6416 away from the first channel 6412 and towards the second channel 6414 (e.g., towards the magnet array 6420). Similarly, a second fluid 6470 (e.g., buffer) may flow through the second channel 6414. As the cells 6416 flow towards the magnet array 6420, they displace the second fluid 6470 flowing through the third channel 6416 such that a portion of the second fluid 6470 may flow into the first channel 6412. In this manner, magnetically-labeled cells 6416 may be magnetically separated from a first fluid 6462 and the second fluid 6470 may aid removal of the first fluid 642 not including the cells 6416.

Figure 64C:
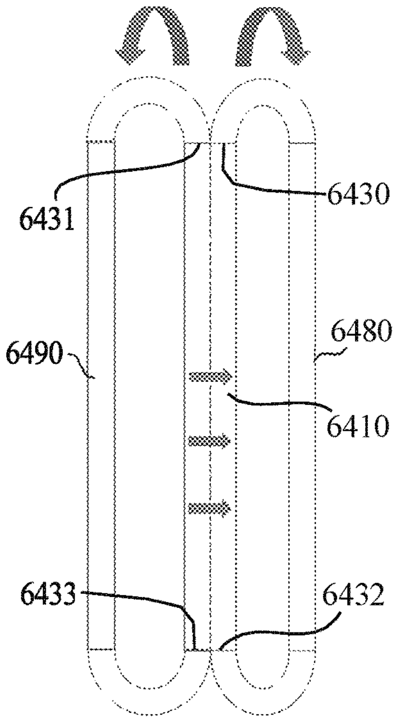
FIG. 64C is a schematic diagram of an illustrative variation of a MACS system.

In some variations, a set of fluidic loops may be coupled to the flow cell to enable a plurality of cell separation cycles. FIG. 64C is a schematic diagram of a MACS module comprising a flow cell 6410, a first fluid conduit 6480 coupled to an inlet 6430 of the flow cell 6410 and an outlet 6432 of the flow cell 6410. The first fluid conduit May 6480 may be configured to receive the set of cells from an outlet 6432 of the flow cell 6410 for recovery and/or recirculation through the inlet 6430 of the flow cell 6410. A second fluid conduit 6490 may be coupled to the inlet 6431 of the flow cell 6410 and the outlet 6433 of the flow cell 6410 to recirculate fluid such as buffer and unrecovered magnetically-labeled cells. The second fluid conduit 6490 may be configured to receive a fluid without the set of cells from the flow cell 6410. Higher purities of labeled cells may be recovered based on a number of cycles performed. For example, a single cell separation cycle may yield about 80% cell purity, a second cell separation cycle may yield about 96% cell purity, a third cell separation cycle may yield about 99.2% cell purity, and a fourth cell separation cycle may yield about 99.84% cell purity.

Figure 65A:
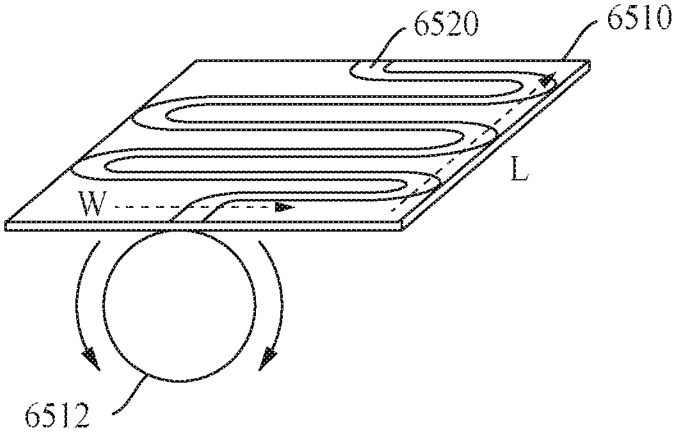
FIGS. 65A-65C are schematic diagrams of an illustrative variation of a flow cell.
Figure 65B:
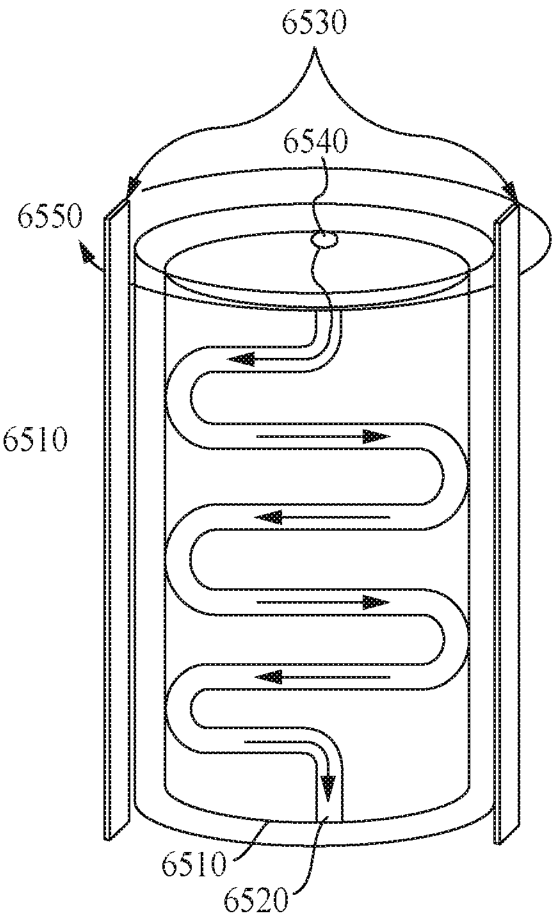
Figure 65C:
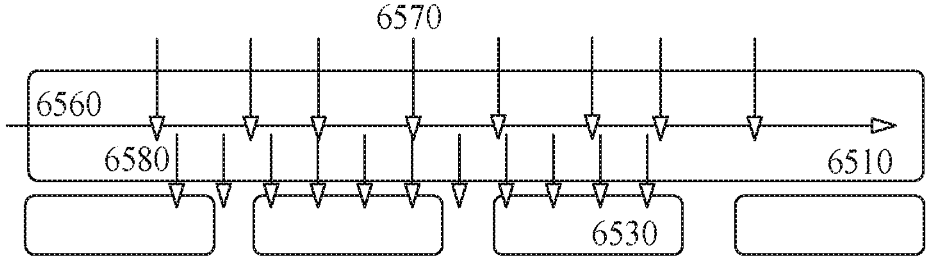

In some variations, applying a centrifugal force to a magnetic cell separation process may further attract labeled cells toward a magnetic array independently of fluid flow rate so as to maintain throughput. FIGS. 65A-65C are schematic diagrams of a MACS module 6500 utilizing centrifugal force to aid a cell separation process. FIG. 65A depicts a flattened flow cell 6510 configured to be wrapped to form a generally cylindrical shape 6512. The flow cell 6510 may comprise a curved flow path 6520.

FIG. 65B illustrates a cylindrical flow cell 6510 concentrically surrounded by (e.g., nested within) a cylindrical magnet array 6530. In FIG. 65B, only a cross-section of the magnet array 6530 is shown for the sake of clarity. The flow cell 6510 may be spaced apart from the magnet array 6530 by a predetermined spacing distance. Accordingly, the flow cell 6510 may be configured to rotate 6550 about a longitudinal axis to generate a centrifugal force on the fluid 6540 within the flow path 6520 in an outward direction towards the magnet array 6530. During a cell separation process, the fluid may be subject to set of forces depicted in FIG. 65C including a bulk fluidic force 6560 in an axial (e.g., bulk flow) direction, a centrifugal force 6570 in a radially outward direction from a center of rotation (e.g., proportional to a net particle system buoyancy), and a magnetic force 6580 extending radially outward from a center of rotation (e.g., proportional to net particle system magnetic attractiveness). In some variations, labeled cells may comprise a higher density than non-labeled cells. Therefore, centrifugal force may preferentially push the labeled cells towards the magnet 6530, further increasing the specificity and efficiency of cell separation.

Figure 66C:
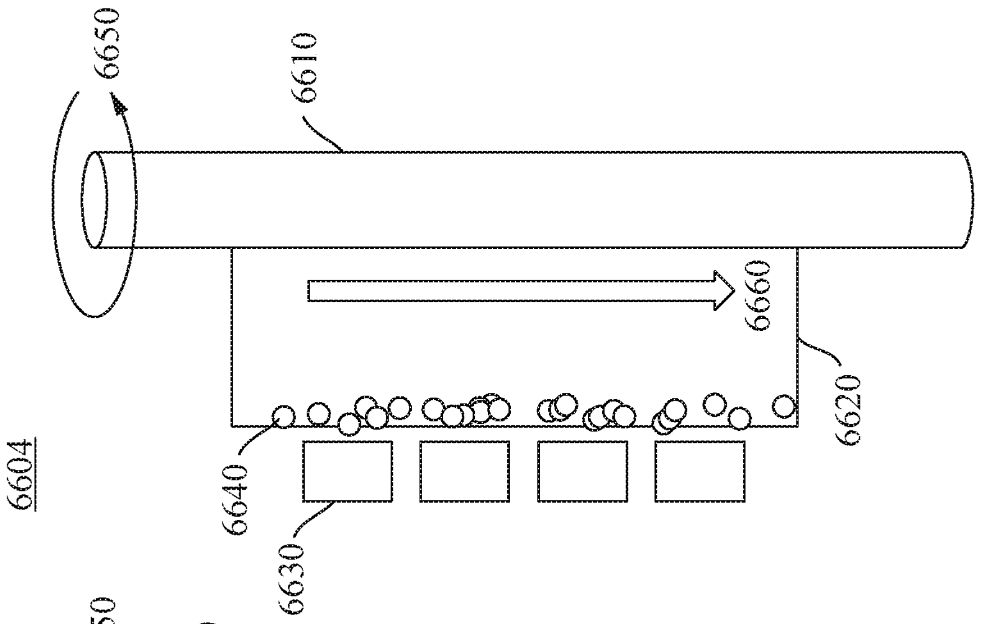
FIGS. 66A-66C are schematic diagrams of an illustrative variation of a cell separation process.
Figure 66B:
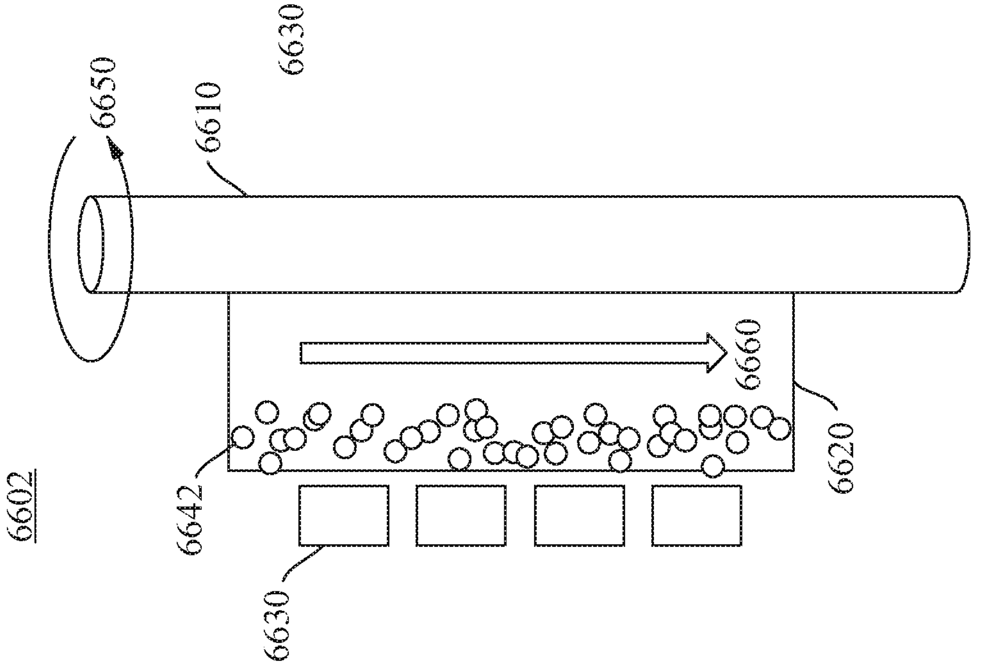
Figure 66A:
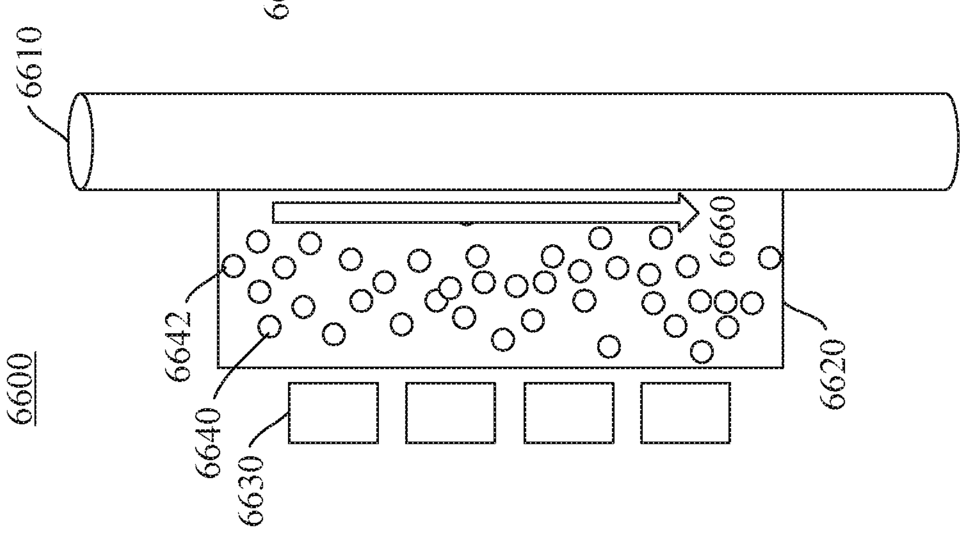

FIGS. 66A-66C are schematic diagrams of a cell separation system and process. A magnetic cell separation system may comprise a flow cell 6610 comprising a flow path 6620 (shown schematically flattened for sake of clarity), and a magnet array 6630. As shown in step 6600, a set of cells 6640, 6642 may comprise labeled cells 6640 (e.g., magnetically labeled cells) and non-labeled cells 6642 may flow into the flow path 6620 of flow cell 6610. For example, a set of the cells 6640 may be labeled with a magnetic-activated cell selection (MACS) reagent. The magnet array 6630 may be disposed external to the flow cell 6610 such that the magnet array 6630 may be moveable relative to the flow cell 6610. For example, the magnet array 6630 may move away from the flow cell 6610 to facilitate flowing the set of cells 6640 out of the flow cell 6610.

At step 6602, the flow cell 6650 may be rotated to generate centrifugal force to push the cells 6640, 6642 toward the magnet array 6630. In some variations, a longitudinal axis of the flow cell 6610 may be oriented substantially perpendicular to ground in order for fluid flow through the flow cell 6610 to be aided by gravity. At step 6604, the magnet array 6630 may magnetically attract the set of cells 6640 towards the magnet array 6630 for a predetermined dwell time as described herein. The non-labeled cells 6642 are not magnetically attracted to the magnet array 6630 and may flow out of the flow cell 6610 into, for example, a waste vessel. In some variations, the fluid (e.g., cells 6160, 6170) within the flow cell may be held statically within the flow cell 6110 for a dwell time before the fluid (e.g., cells 6170) flow from outlet 6132. In some variations, the magnetic coupling between the magnet array 6630 and the cells 6640 may be released after the dwell time, and the cells 6640 may be recovered.

Figure 12A:
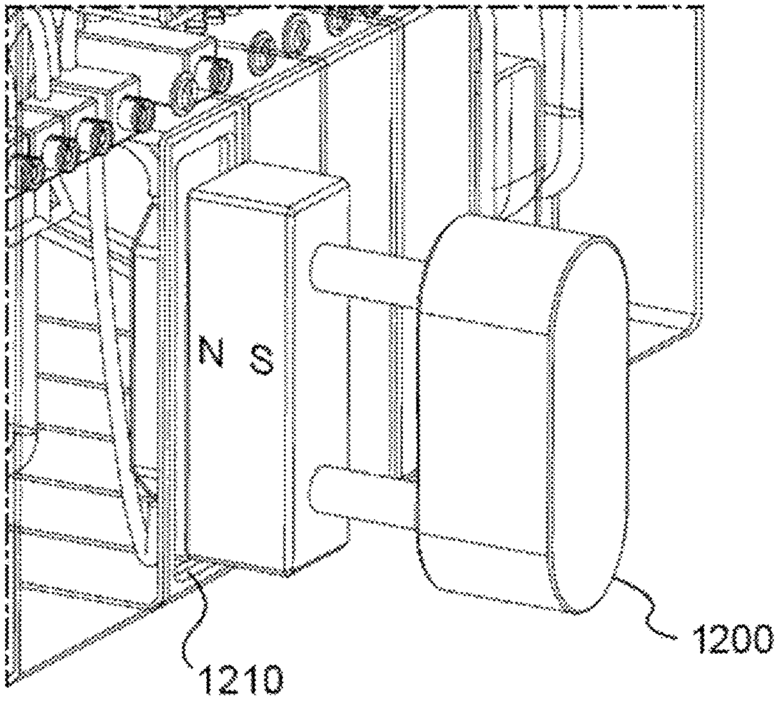
FIG. 12A is a perspective view of an illustrative variation of a magnetic-activated cell sorting (MACS) instrument comprising a magnet in an ON configuration.
Figure 12B:
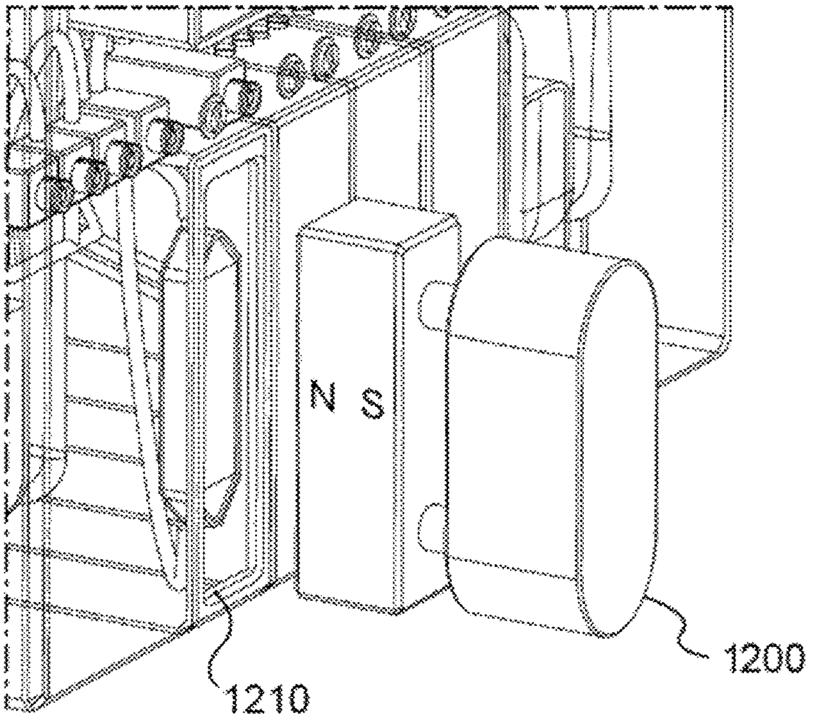
FIG. 12B is a perspective view of an illustrative variation of a MACS instrument comprising a magnet in an OFF configuration.

FIGS. 12A and 12B illustrate the magnet of the MACS instrument 1200 comprising a magnet and a MACS module 1210. The magnet is shown in FIG. 12A in an ON configuration and shown in FIG. 12B in an OFF configuration.

Bioreactor

The bioreactors described herein may comprise a vessel configured to culture mammalian cells. Generally, cell and gene therapy products may be grown in a bioreactor to produce a clinical dose which may subsequently be administered to a patient. A number of biological and environmental factors may be controlled to optimize the proliferation speed and success of cell growth. The bioreactor modules described herein enable one or more of monitoring, adjusting, and/or controlling of cell growth (e.g., to facilitate consistent and efficient cellular proliferation).

Figure 67A:
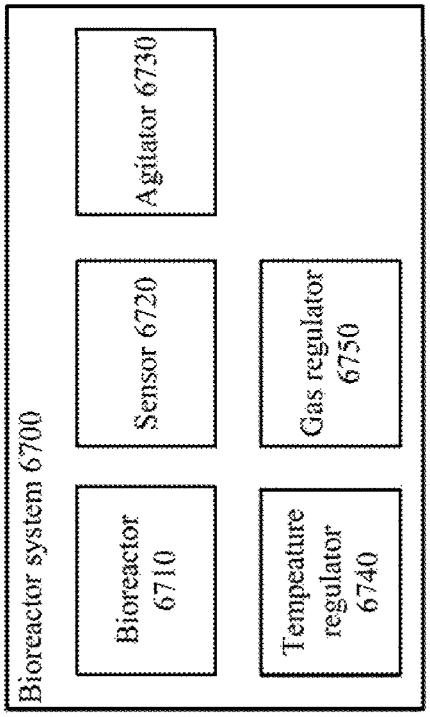
FIGS. 67A-67D are schematic diagrams of an illustrative variation of a cell processing system.

FIG. 67A is a schematic diagram of a cell processing system 6700 (e.g., bioreactor module) comprising one or more of a bioreactor 6710, one or more sensors 6720, an agitator 6730, a temperature regulator 6740, and a gas regulator 6750. In some variations, the sensor 6720 may be configured to monitor (e.g., measure, sense, determine) one or more characteristics of the bioreactor module 6700 and cells in the bioreactor 6710. For example, the sensor 6720 may comprise one or more of a pH sensor, a dissolved oxygen (DO) sensor, a temperature sensor, a glucose sensor, a lactose sensor, a cell density sensor, a humidity sensor, combinations thereof, and the like. One or more of the sensors may be a non-invasive optical sensor.

Figure 67B:
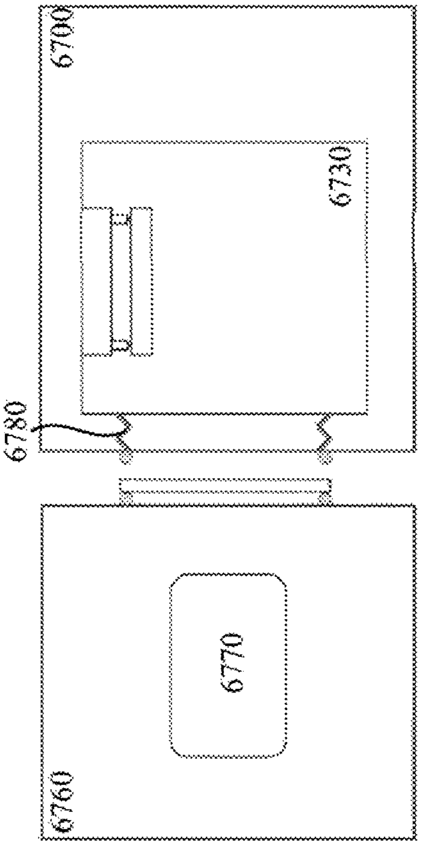
Figure 67C:
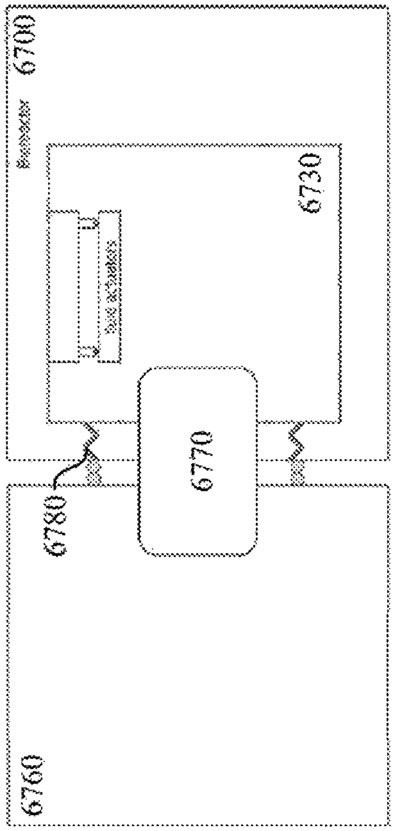
Figure 67D:
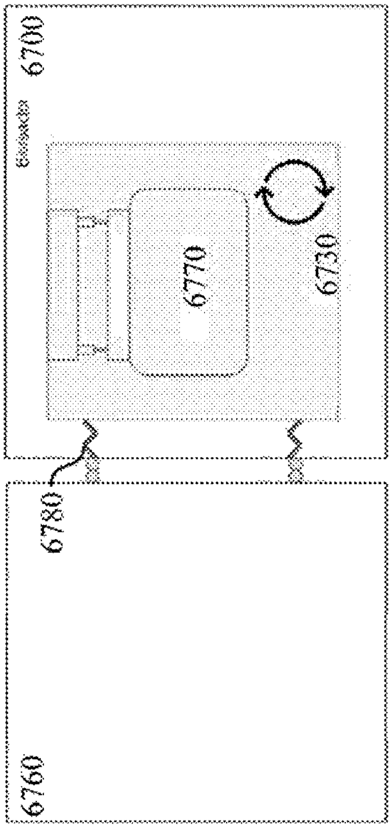

FIGS. 67B-67D are schematic diagrams of a cell processing system comprising a workcell 6760, a bioreactor system 6700 (e.g., bioreactor instrument), a cartridge 6770, an agitator 6730, and a fluid connector 6780. In some variations, a cartridge 6770 for cell processing may comprise a liquid transfer bus and a plurality of modules (e.g., bioreactor module, CCE module, MACS module, EP module). Each module may be fluidically linked to the liquid transfer bus. The bioreactor module may comprise at least one bioreactor.

The bioreactor instrument 6700 may be configured to interface with the cartridge 6770. In some variations, the bioreactor instrument 6700 may comprise the agitator 6730 configured to couple to the bioreactor. The agitator may be configured to agitate cell culture media comprising cells. In some variations, the fluid connector 6780 may be configured to couple the bioreactor system 6700 and workcell 6760.

FIG. 67B depicts a cartridge 6770 comprising a bioreactor disposed within a workcell 6760. The bioreactor 6700 may be uncoupled from the workcell 6760. Once the fluid connector 6780 couples (e.g., to create a sterile flow path) the workcell 6760 to the bioreactor 6700, the cartridge 6770 may be moved into the bioreactor 6700, as shown in FIG. 67C. For example, the cartridge 6770 may be coupled to (e.g., disposed on) an agitator 6730 and then agitated, as shown in FIG. 67D. In some variations, the fluid connector 6780 may comprise a set of foldable sidewalls (e.g., like an accordion) configured to receive and dissipate the agitation of the agitator 6730 without transmitting such motion to the workcell 6760. That is, the fluid connector 6780 may function as a bellows to maintain the connection between the workcell 6760 and bioreactor 6700 without agitating the workcell 6760. In some variations, the fluid connector 6780 may couple the bioreactor (e.g., of cartridge 6770) to a liquid transfer bus.

In some variations, an agitator may be configured to generate motion (e.g., orbital, rotary, linear) to the bioreactor in order to mix the culture in instances where it is required to encourage interactions with a reagent and cells. For example, orbital motion may be used to create a homogenous culture volume such that a small sample taken from the culture may be representative of the culture at large. In some variations, the agitator 6730 may comprise one or more impellers. The agitator 6730 may be configured to provide variable-intensity mixing during culture at defined periods.

In some variations, orbital motion may encourage increased interactions within the cell culture, such as in the toroidal bioreactors described herein that comprise a geometry that may encourage the continuous and gentle flow of fluid around the bioreactor, thereby aiding homogenous mixing with minimal shear stress transferred to the cells.

In some variations, the temperature regulator 6740 may be configured to control a temperature of a bioreactor and corresponding processes. The temperature regulator 6740 may be coupled to the bioreactor. For example, the temperature regulator 6740 may control a temperature of a cell culture to be between about 2° C. and about 40° C. and thereby ensure that a culture is heated to physiological conditions and cooled to slow metabolic processes (e.g., to keep cells in a dormant state) as desired. For example, the thermal regulator 6740 may comprise a circulating coolant coupled to a heat exchanger coupled to a thermal interface (e.g., heating/cooling plate).

In some variations, the gas regulator 6750 may be coupled to the bioreactor and configured to control a gas composition of a bioreactor and corresponding processes using one or more of Clean Dry Air (CDA), carbon dioxide, and nitrogen. The gas regulator 6750 may be coupled to the bioreactor. For example, the sensors 6720 and gas regulator 6750 may provide closed-loop gas control of the bioreactor module 6700. In some variations, CDA may comprise oxygen such as pure oxygen. In some variations, the gas regulator may comprise a manifold coupled to one or more gas sources. The manifold may include a solenoid coupled to a valve (e.g., restrictive orifice) configured to control gas flow through the bioreactor 6710. The solenoid may be configured to pulse to control a quantity and composition of gas received through the manifold. Additionally or alternatively, one or more of a proportional valve and Mass Flow Controller (MFC) may be configured to meter and control the flow of gas to a manifold. In some variations, the gas regulator 6750 may comprise one or more sensors to measure the gas mixture and/or flow rate. Additionally or alternatively, the sensors may be configured for closed-loop control of gas flow through the gas regulator.

In some variations, measured pH from a pH sensor may be used to control a pH of the bioreactor 6710 using the gas regulator 6750. For example, in response to the measured pH, gas regulator 6750 may control a $CO_2$ concentration of the gas contacting the cell culture to control the free hydrogen ions and pH of the culture. In some variations, a pH of the bioreactor 6710 may be between about 5.5 and about 8.5. One or more of $CO_2$ composition of the gas in the bioreactor 6710, buffer, and reagents (e.g., acid, base) may be used to regulate pH. In some variations, a dissolved oxygen concentration of the bioreactor 6710 may be between about 0% and about 21%. Nitrogen composition of the gas in the bioreactor 6710 may be used to regulate the dissolved oxygen concentration. For example, control of both the agitator in the bioreactor and the flow rate and composition of the gas contacting the cell culture may regulate the dissolved carbon dioxide concentration.

In some variations, measured dissolved oxygen from a dissolved oxygen sensor may be used to control an oxygen concentration (e.g., below atmospheric levels) of the bioreactor 6710 using the gas regulator 6750. For example, gas regulator 6750 may control a nitrogen concentration of the gas contacting the cell culture to create hypoxic conditions.

Figure 68A:
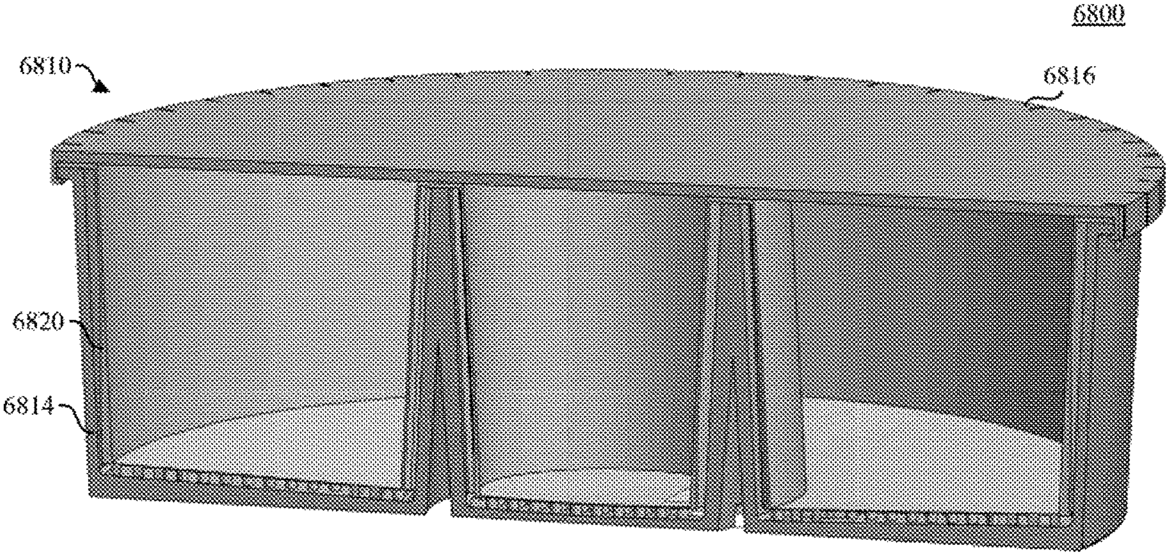
FIG. 68A is a cross-sectional perspective view of an illustrative variation of a bioreactor.
Figure 68B:
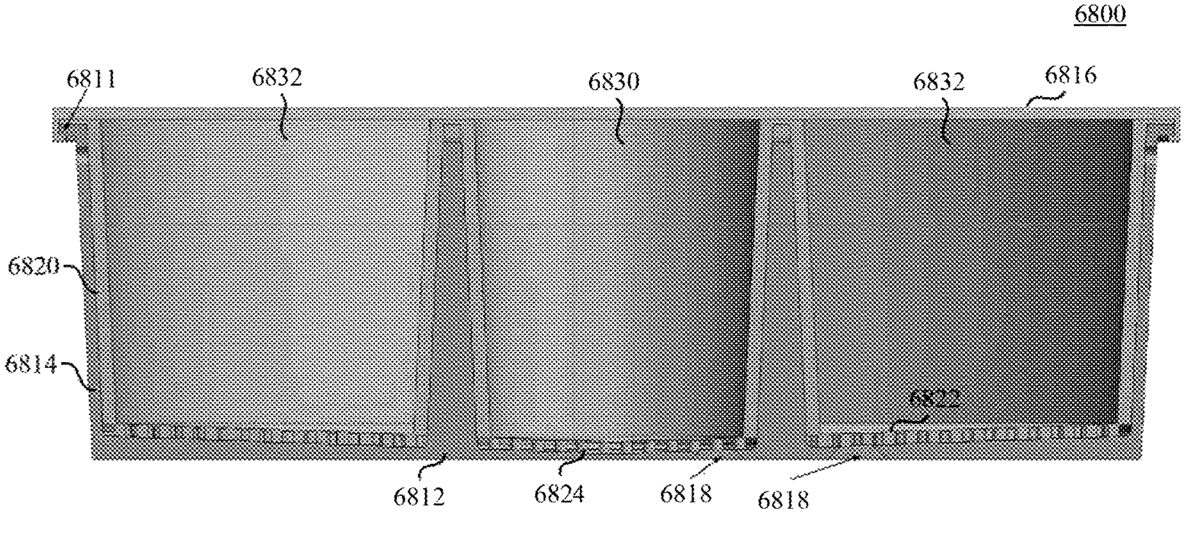
FIG. 68B is a cross-sectional side view of an illustrative variation of a bioreactor.

FIGS. 68A and 68B are cross-sectional perspective views of a bioreactor 6800 comprising an enclosure 6810 comprising a base 6812, a sidewall 6814, and a top 6816. A gas-permeable membrane 6820 may be coupled to one or more of the base 6812 and the sidewall 6814 of the enclosure 6810. In some variations, the enclosure 6810 may comprise a first chamber 6830 having a first volume and a second chamber 6832 having a second volume, the first chamber 6830 separated from the second chamber 6832, and the first volume smaller than the second volume. In some variations, the first chamber 6830 may be concentrically nested within the second chamber 6832. For example, nesting the chambers may enable larger overall working volume ranges (e.g., 100:1). The first chamber 6830 may comprise a well shape with an angled base surface to promote fluid pooling at a center of the first chamber 6830 during aspiration. In some variations, the base 6812 may be disposed on a thermal regulator (not shown) such as a thermoelectric element. In some variations, the enclosure 6810 may be composed of a thermally conductive material such as a metal (e.g., aluminum).

In some variations, the bioreactor 6800 may be coupled to a gas regulator (not shown) to facilitate gas transfer through the gas-permeable membrane 6820 (e.g., into and out of the culture). The gas-permeable membrane 6820 may be configured to hold a cell culture. Gas may diffuse through the surfaces of the culture that contact the gas-permeable membrane to enable increased oxygenation of the cell culture and removal of gaseous metabolic byproducts of the cell culture, and thus increase the potential for metabolic activity. For example, the gas-permeable membrane 6820 enables dissolved oxygen to diffuse into the culture in close proximity to a cell bed where the oxygen may be consumed. In some variations, the bioreactor may be coupled to both a first gas regulator to facilitate gas transfer through the gas-permeable membrane and a second gas regulator to facilitate control of headspace gas composition.

In addition to gas transfer, the bioreactors described herein may be configured to efficiently control a temperature of a cell culture using a conductive thermal interface (e.g., gas-permeable membrane 6820, enclosure 6810) along both a base and sidewall of the bioreactor.

In some variations, the first chamber 6830 may comprise a working volume of between about 10 ml and about 100 ml. In some variations, the first chamber 6830 may comprise a total volume of between about 10 ml and about 130 ml. In some variations, the second chamber 6832 may comprise a working volume of between about 100 ml and about 1000 ml. In some variations, the second chamber 6832 may comprise a total volume of between about 100 ml and about 1400 ml. In some variations, the first chamber 6830 may comprise a diameter of between about 10 mm and about 100 mm, and a height of between about 10 mm and about 100 mm. In some variations, the second chamber 6832 may comprise a diameter of between about 100 mm and about 250 mm, and a height of between about 10 mm and about 100 mm.

Figure 69A:
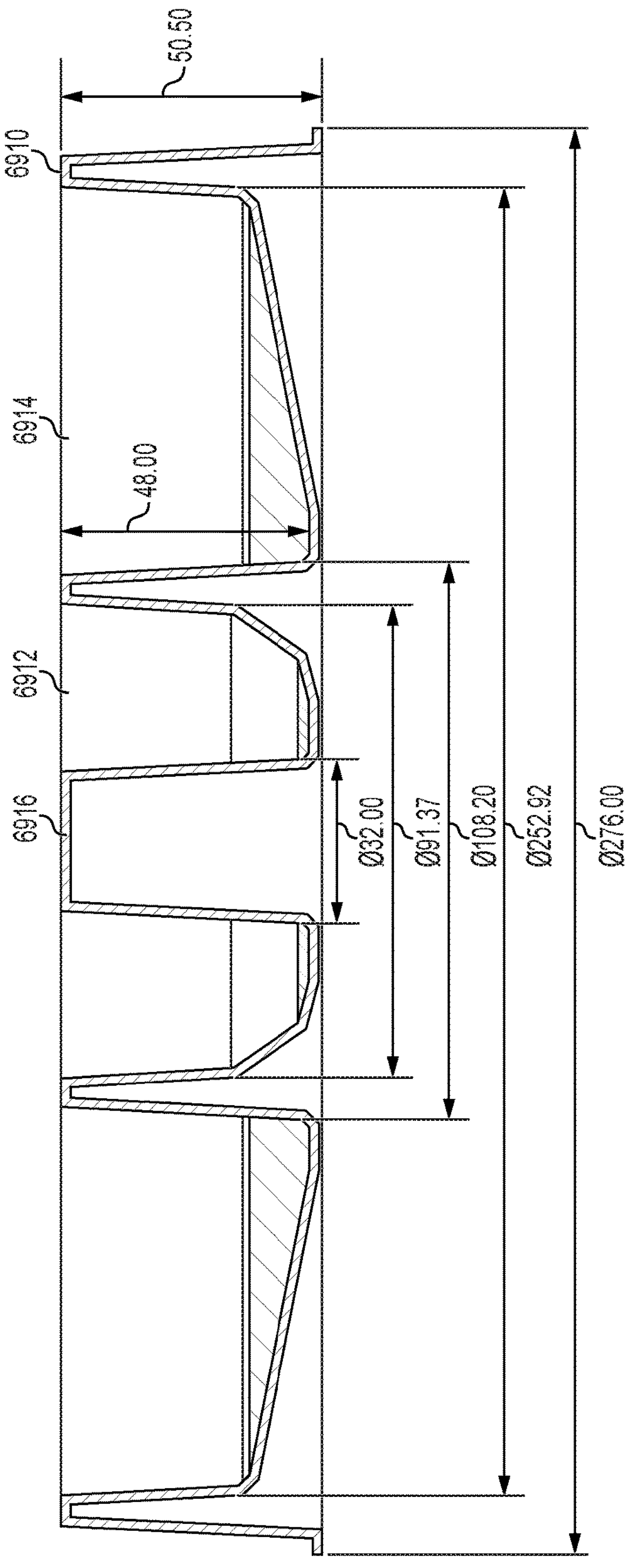
FIG. 69A is a cross-sectional side view of an illustrative variation of an enclosure of a bioreactor.
Figure 69B:
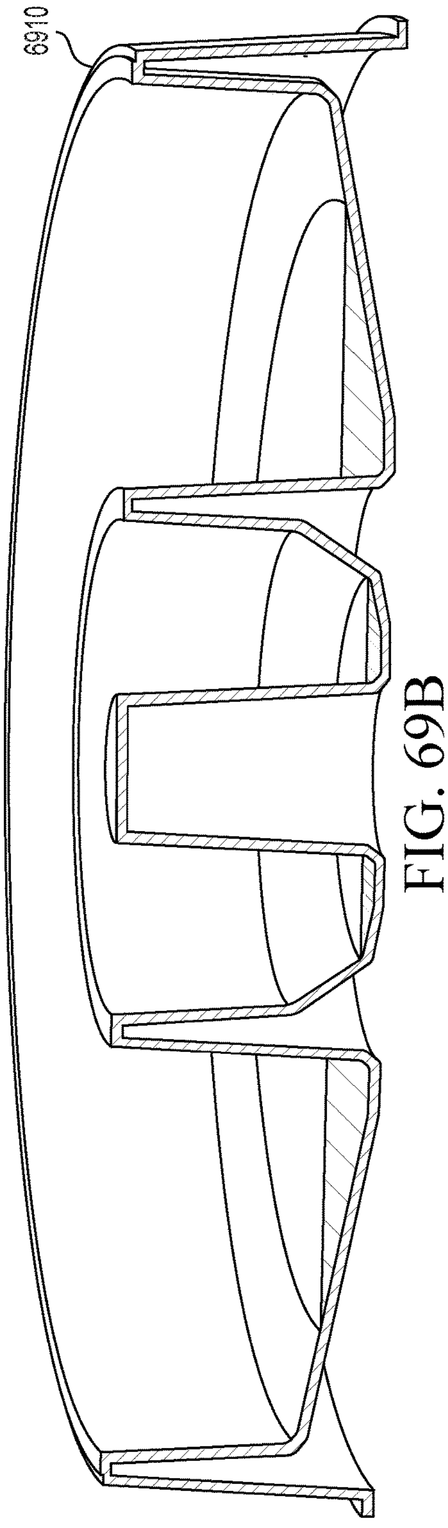
FIG. 69B is a cross-sectional perspective view of an illustrative variation of an enclosure of a bioreactor.

As shown in FIG. 68B, a base 6822 of the gas-permeable membrane 6820 may comprise an angle between about 3 degrees and about 10 degrees relative to the base 6812 of the enclosure 6810. Similarly, FIGS. 69A and 69B depict a sloped base. For example, due to a slope of the base 6822, the chambers 6830, 6832 are deeper towards a center of the bioreactor 6800. This may encourage cell growth towards a center of the bioreactor 6800, which may aid one or more of cell sampling, cell transfer, cell recovery, and the like. In some variations, orbital motion of the bioreactor 6800 may promote cell congregation toward a center of the bioreactor 6800, thereby increasing interaction between the cells.

In some variations, the gas-permeable membrane 680 may comprise a curved surface. In some variations, the gas-permeable membrane may comprise a set of patterned curved surfaces. For example, the set of patterned curved surfaces may comprise a radius of curvature of between about 50 mm and about 500 mm.

Figure 68C:
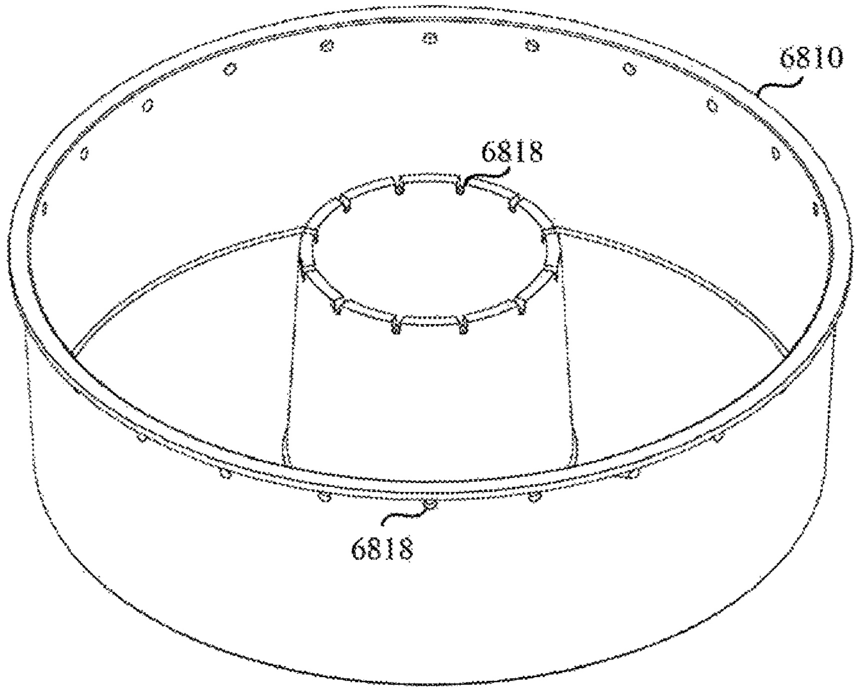
FIG. 68C is a perspective view of an illustrative variation of an enclosure of a bioreactor.
Figure 68D:
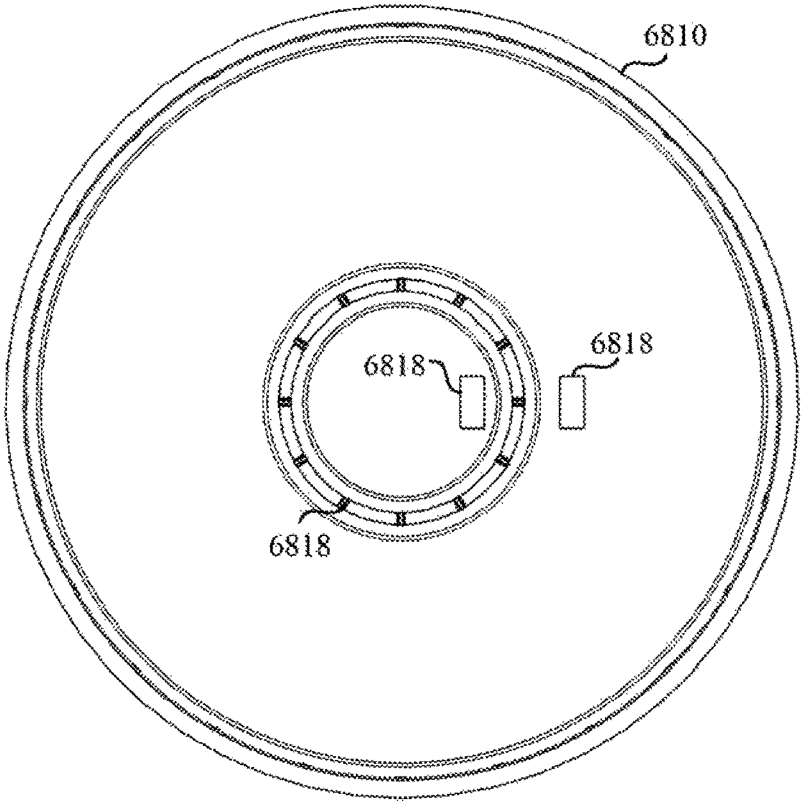
FIG. 68D is a plan view of an illustrative variation of an enclosure of a bioreactor.

In some variations, the bioreactor may be configured to facilitate monitoring (e.g., temperature, pH, dissolved oxygen) and fluid flow (e.g., gas composition, fluid transfer) between the chambers. As shown in FIG. 68C, the enclosure 6810 may comprise one or more nested surfaces curved around a longitudinal axis (e.g., center) of the enclosure 6810. For example, the nested surfaces may comprise a set of concentric toroids. The enclosure 6810 may comprise a toroid shape. FIG. 68C is a perspective view and FIG. 68D is a bottom view of enclosure 6810 comprising a set of apertures 6818 (e.g., holes, openings, slits, slots). In some variations, the apertures 6818 may enable gas and/or heat transfer between the components and chambers of the bioreactor 6800. Additionally or alternatively, one or more sensors may be coupled to the apertures 6818. For example, the apertures 6818 may be coupled to a non-contact sensor (e.g., pH, DO) such as an optical sensor (not shown) configured to determine a fluorescent spot disposed on a surface of the bioreactor. In some variations, one or more of a sensor and fluid connector may be introduced through the apertures 6818.

Figure 68E:
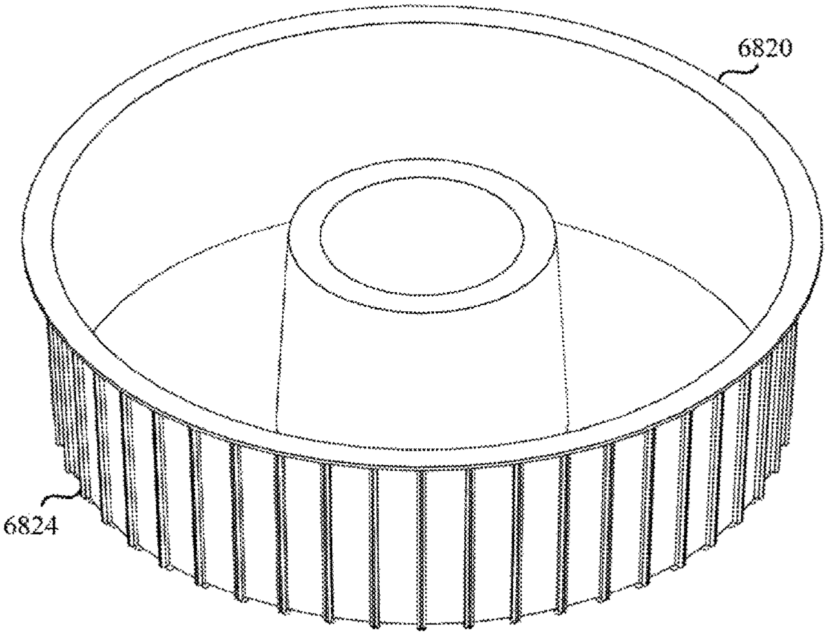
FIG. 68E is a perspective view of an illustrative variation of a membrane of a bioreactor.
Figure 68F:
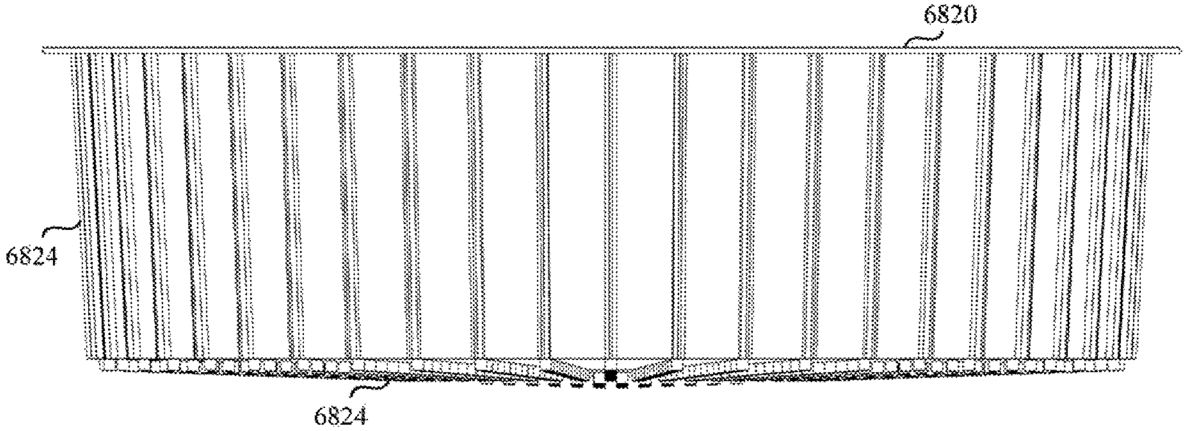
FIG. 68F is a side view of an illustrative variation of a membrane of a bioreactor.
Figure 68G:
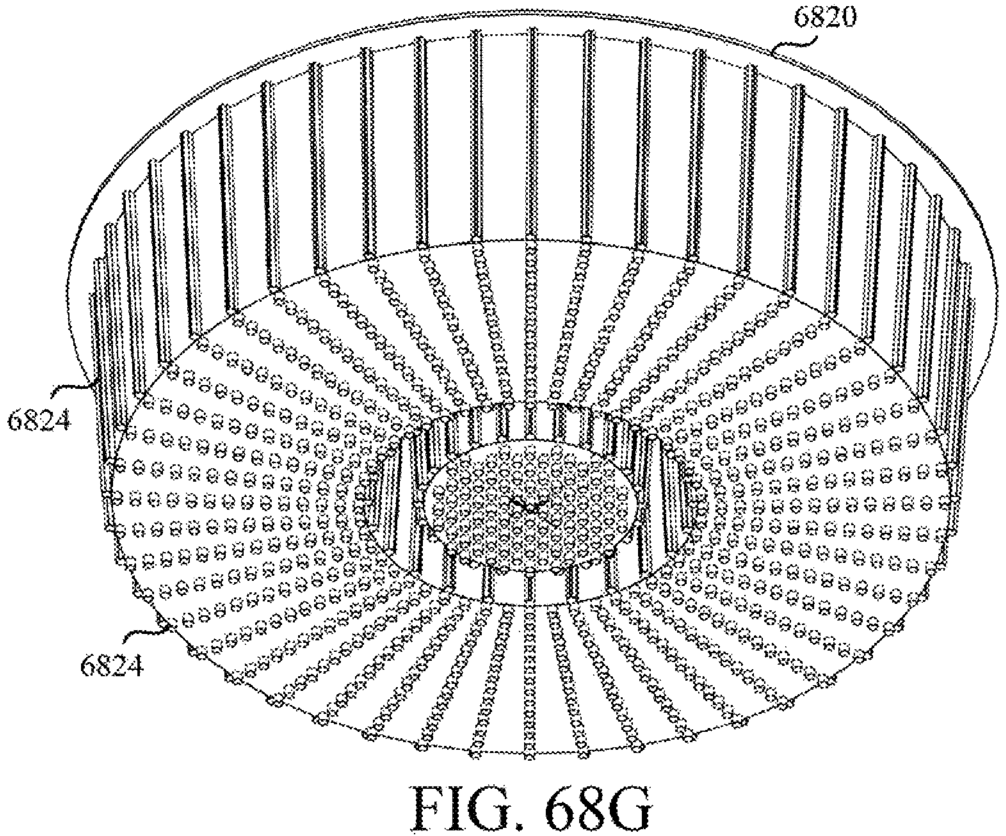
FIG. 68G is a perspective view of an illustrative variation of a membrane of a bioreactor.
Figure 68H:
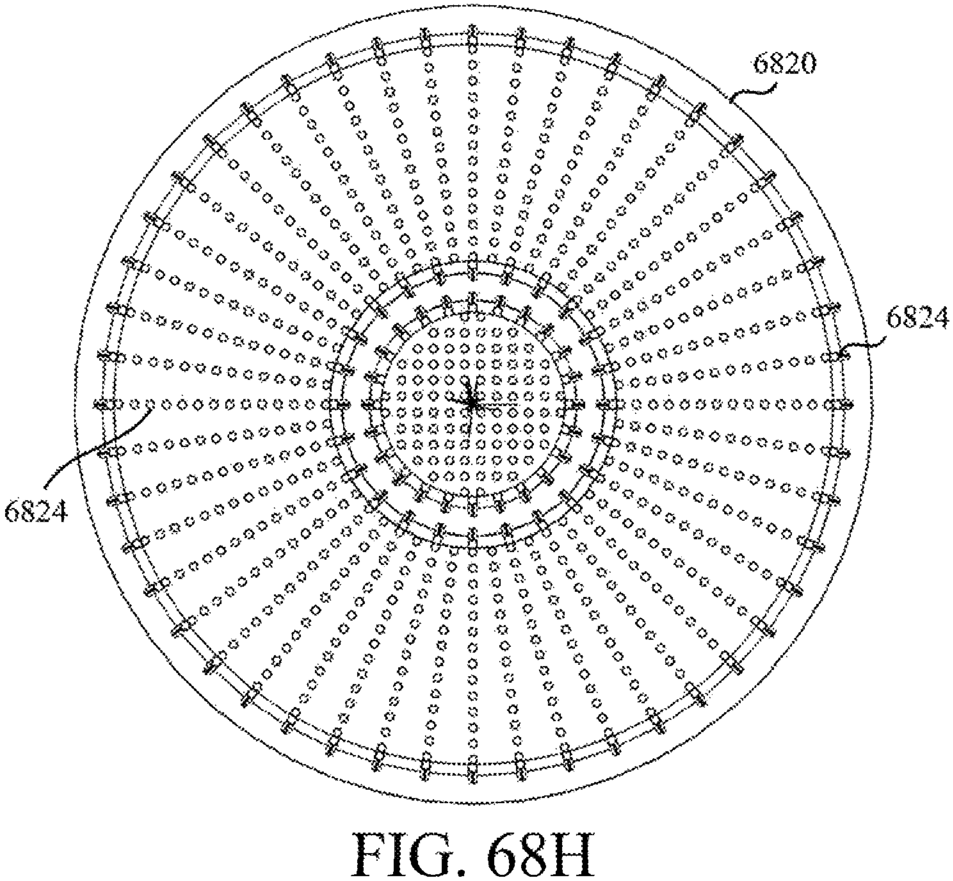
FIG. 68H is a bottom view of an illustrative variation of a membrane of a bioreactor.

In some variations, the gas-permeable membrane extends along the base 6812 and the sidewall 6814 of the enclosure 6810, as shown in FIG. 68B. In some variations, the gas-permeable membrane extends only along the base 6812 of the enclosure 6810. FIG. 68E is a perspective view and FIG. 68F is a side view of the gas-permeable membrane 6820 where an outer surface of the gas-permeable membrane 6820 comprises one or more projections 6824 (e.g., projections, spacers, ribs). The projections 6824 are also depicted in the perspective view of FIG. 68G and bottom view of FIG. 68H. The projections 6824 contact the enclosure 6810 and define a cavity between the enclosure 6810 and the gas-permeable membrane 6820. That is, the projections 6824 may be configured to mechanically space away the enclosure 6810 from a portion of the gas-permeable membrane 6820 to facilitate thermal transfer from the enclosure 6810 to the cell culture. In some variations the gas-permeable membrane may comprise polydimethylsiloxane (PDMS) (e.g., silicone), fluorinated ethylene propylene (FEP), polyolefin (PO), polystyrene (PS), ethyl vinyl acetate (EVA) and have a thickness of between about 0.1 mm and about 0.4 mm, between about 0.2 mm and about 0.3 mm, and about 0.25 mm, including all ranges and sub-values in-between.

FIG. 69A is a cross-sectional side view of an enclosure 6910 of a bioreactor comprising a first chamber 6912, a second chamber 6914, and a column 6916 extending along a longitudinal axis of the enclosure 6910. FIG. 69B is a cross-sectional perspective view of the enclosure 6910 showing the nested curves of the enclosure 6910. The column 6916 may be configured to promote cell culture in combination with agitation such as orbital motion.

Figure 70:
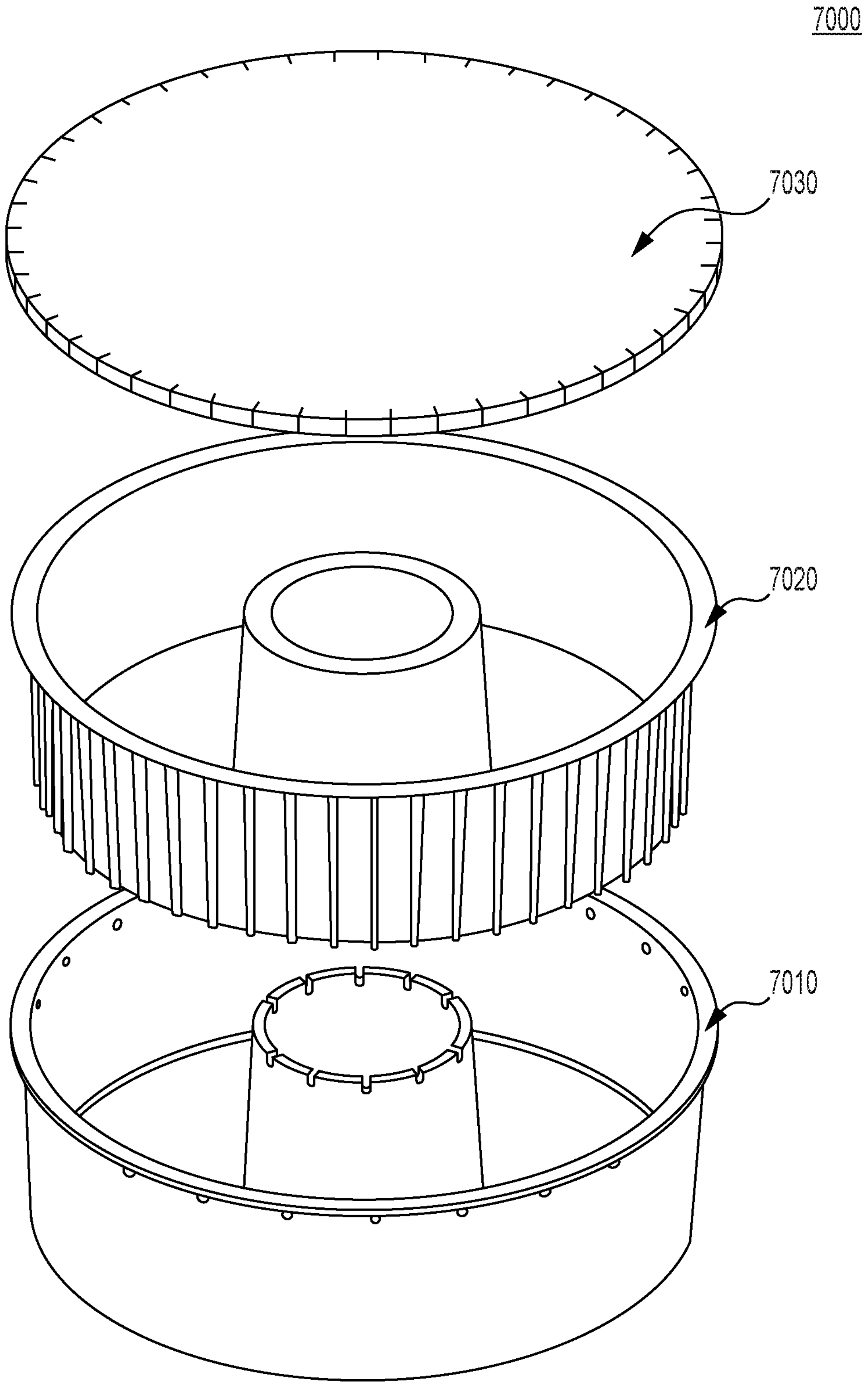
FIG. 70 is an exploded perspective view of an illustrative variation of a bioreactor.

FIG. 70 is an exploded perspective view of a bioreactor 7000 comprising an enclosure 7010, a gas-permeable membrane 7020, and a top 7030. The top 7030 may be composed of a material such as polyethylene.

Figure 71A:
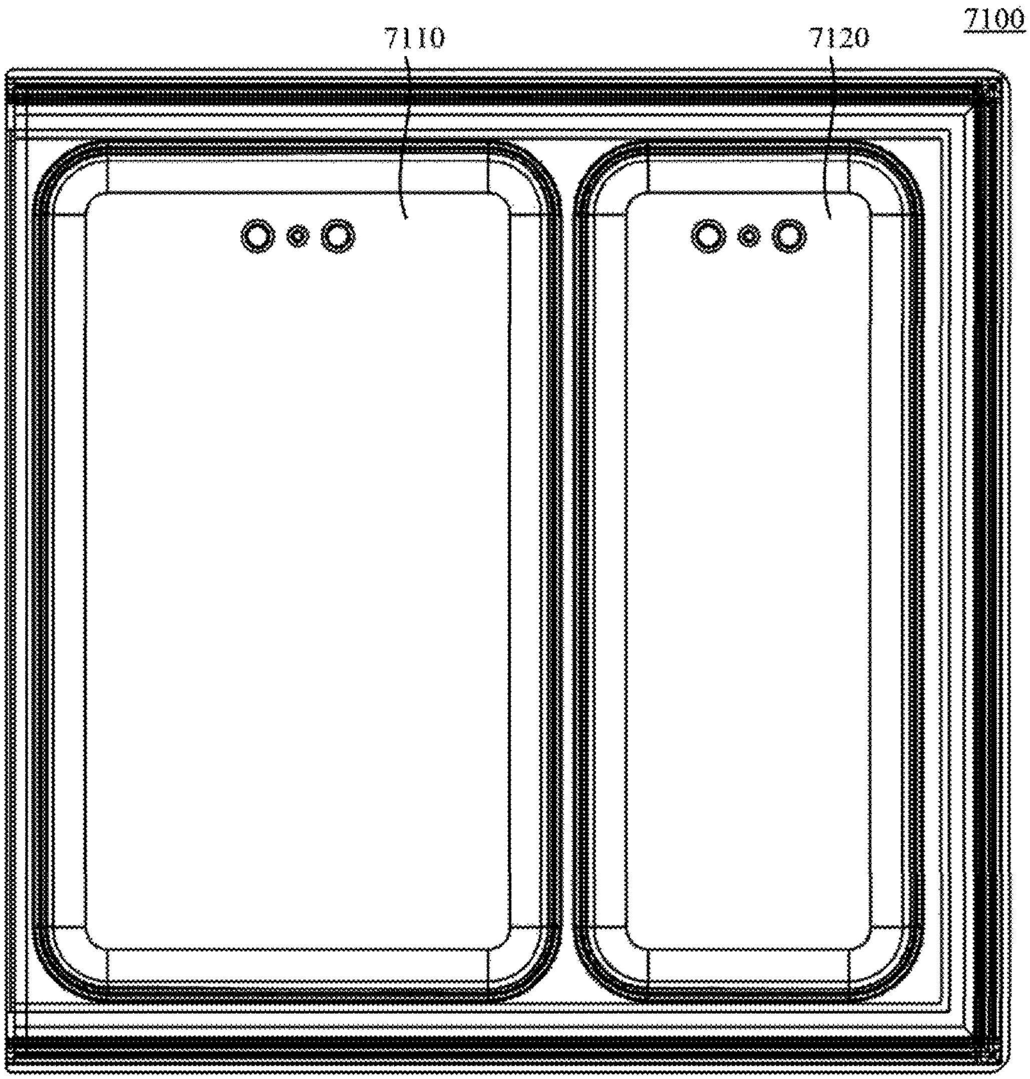
FIG. 71A is a plan view of an illustrative variation of a bioreactor.
Figure 71B:
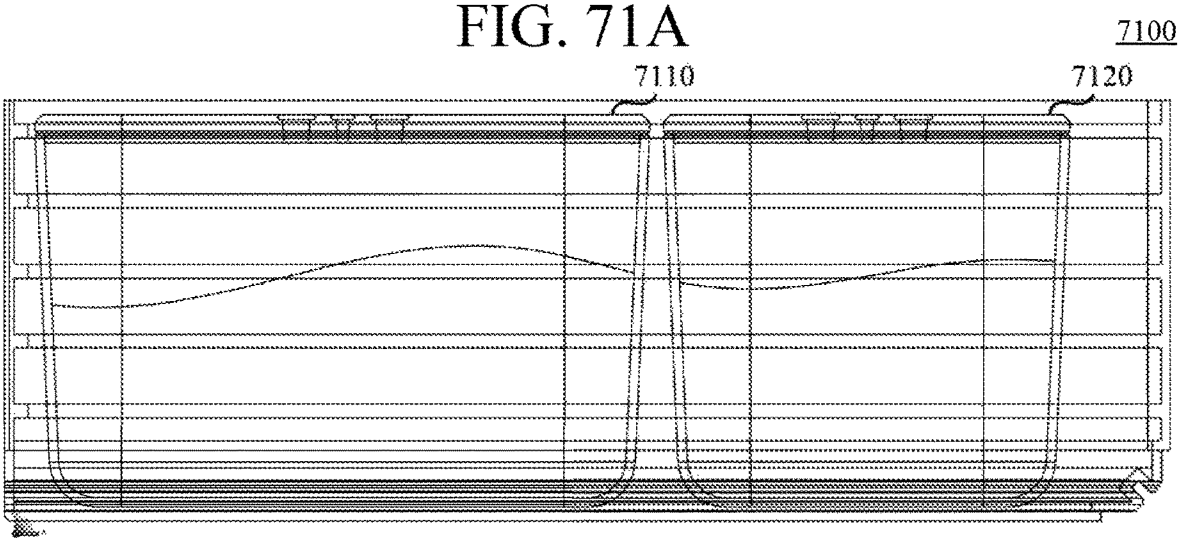
FIG. 71B is a cross-sectional side view of an illustrative variation of a bioreactor.

FIG. 71A is a plan view of a bioreactor 7100 comprising a first chamber 7110 and a second chamber 7120. FIG. 71B is a cross-sectional side view of the bioreactor 7100.

Figure 13A:
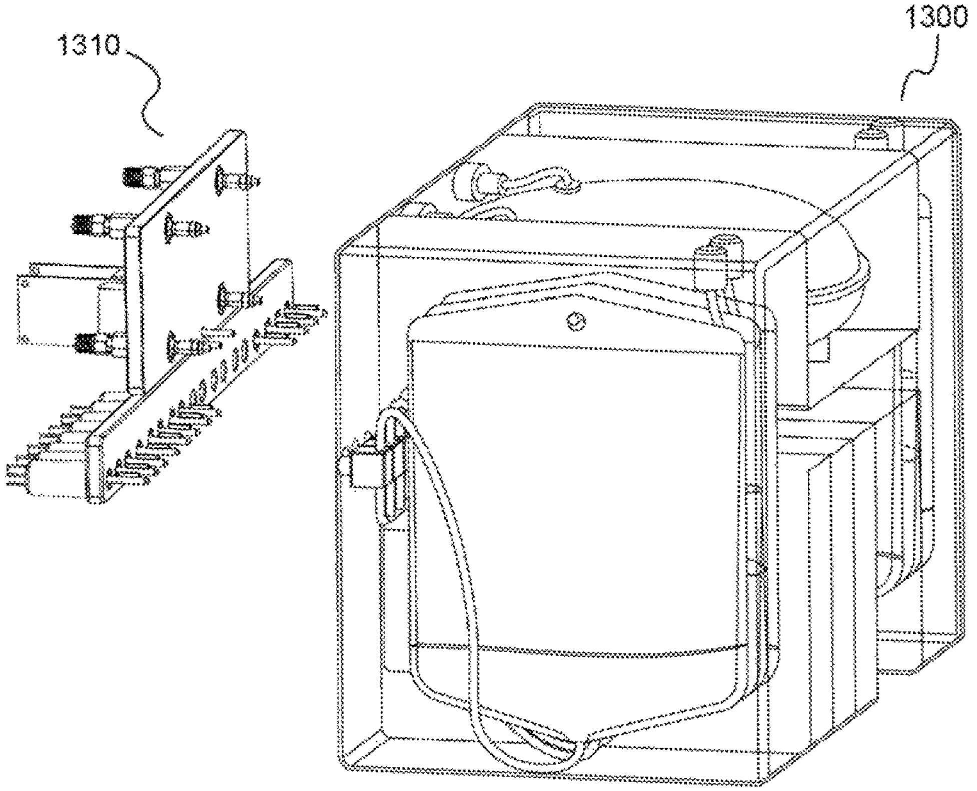
FIG. 13A is a perspective view of an illustrative variation of a cartridge and a bioreactor instrument.
Figure 13B:
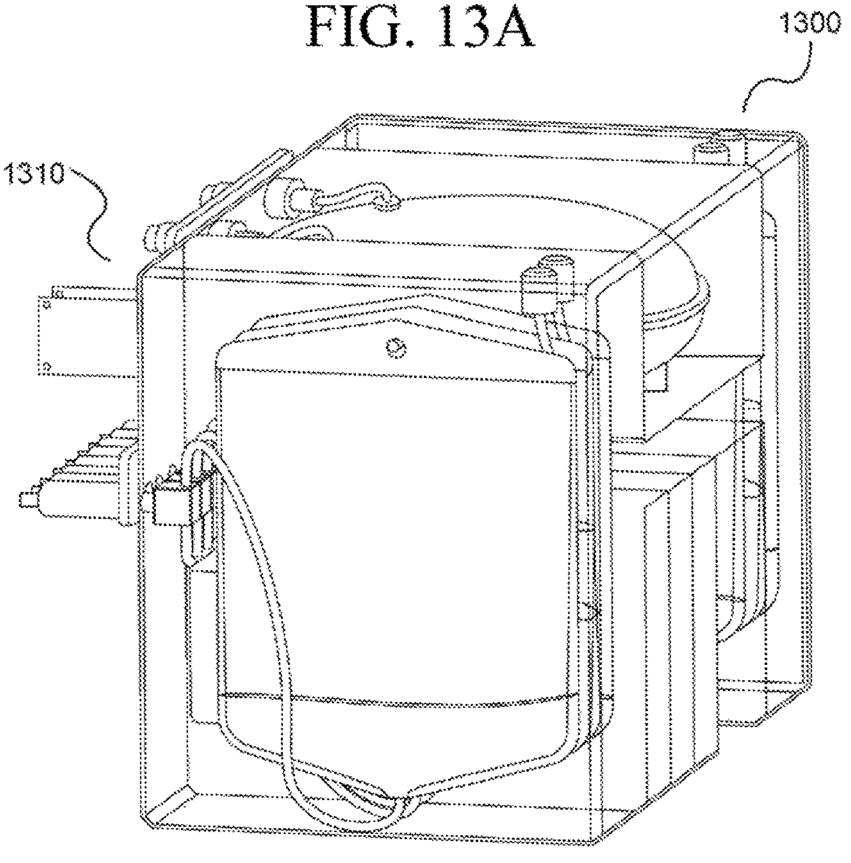
FIG. 13B is a perspective view of an illustrative variation of a cartridge coupled to a bioreactor instrument.

FIGS. 13A and 13B are perspective views of a cartridge 1300 and bioreactor instrument interface 1310. The bioreactor instrument interface 1310 is coupled to the cartridge 1300 in FIG. 13B.

Figure 14:
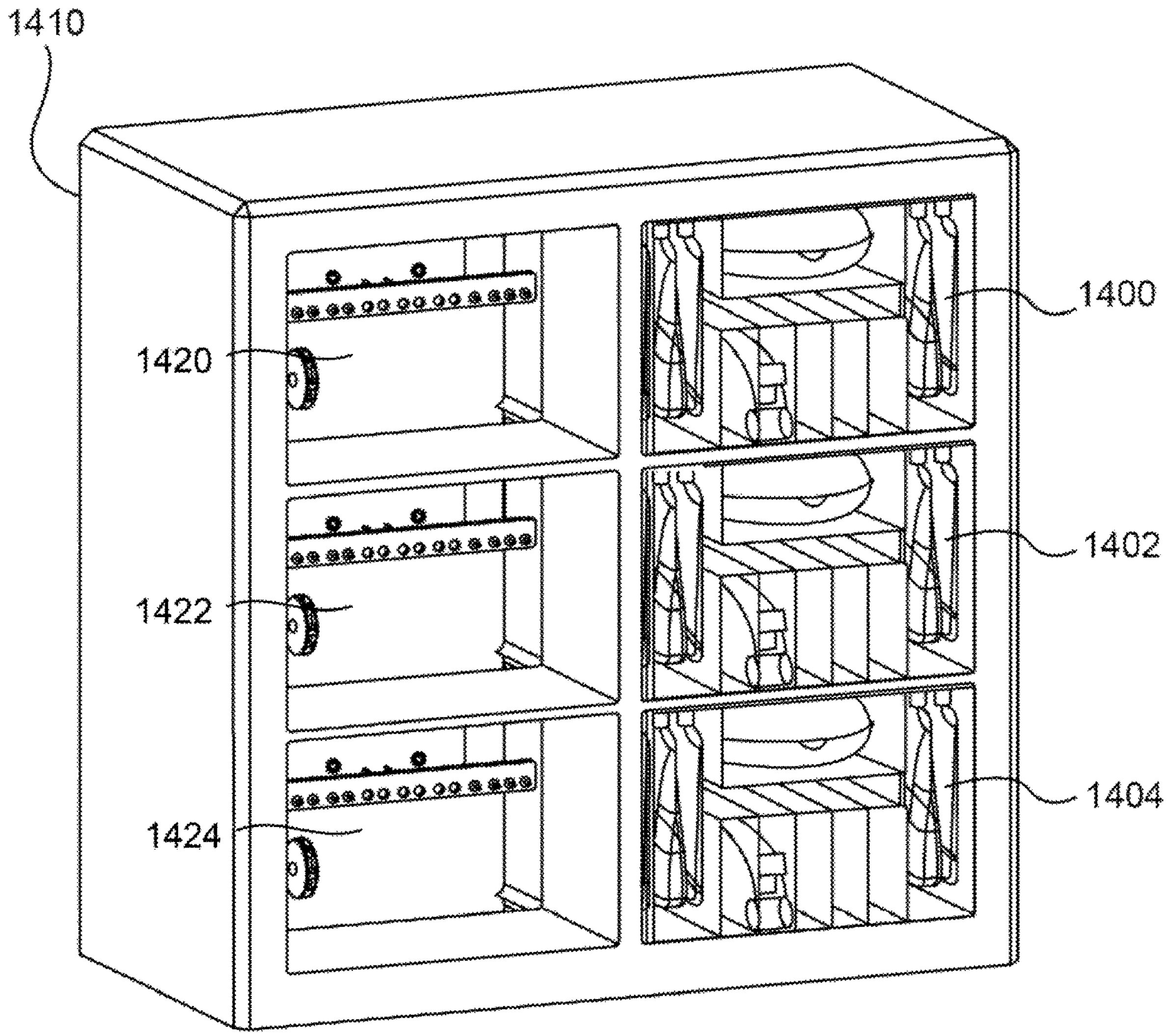
FIG. 14 is a perspective view of an illustrative variation of a bioreactor instrument comprising a set of cartridges and cavities configured to receive cartridges.

FIG. 14 is a perspective view of a bioreactor instrument 1410 comprising a set of cartridges 1400, 1402, 1404 and cavities 1420, 1422, 1424 configured to receive a respective cartridge. In some variations, each cartridge may be docked to enable simultaneous expansion, culturing, or resting steps.

Electroporation Module

In some variations, an electroporation module may be configured to facilitate intracellular delivery of macromolecules (i.e., transfection by electroporation). An electroporation module may contain a continuous flow or batch mode chamber and one or more sets of electrodes for applying direct or alternating current to the chamber. An electrical discharge from one or more capacitors, or current sources, may generate sufficient current in the chamber to promote transfer of a polynucleotide, protein, nucleoprotein complex, or other macromolecule into the cells in the cell product. As with other modules described herein, one or more components used for the process step (here, electroporation) may be provided on the cartridge or in the instrument to which the cartridge interfaces. For example, the capacitor(s) and/or batteries may be provided in the module on the cartridge or in the instrument. The electroporation module may, in some variations, be configured to apply an electric field to a cell suspension under continuous flow in a microfluidic device, e.g., as described in Garcia et al. Sci. Rep. 6:21238 (2016).

Additionally or alternatively, intracellular delivery of macromolecules may also be achieved by other methods, such as mechanoporation. It should be understood that throughout the disclosure variations comprising an electroporation module may instead or in addition comprise a mechanoporation module, or another module configured to perform any suitable method of delivering macromolecules into cells. Mechanoporation can be achieved by, for example, applying transient, fluidic pressure to a solution containing cells, or by applying physical pressure to the cells (e.g., by microneedles). Illustrative methods of mechanoporation by passing a cell suspension through a constriction are provided, e.g., in International Patent Publication No. WO 2017/041051 and WO 2017/123663, and are incorporated by reference herein. Mechanoporation can also be achieved by applying a vortex to a cell suspension in a microfluidic device.

Figure 72:
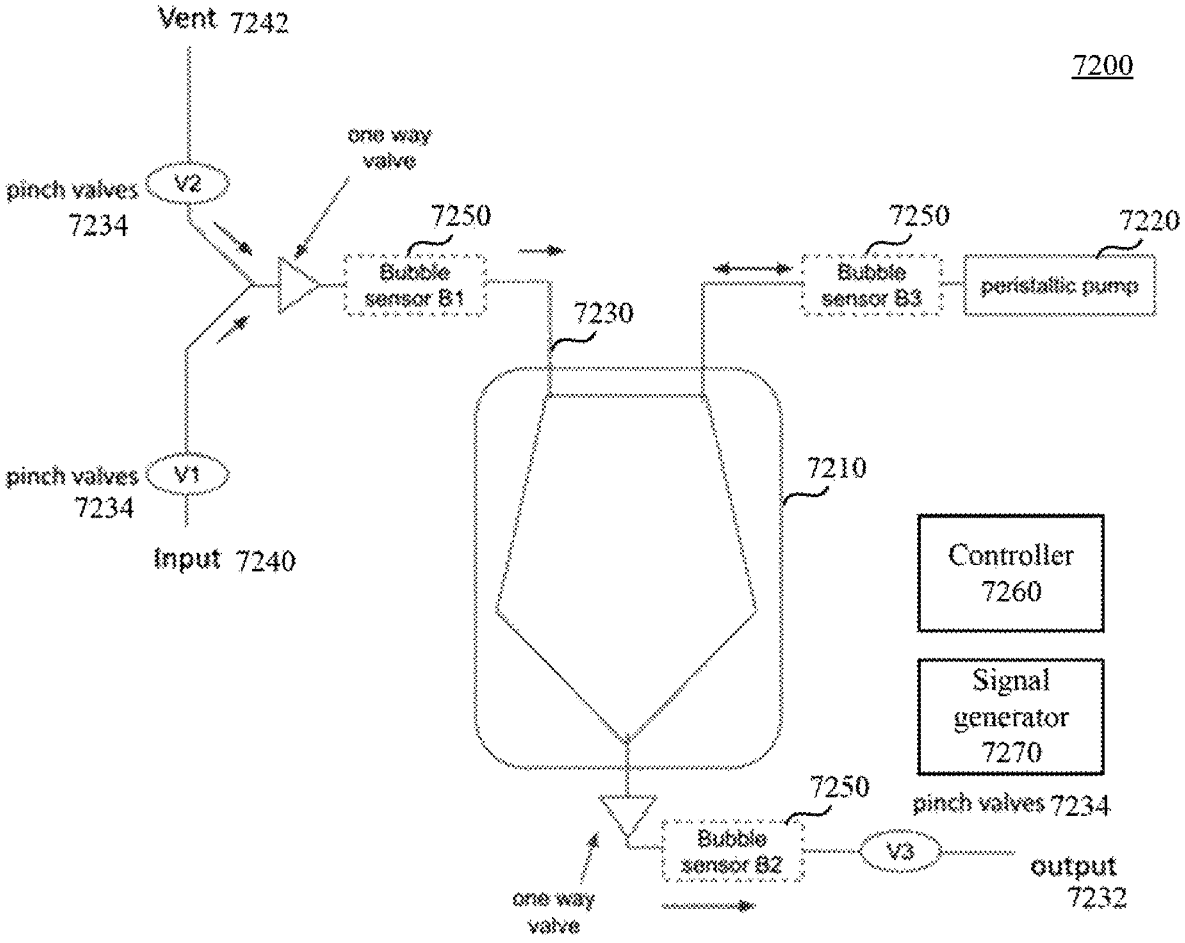
FIG. 72 is a schematic diagram of an illustrative variation of an electroporation system.

FIG. 72 is a schematic diagram of an electroporation module 7200 (e.g., electroporation system) comprising an electroporation chamber 7210 (which may comprise a fluid conduit), a pump 7220, an inlet 7230, an outlet 7232, a set of pinch valves 7234, a first fluid source 7240 (e.g., fluid reservoir, cell reservoir), a second fluid source 7242 (e.g., vent, gas source), a set of sensors 7250 (e.g., bubble sensors), and a controller (e.g., processor and memory) configured to control the module 7200, and a signal generator 7270 configured to deliver an electroporation signal (e.g., voltage pulse) to the electroporation chamber 7210.

In some variations, the fluid conduit 7210 may be configured to receive a first fluid comprising cells and a second fluid. A set of electrodes may be coupled to the fluid conduit 7210. A pump may be coupled to the fluid conduit 7210. The controller 7260 may be configured to generate a first signal to introduce the first fluid into the fluid conduit 7210 using the pump 7220, generate a second signal to introduce the second fluid into the fluid conduit 7210 such that the second fluid separates the first fluid from a third fluid, and generate an electroporation signal to electroporate the cells in the fluid conduit 7210 using the set of electrodes.

In some variations, the second fluid may comprise a gas or oil. In some variations, the controller may be configured to generate a third signal to introduce the third fluid into the fluid conduit 7210. The third fluid may be separated from the first fluid by the second fluid. In some variations, a cartridge for cell processing may comprise a liquid transfer bus and a plurality of modules such as the electroporation module 7200. Each module may be fluidically linked to the liquid transfer bus.

The set of sensors 7250 may be configured to measure fluid changes in a fluid conduit such as a change from a first fluid to a second fluid (e.g., liquid to air) in the fluid conduit. The module 7200 may further comprise a set of valves configured to ensure fluid does not backflow into the electroporation chamber 7210 and/or fluid source 7240. The electroporation chamber 7210 may comprise a cavity configured to hold a fluid to be electroporated and a set of electrodes to apply an electroporation signal to the fluid. For example, the signal generator 7270 may generate a square valve pulse as described in more detail herein.

In some variations, the electroporation module 7200 (e.g., valves 7234, pump 7220, sensors 7250, and controller 7260) may be configured to control fluid flow through the electroporation chamber 7210 in a discontinuous (e.g., batch process) manner. For example, a first batch of cells may undergo electroporation and be physically separated from a second batch of cells by an intermediate fluid such as air or fluid such as oil. Separating cell batches may reduce mixing of transfected and non-transfected cells, and further ensure fixed batch volume. That is, a fluid gap may form a visually verifiable boundary between cell batches to reduce diffusion and mixing between electroporated and non-electroporated cells. Separating cell batches may reduce the duration of time that cells are exposed to certain cytotoxic reagents (e.g., electroporation buffer), thereby increasing performance.

In some variations, a batch of cells may be electroporated when substantially static (e.g., substantially no fluid flow state). By contrast, conventional continuous flow electroporation has an upper fluid flow rate limit correlated to a transfection efficiency. In the batch processing described herein, cell batches may be transferred into and out of the electroporation chamber 7210 at a predetermined rate to increase the overall throughput of the system 7200 without a decrease in electroporation efficiency. Furthermore, the electroporation system 7200 does not utilize a precisely controlled flow rate/pulse rate such as those needed for continuous flow electroporation systems.

Figure 73:
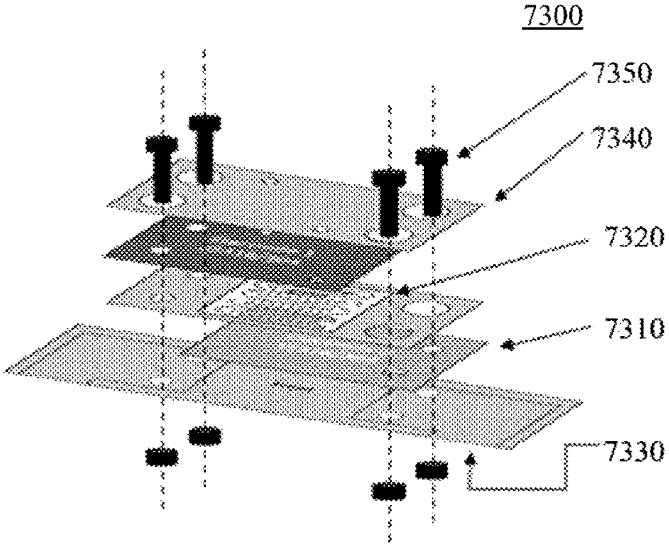
FIG. 73 is an exploded perspective view of an illustrative variation of an electroporation module.

FIG. 73 is an exploded perspective view of an electroporation module 7300 may comprise ah electrode 7310, a fluid conduit 7320 (e.g., electroporation chamber), a substrate 7330 (e.g. alloy busbar), a housing 7340, and a fastener 7350. In some variations, the fluid conduit 7320 may be configured to hold a volume of fluid between about 0.4 ml and about 3.5 ml. The electroporation module 7300 is a parallel-plate design. In some variations, the electrodes may comprise stainless steel and may be separated by an insulating gasket. In some variations, the electrodes may be polished and/or coated with nonreactive materials (e.g., gold, platinum) to reduce gradual buildup of biological matter (e.g., charged molecules, DNA, proteins) on the electrode surface.

Generally, a method of electroporating cells may comprise receiving a first fluid comprising cells in a fluid conduit, receiving a second fluid in the fluid conduit to separate the first fluid from a third fluid, applying an electroporation signal to the first fluid to electroporate the cells. In some variations, the third fluid may be received in the fluid conduit separated from the first fluid by the second fluid. In some variations, the first fluid may be substantially static when applying the electroporation signal.

Figure 74A:
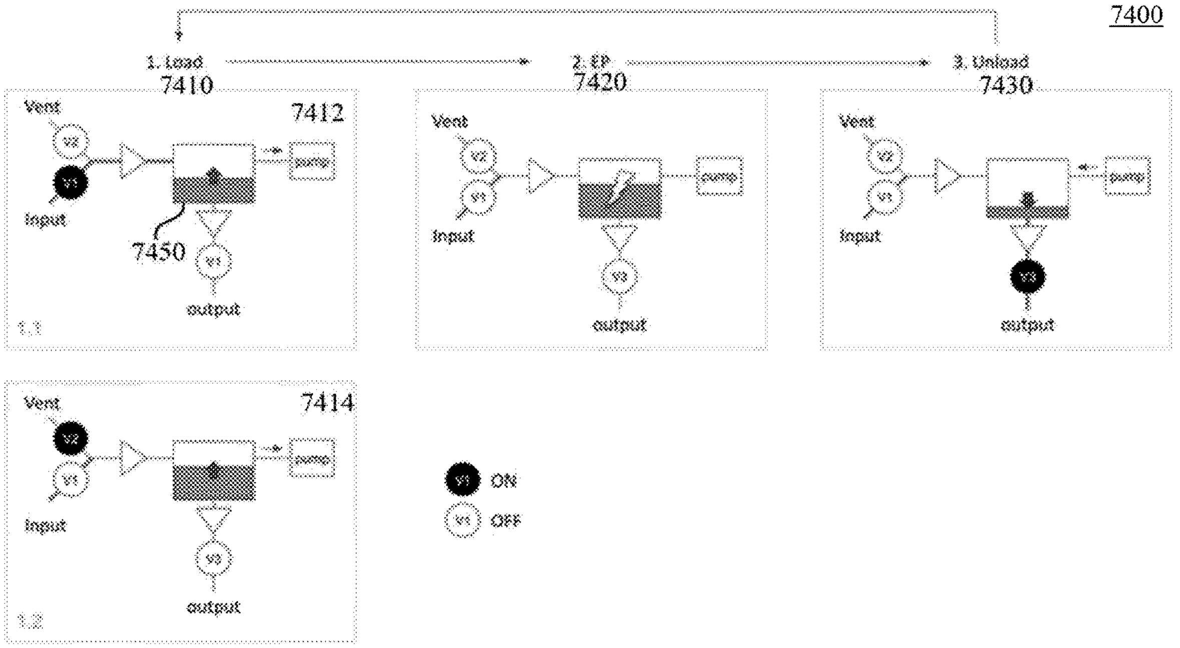
FIGS. 74A-74B are schematic diagrams of illustrative variation of an electroporation process.
Figure 74B:
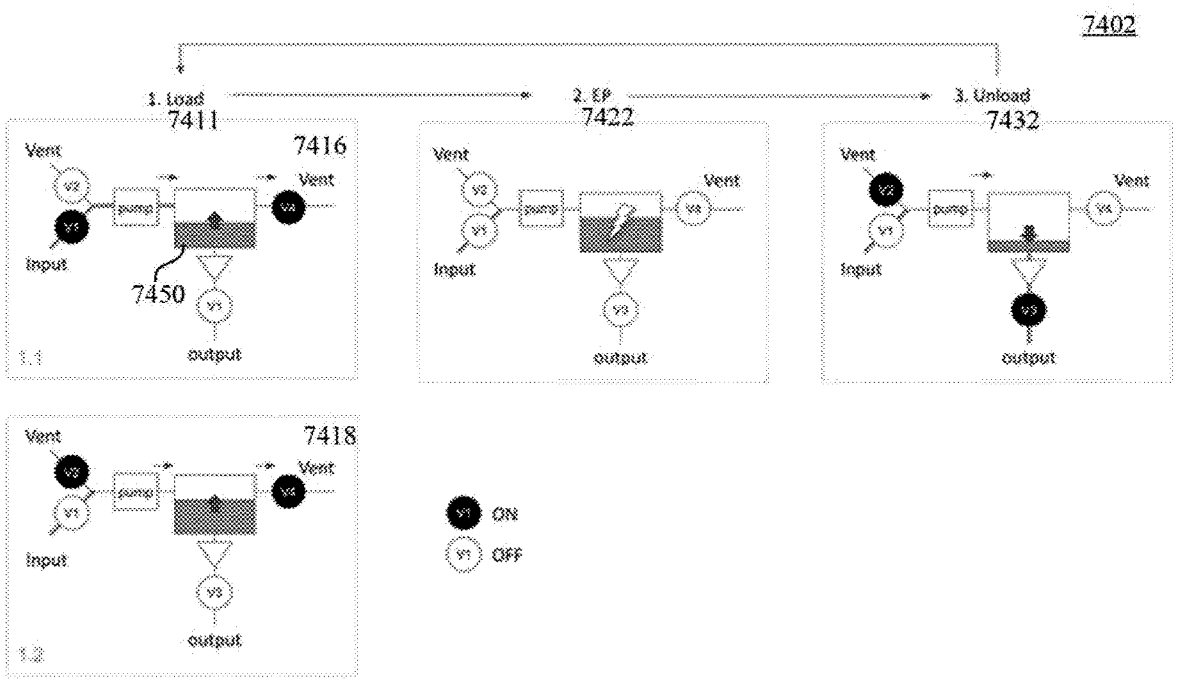

FIGS. 74A-74B are schematic diagrams of variations of an electroporation process 7400, 7402. A method 7400 may include loading cells 7410 into an electroporation chamber 7450. For example, at step 7412, a first fluid may be pumped into the electroporation by opening valve v1 and the pump generating negative pressure (valves v2 and v3 are closed). At step 7414, a second fluid (e.g., gas, oil) may separate the first fluid from a third fluid to create a first batch of cells to electroporate. For example, valves v1 and v3 may be closed with valve v2 open and the pump generating negative pressure. In some variations, a loading volume may be between about 1 ml and about 3 ml with a pumping time of between about 8 seconds and about 15 seconds (at a rate of about 20 ml/min). At step 7420, the cells of the first fluid may be electroporated with each of the valves closed and the pump off. At step 7430, the cells of the first fluid may be flowed out of the electroporation chamber 7450 to output where valves v1 and v2 are closed, valve v3 is open, and the pump generates positive pressure.

FIG. 74B depicts another configuration where a pump is disposed between an input and the electroporation chamber such that the pump may be configured to pump in a single direction. A method 7402 may include loading cells 7411 into an electroporation chamber 7450. For example, at step 7416, a first fluid may be pumped into the electroporation by opening valve v1 and v4, and the pump generating positive pressure (valves v2 and v3 are closed). At step 7418, a second fluid (e.g., gas, oil) may separate the first fluid from a third fluid to create a first batch of cells to electroporate. For example, valves v1 and v3 may be closed with valves v2 and v4 open, and the pump generating positive pressure. At step 7422, the cells of the first fluid may be electroporated with each of the valves closed and the pump off. At step 7432, the cells of the first fluid may be flowed out of the electroporation chamber 7450 to output where valves v1 and v4 are closed, valves v2 and v3 are open, and the pump generates positive pressure.

In some variations, an impedance/resistance across electrodes of an electroporation system may increase over time due to electrode passivation/degradation due to charged biological matter (e.g., charged molecules, DNA, proteins) attaching to the electrode surface. Active electrical field compensation may be applied to ensure a consistent electrical field strength applied to cells over multiple batches of cells. This may reduce the need for electrode surface modification to reduce passivation.

Figure 75:
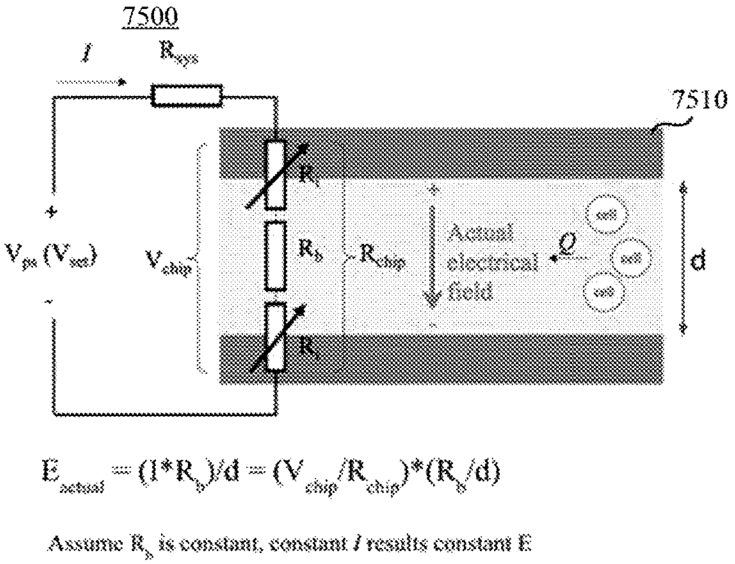
FIG. 75 is a circuit diagram of an illustrative variation of an electroporation process.

FIG. 75 is a circuit diagram of a resistor divider network for an electroporation process 7500. For example, a set of cells may be introduced into an electroporation chamber 7510 to which a voltage $V_{chip}$ may be applied. Fluid resistance $R_b$ corresponds to a fluid (e.g., cell mixture) resistance. Assuming a uniform cell distribution, the fluid resistance $R_b$ should be consistent, also assuming the same volume of each fluid batch being electroporated. $R_i$ corresponds to a resistance between fluid and electrode, which increases over time through the electroporation process. In a conventional electroporation process, voltage $V_{ps}$ is constant. However, due to the increasing $R_i$ over time, the voltage applied to the fluid will decrease over time, leading to lower electrical field strength.

Due to variations in fluid resistance $R_b$ and the low number of pulses that may be applied, interpolation to compensate for reduced electrical field strength may not accurately compensate for electrode passivation.

In some variations, a method of electroporating cells may comprise receiving a first fluid comprising cells in a fluid conduit, applying a resistance measurement signal to the first fluid using a set of electrodes, measuring a resistance between the first fluid and the set of electrodes, and applying an electroporation signal to the first fluid based on the measured resistance. In some variations, a second fluid comprising a gas may be received in the fluid conduit before applying the electroporation signal to the fluid. The first fluid may be separated from a third fluid by the second fluid.

Figure 76A:
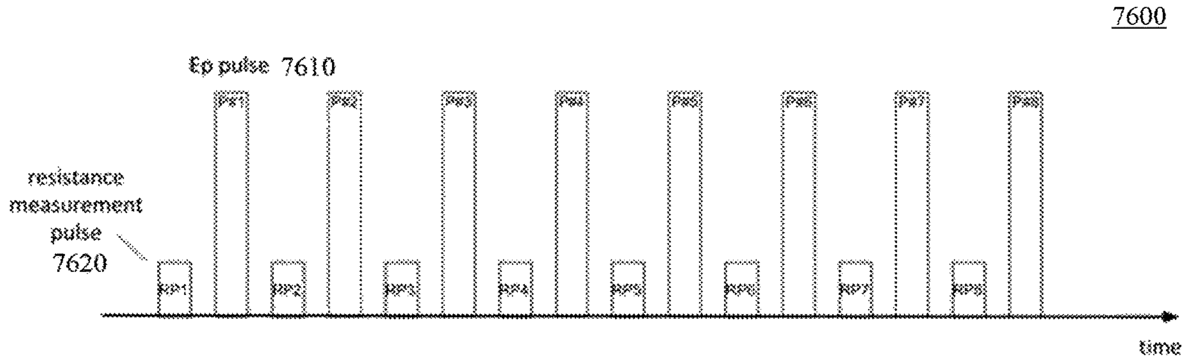
FIGS. 76A-76D are plots of illustrative variations of an electroporation process.
Figure 76B:
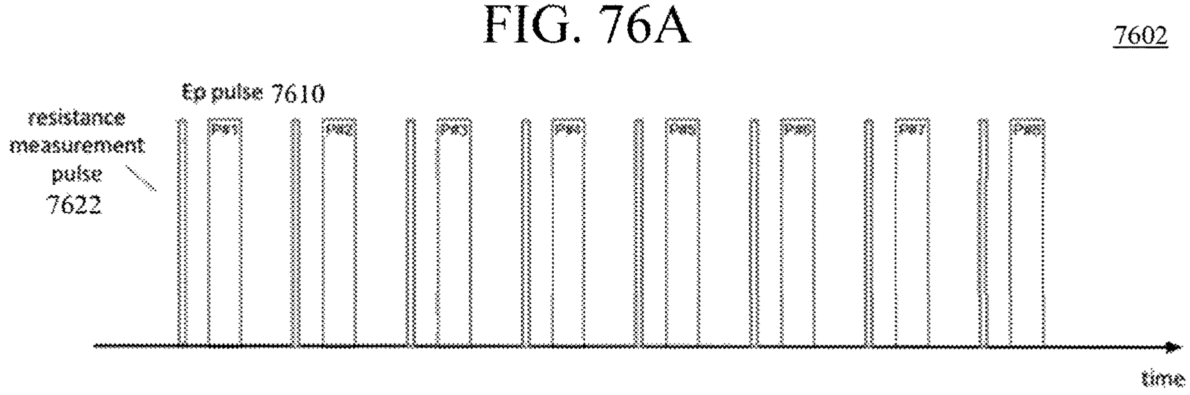
Figure 76C:
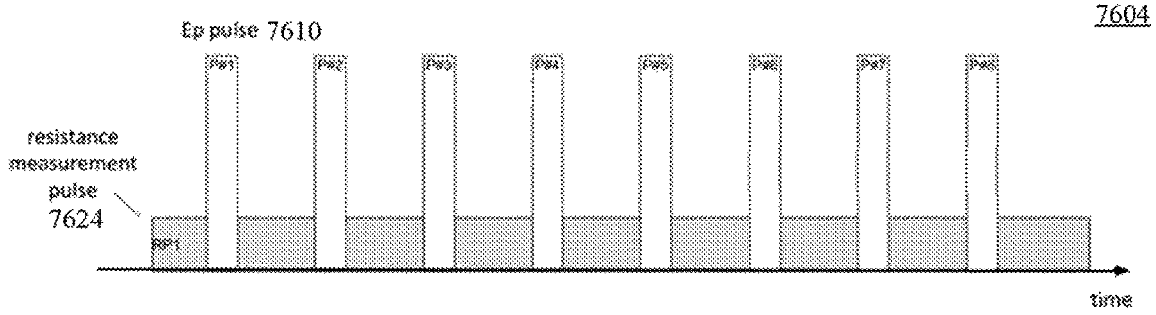
Figure 76D:
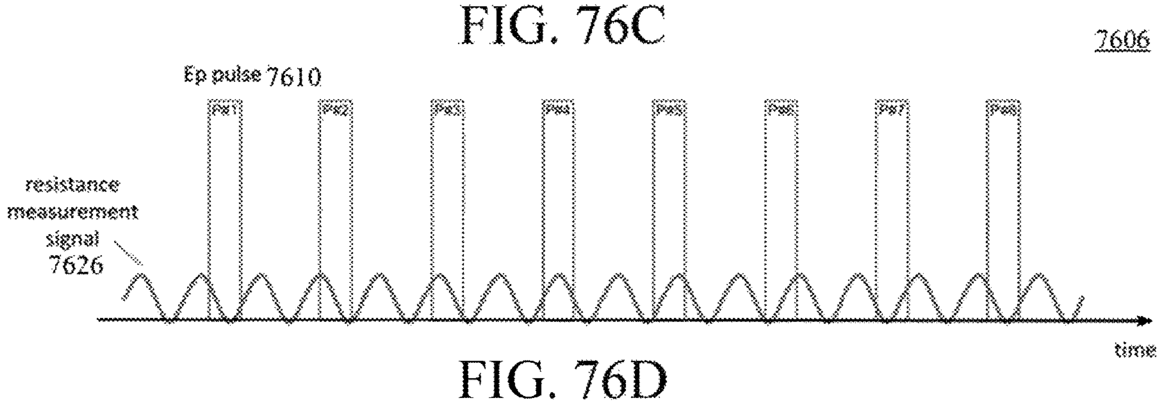

FIGS. 76A-76D are plots 7600, 7602, 7604, 7606 of measurement waveforms and electroporation waveforms. FIG. 76A depicts a first resistance measurement pulse 7620 with a low voltage and a wide pulse width. FIG. 76B depicts a second resistance measurement pulse 7622 with a high voltage and a short pulse width. FIG. 76C depicts a third resistance measurement pulse 7624 with a continuous low voltage waveform to monitor an impedance change continuously over time. FIG. 76D depicts a fourth resistance measurement pulse 7626 with a low AC voltage waveform to monitor an impedance change continuously over time. Each of the resistance measurement pulses avoid inducing electroporation in the cells by reducing voltage and/or pulse width. By monitoring the voltage current of the applied resistance measurement pulse, a change in resistance may be measured and the electroporation pulse applied to a cell batch may be compensated accordingly.

In some variations, an electroporation signal may comprise between about 1 pulse and about 50 pulses, a voltage of between about 100 V and about 700 V, a pulse width of between about 100 us and about 1 ms, a pulse spacing between about 5 second to about 30 seconds, a resistance pulse voltage of between about 10 V and about 40 V, and a resistance pulse width of between about 10 us and about 50 µs.

For example, an eight-batch electroporation run may receive one electroporation pulse per batch. Each electroporation pulse may have an electrical field strength between about 0.5 kV/cm and about 2.0 kV/cm. The resistance measurement pulse applied before each batch may have an electrical field strength less than about 0.2 kV/cm such that electroporation is not induced by the resistance measurement pulse.

Sterile Liquid Transfer Device

Generally, the sterile liquid transfer devices described herein may be configured to store fluid for transfer to another component of a cell processing system such as a cartridge, bioreactor, and the like. In some variations, the sterile liquid transfer device may comprise a portable consumable configured to be moved using a robot. For example, a robot may be configured to move a sterile liquid transfer device from a reagent vault to an ISO 7 space to a sterile liquid transfer instrument within a cell processing system. The sterile liquid transfer device enables the transfer of fluids in an automated, sterile, and metered manner for automating cell therapy manufacturing.

Figure 103A:
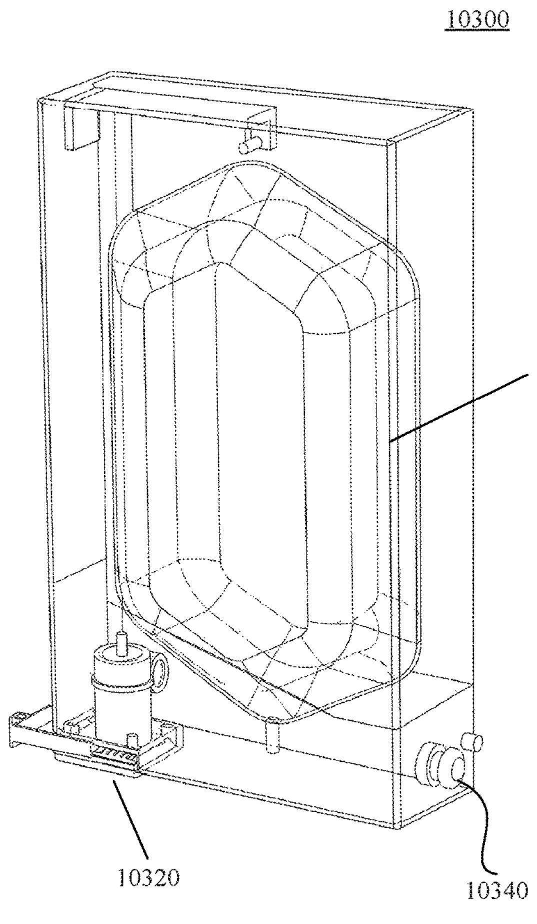
FIGS. 103A and 103B are perspective views of an illustrative variation of a sterile liquid transfer device.
Figure 103B:
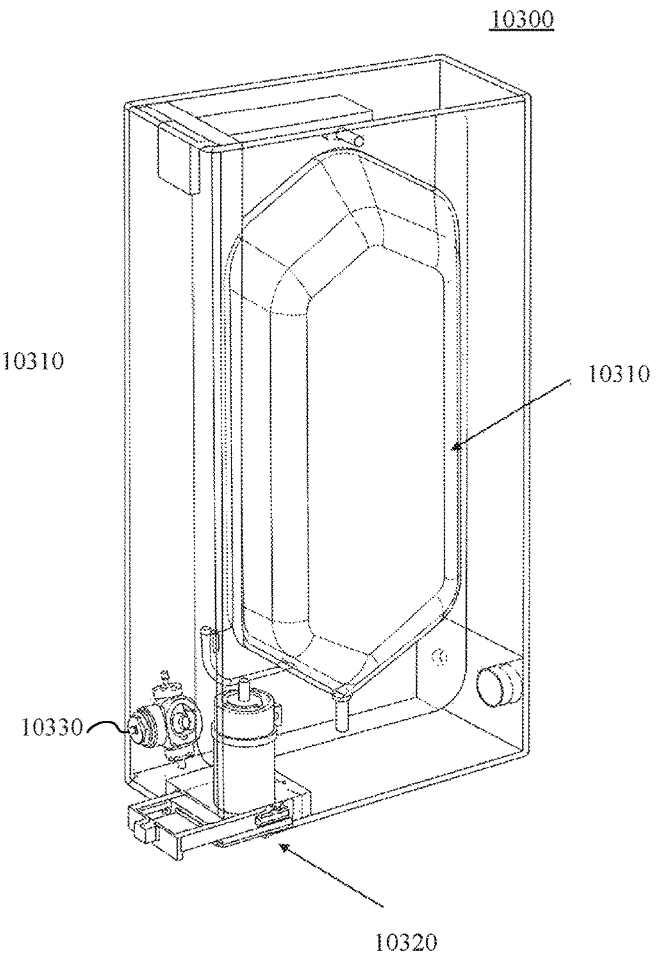

FIGS. 103A and 103B are perspective views of a sterile liquid transfer device 10300 comprising a fluid cavity 10310 (e.g., container, vessel), fluid connector 10320 (e.g., fluid connector), and pump 10330. Fluid stored within fluid cavity 10310 may be transferred in and out of the sterile liquid transfer device 10300 through the fluid connector 10320 using the pump 10330. In some variations, the sterile liquid transfer device 10300 may comprise an engagement feature 10340 (e.g., robot mount) to facilitate robotic arm control.

Fluid Connector

Generally, the aseptic fluid connectors described herein may form a sterile fluid pathway between at least two fluid devices to enable fluid transfer that may be one or more of sterile, fully automated, and precisely metered (e.g., precise control of a transferred fluid volume). In some variations, the robot may be configured to couple a fluid connector between at least two of the plurality of instruments and one or more cartridge. In some variations, the robot may be configured to operate the fluid controller to open and close a set of ports and valves of the fluid connector. The use of a robot and controller to operate the fluid connector may facilitate automation and sterility of a cell processing system.

In some variations, a system may comprise a robot configured to operate a fluid connector as described herein, and a controller comprising a memory and processor. The controller may be coupled to the robot. The controller may be configured to generate a port signal to couple the first port to the second port using the robotic arm, generate a first valve signal to translate the first valve relative to the second valve using the robotic arm, and generate a second valve signal to transition the first valve and the second valve to the open configuration.

In some variations, a fluid pump may be coupled to the sterilant source, and the controller may be configured to generate a first fluid signal to circulate a fluid into the chamber through the sterilant port. The controller may be configured to generate a second fluid signal to circulate the sterilant into the chamber through the sterilant port to sterilize at least the chamber. The controller may be configured to generate a third fluid signal to remove the sterilant from the chamber.

In some variations, the controller may be configured to generate a port signal to couple the first port to the second port using the robotic arm, generate a first valve signal to translate the first valve relative to the second valve using the robotic arm, and generate a second valve signal to transition the first valve and the second valve to the open configuration.

Figure 15:
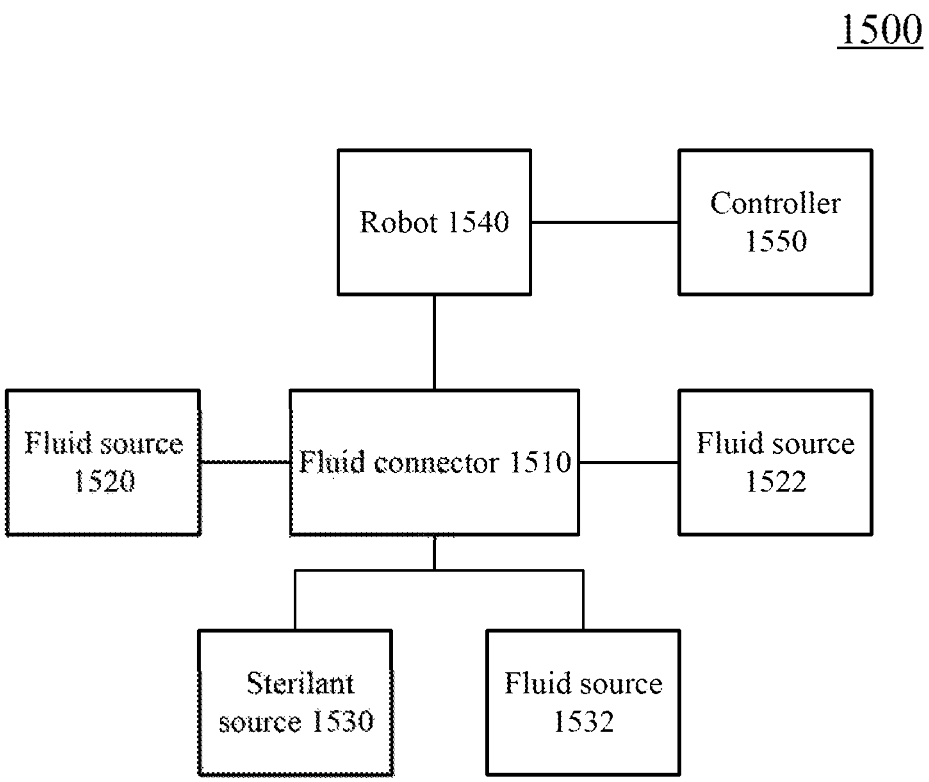
FIG. 15 is a block diagram of an illustrative variation of a fluid connector system.

The fluid connector may further allow for a plurality of connection cycles in a sterile system and may be controlled without human intervention. For example, the fluid connector may comprise one or more of engagement features to facilitate robotic arm control and alignment features to ensure proper connection between connector components. FIG. 15 is a block diagram of an illustrative variation of a fluid connector system 1500 comprising a fluid connector 1510, first fluid device 1520, second fluid device 1522, sterilant source 1530, fluid source 1532, robot (e.g., robotic arm) 1540, and controller 1550. The fluid connector 1510 may be removably coupled (e.g., connected/disconnected, attached/detached) to each of the first fluid device 1520, second fluid device 1522, sterilant source 1532, fluid source 1532, and robot 1540. In some variations, a fluid device may comprise one or more of a cartridge and sterile liquid transfer device. For example, a sterile liquid transfer device may be in fluid communication with a cartridge via the fluid connector. As described in more detail herein, separate portions (e.g., male connector, female connector) of the fluid connector 1510 may be removably coupled to each other. The robot 1540 may be configured to physically manipulate (e.g., removably couple) one or more of the fluid connector 1510, first fluid device 1520, second fluid device 1522, sterilant source 1530, and fluid source 1532 in a predetermined manner. For example, the robot 1540 may connect the fluid connector 1510 between the first fluid device 1520 and the second fluid device 1522. The robot 1540 may also connect the sterilant source 1530 and/or fluid source 1532 to a sterilant port of the fluid connector 1510. In some variations, the robot 1540 may control one or more valves and/or ports of the fluid connector 1510, and thereby initiate a sterilization process for one or more portions of the fluid connector 1510 using, for example, sterilant from the sterilant source 1530. The controller 1550 may be coupled to one or more of the robot 1540, sterilant source 1530, and fluid source 1532 to control one or more of fluid transfer and sterilization.

Figure 16A:
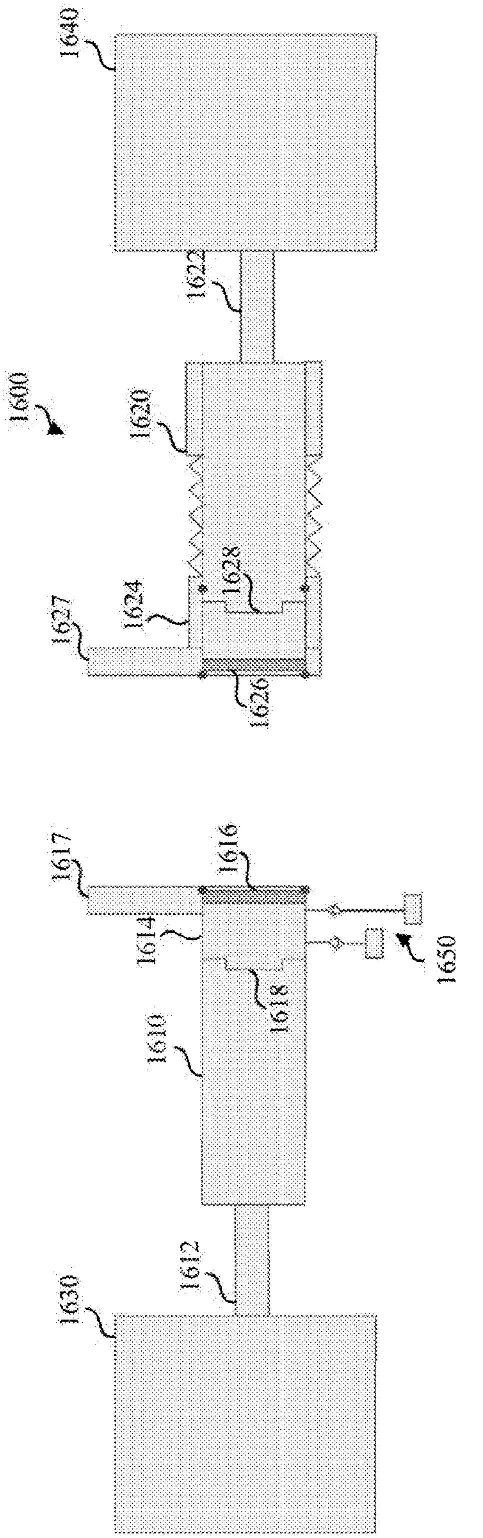
FIG. 16A is a schematic diagram of an illustrative variation of a fluid connector.

FIG. 16A is a schematic diagram of an illustrative variation of a fluid connector 1600. The fluid connector 1600 may comprise a lumen extending along its length and be disposed between a first fluid device 1630 and a second fluid device 1640 to enable fluid flow through the fluid connector 1600. In some variations, the first fluid device 1630 and second fluid device 1640 may be aseptically connected and disconnected using the fluid connector 1600. The fluid devices 1630, 1640 may comprise a closed sterile device, and may be the same or different types of fluid devices. For example, the fluid devices 1630, 1640 may comprise one or more of a sterile liquid transfer device and consumable. In some variations, the fluid connector 1600 may comprise a first connector 1610 including a first proximal end 1612 and a first distal end 1614. The first proximal end 1612 may be configured to couple to the first fluid device 1630. The first distal end 1614 may include a first port 1616, first housing 1617, and a first valve 1618. The first housing 1617 may be configured to receive the first port 1616 in a closed configuration as described in more detail herein.

The fluid connector 1600 may further comprise a second connector 1620 including a second proximal end 1622 and a second distal end 1624. The second proximal end 1622 may be configured to couple to the second fluid device 1640. The second distal end 1624 may include a second port 1626, second housing 1627, and a second valve 1628. The second housing 1627 may be configured to receive the second port 1626 in a closed configuration. In FIG. 16A, the first connector 1610 comprises a sterilant port 1650 configured to couple to a sterilant source (not shown). Additionally or alternatively, the second connector 1620 may comprise the sterilant port 1650. The sterilant port 1650 may be configured to be in fluid communication with the first distal end 1614 and the second distal end 1624 when the second port 1626 is coupled to the first port 1616 as described in more detail herein.

In some variations, a fluid device 1630, 1640 may comprise a sterilant chamber and a sterilant port configured to receive a sterilant. The sterilant chamber may enclose a fluid device connector (not shown) configured to couple to a proximal end of a first connector 1610 or second connector 1620. The fluid device 1630, 1640 may receive a sterilant in a similar manner as the fluid connector 1600.

Figure 16B:
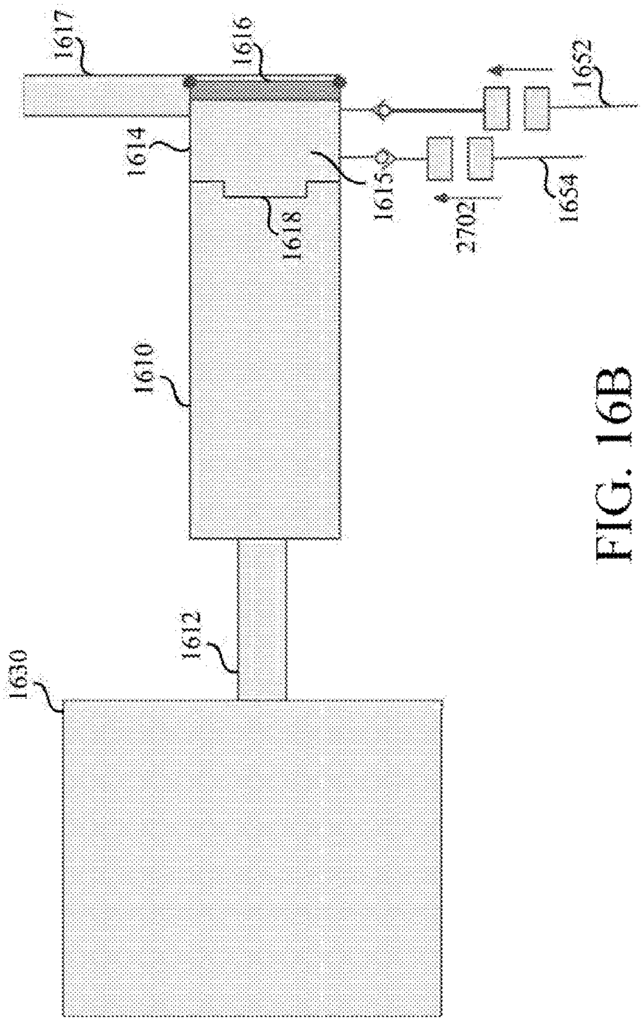
FIG. 16B is a detailed schematic diagram of the fluid connector depicted in FIG. 16A.
Figure 16C:
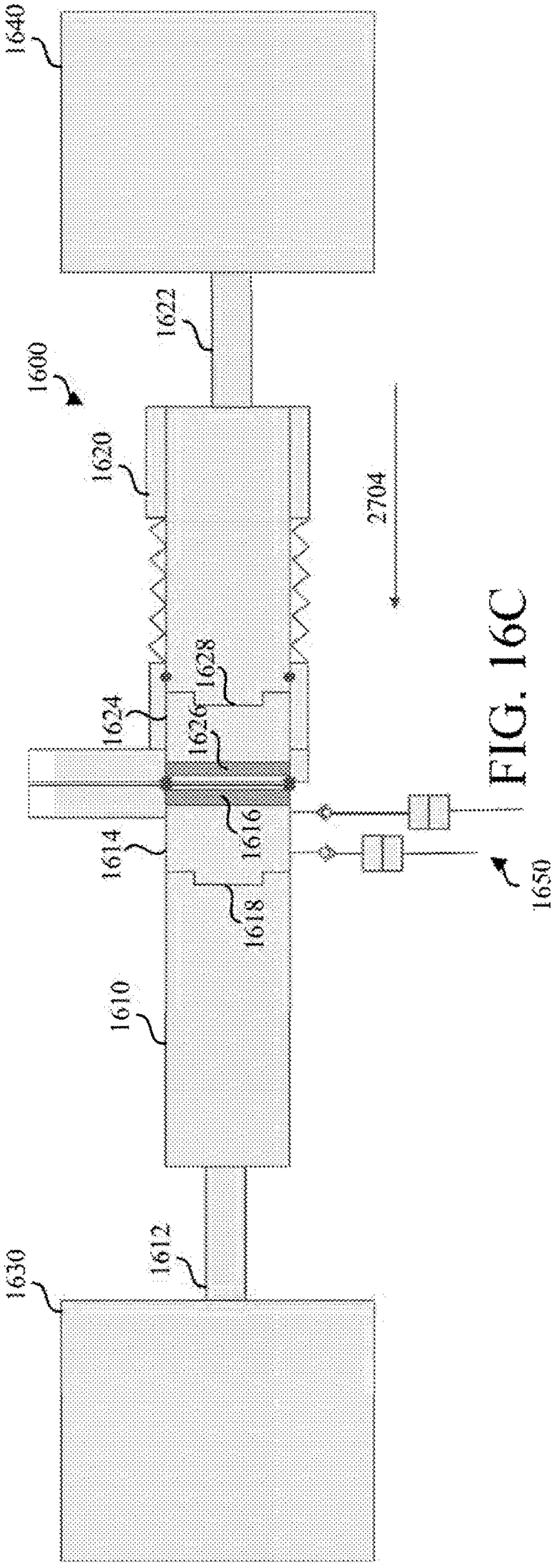
FIG. 16C is a schematic diagram of the fluid connector depicted in FIG. 16A in a coupled configuration.
Figure 16D:
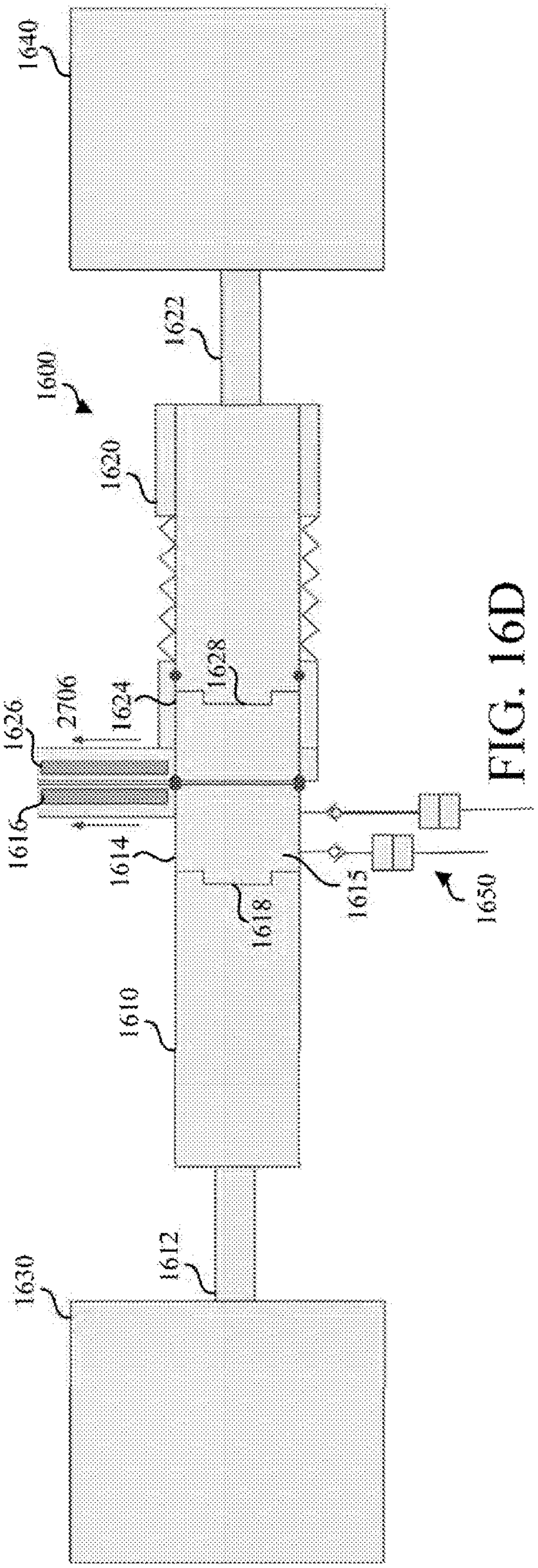
FIG. 16D is a schematic diagram of the fluid connector depicted in FIG. 16A in an open port configuration.

FIG. 16B is a detailed schematic diagram of the first connector 1610 including a first port housing 1617 and a chamber 1615. The chamber 1615 may be defined by the cavity enclosed by one or more of the distal ends 1614, 1624. For example, the chamber 1615 in FIG. 16B may comprise the portion of the first connector 1610 between the first valve 1618 and the first port 1616 in the closed configuration (e.g., the first distal end 1614). In some variations, the first chamber 1615 may comprise a volume of between about 1 $cm^3$ and about 5 $cm^3$. When the first connector 1610 is coupled to the second connector 1620 and the ports 1616, 1626 are in an open configuration (as shown in FIG. 16D), the chamber 1616 may comprise the portion of the fluid connector 1600 between the first valve 1618 and the second valve 1628 (e.g., the first distal end 1614 and second distal end 1624). The chamber 1615 may comprise an enclosed volume configured to receive a fluid such as a sterilant from the sterilant port 1650. In some variations, the sterilant port 1650 may comprise an inlet 1652 and outlet 1654. Methods of using a fluid connector are described in more detail with respect to FIGS. 16C-16L and 27.

In some variations, the fluid connector 1600 may comprise one or more alignment features and robot engagement features configured to facilitate robotic manipulation, as described in more detail herein. In some variations, the fluid connector 1600 may be coupled to one or more sensors, pumps, and valves to facilitate fluid transfer and monitoring.

In some variations, the components of the fluid connector in contact with fluid may be USP Class VI compatible for cell processing and/or GMP applications. In some variations, the components of the fluid connector may be composed of a material including, but not limited to, one or more of cyclic olefin copolymer (COC), polychlorotrifluoroethylene, polyetherimide, polysulfone, polystyrene, polycarbonate, polypropylene, silicone, polyetheretherketone, polymethylmethacrylate, nylon, acrylic, polyvinylchloride, vinyl, phenolic resin, petroleum-derived polymers, glass, polyethylene, terephthalate, metal, stainless steel, titanium, aluminum, cobalt-chromium, chrome, silicates, glass, alloys, ceramics, carbohydrate polymer, mineraloid matter, and combinations or composites thereof.

Figures 17A, 17B, 17C:
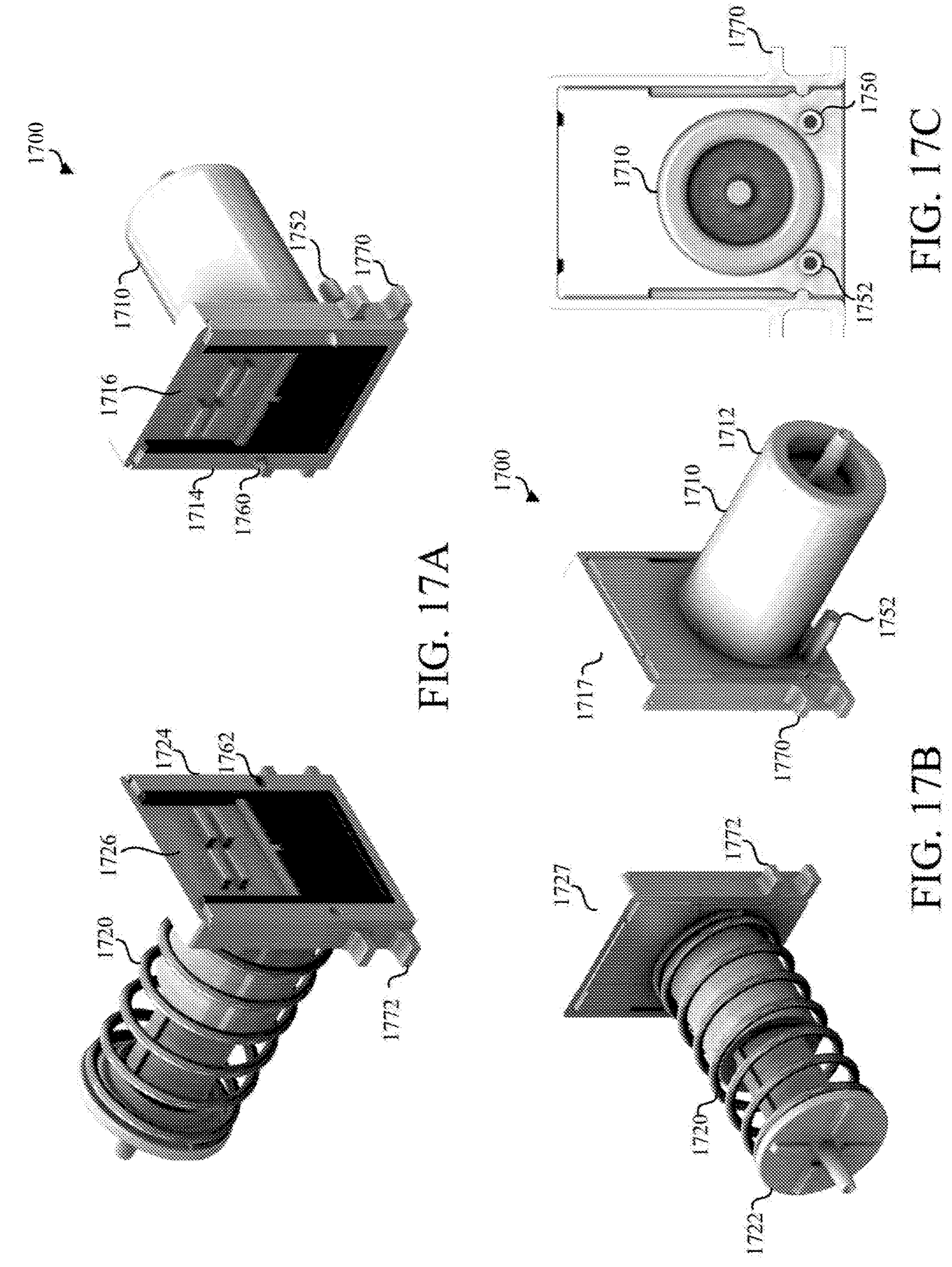
FIG. 17A is a front perspective view of a fluid connector in a closed port configuration.
FIG. 17B is a rear perspective view of the fluid connector depicted in FIG. 17A in the closed port configuration.
FIG. 17C is a rear view of the fluid connector depicted in FIG. 17B in the closed port configuration.

FIGS. 17A-18D depict external and internal views of variations of a fluid connector. FIG. 17A is a front perspective view of a fluid connector 1700 in a closed port configuration. FIG. 17B is a rear perspective view and FIG. 17C is a rear view of the fluid connector 1700. Generally, the fluid connector may comprise a plurality of internal seals to reduce contamination and aid sterilization, as well as alignment features to aid proper registration of the fluid connector components.

The fluid connector 1700 may comprise a lumen extending along its length. In some variations, the fluid connector 1700 may comprise a first connector 1710 including a first proximal end 1712 and a first distal end 1714. The first proximal end 1712 may be configured to couple to a first fluid device (not shown for the sake of clarity). The first proximal end 1712 may comprise a Luer connector or any other suitable connector. The first distal end 1714 may include a first port 1716 and first housing 1717. The first housing 1717 is shown in FIG. 17A holding the first port 1716 in a closed configuration. The first connector 1710 further comprises a sterilant port 1750, 1752 configured to couple to a sterilant source (not shown for the sake of clarity). In some variations, the sterilant port may comprise an inlet and outlet. In some variations, the sterilant port may optionally comprise one or more of a check valve and particle filter configured to reduce contamination into the sterilant port when not connected to a robot or actuator. The first connector 1710 may comprise a first alignment feature 1760 such as a set of protrusions on the first distal end 1714 of the first connector 1710. The alignment features may ensure that small positioning errors due to robotic manipulation do not impact the operation of the fluid connector.

The fluid connector 1700 may further comprise a second connector 1720 including a second proximal end 1722 and a second distal end 1724. The second proximal end 1722 may be configured to couple to the second fluid device (not shown for the sake of clarity). The second proximal end 1722 may comprise a Luer connector or any other suitable connector. The second distal end 1724 may include a second port 1726 and second housing 1727. The second housing 1727 is shown in FIG. 17A holding the second port 1726 in the closed configuration. The second connector 1720 may comprise a second alignment feature 1762 such as a set of holes on the second distal end 1724 of the second connector 1720. The second alignment feature 1762 may be configured to couple to the first alignment feature 1760 in a predetermined axial and rotational configuration to aid mating of the first connector 1710 and the second connector 1720.

The first port 1716 and the second port 1726 retained within respective first housing 1717 of the first distal end 1714 and second housing 1727 of the second distal end 1724 facilitates robotic control as the ports 1716, 1726 are not separable from the fluid connector 1700, and therefore reduces the risk of failure of automated handling by a robot.

In some variations, the first connector 1710 may comprise a first robot engagement feature 1770 and the second connector 1720 may comprise a second robot engagement feature 1772. The robot engagement features 1770, 1772 may be configured to be manipulated by a robot (e.g., robot 1540) such a robotic arm. In some variations, the robot engagement features 1770, 1772 may be operatively coupled to a respective first port 1716 and second port 1726 and configured to actuate the ports 1716, 1726 between a closed port configuration and an open port configuration, as shown in FIGS. 17A-17F. Additionally or alternatively, a user may manually actuate the robot engagement features 1770, 1772 to actuate respective ports 1716, 1726.

Figure 17D:
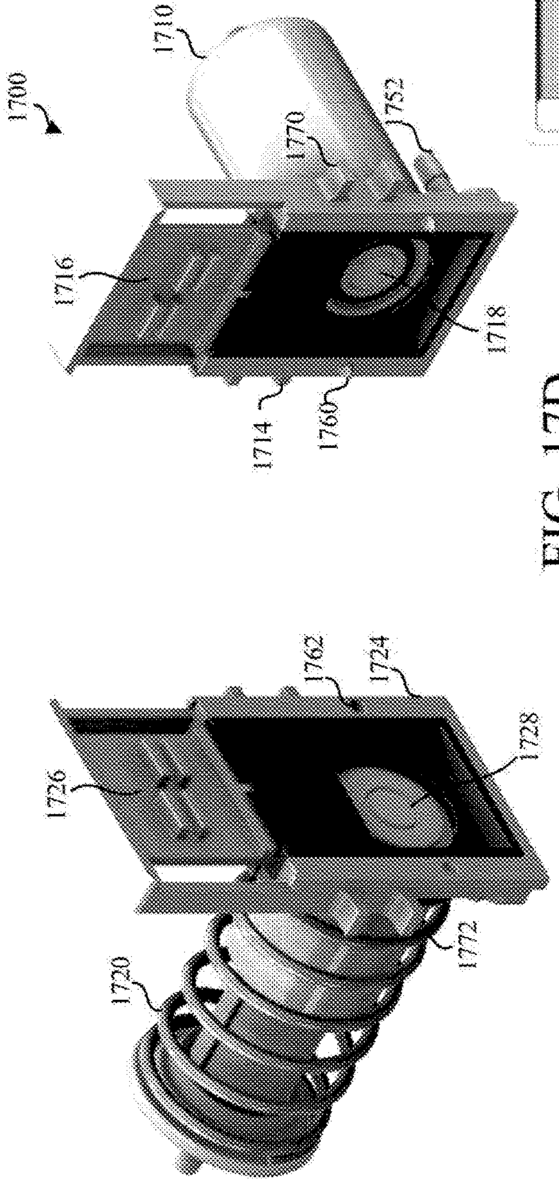
FIG. 17D is a front perspective view of a fluid connector in an open port configuration.
Figure 17E:
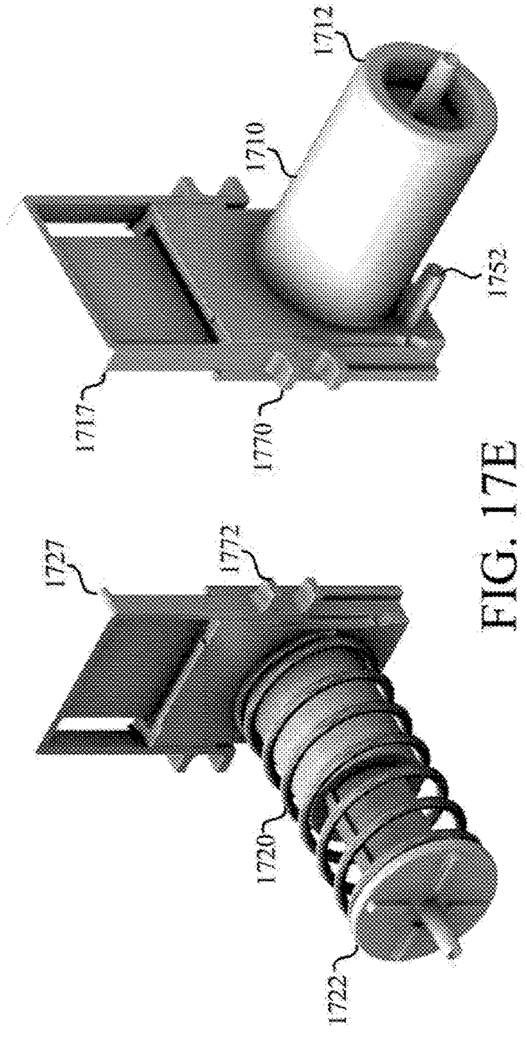
FIG. 17E is a rear perspective view of the fluid connector depicted in FIG. 17D in the open port configuration.
Figure 17F:
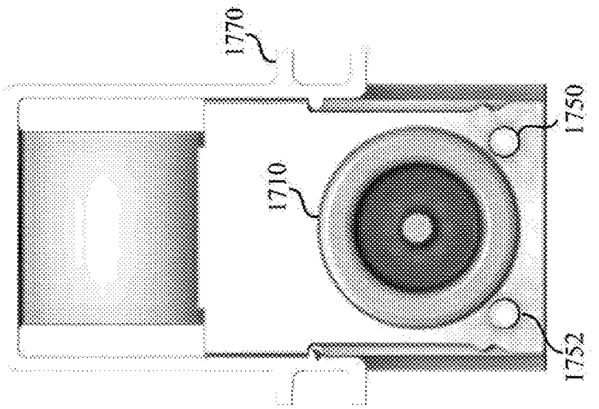
FIG. 17F is a rear view of the fluid connector depicted in FIG. 17E in the open port configuration.

FIG. 17D is a front perspective view of the fluid connector 1700 in an open port configuration. FIG. 17E is a rear perspective view and FIG. 17F is a rear view of the fluid connector 1700 in the open port configuration. In the open port configuration, the first valve 1718 of the first connector 1710 and the second valve 1728 of the second connector 1720 are shown in FIG. 17D.

Figure 18A:
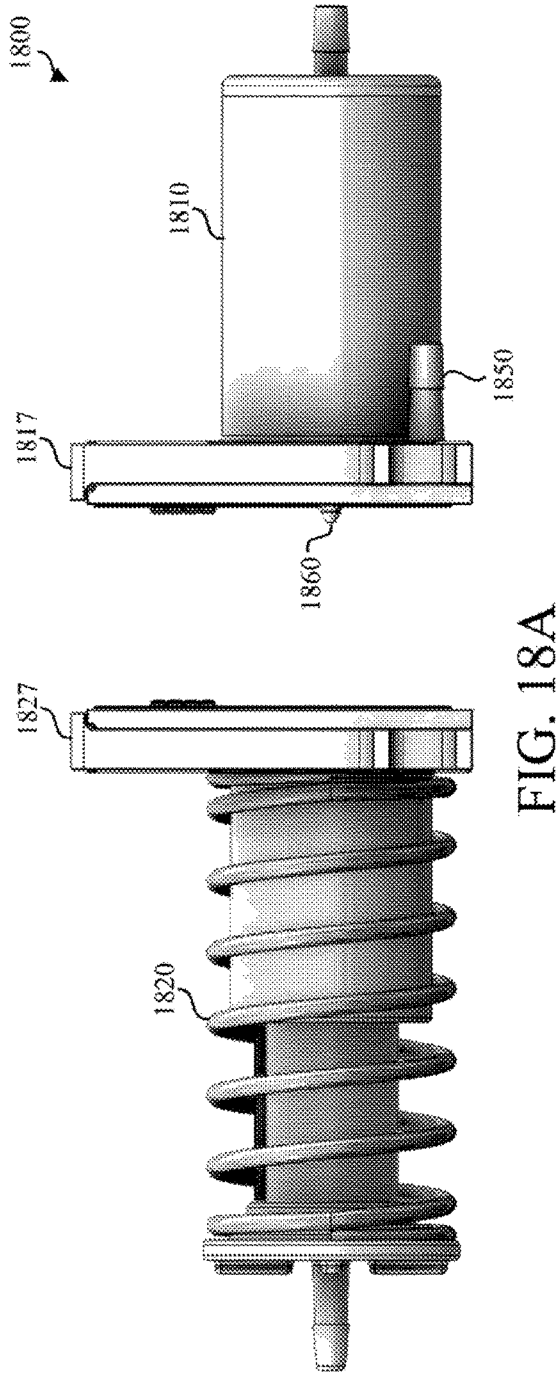
FIG. 18A is a side view of a fluid connector in an uncoupled configuration.
Figure 18B:
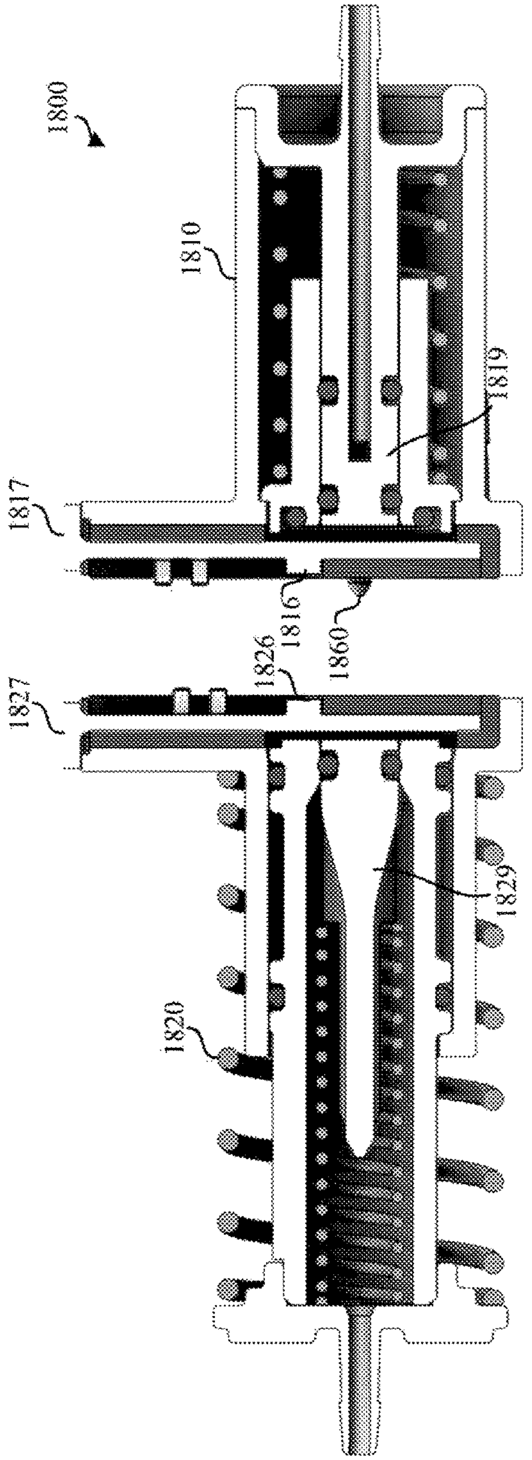
FIG. 18B is a cross-sectional side view of a fluid connector in an uncoupled configuration.

FIG. 18A is a side view and FIG. 18B is a cross-sectional side view of a fluid connector 1800 in an uncoupled configuration. In some variations, the fluid connector 1800 may comprise a first connector 1810 including a first housing 1817 comprising a first port 1816, a sterilant port 1850 configured to couple to a sterilant source (not shown), a first alignment feature 1860 configured to couple to a corresponding alignment feature (not shown) of the second connector 1820. The fluid connector 1800 may comprise a second connector 1820 including a second housing 1827 comprising a second port 1826. The first connector 1810 and second connector 1820 may be axially aligned and alignment features may aid rotational alignment of the first connector 1810 to the second connector 1820. The first valve 1818 may comprise a first valve stem 1819 and the second valve 1828 may comprise a second valve stem 1829.

Figure 18C:
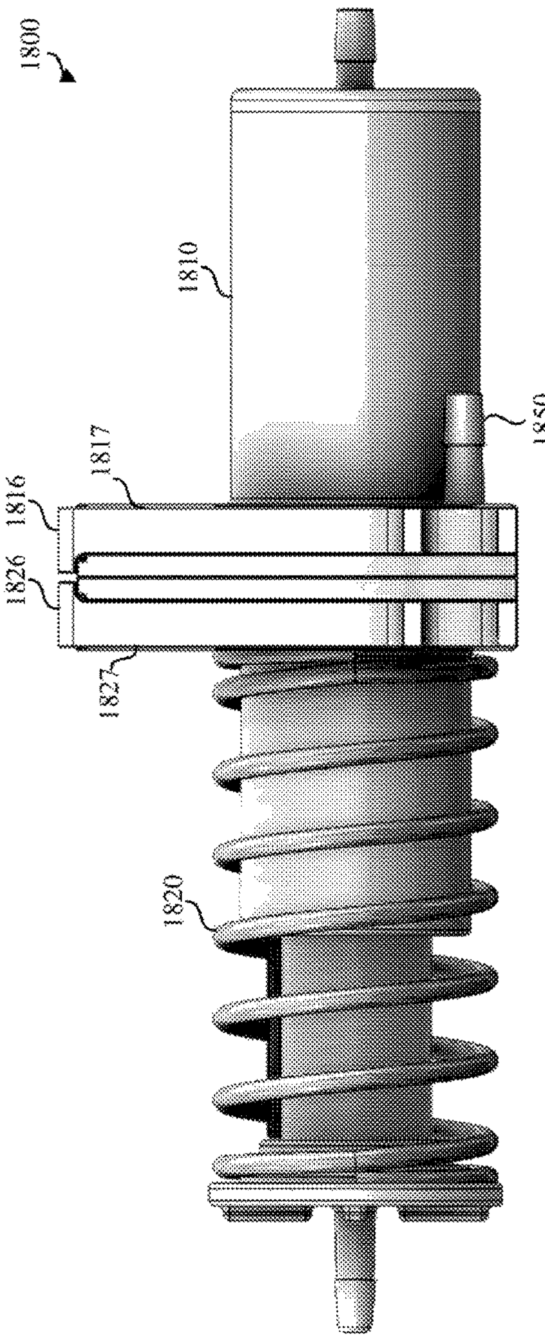
FIG. 18C is a side view of a fluid connector in a coupled configuration.
Figure 18D:
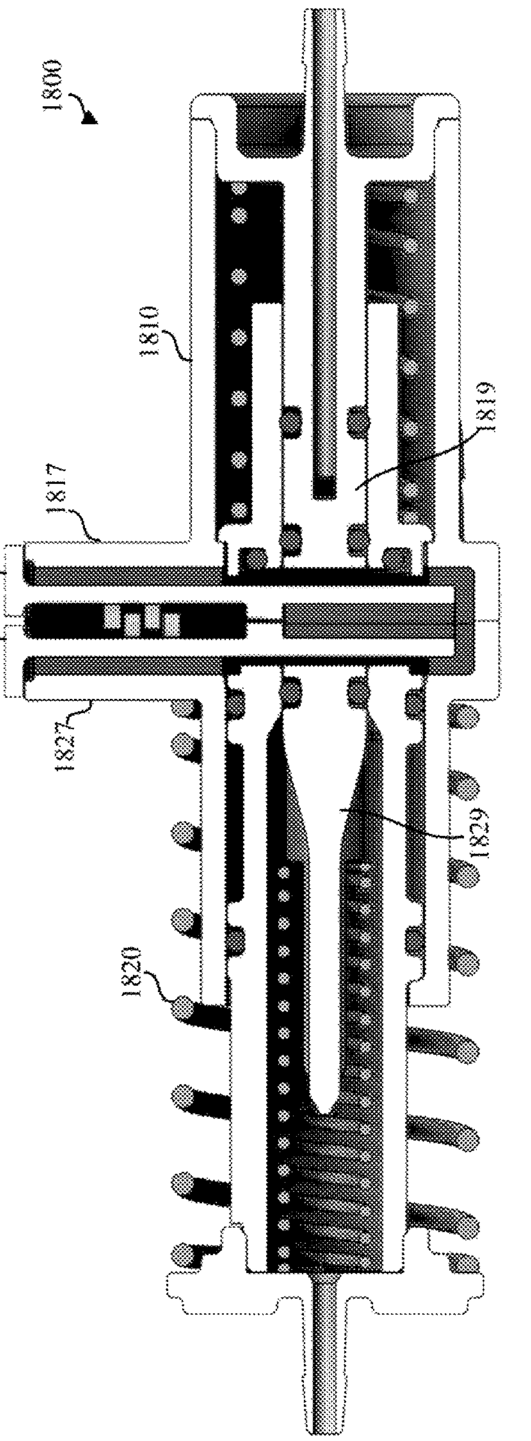
FIG. 18D is a cross-sectional side view of a fluid connector in a coupled configuration.

FIG. 18C is a side view and FIG. 18D is a cross-sectional side view of the fluid connector 1800 in a coupled configuration where the first housing 1817 and the second housing 527 are brought together but where the first connector 1810 and the second connector 1820 are not in fluid communication since the first port 1816 and the second port 1826 are both in the closed configuration. The first alignment features on each connector 1810, 1820 may be configured to ensure axial and/or rotational alignment between the first connector 1810 and the second connector 1820.

Figure 18E:
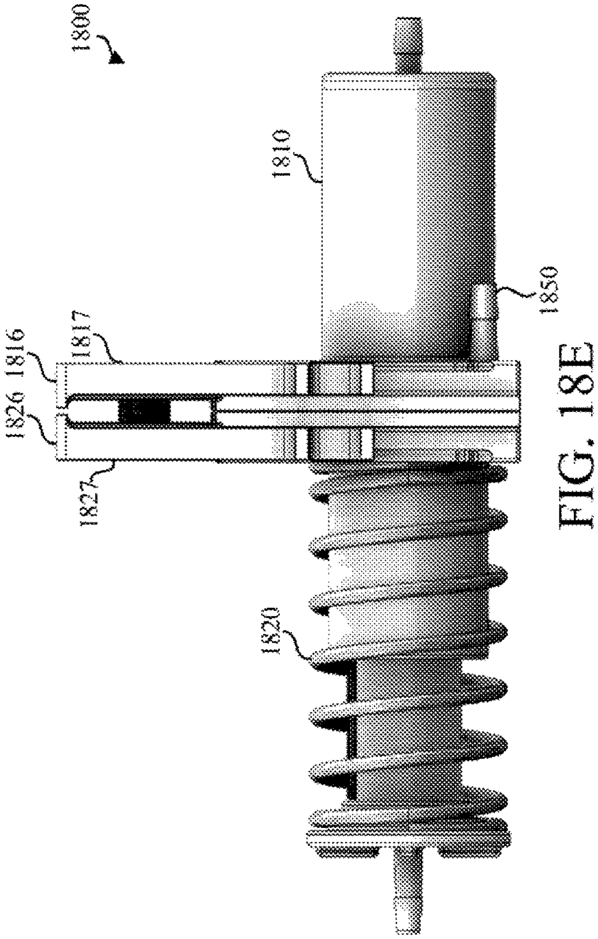
FIG. 18E is a side view of a fluid connector in an open port configuration.
Figure 18F:
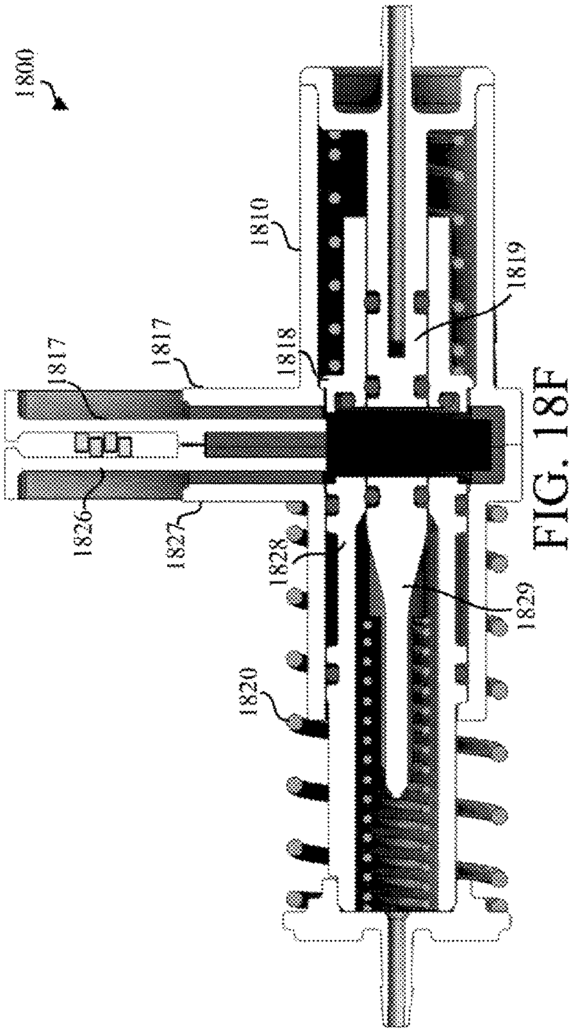
FIG. 18F is a cross-sectional side view of a fluid connector in an open port configuration.

FIG. 18E is a side view and FIG. 18F is a cross-sectional side view of the fluid connector 1800 in an open port configuration. Each of the first port 1817 and the second port 1827 are transitioned from the closed configuration to an open configuration. This creates a closed internal volume within respective distal ends of each connector 1810, 1820. Each of first valve 1818 and second valve 1828 is in a closed configuration such that fluid flow is inhibited between the first connector 1810 and the second connector 1820. still restricted on each half on account of the auto-shutoff valves in both sides.

Figure 18G:
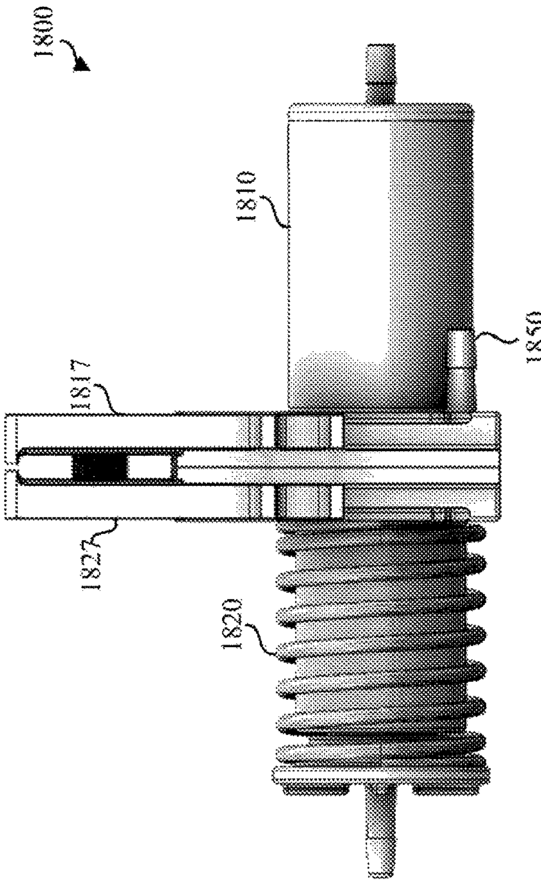
FIG. 18G is a side view of a fluid connector in an open valve configuration.
Figure 18H:
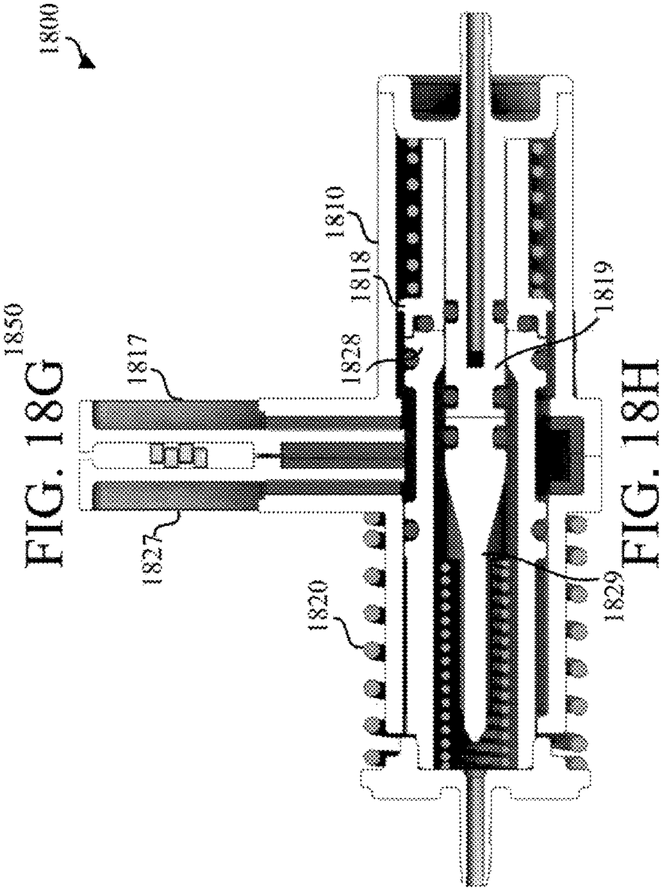
FIG. 18H is a cross-sectional side view of a fluid connector in an open valve configuration.

FIG. 18G is a side view and FIG. 18H is a cross-sectional side view of the fluid connector 1800 in an open valve configuration where the first valve 1818 is coupled to the second valve 1828. For example, the second valve 1828 may be translated along a longitudinal axis of the second connector 1820 towards the first valve 1818. As shown in FIGS. 18G and 18H, the second connector 1820 may be axially compressed to translate the second valve 1828 towards the first valve 1818. The first valve 1818 coupled to the second valve 1828 may form a radial seal, and the first valve stem 1819 and the second valve stem 1829 may be in contact to enable fluid communication between the first connector 1810 and the second connector 1820.

Figure 19:
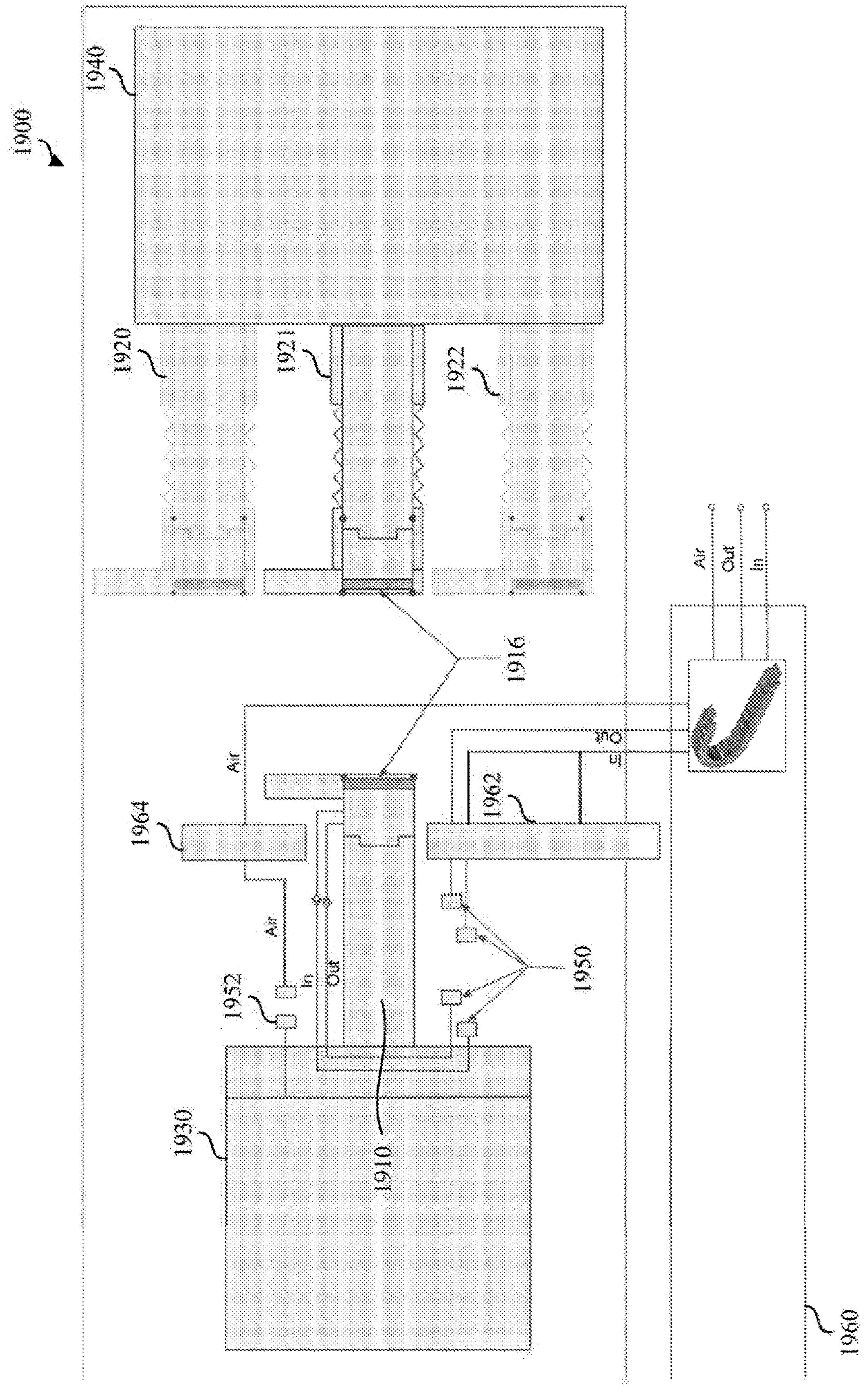
FIG. 19 is a schematic diagram of an illustrative variation of a fluid connector system.

FIGS. 19-26B are schematic diagrams of variations of fluid connector systems for coupling fluid devices. In some variations, a fluid connector may comprise a first connector configured to couple to any one of a plurality of second connectors. FIG. 19 is a schematic diagram of an illustrative variation of a fluid connector system 1900 comprising a first connector 1910, a plurality of second connectors 1920, 1921, 1922, a first fluid device 1930 (e.g., sterile liquid transfer device), a second fluid device 1940 (e.g., consumable), and a robot 1960 (e.g., robotic arm, 3DOF robot). The first connector 1910 may be coupled in fluid communication with the first fluid device 1930, and the second connectors 1920, 1921, 1922 may be coupled in fluid communication with the second fluid device 1940. The first connector 1910 and the second connectors 1920, 1921, 1922 may each comprise a port 1916 configured to couple to a corresponding port as described in more detail herein. The robot 1960 may comprise one or more end effectors 1962, 1964 configured to manipulate and/or couple to one or more of the first fluid device 1930 and first connector 1910. For example, the first connector 1910 may comprise one or more sterilization ports 1950 configured to couple to an end effector 1962 (e.g., gripper). Similarly, the first fluid device 1930 may comprise one or more fluid ports 1952 configured to couple to an end effector 1964.

Figure 96A:
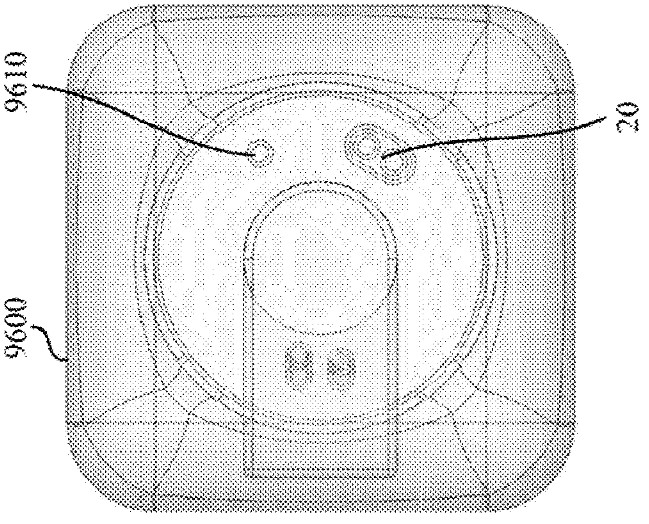
FIG. 96A is a plan view of an illustrative variation of a fluid device.
Figure 96B:
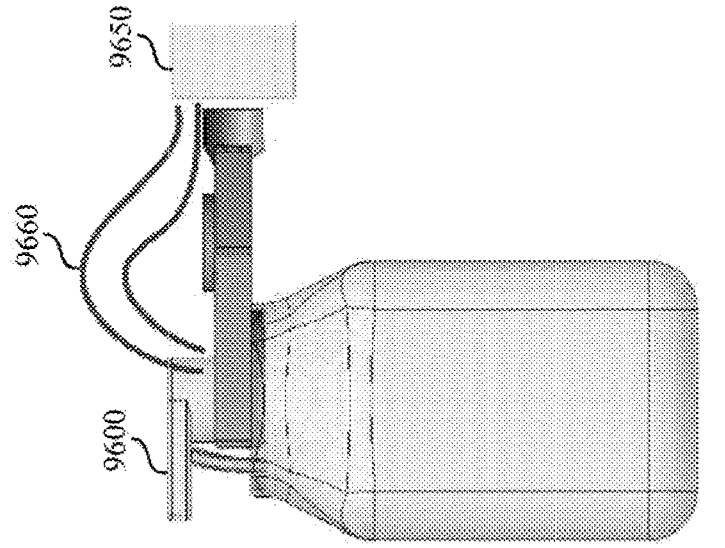
FIG. 96B is a side view of an illustrative variation of a fluid device coupled to a robot.
Figure 96C:
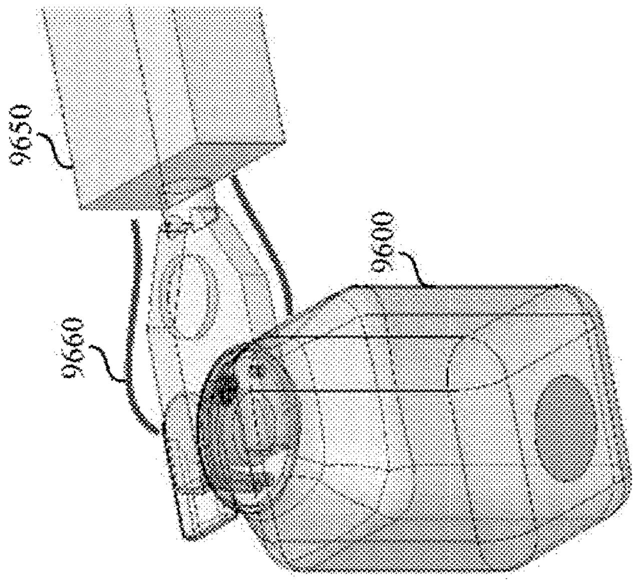
FIG. 96C is a perspective view of an illustrative variation of a fluid device held by a robot.

In some variations, the robot 1960 may be configured to couple to one or more of a sterilant source, fluid source, and pump in order to facilitate efficient and shared fluidic connections between the fluid device, fluid connector, and a sterilization system. For example, FIG. 96A is a plan view of a fluid device 9600 (e.g., sterile liquid transfer device) comprising a fluid port 9610 configured to couple to a fluid source (not shown) and a sterilization port 9620 configured to couple to a sterilant source (not shown). The FIGS. 96B and 96C are respective side and perspective views of a fluid device 9600 coupled to a robot 9650. In some variations, the robot 9650 may comprise one or more fluid conduits 9660 configured to couple to one or more of the fluid port 9610 and sterilization port 9620 of the fluid device 9600.

Figure 20A:
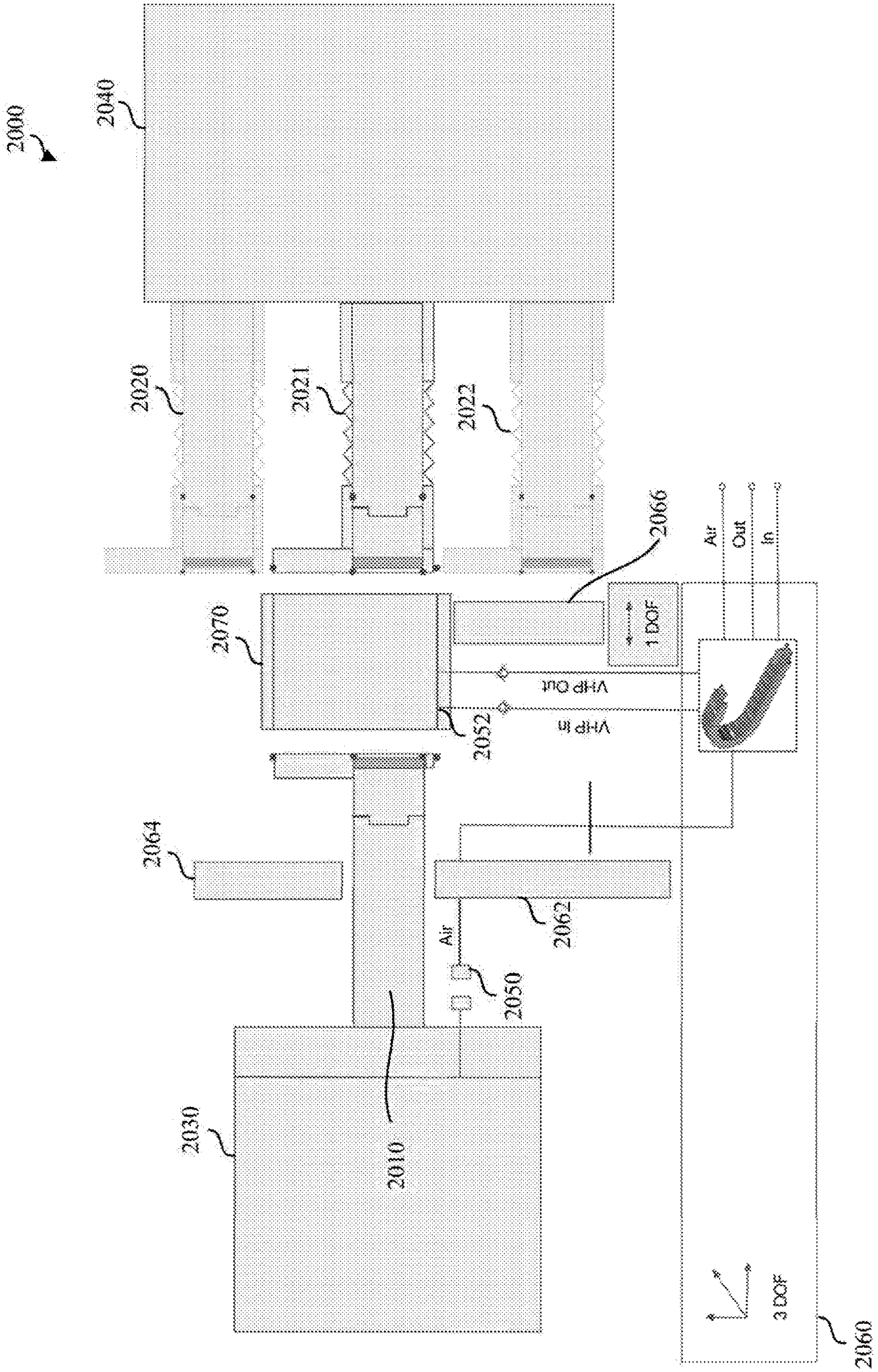
FIG. 20A is a schematic diagram of an illustrative variation of a fluid connector system.

In some variations, a fluid connector may comprise a third connector disposed between a first connector and a second connector. FIG. 20A is a schematic diagram of an illustrative variation of a fluid connector system 2000 comprising a first connector 2010, a plurality of second connectors 2020, 2021, 2022, a third connector 2070 (e.g., instrument, sterilization enclosure), a first fluid device 2030 (e.g., sterile liquid transfer device), a second fluid device 2040 (e.g., consumable), and a robot 2060 (e.g., robotic arm, 3 DOF robot, 1 DOF robot). The first connector 2010 may be coupled in fluid communication with the first fluid device 2030, and the second connectors 2020, 2021, 2022 may be coupled in fluid communication with the second fluid device 2040. The third connector 2070 may be coupled between the first connector 2010 and one of the second connectors 2020, 2021, 2022. The third connector 2070 may comprise a lumen configured to receive and circulate a sterilant through one or more portions of the first connector 2010, second connector 2020, 2021, 2022, and third connector 2070. In some variations, the sterilization port 2052 may be non-removably coupled to a sterilant source and/or fluid source, thereby simplifying one or more of the first fluid device 2030 and first connector 2010.

The robot 2060 may comprise one or more end effectors 2062, 2064, 2066 configured to manipulate and/or couple to one or more of the first fluid device 2030, first connector 2010, and third connector 2070. For example, the first fluid device 2030 may comprise one or more fluid ports 2050 configured to couple to an end effector 2062. Similarly, the third connector 2070 may comprise one or more sterilization ports 2052 configured to couple to robot 2060 (e.g., end effector 2064). In some variations, the robot 2060 may be configured to couple to one or more of a sterilant source, fluid source, and pump in order to facilitate efficient and shared fluidic connections between the fluid device, fluid connector, and a sterilization system.

Figure 20C:
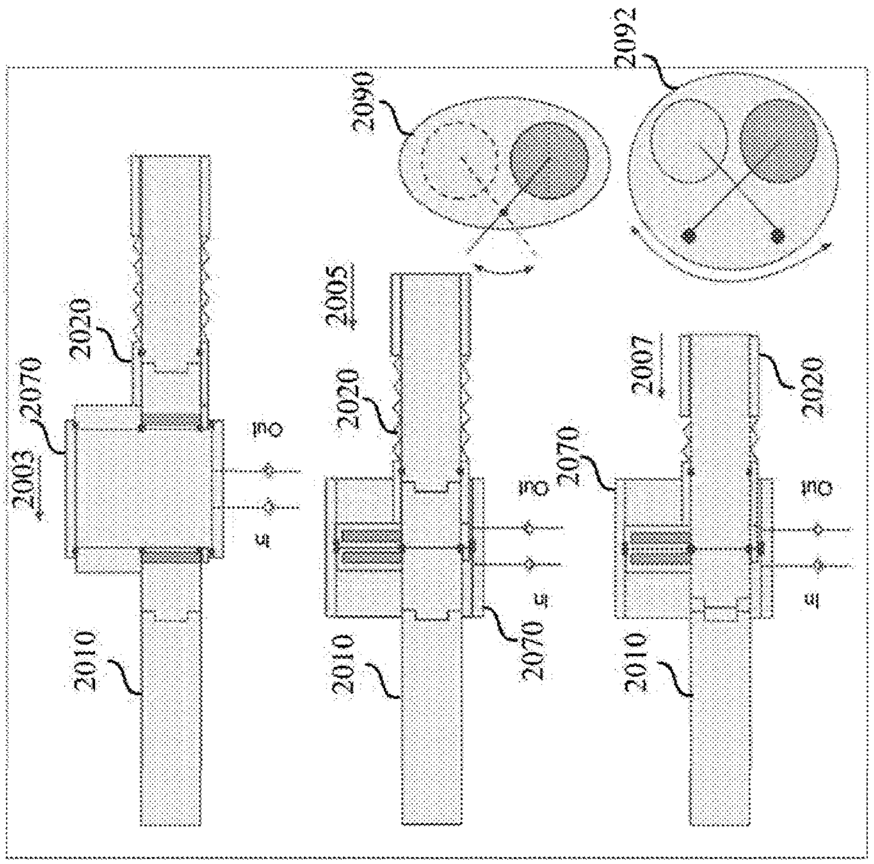
FIGS. 20B and 20C are schematic diagrams of an illustrative variation of a fluid connector connection process.
Figure 20B:
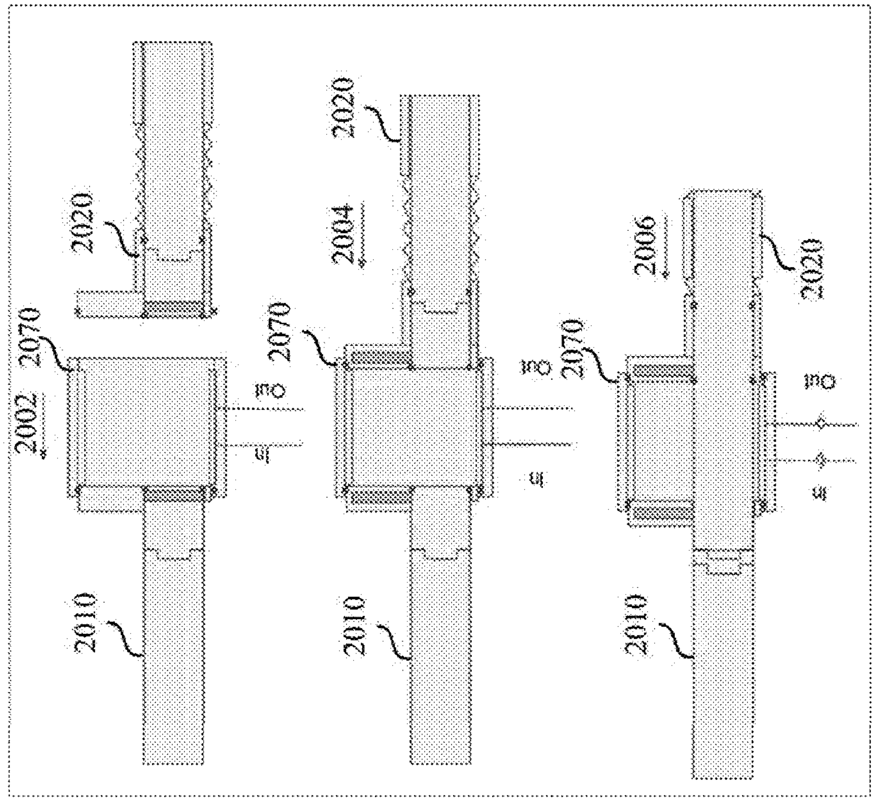

FIGS. 20B and 20C are schematic diagrams of a fluid connector connection process. In FIG. 20B, a third connector 2070 may be coupled to a distal end of a first connector 2010, at 2002. A distal end of the second connector 2020 may be coupled to the third connector 2070, at 2004. The second connector 2020 may be translated through the third connector 2070 to directly couple the second connector 2020 to the first connector 2010, at 2006.

In FIG. 20C, a third connector 2070 may be coupled to a distal end of the first connector 2010 and a distal end of the second connector 2020, at 2002. Each of the first connector 2010 and the second connector 2020 may be translated toward each other through the third connector 2070, at 2005. The second connector 2020 may be further translated towards the first connector 2010 to directly couple the first connector 2010 to the second connector 2010, at 2007. FIG. 20C further illustrates a first port 2090 and a second port 2092 that may transition between a closed port configuration and an open port configuration.

Figure 21:
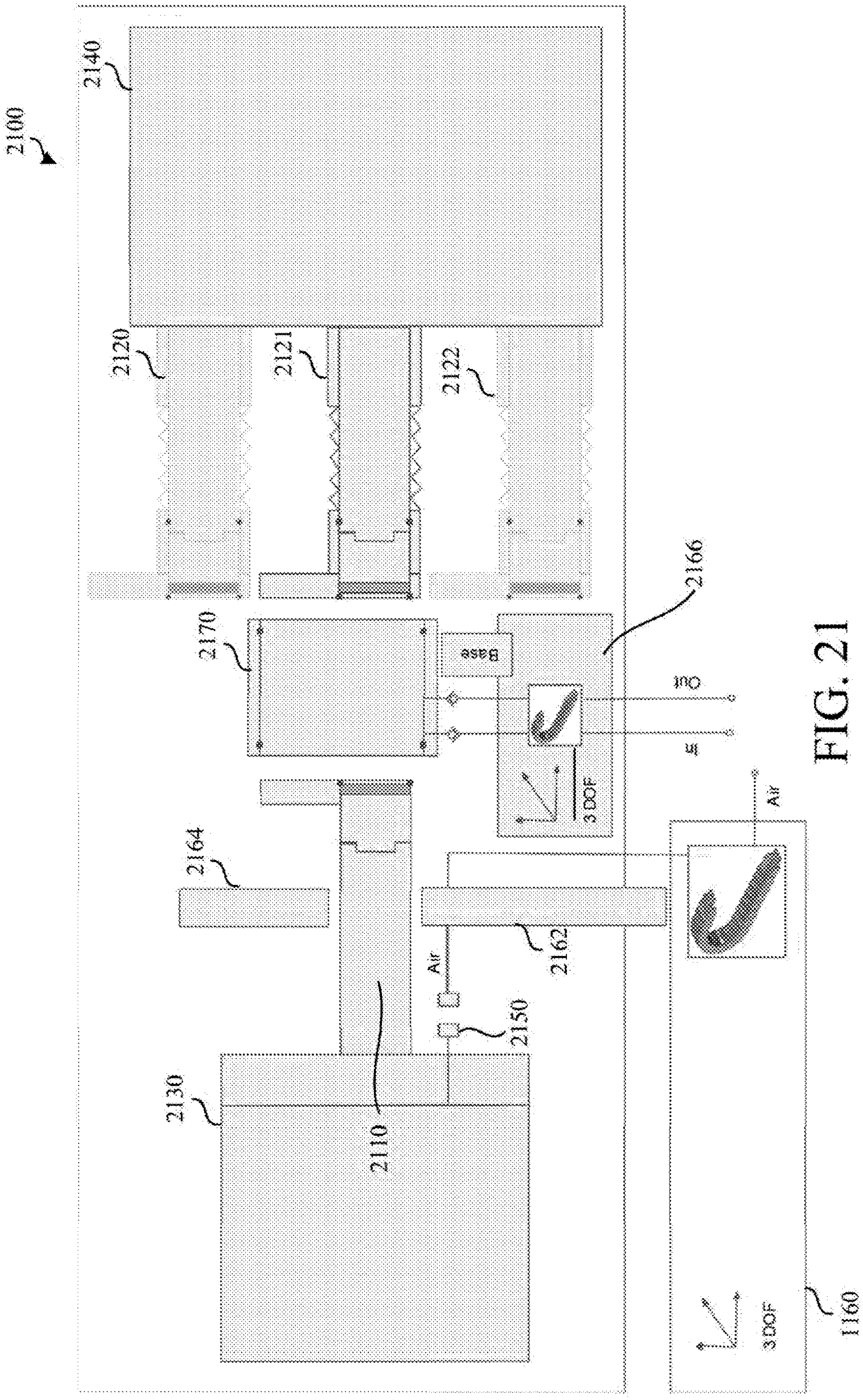
FIG. 21 is a block diagram of an illustrative variation of a fluid connector system.

In some variations, a fluid connector may comprise a third connector disposed between a first connector and a second connector. The third connector may be coupled to a second robot different from a first robot coupled to the first connector. FIG. 21 is a block diagram of an illustrative variation of a fluid connector system 2100 comprising a first connector 2110, a plurality of second connectors 2120, 2121, 2122, a third connector 2170 (e.g., instrument, sterilization enclosure), a first fluid device 2130 (e.g., sterile liquid transfer device), a second fluid device 2140 (e.g., consumable), a first robot 2160, and a second robot 2166. The first connector 2110 may be coupled in fluid communication with the first fluid device 2130, and the second connectors 2120, 2121, 2122 may be coupled in fluid communication with the second fluid device 2140. The third connector 2170 may be coupled between the first connector 2110 and one of the second connectors 2120, 2121, 2122. The third connector 2170 may comprise a lumen configured to receive and circulate a sterilant through one or more portions of the first connector 2110, second connector 2120, 2121, 2122, and third connector 2170. In some variations, the third connector 2170 may be non-removably coupled to a sterilant source and/or fluid source, thereby simplifying one or more of the first fluid device 2130 and first connector 2110.

The first robot 2160 may comprise one or more end effectors 2162, 2164 configured to manipulate and/or couple to one or more of the first fluid device 2130 and first connector 2110. For example, the first fluid device 2130 may comprise one or more fluid ports 2150 configured to couple to an end effector 2162. The third connector 2170 may be coupled to a second robot 2166 (e.g., 3 DOF robot). In some variations, the robot 2160, 2166 may be configured to couple to one or more of a sterilant source, fluid source, and pump in order to facilitate efficient and shared fluidic connections between the fluid device, fluid connector, and a sterilization system.

Figure 22:
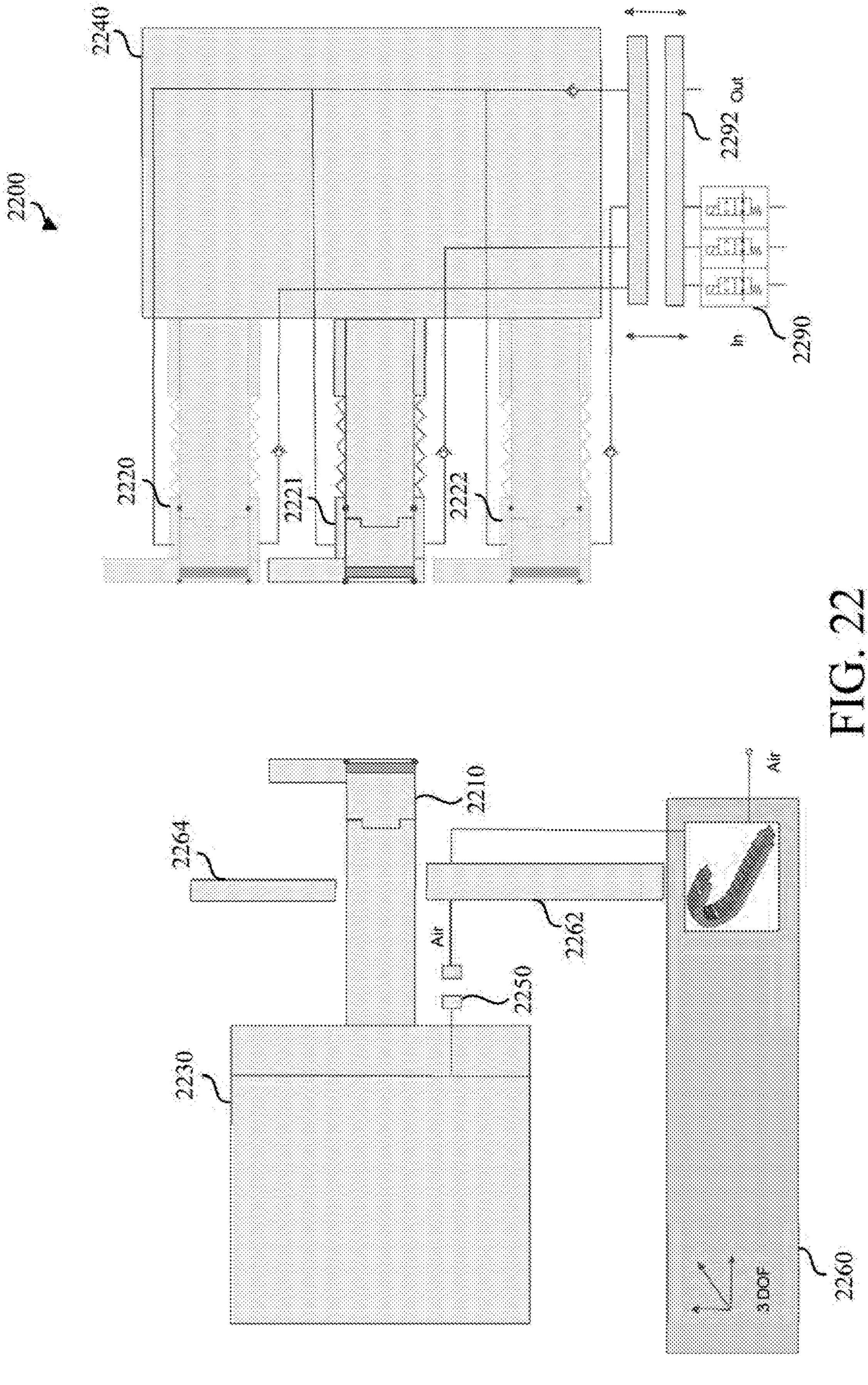
FIG. 22 is a block diagram of an illustrative variation of a fluid connector system.

In some variations, a fluid connector may comprise a sterilant source coupled to a plurality of second connectors. FIG. 22 is a block diagram of an illustrative variation of a fluid connector system 2200 comprising a first connector 2210, a plurality of second connectors 2220, 2221, 2222, a first fluid device 2230 (e.g., sterile liquid transfer device), a second fluid device 2240 (e.g., consumable), a robot 2260, a sterilant source 2290 comprising one or more valves, and a sterilant switch 2292. The first connector 2210 may be coupled in fluid communication with the first fluid device 2230, and the second connectors 2220, 2221, 2222 may be coupled in fluid communication with the second fluid device 2240. The robot 2260 may comprise one or more end effectors 2262, 2264 configured to manipulate and/or couple to one or more of the first fluid device 2230 and first connector 2210. For example, the first fluid device 2230 may comprise one or more fluid ports 2250 configured to couple to an end effector 2262. In some variations, the sterilant source 2290 may be coupled to the switch 2292. The switch 2292 may be coupled to each of the second connectors 2220, 2221, 2222 in order to facilitate efficient and shared fluidic connections between the fluid device, fluid connector, and sterilization system. In some variations, a sterilant conduit may be routed from the switch 2292 through the second fluid device 2240 to a respective second connector 2220, 2221, 2222.

Figure 23:
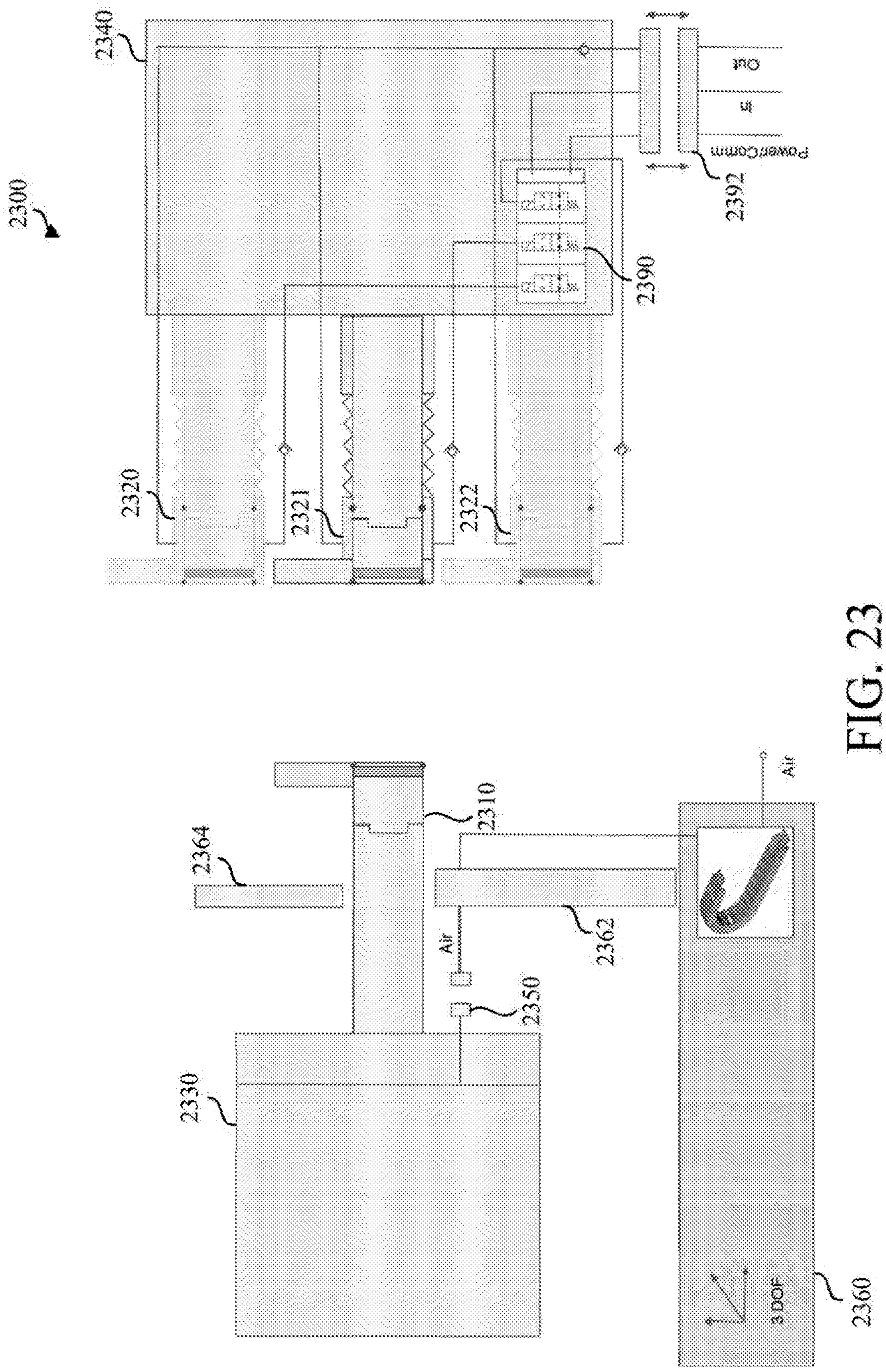
FIG. 23 is a block diagram of an illustrative variation of a fluid connector system.

In some variations, a fluid device may comprise one or more sterilant valves coupled to a plurality of second connectors. FIG. 23 is a block diagram of an illustrative variation of a fluid connector system. FIG. 23 is a block diagram of an illustrative variation of a fluid connector system 2300 comprising a first connector 2310, a plurality of second connectors 2320, 2321, 2322, a first fluid device 2330 (e.g., sterile liquid transfer device), a second fluid device 2340 (e.g., consumable), a robot 2360, a set of sterilant valves 2390 disposed within a housing of the second fluid device 2340, and a sterilant switch 2392. The first connector 2310 may be coupled in fluid communication with the first fluid device 2330, and the second connectors 2320, 2321, 2322 may be coupled in fluid communication with the second fluid device 2340. The robot 2360 may comprise one or more end effectors 2362, 2364 configured to manipulate and/or couple to one or more of the first fluid device 2330 and first connector 2310. For example, the first fluid device 2330 may comprise one or more fluid ports 2350 configured to couple to an end effector 2362. In some variations, the sterilant valves 2390 may be coupled to the switch 2392. The switch 2392 may be coupled to each of the second connectors 2320, 2321, 2322 via the sterilant valves 2390 in order to facilitate efficient and shared fluidic connections between the fluid device, fluid connector, and sterilization system. In some variations, a sterilant conduit may be routed from the switch 2392 through the second fluid device 2340 to a respective second connector 2320, 2321, 2322.

Figure 24A:
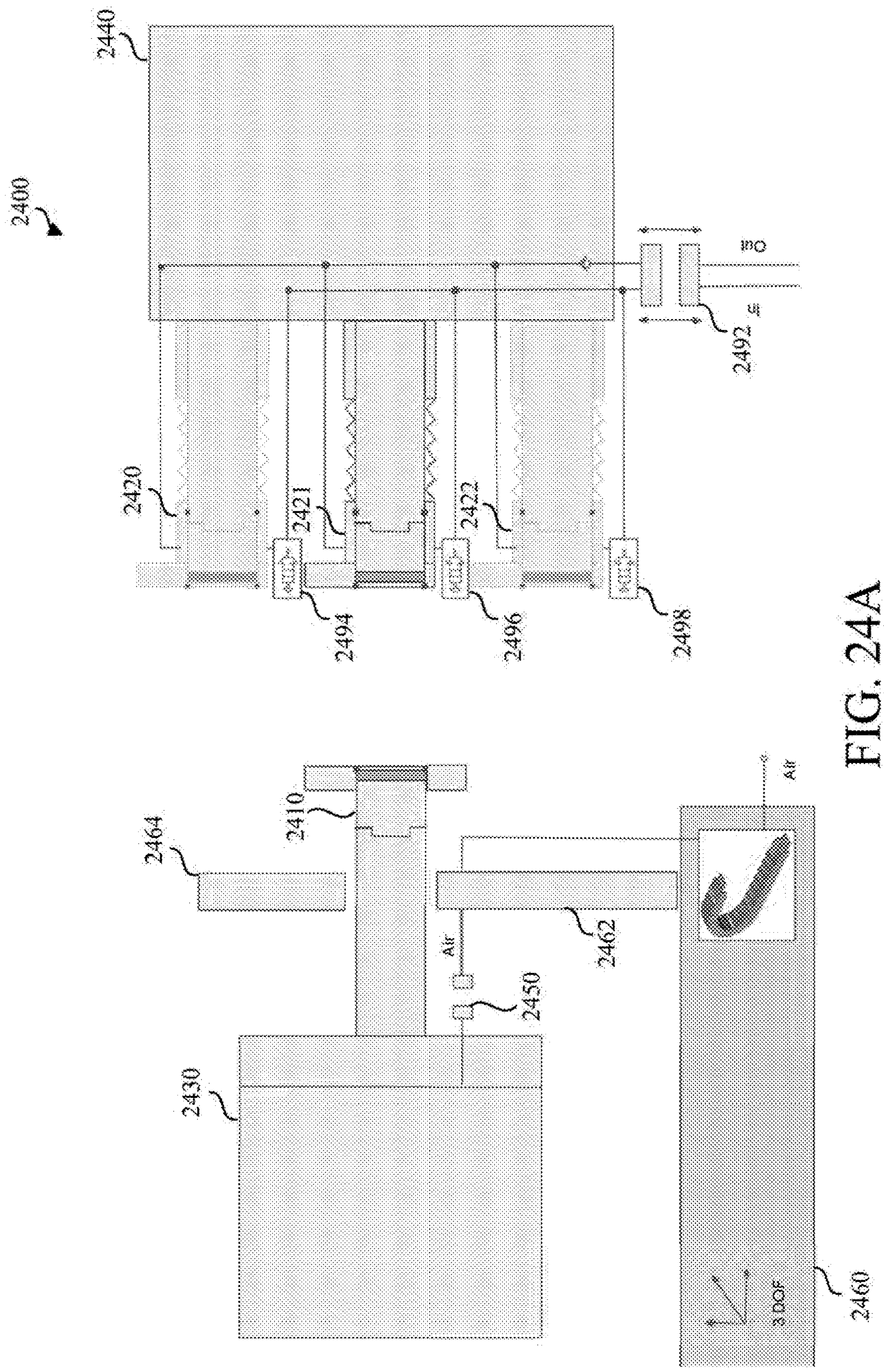
FIG. 24A is a block diagram of an illustrative variation of a fluid connector system.

In some variations, a fluid connector may comprise a sterilant source coupled to a plurality of second connectors each having a sterilant port (e.g., sterilant valve) and a sterilant conduit through a fluid device. FIG. 24A is a block diagram of an illustrative variation of a fluid connector system 2400 comprising a first connector 2410, a plurality of second connectors 2420, 2421, 2422, a first fluid device 2430 (e.g., sterile liquid transfer device), a second fluid device 2440 (e.g., consumable), a robot 2460, and a sterilant switch 2492 coupled to a sterilant source (not shown). The first connector 2410 may be coupled in fluid communication with the first fluid device 2430, and the second connectors 2420, 2421, 2422 may be coupled in fluid communication with the second fluid device 2440. The robot 2460 may comprise one or more end effectors 2462, 2464 configured to manipulate and/or couple to one or more of the first fluid device 2430 and first connector 2410. For example, the first fluid device 2430 may comprise one or more fluid ports 2450 configured to couple to an end effector 2462.

In some variations, each of the second connectors 2420, 2421, 2422, may comprise a respective sterilant port 2494, 2496, 2498 comprising a valve coupled to a distal end of the second connector 2420, 2421, 2422. In some variations, a sterilant conduit may be routed from the switch 2492 through the second fluid device 2440 to a respective sterilant port 2494, 2496, 2498. In some variations, a sterilant source (not shown) may be coupled to the switch 2492. The switch 2492 may be coupled to each of the second connectors 2420, 2421, 2422 via the sterilant ports 2494, 2496, 2498 in order to facilitate efficient and shared fluidic connections between the fluid device, fluid connector, and sterilization system.

Figure 24B:
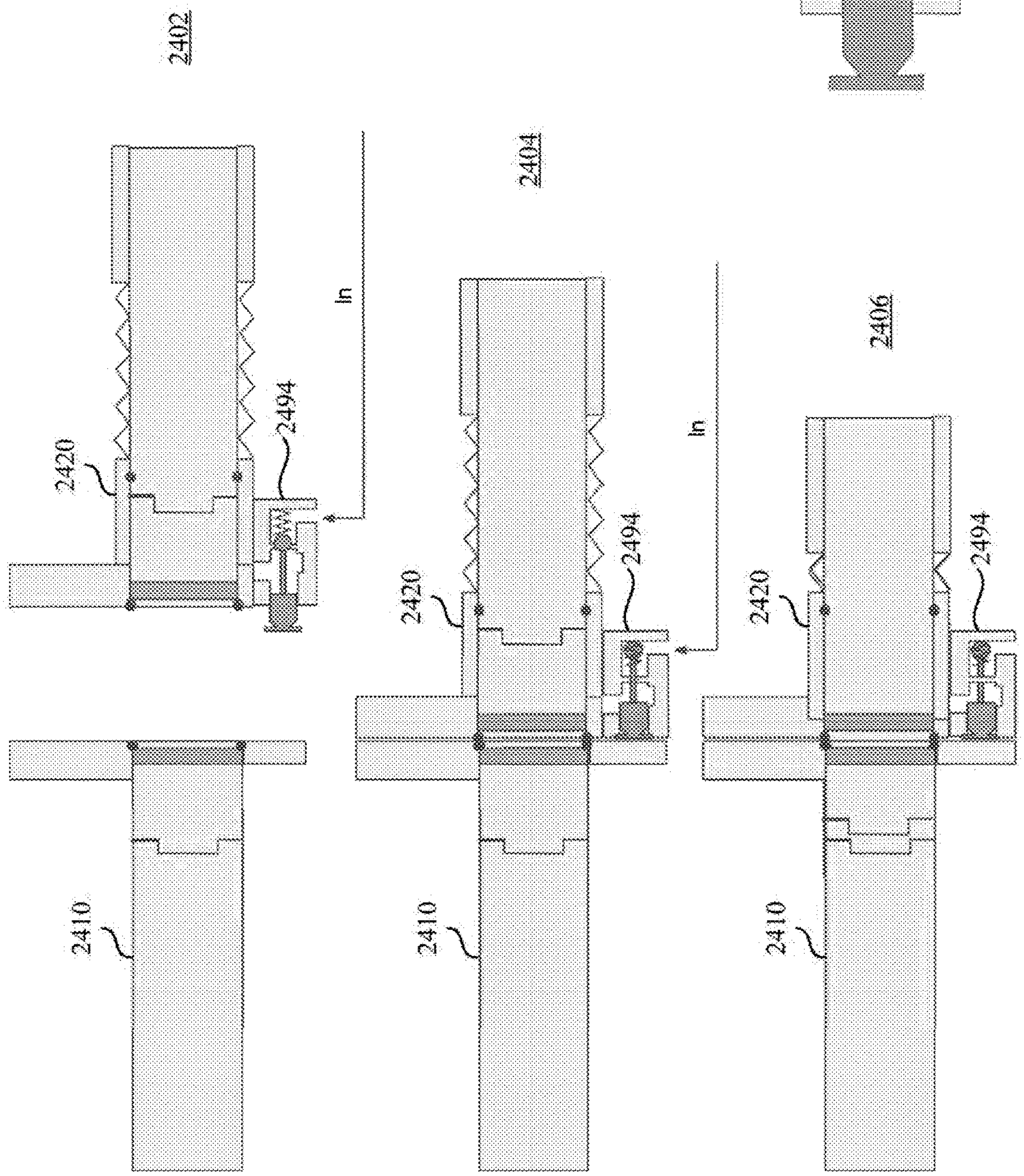
FIG. 24B is a schematic diagram of an illustrative variation of a fluid connector connection process.
Figure 24C:
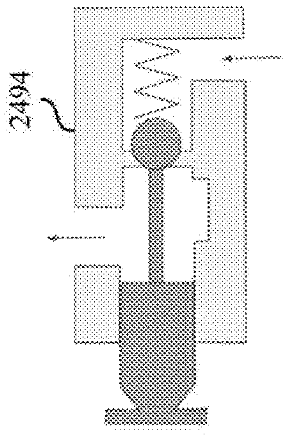
FIG. 24C is a schematic diagram of an illustrative variation of a valve.

FIG. 24B are schematic diagrams of a fluid connector connection process 2402, 2404, 2406 where a first connector 2410 is coupled to a second connector 2420. For example, the sterilant port 2494 is in a closed valve configuration when the first connector 2410 and the second connector 2420 are separated and uncoupled 2402. FIG. 24C is a detailed schematic diagram of the sterilant valve 2494. In some variations, the valve 2494 may transition to an open valve configuration when the first connector 2410 is coupled to the second connector 2420, at 2404 and 2406.

Figure 25A:
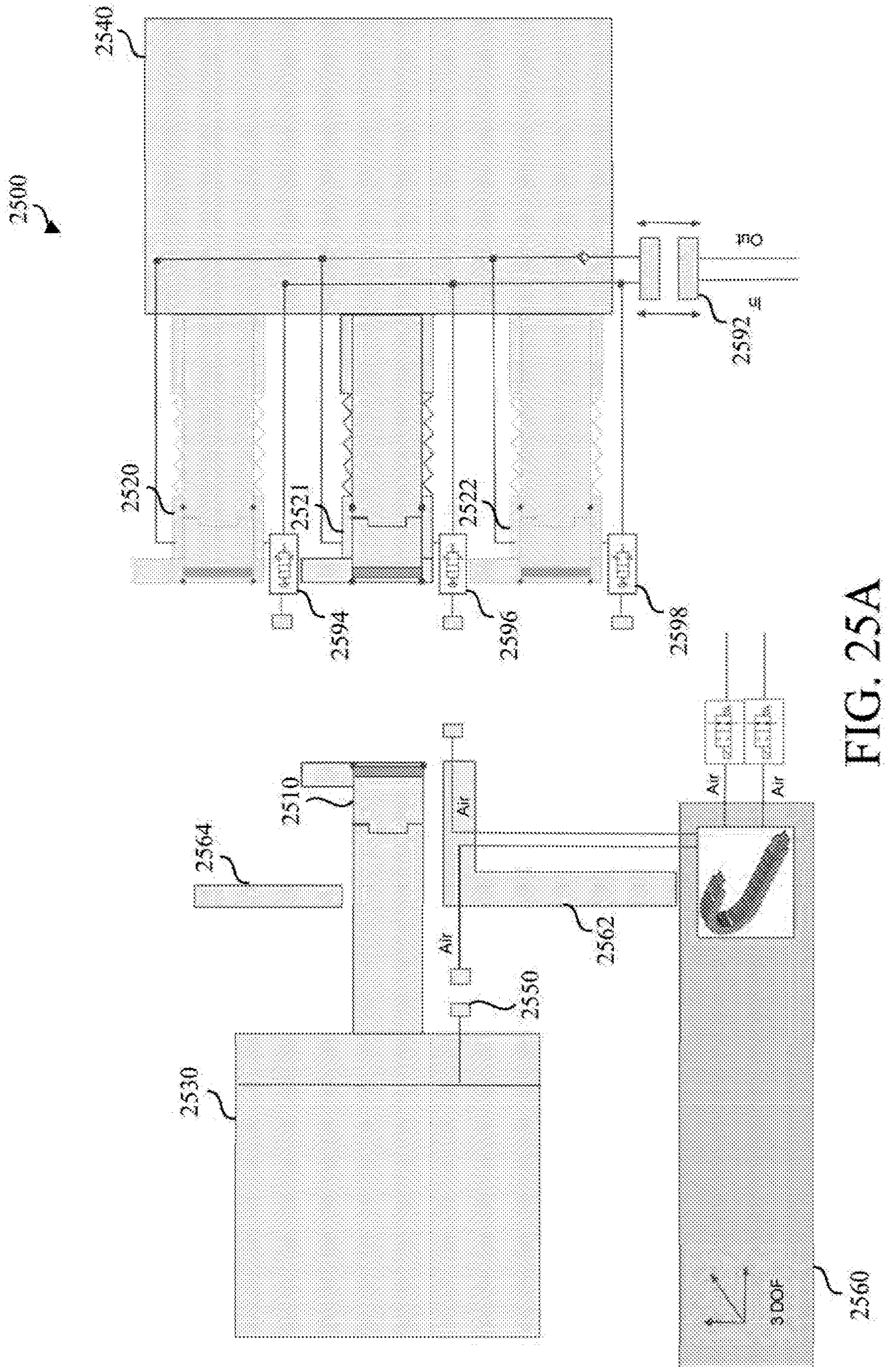
FIG. 25A is a block diagram of an illustrative variation of a fluid connector system.

In some variations, a plurality of second connectors may comprise one or more pneumatic sterilant valves and a sterilant path through a fluid device. FIG. 25A is a block diagram of an illustrative variation of a fluid connector system 2500 comprising a first connector 2510, a plurality of second connectors 2520, 2521, 2522, a first fluid device 2530 (e.g., sterile liquid transfer device), a second fluid device 2540 (e.g., consumable), a robot 2560, and a sterilant switch 2592 coupled to a sterilant source (not shown). The first connector 2510 may be coupled in fluid communication with the first fluid device 2530, and the second connectors 2520, 2521, 2522 may be coupled in fluid communication with the second fluid device 2540.

In some variations, each of the second connectors 2520, 2521, 2522, may comprise a respective pneumatic sterilant port 2594, 2596, 2598 comprising a valve coupled to a distal end of the second connector 2520, 2521, 2522. In some variations, a sterilant conduit may be routed from the switch 2592 through the second fluid device 2540 to a respective sterilant port 2594, 2596, 2598. In some variations, a sterilant source (not shown) may be coupled to the switch 2592. The switch 2592 may be coupled to each of the second connectors 2520, 2521, 2522 via the sterilant ports 2594, 2596, 2598 in order to facilitate efficient and shared fluidic connections between the fluid device, fluid connector, and sterilization system.

The robot 2560 may comprise one or more end effectors 2562, 2564 configured to manipulate and/or couple to one or more of the first fluid device 2530, first connector 2510, and sterilant ports 2594, 2596, 2598. For example, the first fluid device 2530 may comprise one or more fluid ports 2550 configured to couple to an end effector 2562. Similarly, sterilant ports 2594, 2596, 2598 may be configured to couple to the end effector 2562 to pneumatically actuate the sterilant ports 2594, 2596, 2598. A pneumatically actuated sterilant port may enable the sterilant conduit to be formed with a fewer number of check valves between the sterilant ports 2594, 2596, 2598 and switch 2592.

Figure 25C:
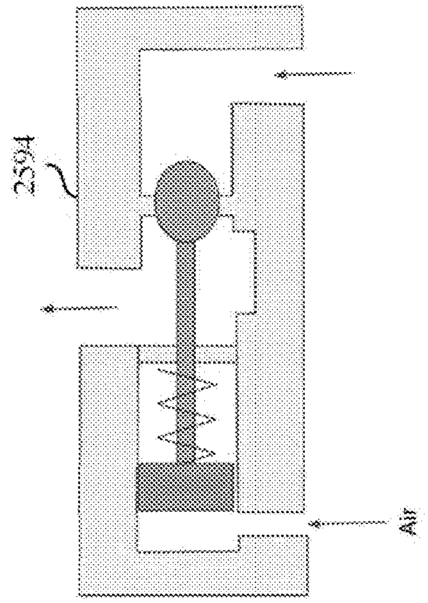
FIG. 25C is a schematic diagram of an illustrative variation of a valve.
Figure 25B:
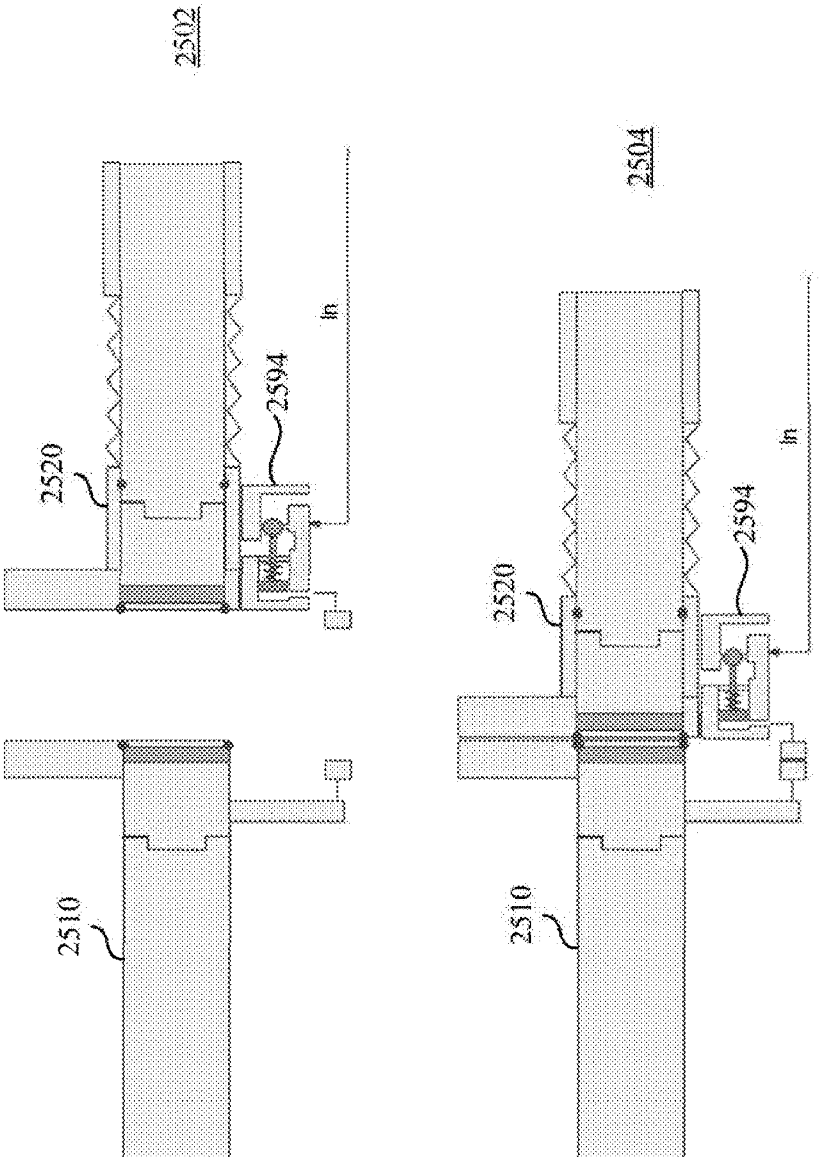
FIG. 25B is a schematic diagram of an illustrative variation of a fluid connector connection process.

FIG. 25B are schematic diagrams of a fluid connector connection process 2502 and 2504, where a first connector 2510 is coupled to a second connector 2520. For example, the sterilant port 2594 is in a closed valve configuration when the first connector 2510 and the second connector 2520 are separated and uncoupled 2502. FIG. 25C is a detailed schematic diagram of the sterilant valve 2594. In some variations, the valve 2594 may transition to an open valve configuration when the first connector 2510 is coupled to the second connector 2520 and the valve 2594 is pneumatically actuated, at 2504.

Liquid Transfer Bus

Generally, to permit transfer of one or more of a cell product (that is, solution(s) containing cell product), fluids, and reagents between the modules, the modules of the cartridge may be fluidically coupled to one another either directly or via one or more liquid transfer buses. In some variations, a liquid transfer bus may comprise a portion of the cartridge configured to control the flow and distribution of the cell product between modules and reservoirs. A liquid transfer bus may comprise one or more of a fluid manifold, fluid conduit (e.g., tubing), and one or more valves (including but not limited to 2/2 valves, 3/2 valves, 3/3 valves, 4/2 valves, and rotary selector valves).

Transfer of the cell product, reagents, or fluids within the cartridge may be achieved by any pump or other structure that generates a pressure differential between fluid in one portion of the cartridge and fluid in another portion of the cartridge. For example, the cartridge may comprise one or more pump; the cartridge may be pre-loaded with pressurized fluid contained behind a valve; the cartridge may be connected to a fluid source or a fluid sink. The cartridge may contain one or more mechanical pumps (e.g., linear pump, peristaltic pump, gear pump, screw pump, plunger pump) or portions of a pump (i.e. the pump may interface with a pump actuator). External pressure may be applied to the cartridge, to tubing within the cartridge, or to a bag within the cartridge (that is, applying pressure either to the liquid in the bag or to headspace gas of the bag). In some variations, an arrangement of the components of the cartridge may facilitate gravity-based fluid transfer within the cartridge (e.g., gravity-fed pumping). Although one advantage of the disclosed variations may be reduced operator intervention, the systems and methods of the disclosure may use manual operation in the designed workflow or as an adjunct to automated operation in case of imperfect automated system operation. For example, a process step may include manual intervention, such as fluid input or output. An operator may intervene in an automated process to correct device operation, (e.g. manually compressing a bag to flush remaining fluid into the system). Fluid may comprise liquid and/or gas, as compressed gases supplied externally or provided in pressurized chambers may be used to generate liquid flow, e.g., transfer of solution containing a cell product from one module to another.

In some variations, the liquid transfer bus may be configured to deliver the cell product(s) to each of a series of modules in an order set by the design of the cartridge, or in an order determined by operation of the system by the processor or processors. Similarly stated, some variations of the cartridge may have the advantage that the order of cell processing steps as well as the process parameters for any of the cell therapy processing steps may not be set by the cartridge but rather are controlled by the controller. In some variations, the liquid transfer bus may be controlled to deliver the cell product to the modules in any of various sequences, or to bypass one or more modules (e.g., by configuring the state of the valve(s) attached to the fluidic bus). In some variations, a module may be used more than once in a method of cell processing. Optionally, the method may comprise performing one or more wash steps. For example, a counterflow centrifugal elutriation (CCE) module may be used more than once. In an illustrative method, the method comprises culturing the cell product in a first bioreactor module, transferring the cell product to the CCE module to enrich for a desired cell type, transferring the cell product to a second bioreactor module for a second culturing step, washing the CCE module using a wash solution, and transferring the cell product to the CCE module for a second enrichment step.

In some variations, the liquid transfer bus or the liquid transfer buses may be fluidically coupled to multiple bags or reservoirs used to provide solutions or reagents, store cell products, or to collect waste solutions or reagents.

Figure 26A:
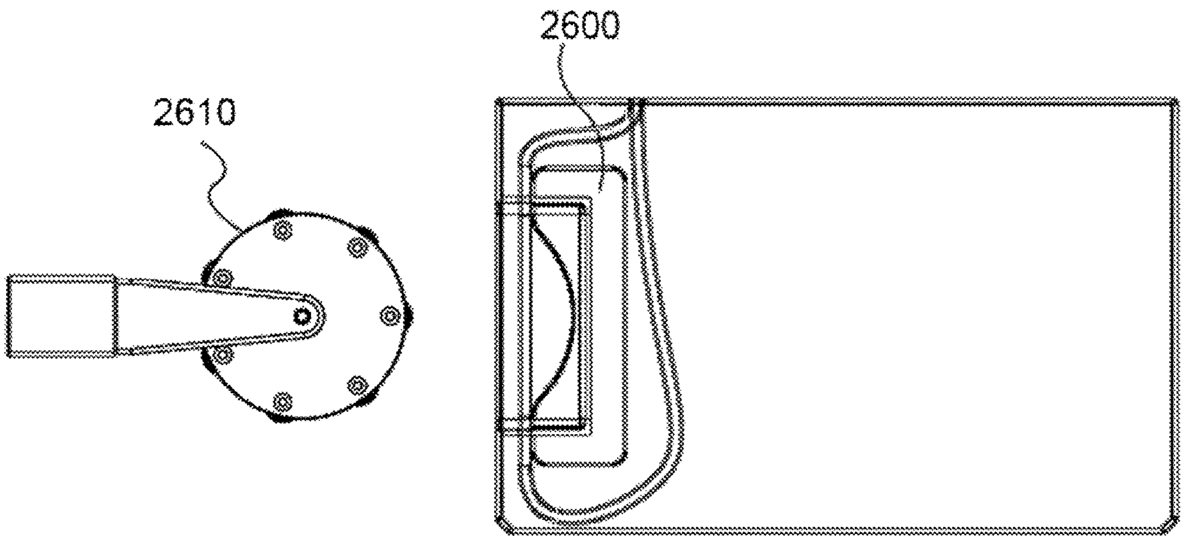
FIG. 26A is a side view of an illustrative variation of a pump actuator and pump.
Figure 26B:
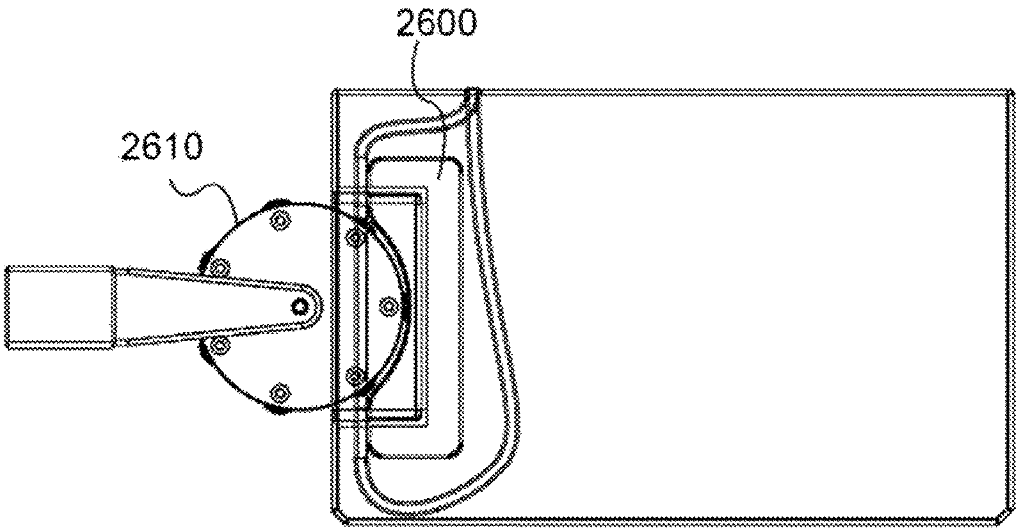
FIG. 26B is a side view of an illustrative variation of a pump actuator coupled to a pump.

In some variations, the cartridge may comprise one or more pumps, which may be fluidically coupled to the liquid transfer bus and/or one or more modules. The pump(s) may include a motor operatively coupled to control circuits and a power source (e.g. a battery or electrical connectors for an off-cartridge power source). In some variations, the pump may be divided into a pump on the cartridge and pump actuators on one or more instruments of the system. The pump may be an opening in the cartridge with tubing arranged around the circumference of the opening and configured to receive a pump actuator (e.g., a peristaltic rotor). By dividing components of the pump that contact the cell product (i.e. tubing) from components of the pump that perform operations of the cell product, (i.e. the pump actuator, e.g., peristaltic rotor), the cartridge may be compact and simplified. For example, FIG. 26A and FIG. 26B illustrate a pump head 2610 and a pump 2610 of a cartridge in an uncoupled configuration (FIG. 13A) and a coupled configuration.

In some variations, one or more pumps 146 (e.g., fluid pump) may generate a predetermined fluid flow rate to circulate a sterilant and/or fluid. In some variations, a pump may comprise one or more of a positive displacement pump (e.g., peristaltic pump, diaphragm pump, syringe pump), centrifugal pump, combinations thereof, and the like. One or more fluid sources may be coupled to the pump.

In some variations, the pump may be configured to receive a pump signal (generated by a controller) configured to circulate a sterilant for a dwell time sufficient to sterilize at least a portion of a fluid connector. For example, the pump may be configured to circulate the sterilant for at least 10 seconds. In some variations, the pump may be configured to receive a pump signal configured to circulate a non-sterilant gas (e.g., inert gas, air) to remove the sterilant.

In some variations, a discontinuous flow pump (e.g., peristaltic pump) may generate pulsatile flow as, for example, a tube contracts and relaxes between rollers. In some variations, closed loop feedback from a flow sensor may be used to compensate for pulsatile flow to generate a substantially continuous flow rate. For example, a flow sensor may be coupled to a fluid conduit to measure the flow rate. A controller may receive the measured flow rate and generate a pump signal to the pump based on a proportional correction function configured to reduce the "ripples" measured by the flow sensor. Additionally or alternatively, a controller may apply periodic error correction to a pump signal to reduce periodic error that may be unique to each pump. For example, a flow sensor may measure and determine a periodic error of a pump. A pump signal comprising the periodic error correction may correspond to a waveform comprising an inverse shape of the error. The resulting pump flow may correct for fluctuations in flow rate.

Controller

In some variations, a system 100 may comprise a controller 120 (e.g., computing device) comprising one or more of a processor 122, memory 124, communication device, 126, input device 128, and display 130. The controller 120 may be configured to control (e.g., operate) the workcell 110. The controller 120 may comprise a plurality of devices. For example, the workcell 110 may enclose one or more components of the controller 120 (e.g., processor 122, memory 124, communication device 126) while one or more components of the controller 120 may be provided remotely to the workcell 110 (e.g., input device 128, display 130).

Processor

The processor (e.g., processor 122) described here may process data and/or other signals to control one or more components of the system (e.g., workcell 110, controller 120). The processor may be configured to receive, process, compile, compute, store, access, read, write, and/or transmit data and/or other signals. Additionally, or alternatively, the processor may be configured to control one or more components of a device and/or one or more components of controller (e.g., console, touchscreen, personal computer, laptop, tablet, server).

In some variations, the processor may be configured to access or receive data and/or other signals from one or more of workcell 110, server, controller 120, and a storage medium (e.g., memory, flash drive, memory card, database). In some variations, the processor may be any suitable processing device configured to run and/or execute a set of instructions or code and may include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data transfer), and/or central processing units (CPU). The processor may be, for example, a general purpose processor, Field Programmable Gate Array (FPGA), an Application Specific Integrated Circuit (ASIC), a processor board, and/or the like. The processor may be configured to run and/or execute application processes and/or other modules, processes and/or functions associated with the system. The underlying device technologies may be provided in a variety of component types (e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and the like.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including structured text, typescript, C, C++, C#, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code Memory The cell processing systems and devices described here may include a memory (e.g., memory 124) configured to store data and/or information. In some variations, the memory may include one or more of a random access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some variations, the memory may store instructions to cause the processor to execute modules, processes, and/or functions associated with the device, such as image processing, image display, sensor data, data and/or signal transmission, data and/or signal reception, and/or communication. Some variations described herein may relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The computer code (also may be referred to as code or algorithm) may be those designed and constructed for the specific purpose or purposes. In some variations, the memory may be configured to store any received data and/or data generated by the controller and/or workcell. In some variations, the memory may be configured to store data temporarily or permanently Input Device In some variations, the display may include and/or be operatively coupled to an input device 128 (e.g., touch screen) configured to receive input data from a user. For example, user input to an input device 128 (e.g., keyboard, buttons, touch screen) may be received and processed by a processor (e.g., processor 122) and memory (e.g., memory 124) of the system 100. The input device may include at least one switch configured to generate a user input. For example, an input device may include a touch surface for a user to provide input (e.g., finger contact to the touch surface) corresponding to a user input. An input device including a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device including at least one switch, a switch may have, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive user movement data from an optical sensor and classify a user gesture as a user input. A microphone may receive audio data and recognize a user voice as a user input.

In some variations, the cell processing system may optionally include one more output devices in addition to the display, such as, for example, an audio device and haptic device. An audio device may audibly output any system data, alarms, and/or notifications. For example, the audio device may output an audible alarm when a malfunction is detected. In some variations, an audio device may include at least one of a speaker, piezoelectric audio device, magnetostrictive speaker, and/or digital speaker. In some variations, a user may communicate with other users using the audio device and a communication channel. For example, a user may form an audio communication channel (e.g., VoIP call).

Additionally or alternatively, the system may include a haptic device configured to provide additional sensory output (e.g., force feedback) to the user. For example, a haptic device may generate a tactile response (e.g., vibration) to confirm user input to an input device (e.g., touch surface). As another example, haptic feedback may notify that user input is overridden by the processor.

Communication Device

In some variations, the controller may include a communication device (e.g., communication device 126) configured to communicate with another controller and one or more databases. The communication device may be configured to connect the controller to another system (e.g., Internet, remote server, database, workcell) by wired or wireless connection. In some variations, the system may be in communication with other devices via one or more wired and/or wireless networks. In some variations, the communication device may include a radiofrequency receiver, transmitter, and/or optical (e.g., infrared) receiver and transmitter configured to communicate with one or more devices and/or networks. The communication device may communicate by wires and/or wirelessly.

The communication device may include RF circuitry configured to receive and send RF signals. The RF circuitry may convert electrical signals to/from electromagnetic signals and communicate with communications networks and other communications devices via the electromagnetic signals. The RF circuitry may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth.

Wireless communication through any of the devices may use any of plurality of communication standards, protocols and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), voice over Internet Protocol (VOIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), EtherCAT, OPC Unified Architecture, or any other suitable communication protocol. In some variations, the devices herein may directly communicate with each other without transmitting data through a network (e.g., through NFC, Bluetooth, WiFi, RFID, and the like).

In some variations, the systems, devices, and methods described herein may be in communication with other wireless devices via, for example, one or more networks, each of which may be any type of network (e.g., wired network, wireless network). The communication may or may not be encrypted. A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication.

Display

Image data may be output on a display e.g., display 130) of a cell processing system. In some variations, a display may include at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

II. Methods

Figure 28:
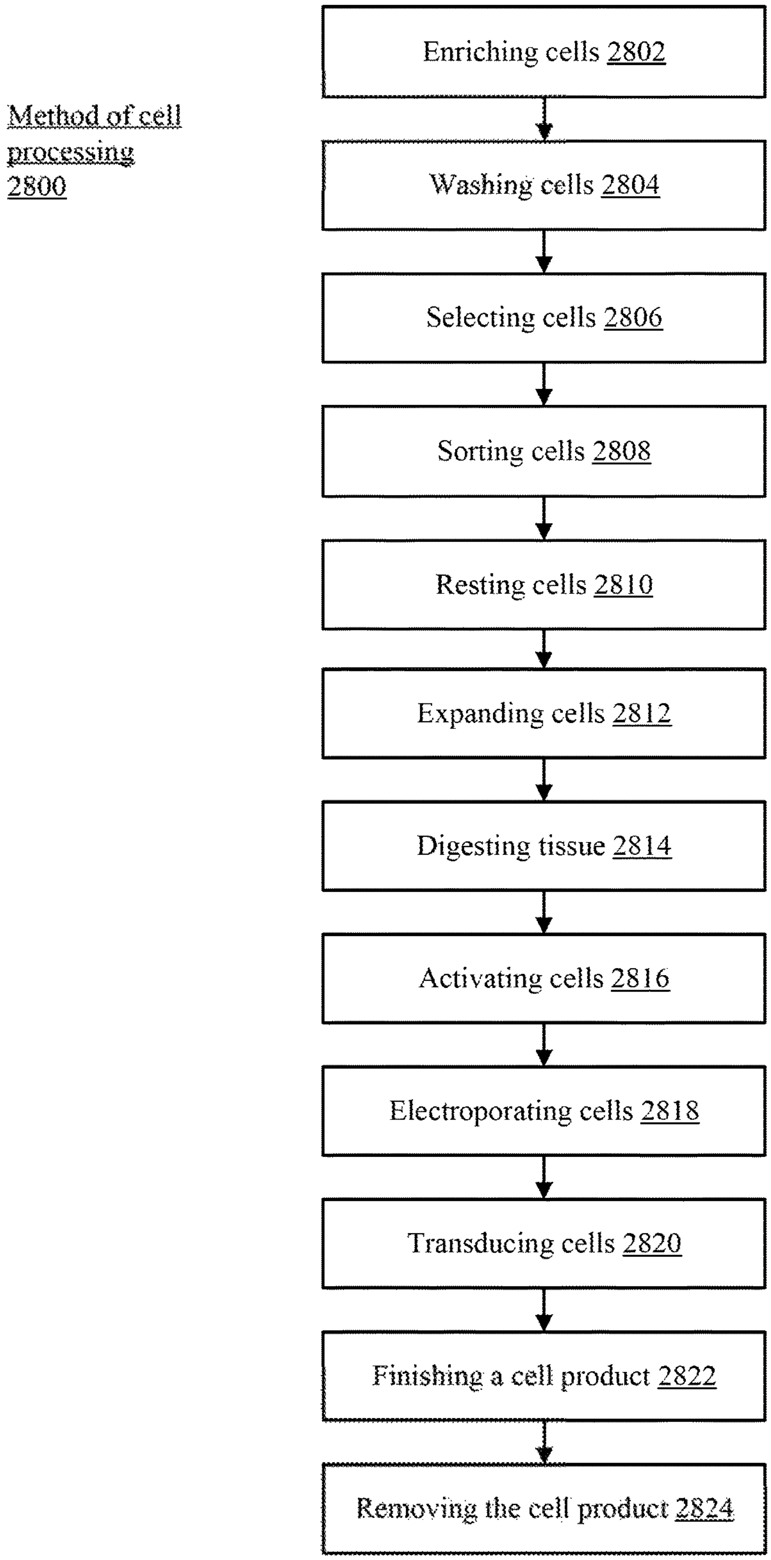
FIG. 28 is a flowchart of an illustrative variation of a method of cell processing.

Generally, the systems and devices described herein may perform one or more cell processing steps to manufacture a cell product. FIG. 28 is a flowchart of a method of cell processing 2800. The method 2800 may include enriching a selected population of cells in a solution (e.g., fluid) 2802. For example, the solution may be conveyed to a CCE module of a cartridge via a liquid transfer bus. A robot may be operated to move the cartridge to a CCE instrument so that the CCE module interfaces with the CCE instrument. The CCE instrument may be operated to cause the CCE module to enrich the selected population of cells. Additionally or alternatively, the cell product may be introduced into and out of the cartridge via a sterile liquid transfer port (either manually or automatically) for any of the steps described herein. In some variations, the cartridge may be sterilized in a feedthrough port (either manually or automatically).

In some variations, a selected population of cells in the solution may be washed 2804. For example, the solution may be conveyed to the CCE module of the cartridge via the liquid transfer bus. A robot may be operated to move the cartridge to the CCE instrument so that the CCE module interfaces with the CCE instrument. The CCE instrument may be operated to cause the CCE module to remove media from the solution, introduce media into the solution, and/or replace media in the solution.

In some variations, a population of cells in the solution may be selected 2806. For example, the solution may be conveyed to a selection module of the cartridge via the liquid transfer bus. The robot may be operated to move the cartridge to a selection instrument so that the selection module interfaces with the selection instrument. The selection instrument may be operated to cause the selection module to select the selected population of cells.

In some variations, a population of cells in the solution may be sorted 2808. For example, the solution may be conveyed to a sorting module of the cartridge via the liquid transfer bus. The robot may be operated to move the cartridge to a sorting instrument so that the sorting module interfaces with the sorting instrument. The sorting instrument may be operated to cause the sorting module to sort the population of cells.

In some variations, the solution may be conveyed to a bioreactor module of the cartridge via the liquid transfer bus to rest 2810. For example, the robot may be operated to move the cartridge to a bioreactor instrument so that a bioreactor module interfaces with the bioreactor instrument. The bioreactor instrument may be operated to cause the bioreactor module to maintain the cells at a set of predetermined conditions.

In some variations, the cells may be expanded in the solution 2812. For example, the solution may be conveyed to the bioreactor module of the cartridge via the liquid transfer bus. The robot may be operated to move the cartridge to the bioreactor instrument so that the bioreactor module interfaces with the bioreactor instrument. The bioreactor instrument may be operated to cause the bioreactor module to expand the cells by cellular replication.

In some variations, tissue may be digested by conveying an enzyme reagent via the liquid transfer bus to a module containing a solution containing a tissue such that the tissue releases a select cell population into the solution 2814.

In some variations, a selected population of cells in the solution may be activated by conveying an activating reagent via the liquid transfer bus to a module containing the solution containing the cell product 2816.

In some variations, the solution may be conveyed to an electroporation module of the cartridge via the liquid transfer bus and receive an electroporation signal to electroporate the cells in the solution 2818. For example, the robot may be operated to move the cartridge to an electroporation instrument so that the electroporation module interfaces with the electroporation instrument. The electroporation instrument may be operated to cause the electroporation module to electroporate the selected population of cells in the presence of genetic material.

In some variations, an effective amount of a vector may be conveyed via the liquid transfer bus to a module containing the solution containing the cell product, thereby transducing a selected population of cells in the solution 2820.

In some variations, a formulation solution may be conveyed via the liquid transfer bus to a module containing the cell product to generate a finished cell product 2822. For example, the finished cell product may be conveyed to one or more product collection bags. In some variations, finishing a cell product may comprise one or more steps of washing cells, concentrating cells, exchanging a buffer of the cells with a formulation buffer, and dosing cells in the formulation buffer in predetermined quantities into one or more product collection bags and/or vessels.

In some variations, the cell product may be removed, either manually or automatically, from the cartridge to harvest the cells 2824.

In some variations, the cell product may comprise one or more of an immune cell genetically engineered chimeric antigen receptor T cell, a genetically engineered T cell receptor (TCR) cell, a hematopoietic stem cell (HSC), and a tumor infiltrating lymphocyte (TIL). In some variations, the immune cell may comprise a natural-killer (NK) cell.

Methods of cell processing may include a subset of cell processing steps in any suitable order. For example, the method of cell processing may include, in order, the enrichment step 2802, the selection step 2806, the activation step 2816, the transduction step 2820, the expansion step 2812, and the harvesting step 2824. In some variations, the method of cell processing may include, in order, the enrichment step 2802, the selection step 2806, the resting step 2810, the transduction step 2820, and the harvesting step 2824. In some variations, the method of cell processing may include, in order, the tissue-digestion step 2820, the washing step 2804, the activation step 2816, the expansion step 2812, and the harvesting step 2824.

Generally, the methods described herein may offload the complex steps performed in cell processing operation to a set of instruments, thereby reducing the cost of the cartridge (which may be a consumable). In some variations, the cartridge may contain the cell product (e.g., solution containing cells) throughout a manufacturing process, with different instruments interfacing with the cartridge at appropriate times to perform one or more cell processing steps. For example, a cell processing step may comprise conveying cells and reagents to each of the modules within the cartridge. A set of instruments interfacing with a cartridge facilitates process flexibility where a workcell may be customized with a predetermined set of instruments for a predetermined cell therapy product. For example, the order of cell processing steps may be customized for each cell product as described in more detail herein with respect to FIGS. 35-55.

In some variations, a cell product may be retained within the cartridge throughout a manufacturing process (e.g., workflow). Additionally or alternatively, the cell product may be removed from the cartridge for one or more cell processing steps, either manually by an operator, or automatically through a fluid connector (e.g., SLTP) or other access ports on the cartridge. The cell product may then be returned to the same cartridge, transferred to another cartridge, or split among several cartridges. In some variations, one or more cell processing steps may be performed outside the cartridge. In some variations, processing within the workcell may facilitate sterile cell processing within the cartridge.

Figure 29:
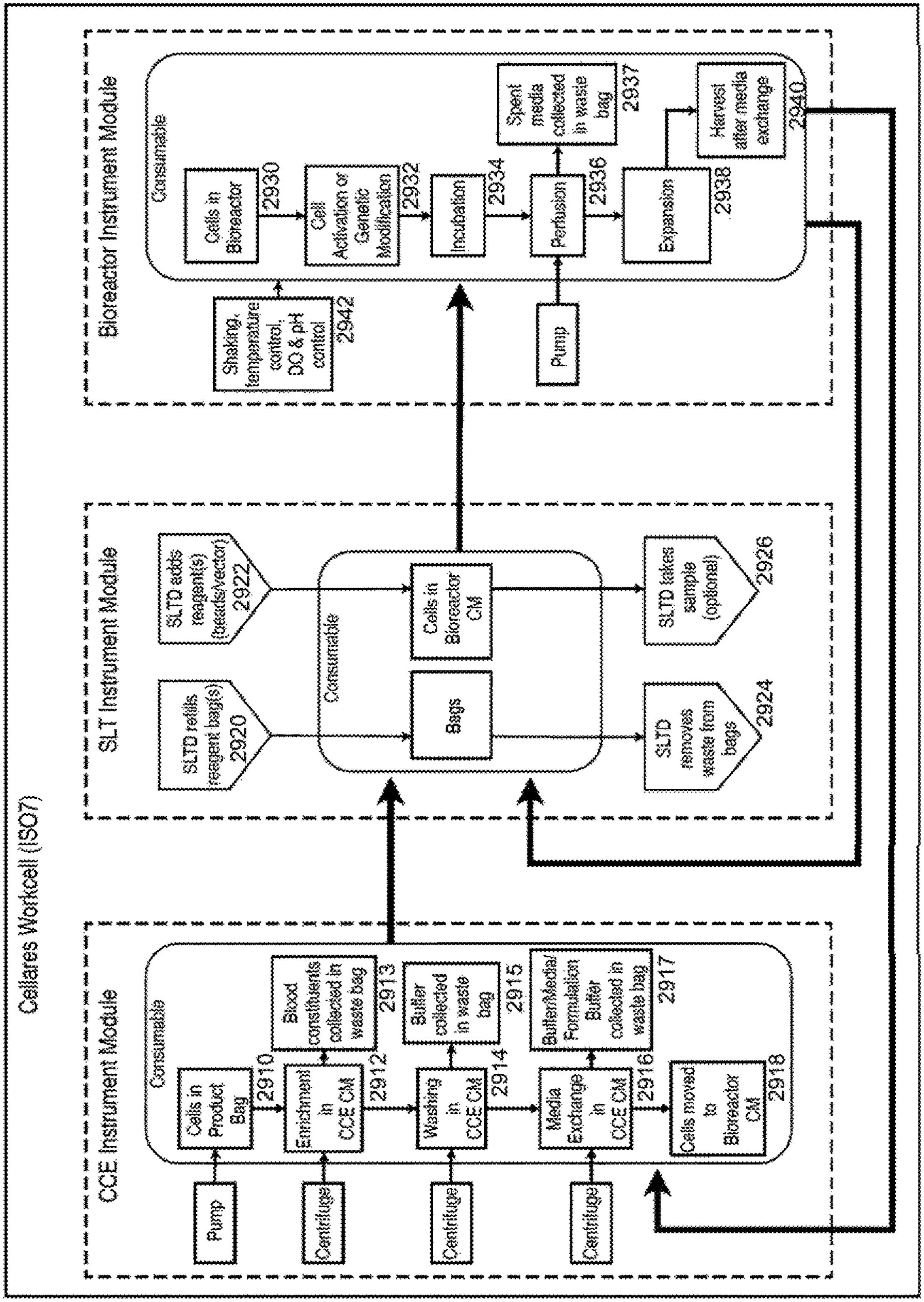
FIG. 29 is a flowchart of an illustrative variation of a method of cell processing.

FIG. 29 is a flowchart of a method of cell processing and illustrates cell processing steps performed on a cartridge (e.g., consumable) within a workcell including a CCE instrument module, a sterile liquid transfer (SLT) instrument module, and a bioreactor instrument module. The consumable may be configured to interface with any of the CCE instrument module, SLT instrument module, and bioreactor instrument module to perform one or more cell processing steps. For example, a robot (or operator) may be configured to move a cartridge between any of the modules of the workcell. A pump head in an instrument may engage the consumable cartridge in order to convey fluids between the modules of the cartridge, into or out of various reservoirs in the cartridge, and/or through ports that permit reagents to be added or removed from the cartridge.

In some variations, the CCE instrument module may comprise a pump and centrifuge configured to interface with a cartridge (e.g., consumable). The SLT instrument module may comprise one or more fluid connectors be configured to interface with one or more of a bag and bioreactor of a cartridge. The bioreactor instrument module may comprise one or more sensors, temperature regulators, pumps, agitators, and the like, and be configured to interface with the cartridge. In some variations, the cell product may be contained within the cartridge throughout cell processing.

A method of cell processing depicted in FIG. 29 may include moving a fluid (e.g., cells in solution) in a product bag to a CCE module (e.g., rotor) of a cartridge (e.g., consumable) using a pump 2910. In some variations, the fluid may be enriched using the CCE module 2912. For example, blood constituents may be collected in a waste bag 2913. In some variations, the fluid may be washed using the CCE module 2914. For example, buffer may be collected in a waste bag 2915. In some variations, media may be exchanged using the CCE module 2916. For example, one or more of buffer (e.g., formulation buffer) and media may be collected in a waste bag 2917. In some variations, fluid may be moved to a bioreactor of the cartridge 2918.

In some variations, a fluid connector may fill a bag with a reagent 2920. In some variations, a reagent (e.g., bead, vector) may be added to a bioreactor of a cartridge 2922. In some variations, a fluid connector removes waste from a bag 2924. In some variations, a fluid connector may optionally remove a sample from a bioreactor.

In some variations, cells may be moved to a bioreactor 2930. In some variations, the cells may undergo activation or genetic modification 2932. In some variations, the cells may undergo incubation 2934. In some variations, the cells may undergo perfusion using a pump 2936. For example, spent media may be collected in a waste bag 2937. In some variations, cells may undergo expansion 2938. In some variations, cells may be harvested after media exchange 2940.

Figure 30A:
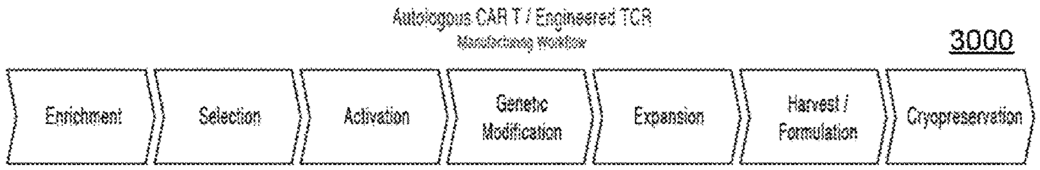
FIG. 30A is a flowchart of an illustrative variation of a method of cell processing for autologous CAR T cells or engineered TCR cells.
Figure 30B:
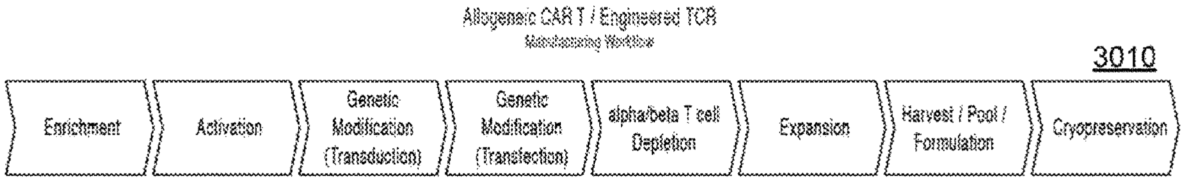
FIG. 30B is a flowchart of an illustrative variation of a method of cell processing for allogeneic CAR T cells or engineered TCR cells.

FIG. 30A is a flowchart of a method of cell processing for autologous CAR T cells or engineered TCR cells. The method 3000 may comprise the steps of enrichment, selection, activation, genetic modification, expansion, harvest/formulation, and cryopreservation. FIG. 30B is a flowchart of a method of cell processing for allogeneic CAR T cells or engineered TCR cells. The method 3010 may comprise the steps of enrichment, activation, genetic modification (e.g., transduction, transfection), alpha/beta T cell depletion, expansion, harvest/pool/formulation, and cryopreservation.

Figure 31:
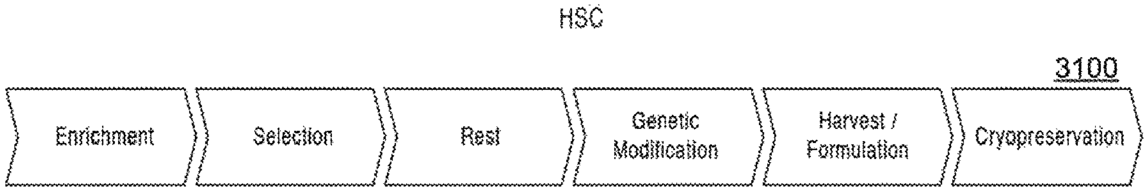
FIG. 31 is a flowchart of an illustrative variation of a method of cell processing for HSC cells.

FIG. 31 is a flowchart of a method of cell processing for hematopoietic stem cell (HSC) cells. The method 3100 may comprise the steps of enrichment, selection, rest, genetic modification, harvest/formulation, and cryopreservation.

Figure 32:
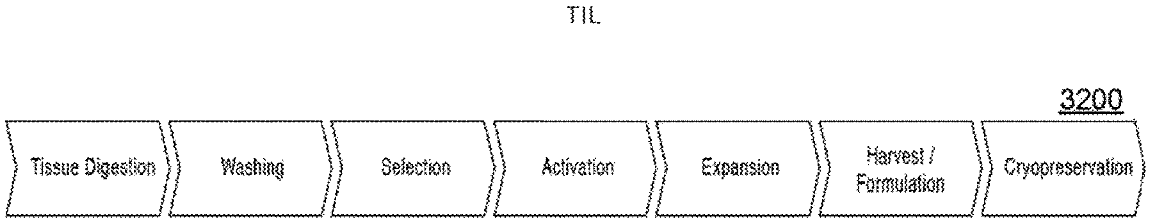
FIG. 32 is a flowchart of an illustrative variation of a method of cell processing for TIL cells.

FIG. 32 is a flowchart of a method of cell processing for tumor infiltrating lymphocyte (TIL) cells. The method 3200 may comprise the steps of tissue digestion, washing, selection, activation, expansion, harvest/formulation, and cryopreservation.

Figure 33:
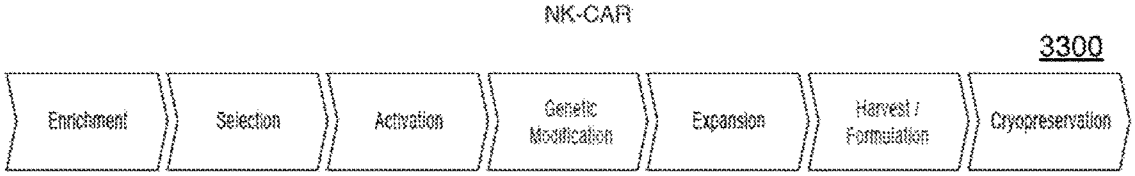
FIG. 33 is a flowchart of an illustrative variation of a method of cell processing for NK-CAR cells.

FIG. 33 is a flowchart of a method of cell processing for natural killing (NK) CAR cells. The method 3300 may comprise the steps of enrichment, selection, activation, genetic modification, expansion, harvest/formulation, and cryopreservation.

Figure 34A:
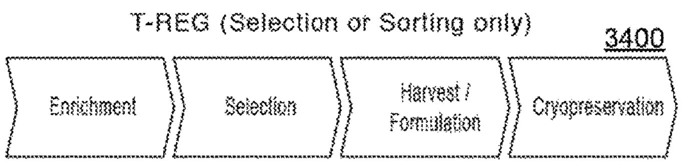
FIGS. 34A-34C are flowcharts of illustrative variations of methods of cell processing for Treg cells.
Figure 34B:
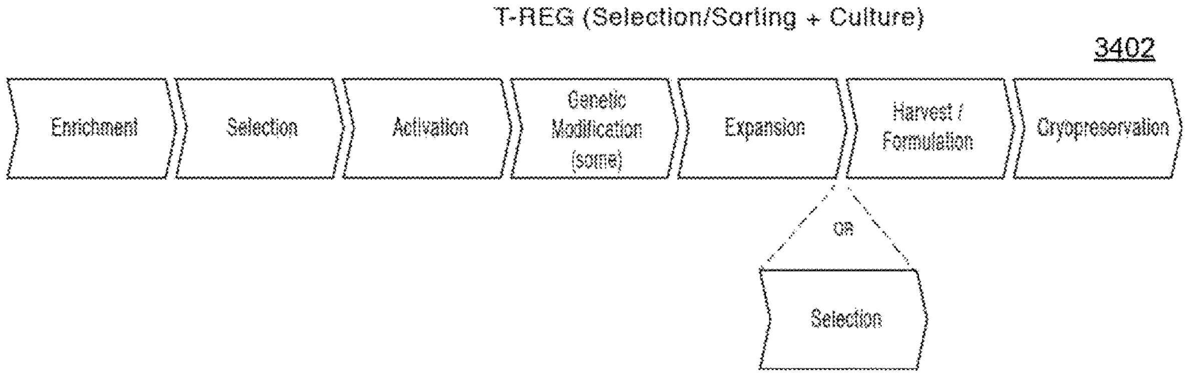
Figure 34C:
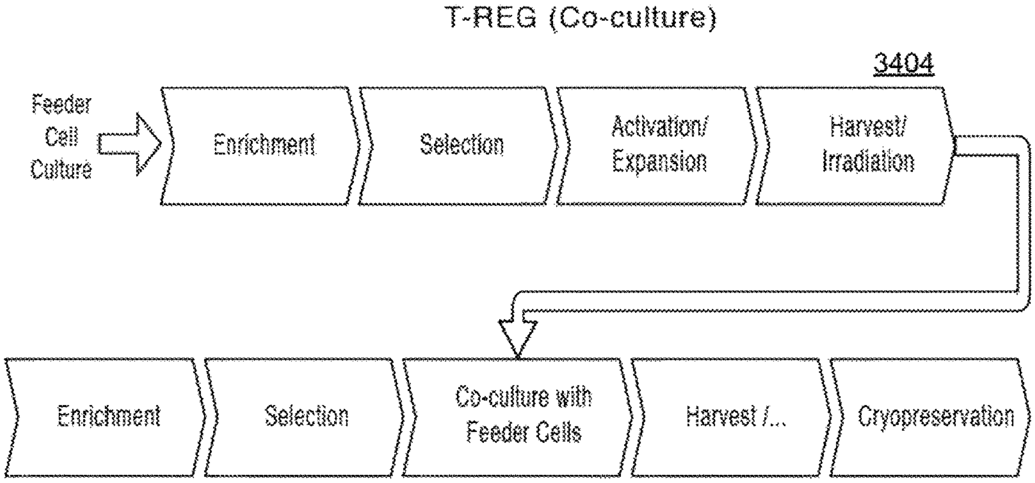

FIGS. 34A-34C are flowcharts of methods of cell processing for regulatory T (Treg) cells. The method 3400 may comprise the steps of enrichment, selection, harvest/formulation, cryopreservation. The method 3402 may comprise the steps of enrichment, selection, activation, genetic modification, expansion, selection (optionally), harvest/formulation, and cryopreservation. The method 3404 may comprise the steps of introducing feeder cell culture for enrichment, selection, activation/expansion, and harvest/irradiation. Another set of cells may undergo enrichment, selection, co-culture with the processed feeder cells, harvest, and cryopreservation.

FIGS. 98-101 are flowcharts of methods of cell processing for cell therapy workflows comprising split (e.g., parallel) processing. The method 9800 may comprise the steps of enrichment, selection, activation, genetic modification, expansion, formulation, and cryopreservation. For example, a cell processing method 9800 (e.g., workflow) may comprise splitting a cell product into two or more portions after an enrichment step. The split portions may be processed in parallel within a single cartridge. In some variations, one or more split portions may be transferred to two or more cartridges and processed in parallel. One or more cell processing parameters (e.g., timing of process steps, types of reagents added, transfection constructs, and the like) may be configured independently for each split portion of the cell product. In some variations, the split portions may be pooled after the expansion step.

The method 9900 may comprise the steps of enrichment, selection, activation, genetic modification, expansion, formulation, and cryopreservation. For example, a cell processing method 9900 (e.g., workflow) may comprise splitting a cell product into two or more portions after an activation step. The split portions may be processed in parallel within a single cartridge. In some variations, one or more split portions may be transferred to two or more cartridges and processed in parallel. One or more cell processing parameters (e.g., timing of process steps, types of reagents added, transfection constructs, and the like) may be configured independently for each split portion of the cell product. In some variations, the split portions may be pooled after the expansion step and/or the genetic modification step.

The method 10000 may comprise the steps of enrichment, selection, activation, genetic modification, expansion, formulation, and cryopreservation. For example, a cell processing method 10000 (e.g., workflow) may comprise splitting a cell product into two or more portions aftera selection step. The split portions may be processed in parallel within a single cartridge. In some variations, one or more split portions may be transferred to two or more cartridges and processed in parallel. One or more cell processing parameters (e.g., timing of process steps, types of reagents added, transfection constructs, and the like) may be configured independently for each split portion of the cell product. In some variations, the split portions may not be pooled.

The method 10100 may comprise the steps of enrichment, selection, activation, genetic modification, expansion, formulation, and cryopreservation. For example, a cell processing method 10100 (e.g., workflow) may comprise splitting a cell product into two or more portions as starting materials. The separate products may remain segregated and processed in parallel as split portions within a single cartridge or a plurality of cartridges. One or more cell processing parameters (e.g., timing of process steps, types of reagents added, transfection constructs, and the like) may be configured independently for each split portion. In some variations, the split portions may be pooled after the expansion step.

Figure 102:
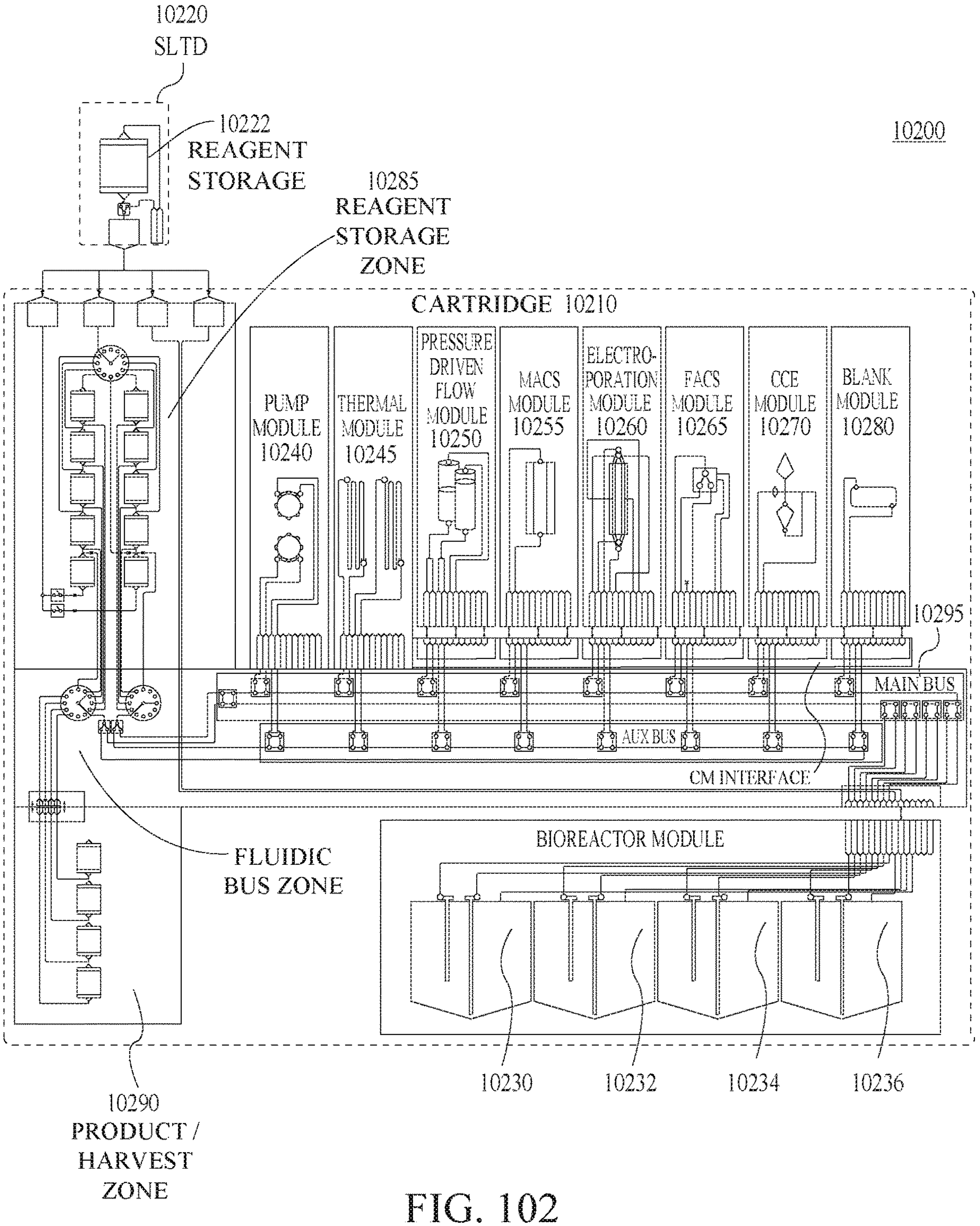
FIG. 102 is a schematic diagram of an illustrative variation of a cell processing system.

FIG. 102 is a schematic diagram of a cell processing system 10200 configured for split processing within a single cartridge. For example, the methods 9800-10100 described with respect to FIGS. 98-101 may be performed within the cartridge 10210. In some variations, the system 10200 may comprise a sterile liquid transfer device 10220 comprising a reagent 10222, and a cartridge 10210 comprising a plurality of bioreactor modules 10230, a pump module 10240, a thermal module 10245, a pressure driven flow module 10250, a MACS module 10255, an electroporation module 10260, a FACS module 10265, a CCE module 10270, and a blank module 10280. The cartridge 10210 may further comprise a reagent storage 10285, a plurality of product bags 10290, and a liquid transfer bus 10295. The liquid transfer bus 10295 may be configured to couple the components of the cartridge 10210 for fluid communication.

In some variations, loading and removing of cell product into and out of the cartridge may be performed in the system or outside the system. In some variations, the cartridge is loaded bedside to the patient or donor and then delivered to a cell processing system in or near the hospital, or shipped to a facility where the cell processing system is installed. Likewise, the cell product may be removed from the cartridge after processing either at a facility or closer to the intended recipient of the cell product (the patient). Optionally the cell product is frozen before, during, or after the methods of the disclosure-optionally after addition of one or more cryoprotectants to the cell product. In some variations, the system comprises a freezer and/or a liquid nitrogen source. In some variations, the system comprises a water bath or a warming chamber containing gas of controlled temperature to permit controlled thawing of the cell product, e.g. a water bath set to between about 20° C. and about 40° C. In some variations, the cartridge is made of materials that resistant mechanical damage when frozen.

Automated Cell Processing

Described here are methods of transforming user-defined cell processing operations into cell processing steps using the automated cell processing systems and devices described herein. In some variations, cell processing operations are received and transformed into cell processing steps to be performed by the system given a set of predetermined constraints. For example, a user may input a set of biologic process steps and corresponding biologic process parameters to be executed by a cell processing system. Optionally, process parameters may be customized for each cartridge or sets of cartridges.

Figure 35:
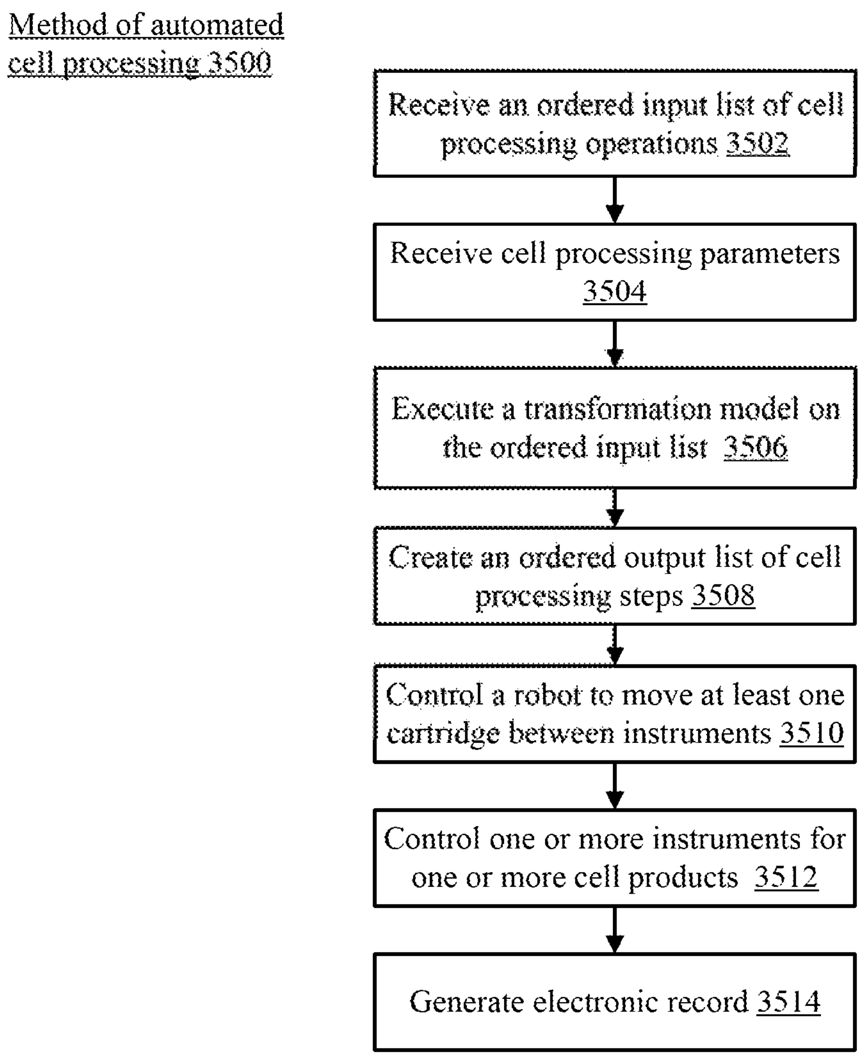
FIG. 35 is a flowchart of an illustrative variation of a method of cell processing.
Figure 52:
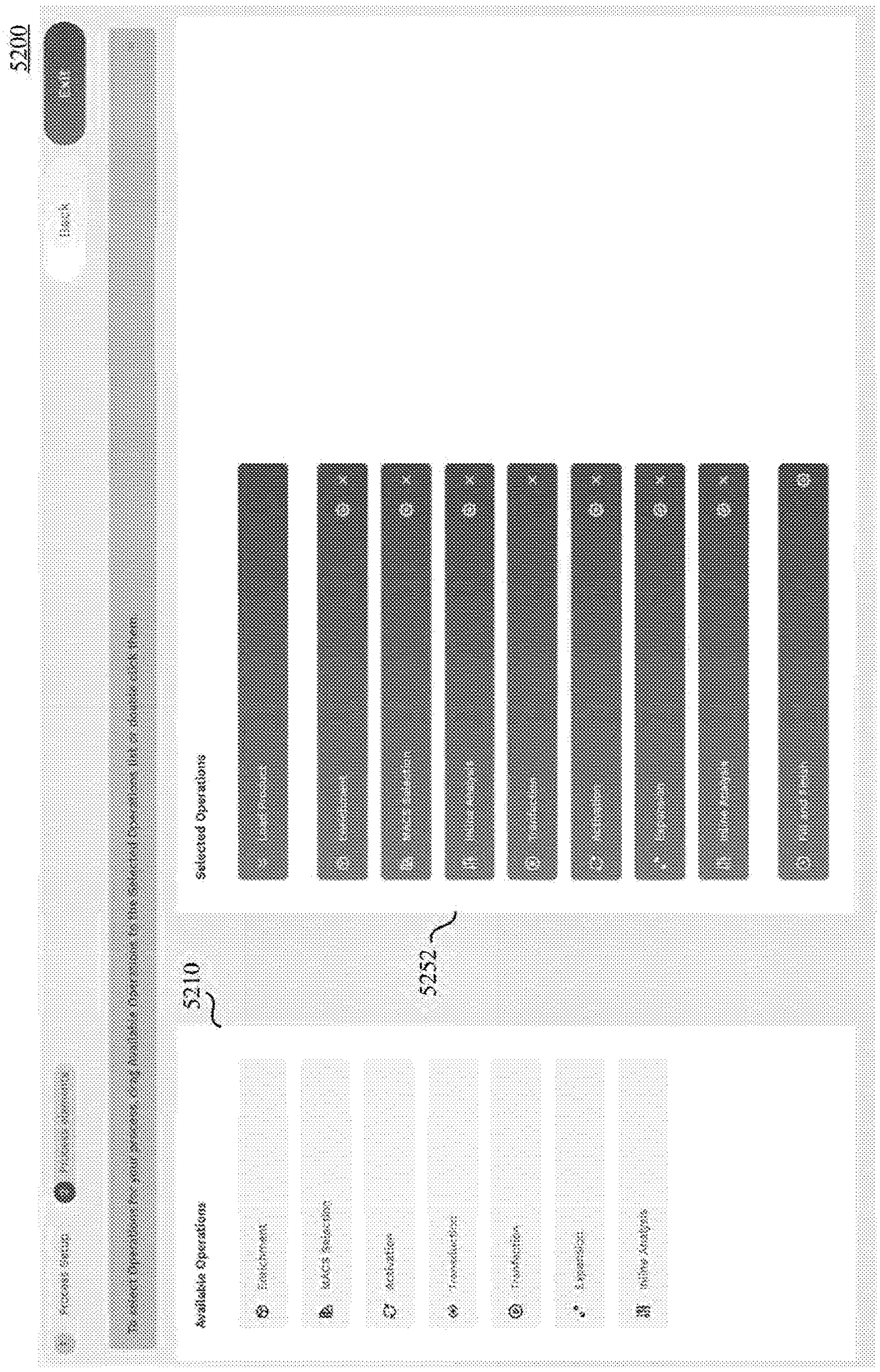
FIG. 52 is an illustrative variation of a graphical user interface relating to a filled process operations.

FIG. 35 is a flowchart that generally describes a variation of a method of automated cell processing. The method 3500 may include receiving an ordered input list of cell processing operations 3502. For example, a set of more than one ordered input list of cell processing operations may be received to be performed on more than one cartridge on an automated cell processing system. For example, as shown in the GUI 4900 of FIG. 49 and described in more detail herein, one or more biologic process inputs (e.g., available operations) such as enrichment, MACS selection, activation, transduction, transfection, expansion, and inline analysis may be selected as an ordered input list of cell processing operations. Furthermore, GUI 5200 of FIG. 52 illustrates a complete ordered input list of cell processing operations (e.g., set of selected operations) 5220 selected by a user.

Figure 40:
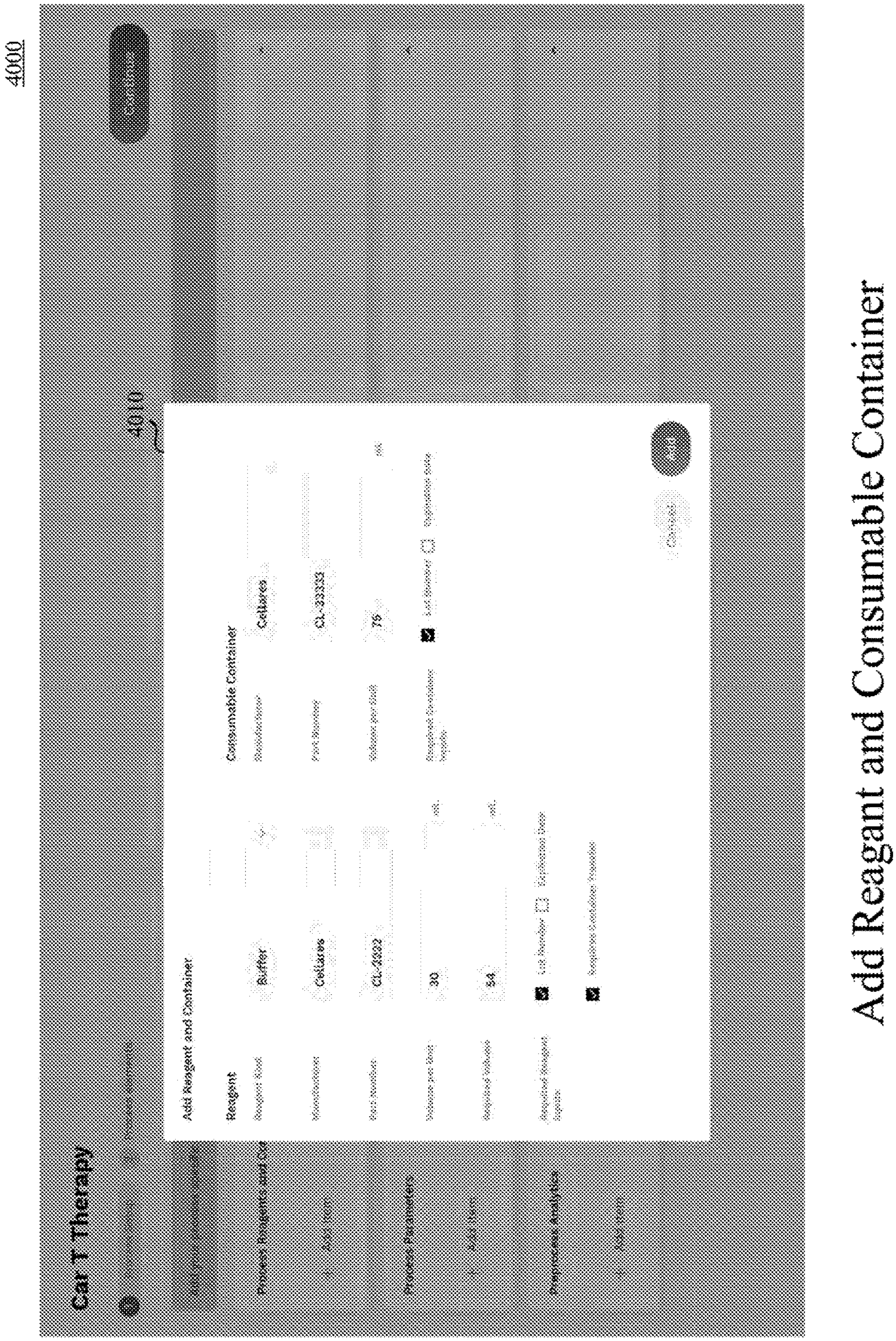
FIG. 40 is an illustrative variation of a graphical user interface relating to adding a reagent and a consumable container.
Figure 42:
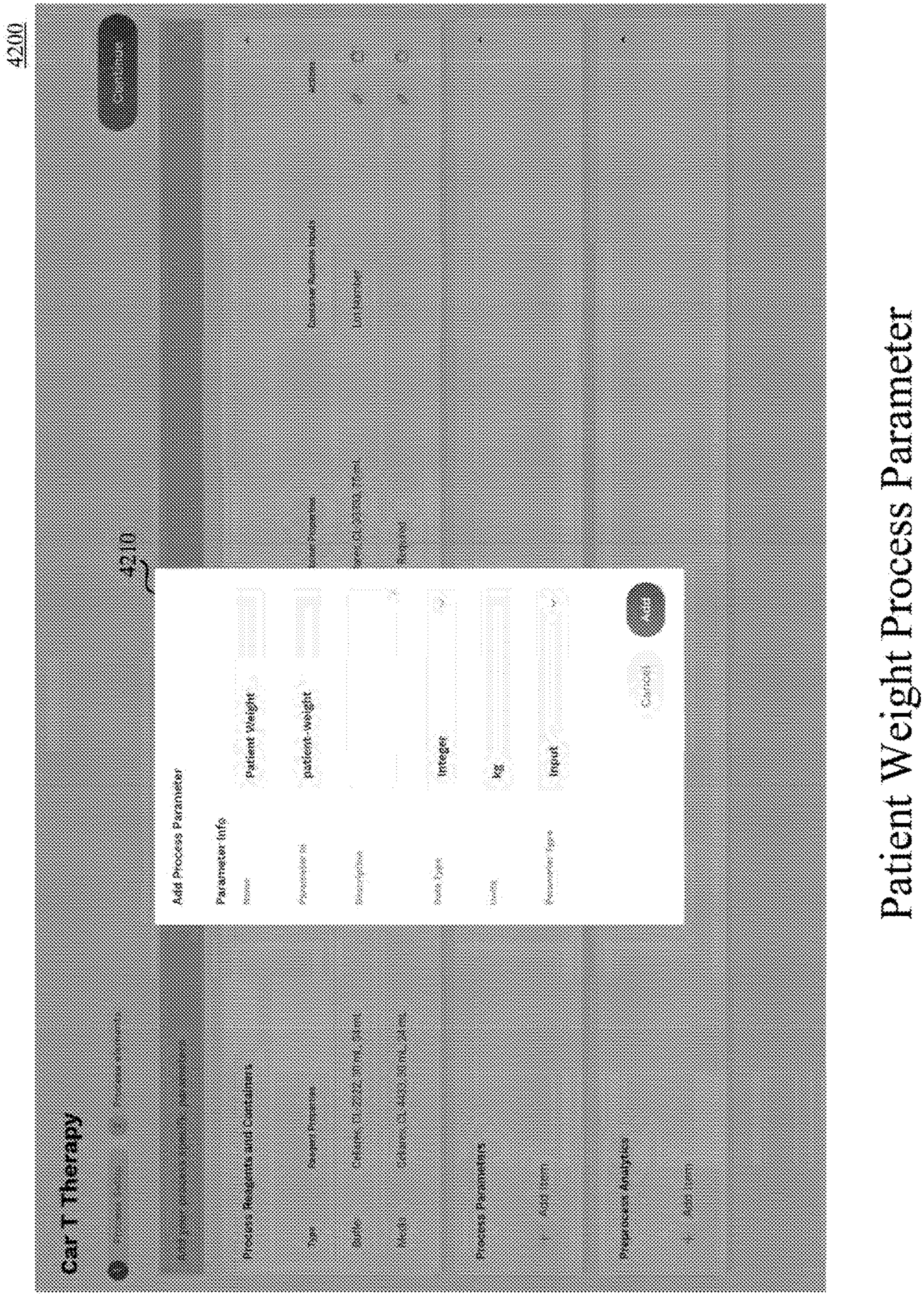
FIG. 42 is an illustrative variation of a graphical user interface relating to a patient weight process parameter.
Figure 44:
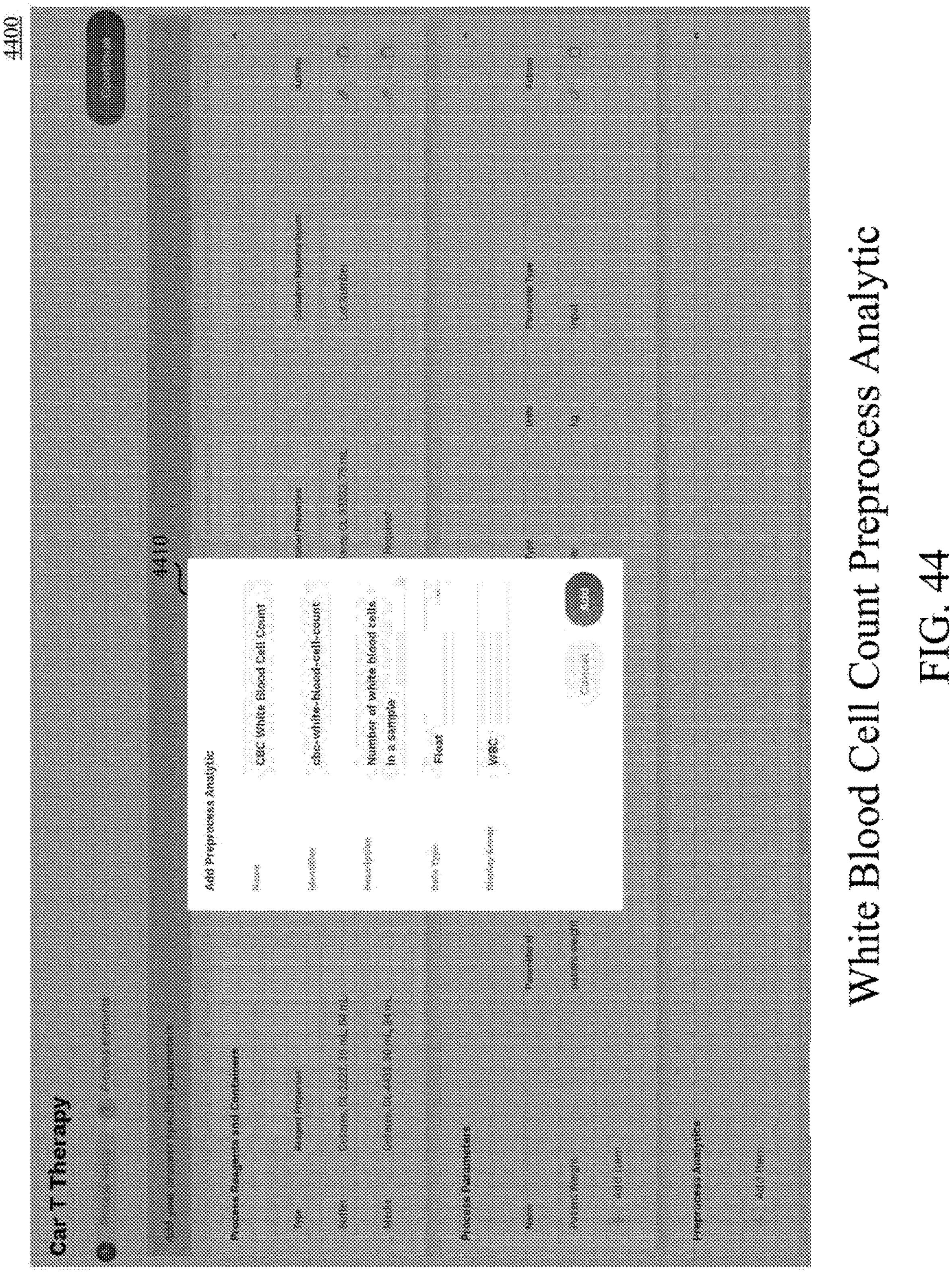
FIG. 44 is an illustrative variation of a graphical user interface relating to a white blood cell count preprocess analytic.
Figure 48:
FIG. 48 is an illustrative variation of a graphical user interface relating to a filled process operations activation settings.

In some variations, one or more sets of cell processing parameters may be received 3504. Each set of cell processing parameters may be associated with one of the cell processing operations. Each set of cell processing parameters may specify characteristics of the cell processing step to be performed by the instrument at that cell processing step. For example, the GUI 4000 of FIG. 40 illustrates reagent and container parameters, the GUI 4200 of FIG. 42 illustrates an example of a process parameter, the GUI 4400 of FIG. 44 illustrates an example of a preprocess analytic, and the GUI 4800 of FIG. 48 illustrates an example of a set of activation settings.

In some variations, a transformation model may be executed on the ordered input list 3506. In some variations, the transformation model may comprise constraints on the ordered output list determined by a predetermined configuration of the automated cell processing system. For example, the constraints may comprise information on the configuration of the automated cell processing system.

In some variations, the constraints may comprise one or more of a type and/or number and/or state of instruments, a type and/or number and/or state of modules on the cartridge, a type and/or number of reservoirs on the cartridge, a type and/or number of sterile liquid transfer ports on the cartridge, and number and position of fluid paths between the modules, reservoirs, and sterile liquid transfer ports on the cartridge.

In some variations, a set of predetermined constraints may be placed on a set of the process control parameters. For example, the volume and/or the type of reagents used may be constrained based on the size of the system and/or products manufactured. Other process parameter constraints may include, but is not limited to, one or more or temperature, volume, time, pH, cell size, cell number, cell density, cell viability, dissolved oxygen, glucose levels, volumes of onboard reagent storage and waste, combinations thereof, and the like. For example, the GUI 4000 of FIG. 40 depicts that a reagent has a volume per unit of 30 ml and a required volume of 54 ml, and a consumable container has a volume per unit of 75 ml. The GUI 4800 of FIG. 48 depicts that an activation concentration is 12 mg/L, an activation culture time is 1600 seconds, activation temperature is 18° C., and a gas mix includes 21% oxygen, 78.06% nitrogen, and 0.04% of carbon dioxide. These constraints may be applied by a transformation model to generate an ordered output list of cell processing steps that affect how one or more of the robot, instrument, and cartridge are operated and the cell product manufactured.

In some variations, the order of operations may be constrained based on hardware constraints. For example, the robot may be limited to moving one cartridge at a time. Similarly, an instrument may be constrained to operating on a predetermined number of cartridges at once.

Figure 49:
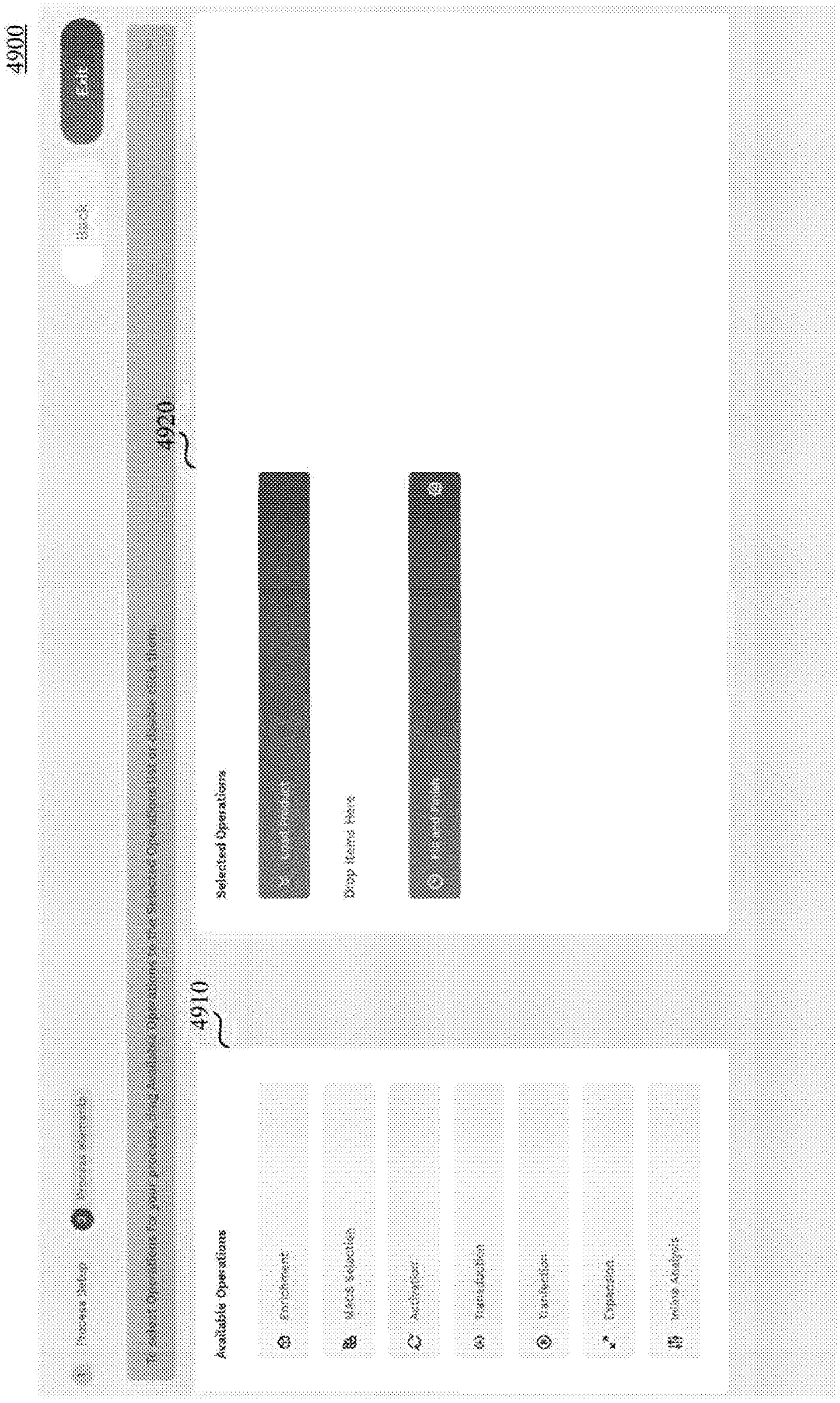
FIG. 49 is an illustrative variation of a graphical user interface relating to an initial process operations.

In some variations, as illustrated in the GUI 4900 of FIG. 49, a load product operation must be the first operation performed, and may be performed once for each process. A fill and finish operation may always be the last operation performed before product completion, and may be performed once for each process.

In some variation, the system may prevent the user from executing a set of operations in an order that cannot be performed by the system.

In some variations, a notification (e.g., warning, alert) may be output if a user orders a set of operations in a "non-standard" manner. For example, a notification may be output if the same type of operation is repeated sequentially (e.g., enrichment immediately followed by enrichment). Similarly, a notification may be output if an operation (e.g., selection, activation) is used two times or more within a given process when such an operation is typically used just once in a given process.

In some variations, an output of the transformation model may correspond to an ordered output list of cell processing steps capable of being performed by the system 3508. For example, the transformation model may be executed on the sets of ordered input lists to create the ordered output list of cell processing steps. The output list of cell processing steps may control a robot, cartridge, and one or more instruments.

In some variations, the ordered output list is performed by the system to control a robot to move one or more cartridges each containing a cell product between the instruments 3510. For example, the MACS selection process selected by the user may correspond to the robot 230 of FIG. 2 moving the cartridge 250 to the cell selection instrument 216 from, for example, another instrument. In some variations, the ordered output list may comprise instructions for a robot to load a cartridge (e.g., single use consumable) into the cell processing system (e.g., workcell). Furthermore, the robot may be configured to move the cartridge to a first instrument position.

In some variations, the ordered output list is further performed by the system to control one or more of the instruments to perform one or more cell processing steps on one or more cell products 3512 of a respective cartridge. For example, the compute server rack 210 (e.g., controller 120) may be configured to control an electroporation module 220 configured to apply a pulsed electric field to a cell suspension of a cartridge 250. In some variations, the ordered output list may comprise instructions for an instrument (e.g., bioreactor) to process the product (e.g., transfer the cell product from a small bioreactor module to a large bioreactor module). Furthermore, the instrument may be further configured to operate under a set of process parameters (e.g., 9 hour duration, pH of 6.7, temperature between 37.3° C. and 37.8° C., mixing mode 3). As another example, the ordered output list may comprise instructions to operate a sterile liquid transfer module to perform one or more of removing waste from a cartridge, adding media to the cartridge, and adding a MACS reagent to the cartridge.

In some variations, one or more electronic batch records may be generated 3514 based on the process parameters and data collected from sensors during process execution. Batch records generated by the system may include process parameters, time logging, sensor measurements from the instruments, QC parameters determined by QC instrumentation, and other records.

Figure 36:
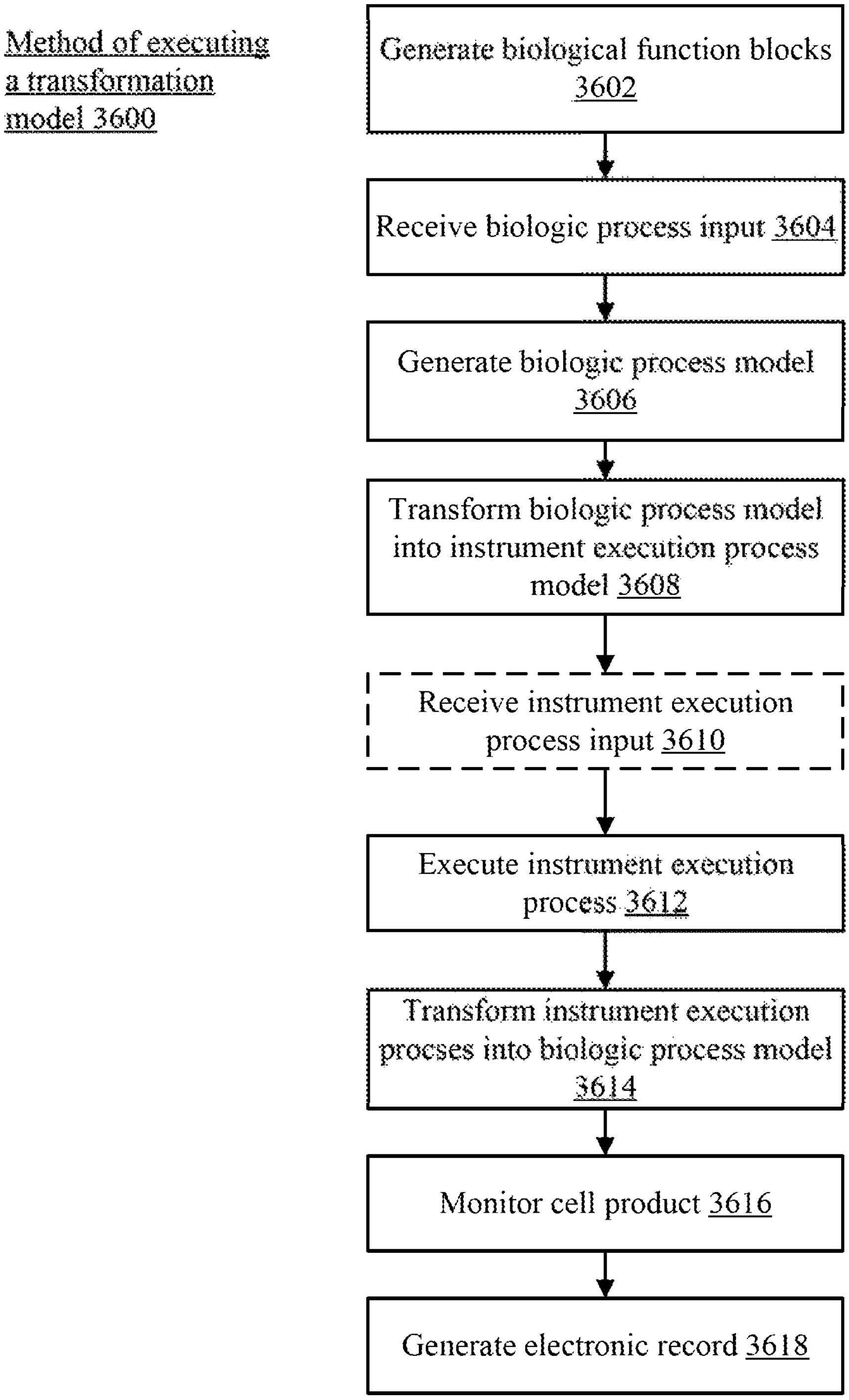
FIG. 36 is a flowchart of an illustrative variation of a method of executing a transformation model.

FIG. 36 is a flowchart that generally describes a variation of a method of executing a transformation model 3600. In some variations, one or more biological functions may be generated and output to a user. For example, a set of configurable biological function blocks may be displayed on a graphical user interface for user selection. The GUI may enable a user to select and order the biological function blocks and define biological control parameters. One or more control parameters of the biologic function blocks may be modified by a user if desired. In some variations, one or more biologic function templates may be generated comprising a predefined sequence of biological function blocks. One or more biological control parameters of the biologic function templates may be modified by a user if desired.

In some variations, a cell processing system may be configured to receive and/or store one or more biologic function (e.g., process) inputs from the user 3604. For example, a user may select one or more predefined biological function templates.

In some variations, a biologic process model (e.g., process definition) may be generated based on the biologic process inputs 3606. In some variations, a biologic process model may include one or more of enrichment, isolation, MACS selection, FACS selection, activation, genetic modification, gene transfer, transduction, transfection, expansion, formulation (e.g., harvest, pool), cryopreservation, T cell depletion, rest, tissue digestion, washing, irradiation, co-culture, combinations thereof, and the like.

In some variations, the biologic process model may be transformed into an instrument execution process model 3608. For example, each biological function block in the biological process model may correspond to an ordered list of cell processing system operations with corresponding hardware control parameters. The instrument execution process model may comprise the sequence of hardware operations corresponding to the biologic process model. As described herein, the transformation model may comprise one or more constraints.

Optionally, in some variations, a cell processing system may be configured to receive and/or store one or more instrument execution process inputs from the user 3610. For example, a user may modify the transformed instrument execution process model if desired. The user may select specific hardware components to perform certain steps, modify timing parameters, and the like.

In some variations, the instrument execution process may be executed to generate the cell product 3612. For example, the cell processing system at run-time may process the cell product through the system as defined by the instrument execution process model.

In some variations, an instrument execution process may be executed 3612. In some variations, an instrument execution process model may be transformed back into a biologic process model 3614. This progress of the biologic process model may be output (e.g., displayed) to a user for monitoring. For example, the instrument execution process model may comprise one or more references (e.g., pointers) back to the biological process model so that run-time execution progress may be reported against the biological process model.

Figure 53:
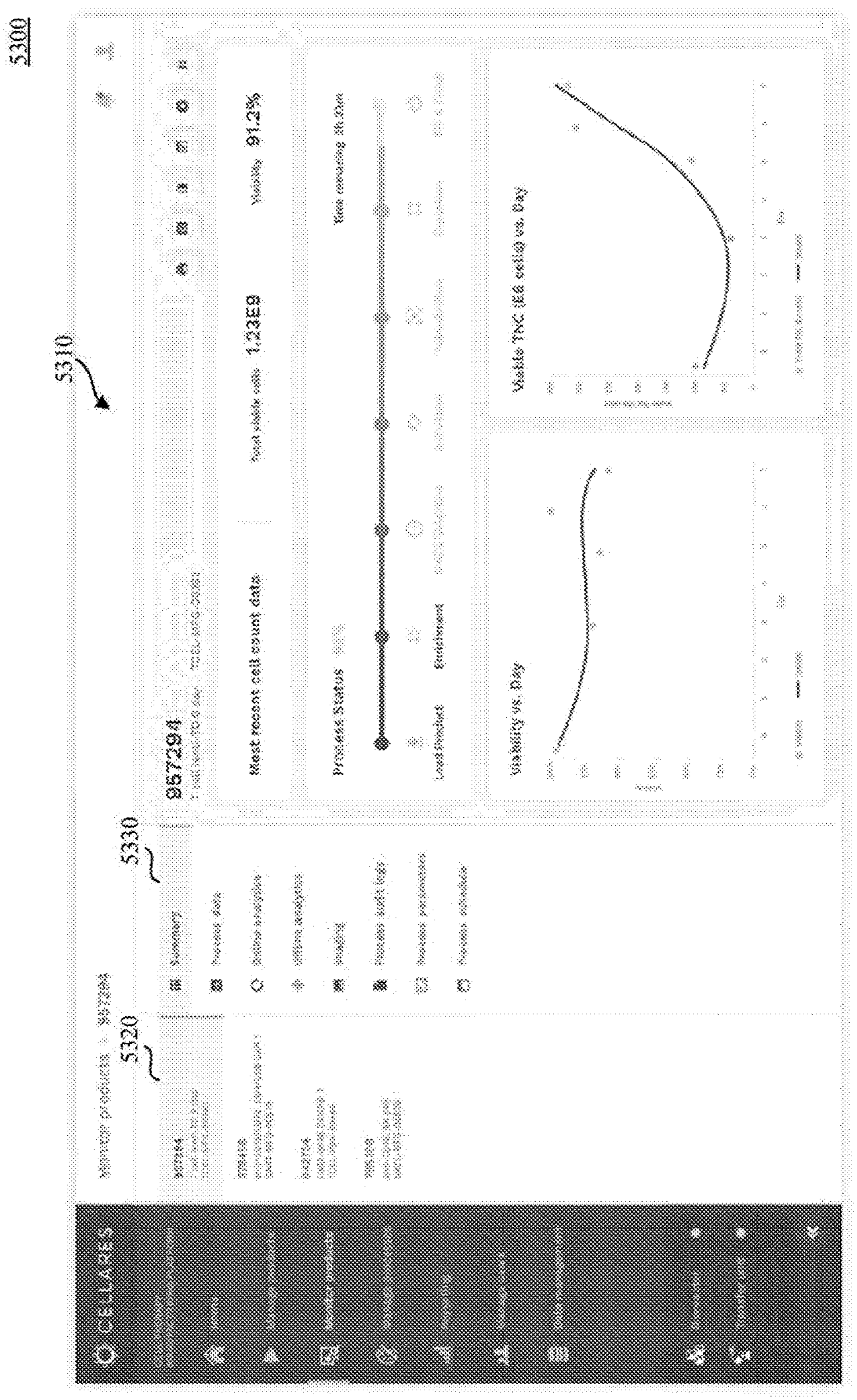
FIG. 53 is an illustrative variation of a graphical user interface relating to product monitoring.
Figure 54:
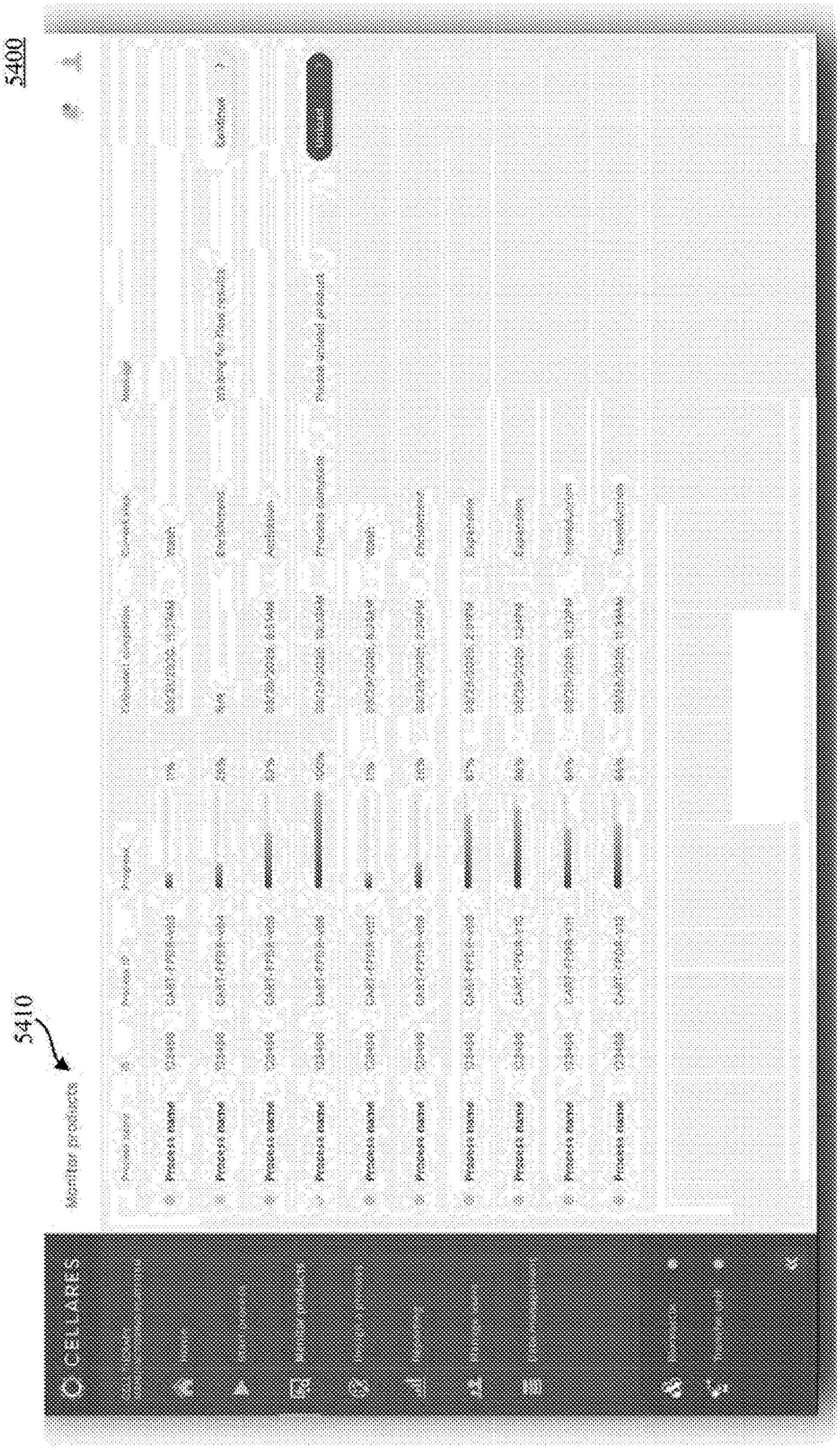
FIG. 54 is another illustrative variation of a graphical user interface relating to product monitoring.

In some variations, a cell product may be monitored 3616. For example, the GUIs 5300 and 5400 of respective FIGS. 53 and 54 illustrate sensor data monitored by the system for a plurality of products. For example, a number of viable cells and a status of a process (e.g., as a function of percentage completion) may be graphically illustrated for a user.

In some variations, an electronic record may be generated based on the monitored data 3618. For example, one or more electronic batch records may be generated in compliance with, for example, 21 CFR regulations.

Figure 55:
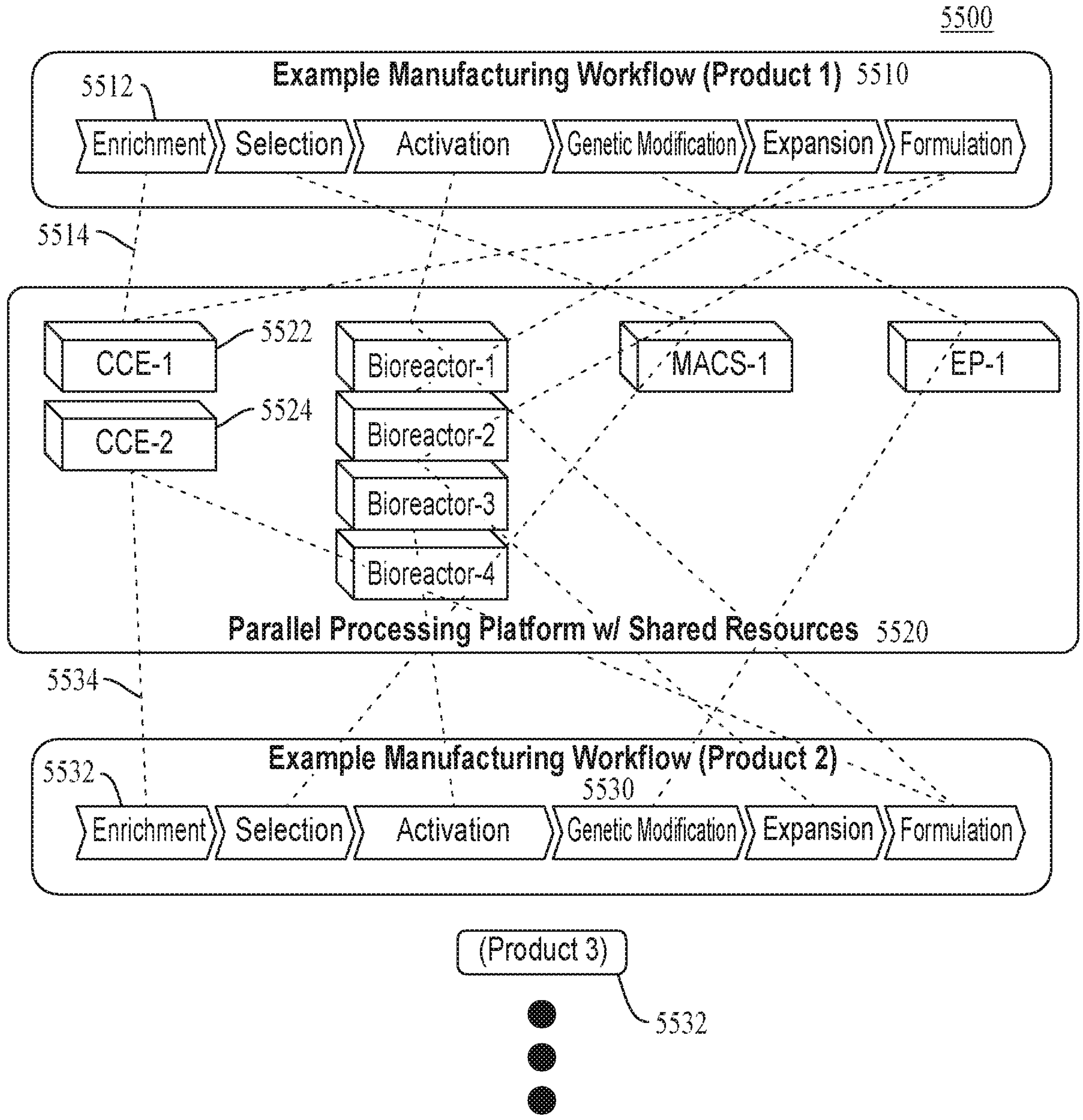
FIG. 55 is a block diagram of an illustrative variation of a manufacturing workflow.

FIG. 55 is a block diagram of an illustrative variation of a manufacturing workflow 5500 comprising a processing platform 5520 (e.g., system 100, workcell 110, 200, 201) configured to generate a plurality of cell products (e.g., first product, second product, third product) in parallel. For example, a first workflow 5510 for a first product may include a plurality of biologic processes 5512 executed in a predetermined sequence using corresponding elements 5522 (e.g., hardware) of the platform 5520. Simultaneously, a second workflow 5530 for a second product may execute a predetermined sequence of biologic processes 5530 using corresponding elements 5524 of the platform 5520. In this manner, hardware resources of the platform 5520 may be efficiently utilized to increase throughput. In some variations, about 2, 3, 4, 5, 6, 7, 8, 9, 10, or more cell products may be manufactured simultaneously on the platform 5520. The transformation model may include hardware constraints that eliminate scheduling conflicts to ensure that, for example, the same instrument is not used for different products at the same time.

Graphical User Interface

Figure 37:
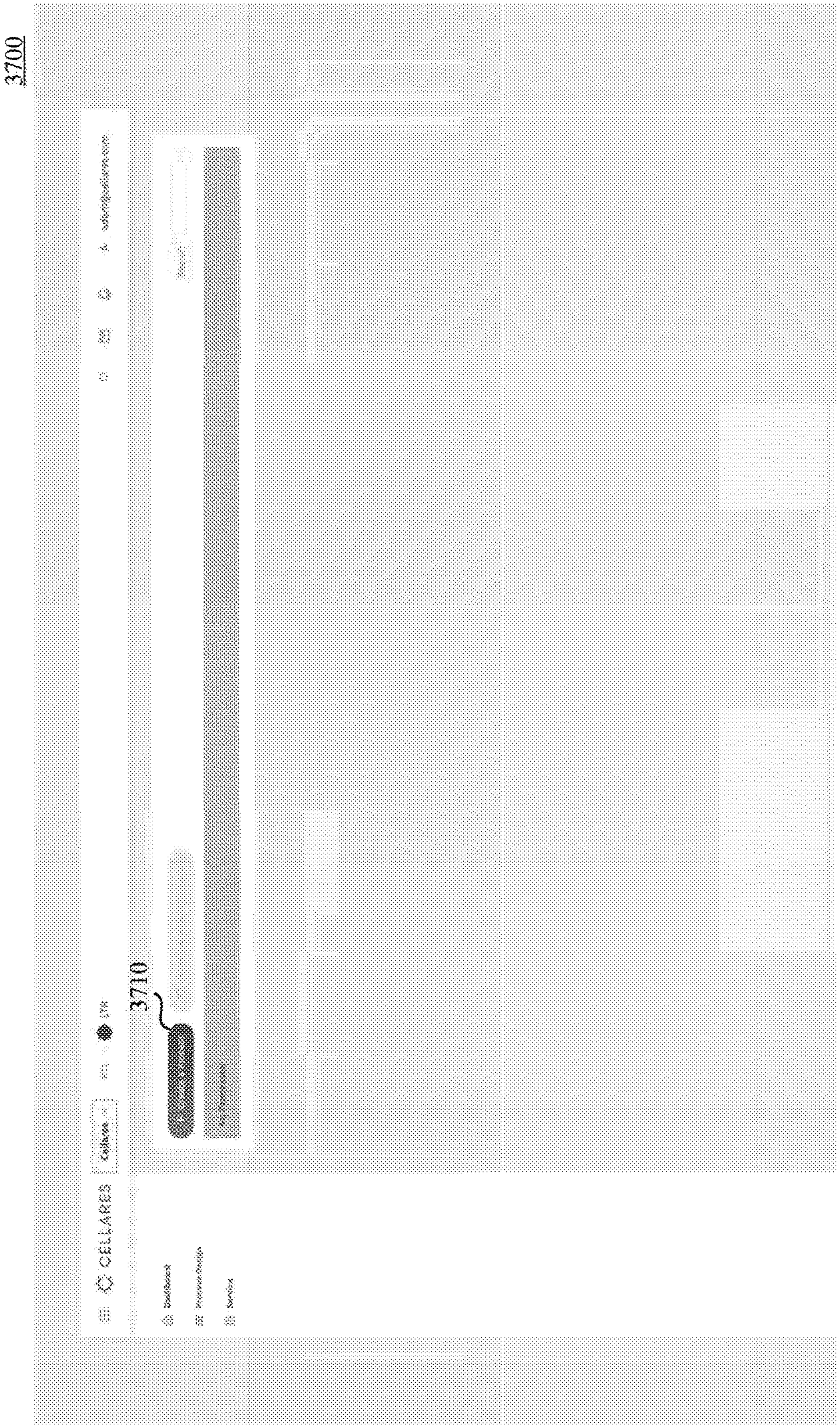
FIG. 37 is an illustrative variation of a graphical user interface relating to an initial process design interface.

In some variations, a graphical user interface (GUI) may be configured for designing a process and monitoring a product. FIG. 37 is a variation of a GUI 3700 comprising an initial process design interface. For example, GUI 3700 may be a process design home page. The GUI 3700 may indicate that no processes have been selected or loaded. A create icon 3710 (e.g., "Create a Process") may be selectable for a user to begin a process design process. In some variations, one or more of the GUIs described herein may include a search bar.

Figure 38:
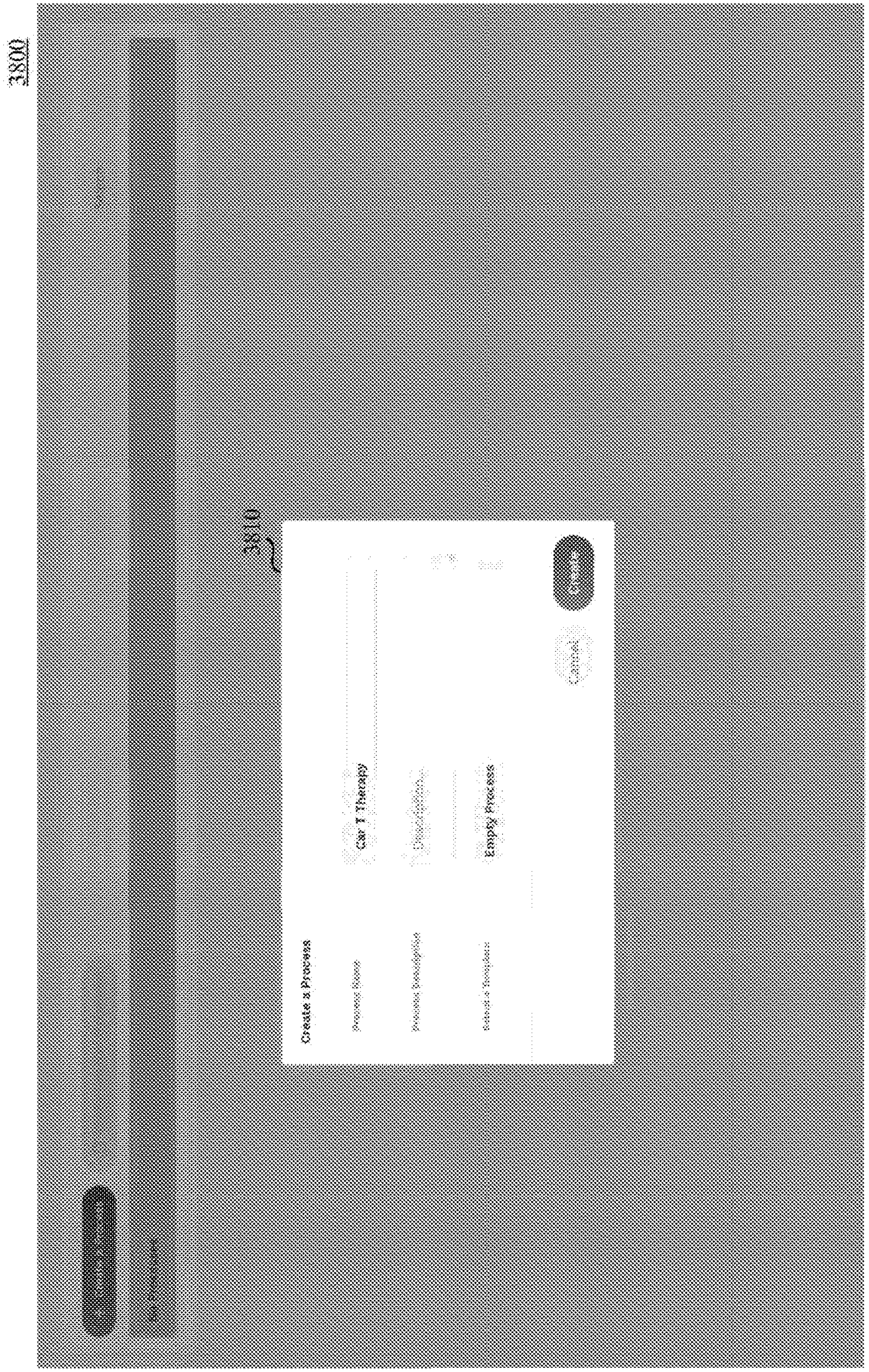
FIG. 38 is an illustrative variation of a graphical user interface relating to creating a process.

FIG. 38 is a variation of a GUI 3800 relating to creating a process. GUI 3800 may be displayed following selection of the create icon 3710 in FIG. 37. For example, GUI 3800 may comprise a process creation window 3810 allowing a user to input and/or select one or more of a process name, process description, and template. In some variations, a user may select from a list of predetermined templates. For example, a user may create a process and save it as a template for later selection.

Figure 39:
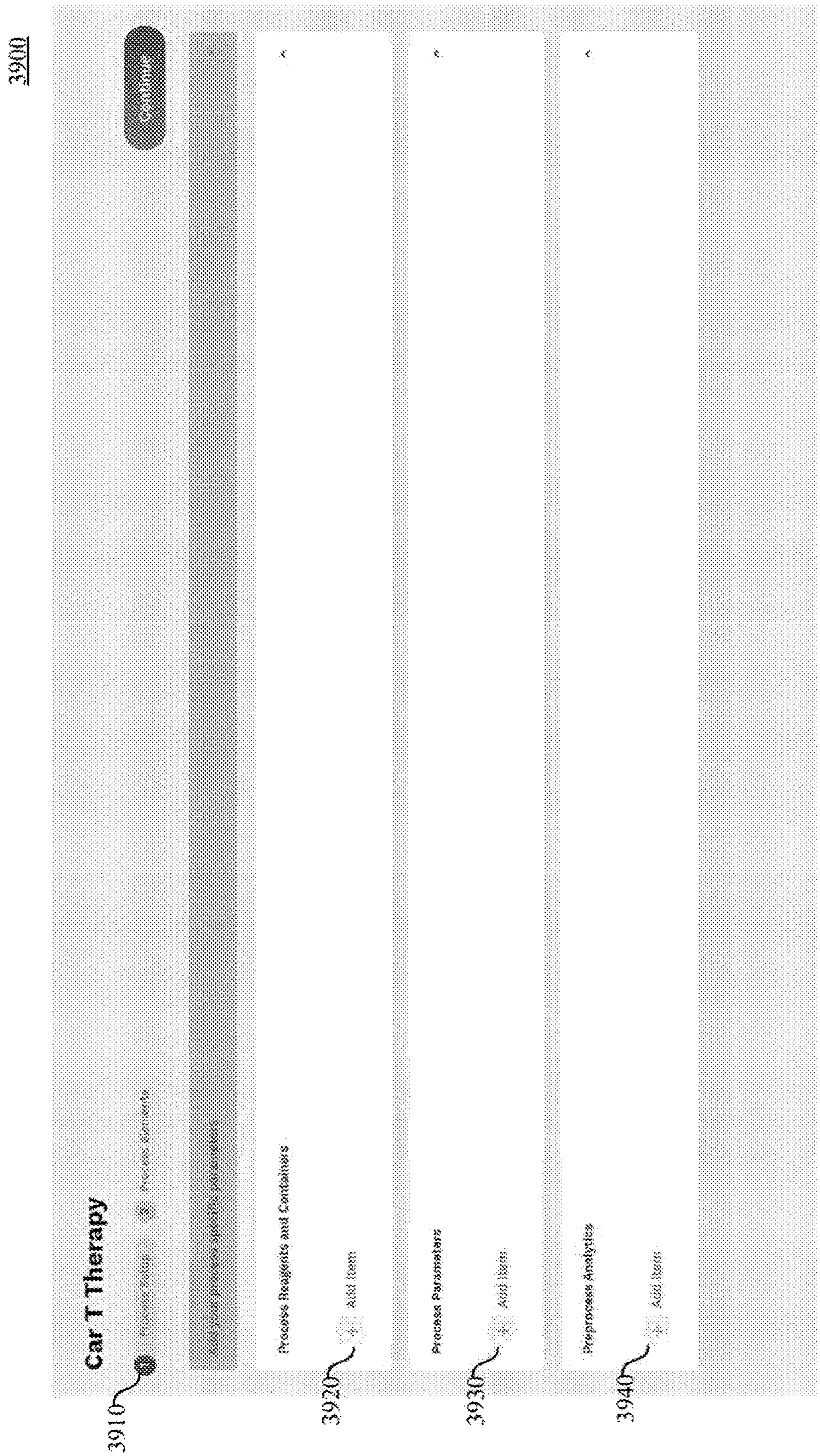
FIG. 39 is an illustrative variation of a graphical user interface relating to an empty process.

FIG. 39 is a variation of a GUI 3900 comprising relating to an empty process. GUI 3900 may be displayed following confirmation in GUI 3800 that a process is to be created. GUI 3900 may indicate the process name (e.g., Car T Therapy) and may highlight Process Setup icon 3910 and allow process specific parameters to be added such as process reagents and containers, process parameters, and preprocess analytics. GUI 3900 may further comprise an Add Process Reagents and Containers icon 3920, Add Process Parameters icon 3930, and Add Preprocess Analytics icon 3940. Once process setup is completed, one or more process elements may be specified.

In some variations, the GUI 3900 may comprise one or more predetermined templates for a set of biological processes (e.g., CAR-T, NK cells, HSC, TIL, etc.). For example, the templates may aid process development and be validated starting points for process development. The templates may be further modified (e.g., customized) based on user requirements.

FIG. 40 is a variation of a GUI 4000 comprising relating to adding a reagent and a consumable container. GUI 4000 may be displayed following selection of an Add Process Reagents and Containers icon 3920 in FIG. 39. For example, GUI 4000 may comprise an Add Reagent and Container window 4010 enabling a user to input and/or select one or more reagents comprising a reagent kind, manufacturer, part number, volume per unit, required volume and required reagent inputs (e.g., lot number, expiration date, requires container transfer). Add Reagent and Container window 4010 may comprise one or more of an input field, selection box, drop-down selector, and the like. Furthermore, the Add Reagent and Container window 3810 may enable a user to input and/or select one or more consumable containers comprising a manufacturer, part number, volume per unit, and required container inputs (e.g., lot number, expiration date). In some variations, a user may select from a list of predetermined templates. For example, a user may create a process and save it as a template.

Figure 41:
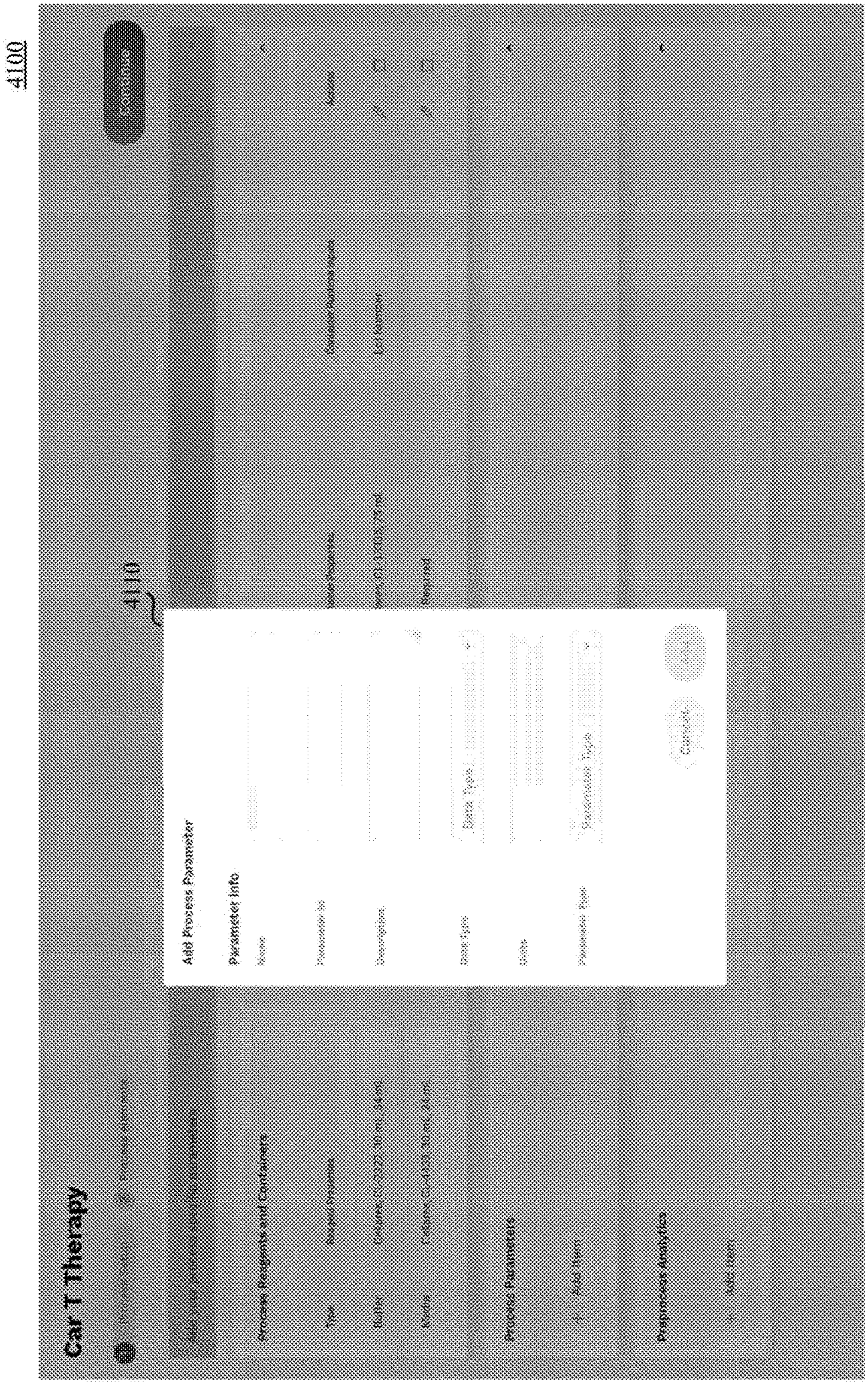
FIG. 41 is an illustrative variation of a graphical user interface relating to a process parameter.

FIG. 41 is a variation of a GUI 4100 comprising relating to a process parameter. GUI 4100 may be displayed following selection of an Add Process Reagents and Containers icon 3930 in FIG. 39. For example, GUI 4100 may comprise an Add Process Parameter window 4110 enabling a user to input and/or select one or more parameters comprising a name, parameter identification, description, data type, units, and parameter type. Add Process Parameter window 4010 may comprise one or more of an input field, selection box, drop-down selector, and the like. In some variations, a user may select from a list of predetermined templates. For example, a user may create a parameter and save it as a template. FIG. 42 is a variation of a GUI 4200 comprising relating to a patient weight process parameter. For example, GUI 4200 may comprise an Add Process Parameter window 4110 having filled in parameter information including patient weight, data type (e.g., integer), units (e.g., kg), and parameter type (e.g., input).

Figure 43:
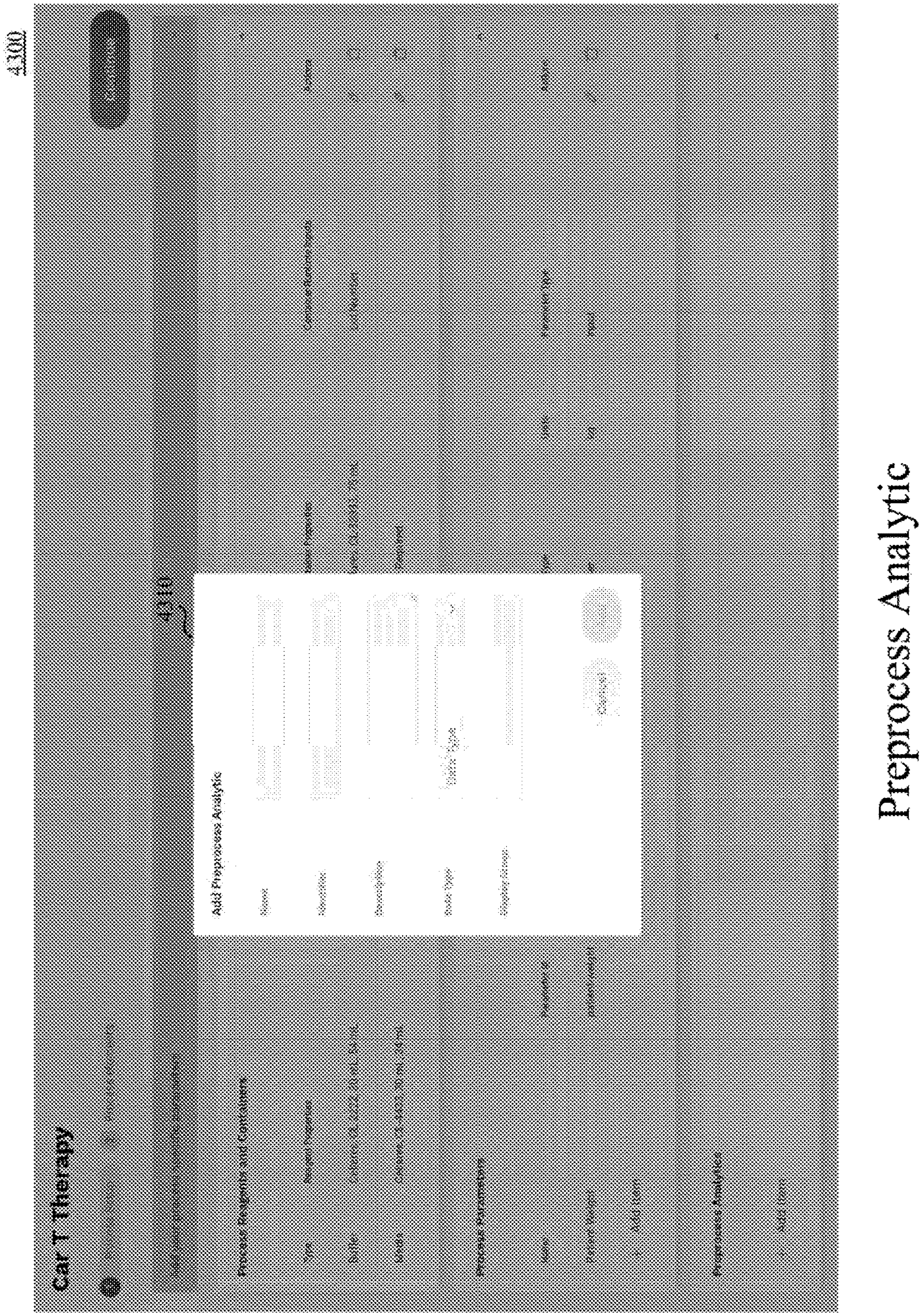
FIG. 43 is an illustrative variation of a graphical user interface relating to a preprocess analytic.

FIG. 43 is a variation of a GUI 4300 relating to a preprocess analytic. GUI 4300 may be displayed following selection of an Add Preprocess analytics icon 3940 in FIG. 39. For example, GUI 4300 may comprise an Add Preprocess Analytic window 4310 enabling a user to input and/or select one or more parameters comprising a name, identifier, description, data type, and display group. Add Preprocess Analytic window 4310 may comprise one or more of an input field, selection box, drop-down selector, and the like. In some variations, a user may select from a list of predetermined templates. For example, a user may create a parameter and save it as a template.

FIG. 44 is a variation of a GUI 4400 relating to a white blood cell count preprocess analytic. For example, GUI 4400 may comprise an Add Preprocess Analytic window 4410 having filled in preprocess analytic information including name (e.g., CBC White Blood Cell Count), identifier (e.g., CBC-white-blood-cell-count), description (e.g., Number of white blood cells in a sample), data type (e.g., float), and display group (e.g., WBC).

Figure 45:
FIG. 45 is an illustrative variation of a graphical user interface relating to process parameter calculation.

FIG. 45 is a variation of a GUI 4500 relating to a process parameter calculation. GUI 4500 may be displayed following selection of an Add Preprocess analytics icon 3940 in FIG. 39 and selection of a "Calculation" parameter type. For example, GUI 4500 may comprise an Add Preprocess Analytic window 4510 enabling a user to input and/or select one or more parameters comprising a name, identifier, description, data type, display group, units, and parameter type. Furthermore, a Calculation Builder may enable a user to define a formula (e.g., algorithm, equation) to perform a predetermined calculation. For example, a Calculation Builder may comprise one or more of a set of available parameters (e.g., patient weight), constant value, equation, and operands.

Figure 46:
FIG. 46 is an illustrative variation of a graphical user interface relating to a completed process setup.

FIG. 46 is a variation of a GUI 4600 relating to a completed process setup. For example, GUI 4600 may comprise a Process Setup window 4610 having a filled in process reagents, containers, process parameters, and preprocess analytics. Once process setup is completed, one or more process elements may be specified.

Figure 47:
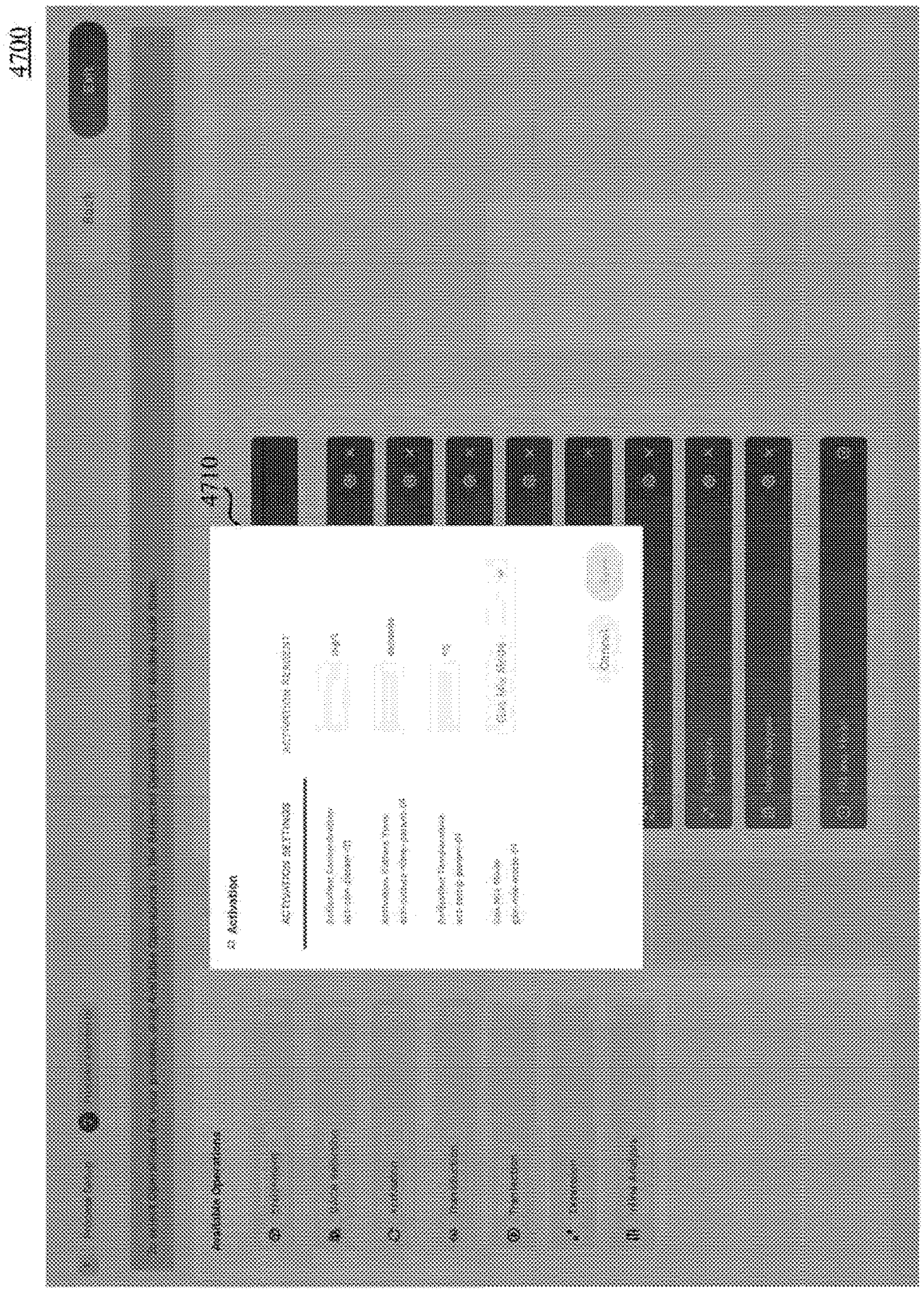
FIG. 47 is an illustrative variation of a graphical user interface relating to process operations activation settings.

FIG. 47 is a variation of a GUI 4700 relating to process operations activation settings. GUI 4700 may be displayed following selection of a Process elements icon 4620 in FIG. 46. For example, GUI 4700 may comprise an Activation settings window 4710 allowing a user to input and/or select one or more of activation concentration (e.g., mg/L), activation culture time (e.g., seconds), activation temperature (e.g., ° C.), and gas mix mode. In some variations, a user may select from a list of predetermined templates. For example, a user may create a set of activation settings and save it as a template for later selection.

FIG. 48 is a variation of a GUI 4800 relating to a filled process operations activation settings. For example, GUI 4800 may comprise an Activation settings window 4810 having filled in Activation setting information. In some variations, a set of gases (e.g., $O_2$, $N_2$, $CO_2$) and corresponding concentrations may be specified.

FIG. 49 is a variation of a GUI 4900 relating to a process operations interface. The GUI 4900 may comprise an Available Operations window 4910 and a Selected Operations window 4920. The available options for selection may include one or more biologic process inputs as described herein including, but not limited to, enrichment, MACS selection, activation, transduction, transfection, expansion, and inline analysis. One or more of the operations may be selected and dragged into the Selected Operations window 4920. The selected operations may be reordered within the Selected Operations window 4920.

Figure 50:
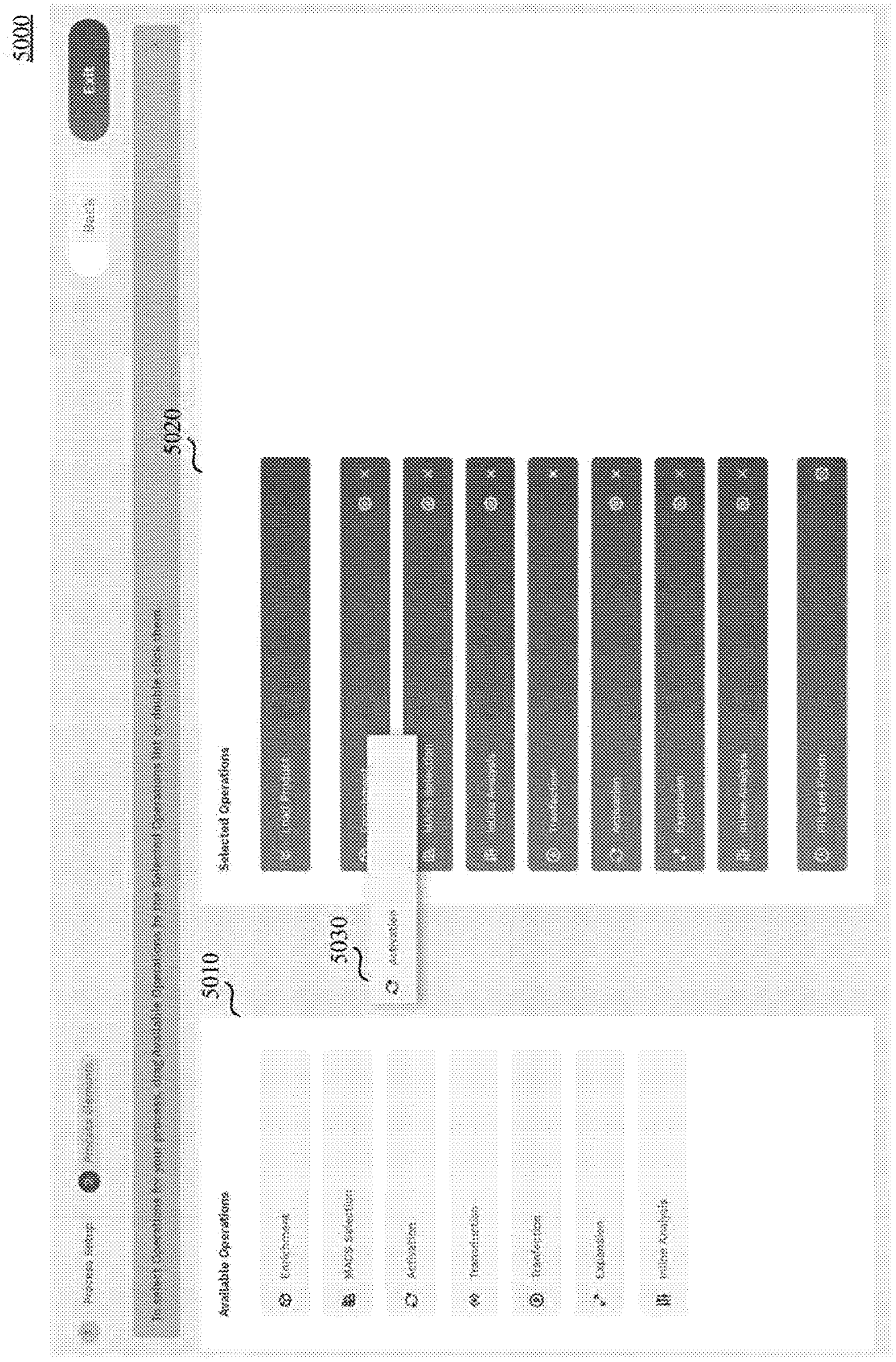
FIG. 50 is an illustrative variation of a graphical user interface relating to dragging in process operations.

FIG. 50 is a variation of a GUI 5000 relating to dragging process operations. The GUI 5000 may comprise an Available Operations window 5010, a Selected Operations window 5020, and a selected (e.g., dragged) operation 5030 that may be drag and dropped between the Available Operations window 5010 and the Selected Operations window 5020. The Selected Operations window 5020 may comprise a plurality of selected operations.

Figure 51:
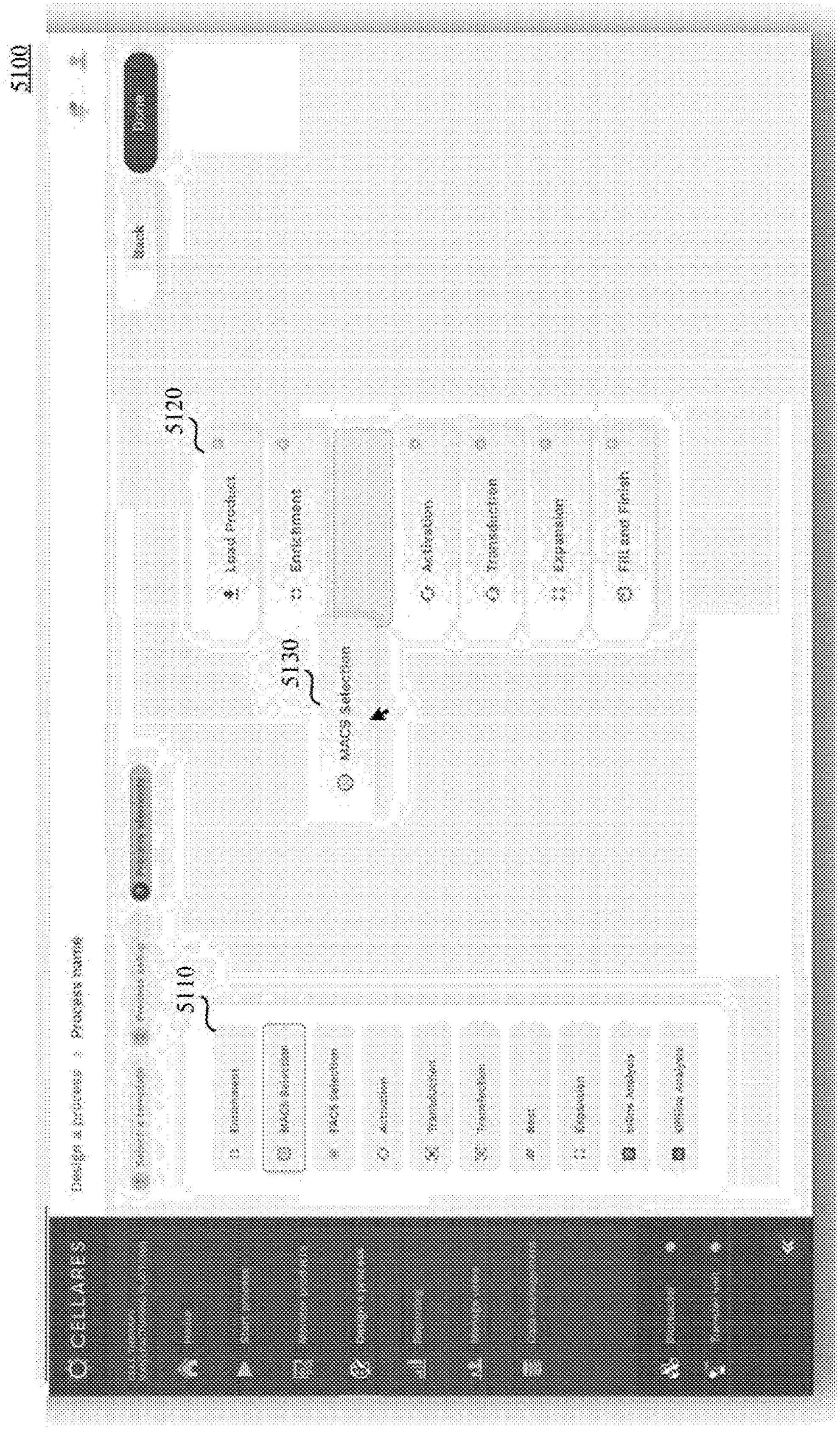
FIG. 51 is another illustrative variation of a graphical user interface relating to dragging in process operations.

FIG. 51 is a variation of a GUI 5100 relating to dragging process operations. The GUI 5100 may comprise an Available Operations window 5110, a Selected Operations window 5120, and a selected (e.g., dragged) operation 5130 that may be drag and dropped between the Available Operations window 5110 and the Selected Operations window 5120.

The Selected Operations window 5120 may comprise a plurality of selected operations.

FIG. 52 is a variation of a GUI 5200 relating to a filled process operations. For example, the GUI 5200 may comprise an Available Operations window 5210 and a Selected Operations window 5220 comprising a completed set of selected operations. In some variations, the settings (e.g., parameters) of each operation may be selectively modified by the user by selecting a corresponding icon (e.g., gear icon).

FIGS. 53 and 54 are variations of a GUI 5300 and 5400 relating to product monitoring. The GUI 5300 and 5400 may comprise respective monitoring windows 5310, 5410. For example, the GUI 5310 may monitor a plurality of products 5320 and output one or more product characteristics 5330 including, but not limited to, a summary, process data, online analytics, imaging, process audit logs, process parameters, and process schedule. The monitoring window 5410 may monitor one or more product characteristics of one or more products. For example, the product characteristics may include, but is not limited to, one or more of a process name, identification, process identification, progress, estimated completion, current step, and message.

Figure 77A:
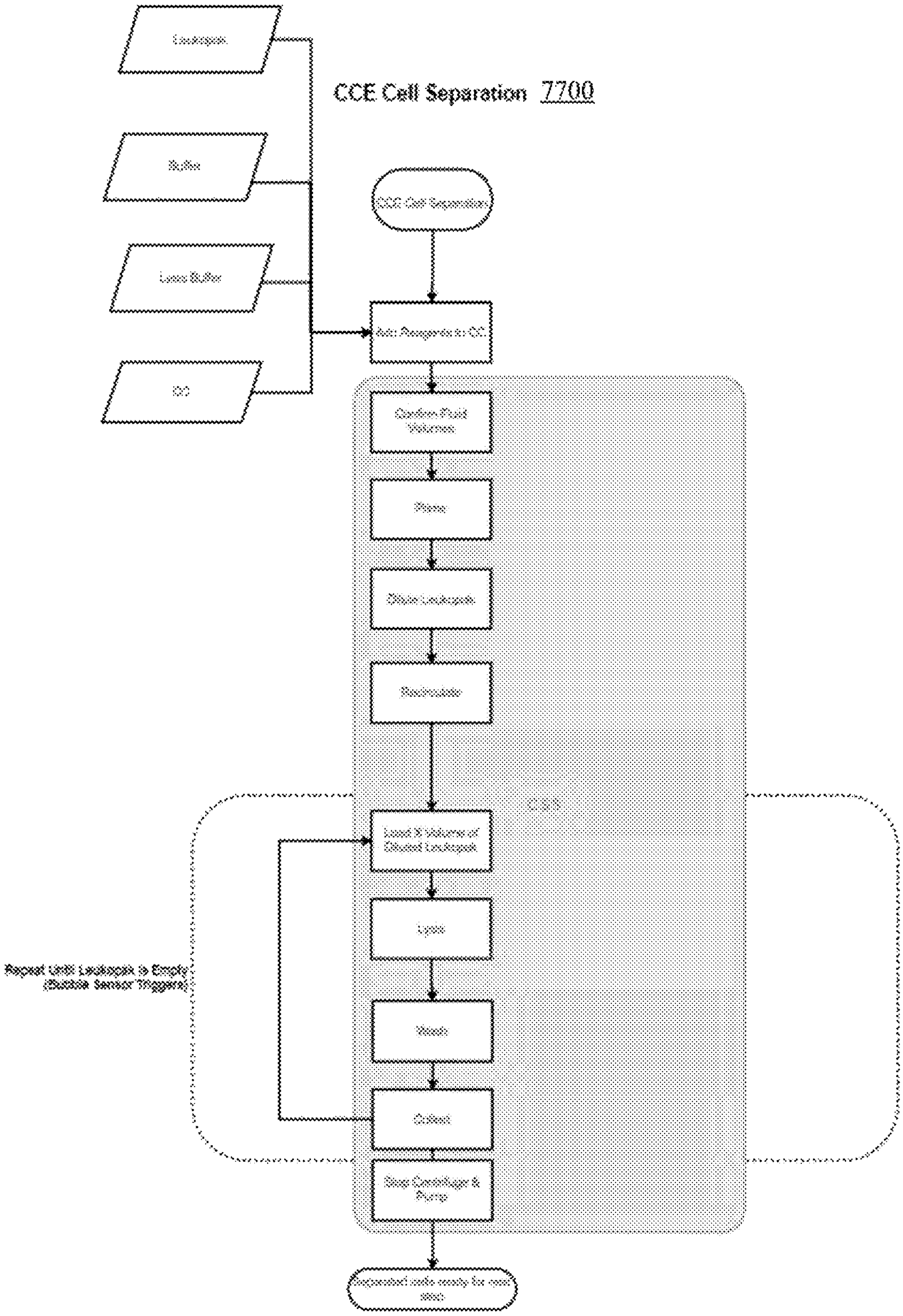
FIG. 77A is a flowchart of an illustrative variation of a method of separating cells.
Figure 77B:
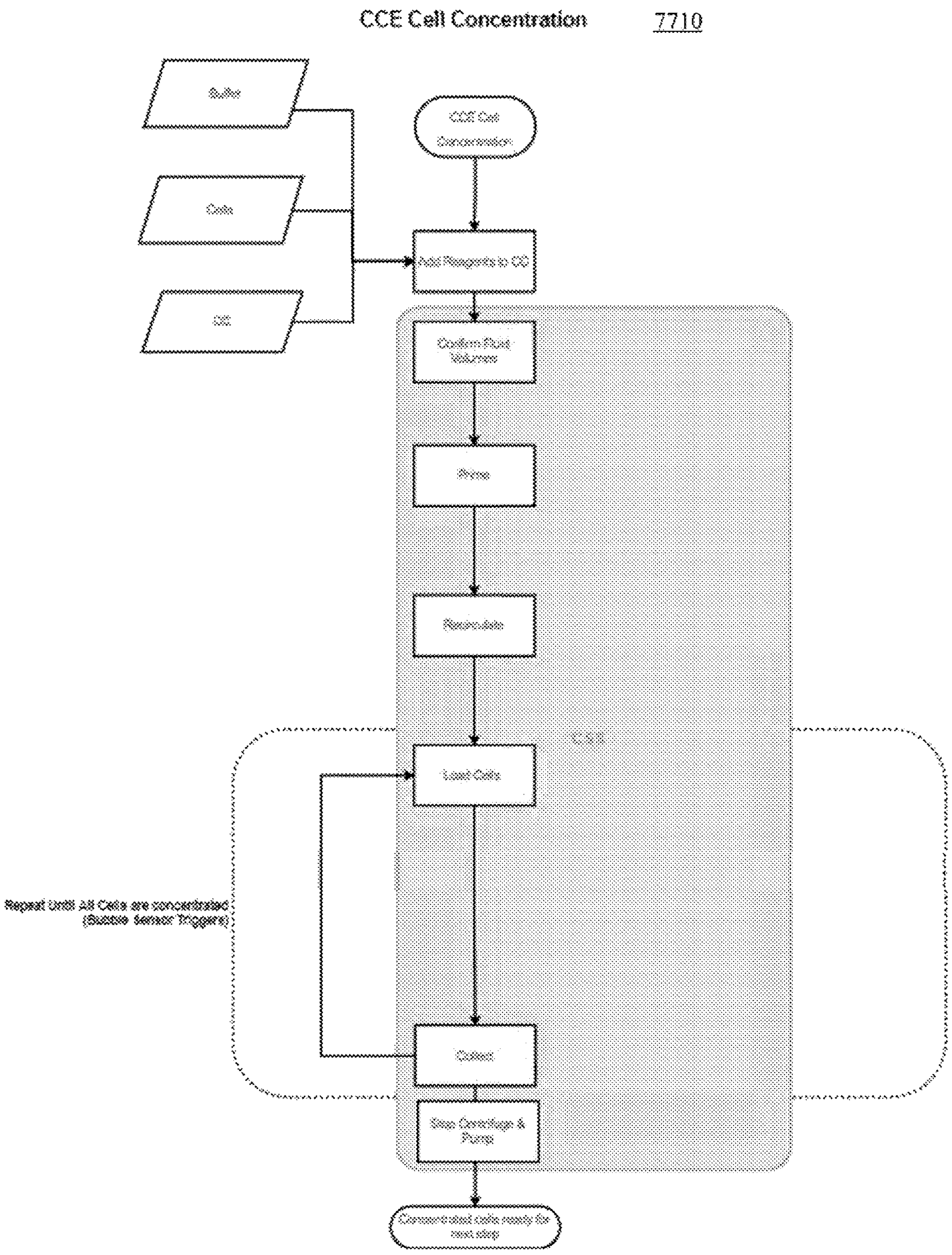
FIG. 77B is a flowchart of an illustrative variation of a method of concentrating cells.
Figure 77C:
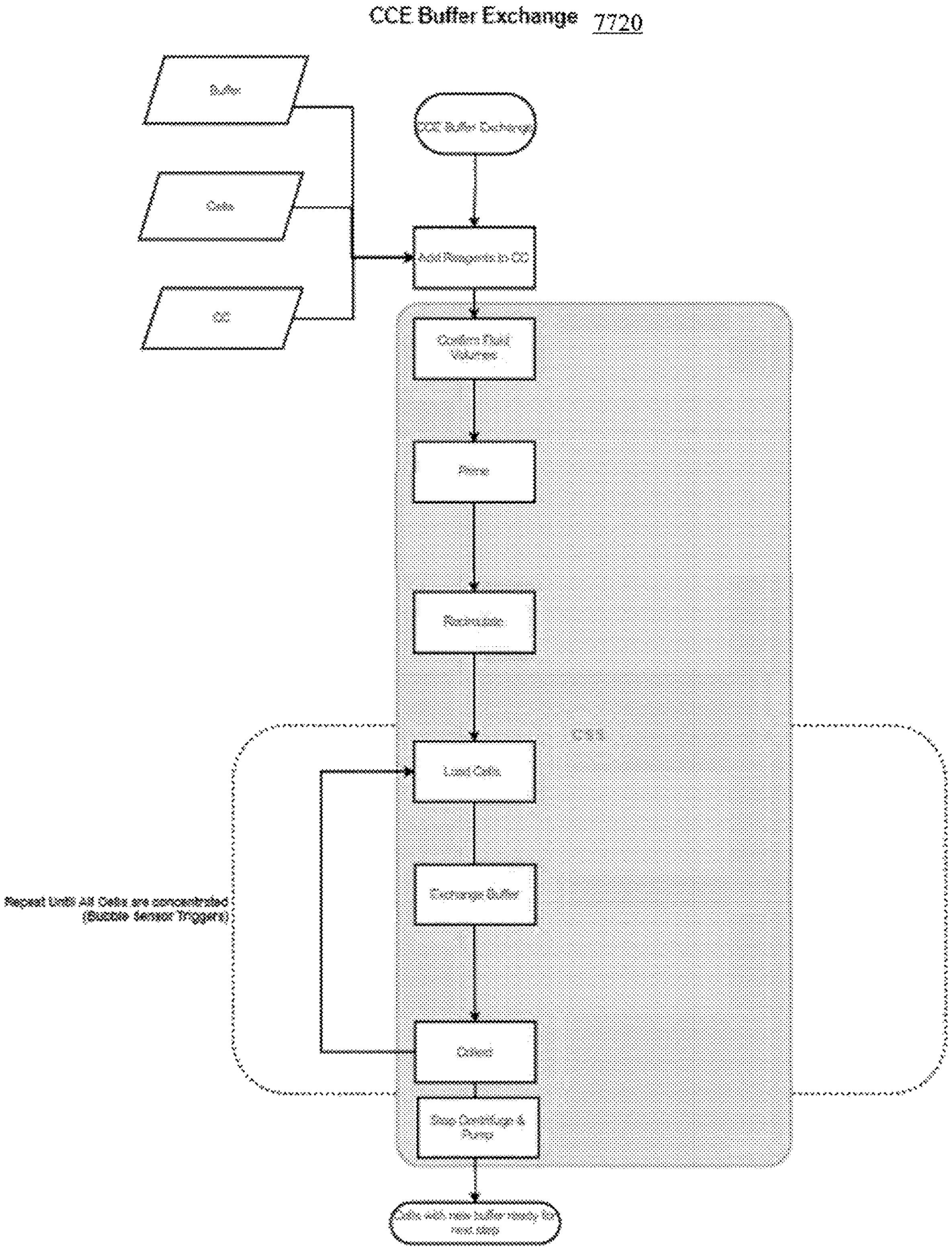
FIG. 77C is a flowchart of an illustrative variation of a method of buffer exchange.

FIG. 77A is a flowchart of a method of separating cells 7700 using a CCE module. FIG. 77B is a flowchart of a method of concentrating cells 7710 using a CCE module. FIG. 77C is a flowchart of a method of buffer exchange 7720 using a CCE module.

Figure 78:
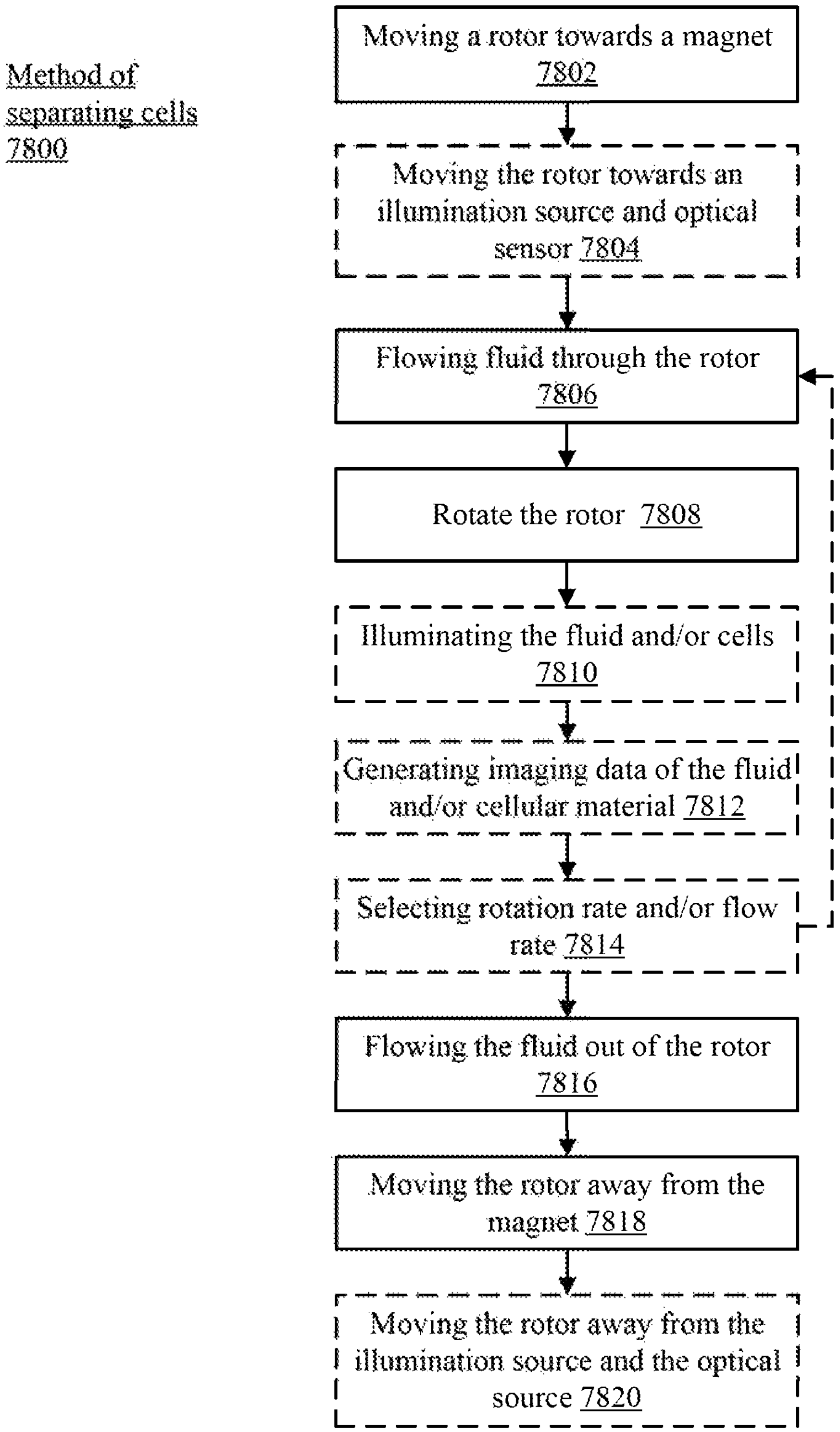
FIG. 78 is a flowchart of another illustrative variation of a method of separating cells.

FIG. 78 is a flowchart of a method of separating cells 7800. A method of counterflow centrifugal elutriation (CCE) 7800 may comprise the step moving a rotor towards a magnet 7802. The rotor may define a rotational axis. In some variations, moving the rotor comprises advancing and withdrawing the magnet relative to the rotor using a robot. The rotor may be optionally moved towards an illumination source and an optical sensor 7804. Fluid may be flowed through the rotor 7806. In some variations, flowing the fluid comprises a flow rate of up to about 150 ml/min while rotating the rotor. The rotor may be magnetically rotated about the rotational axis using the magnet while flowing the fluid through the rotor 7808. In some variations, rotating the rotor comprises a rotation rate of up to 6,000 RPM. One or more of the fluid and the cells may be optionally illuminated using an illumination source 7810. Image data of one or more of the fluid and biological material (e.g., particles, cellular material) in the rotor may optionally be generated using an optical sensor 7812. One or more of a rotation rate of the rotor and a flow rate of the fluid may optionally be selected based at least in part on the image data 7814. The fluid may be flowed out of the rotor 7816. The rotor may be moved away from the magnet 7818. The rotor may optionally be moved away from the illumination source and the optical sensor 7820.

Figure 79A:
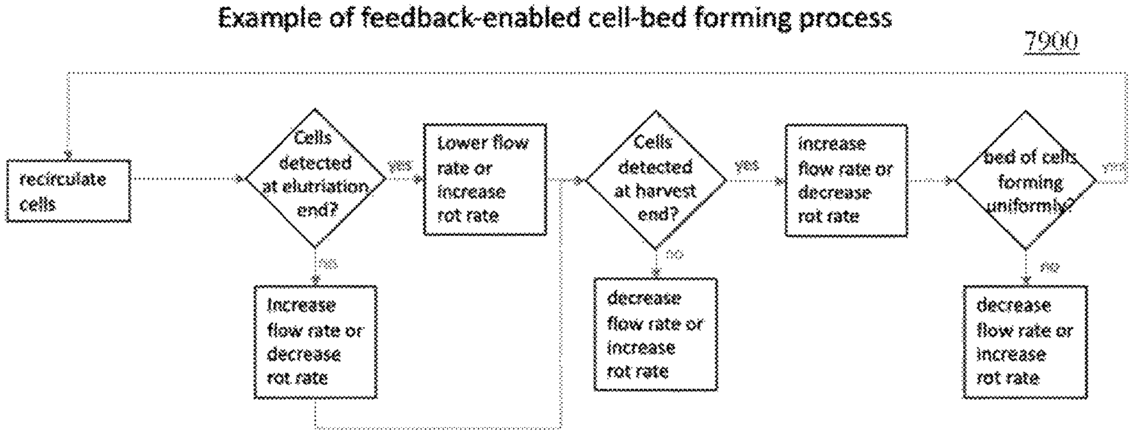
FIG. 79A is a flowchart of an illustrative variation of a closed-loop method of separating cells 7900.
Figure 79B:
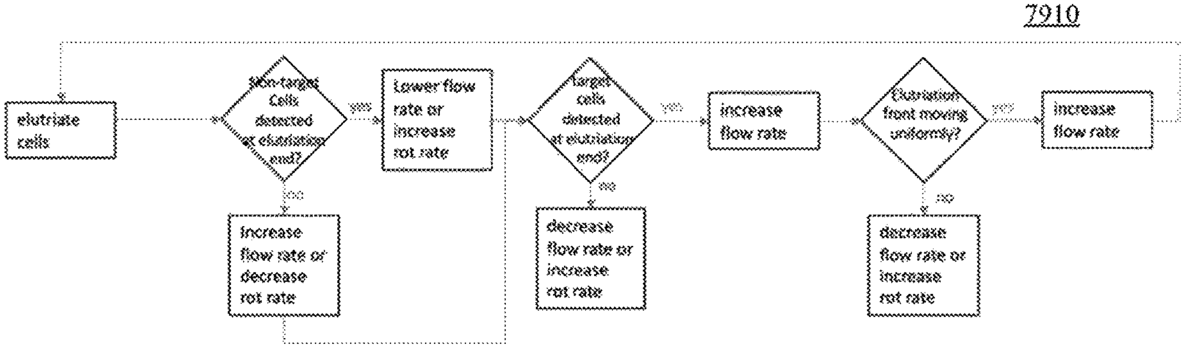
FIG. 79B is a flowchart of an illustrative variation of a closed-loop method of elutriating cells 7910.
Figure 79C:
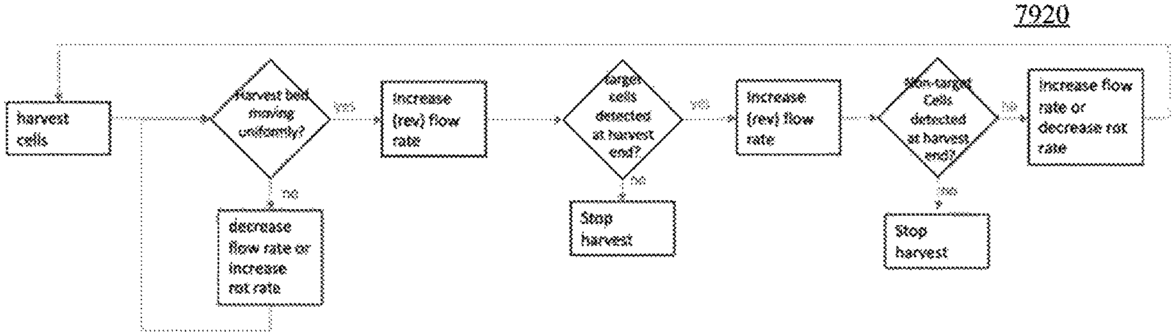
FIG. 79C is a flowchart of an illustrative variation of a closed-loop method of harvesting cells 7920.

FIG. 79A is a flowchart of a closed-loop method of separating cells 7900. FIG. 79B is a flowchart of a closed-loop method of elutriating cells 7910. FIG. 79C is a flowchart of a closed-loop method of harvesting cells 7920.

Figure 80A:
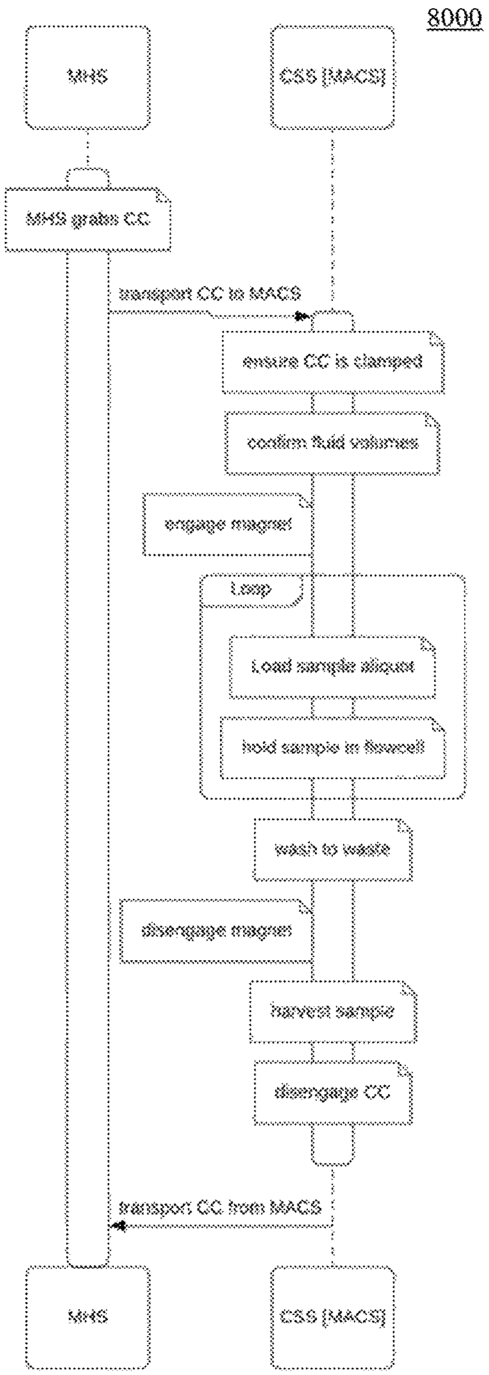
FIG. 80A is a flowchart of an illustrative variation of a method of separating cells.
Figure 80B:
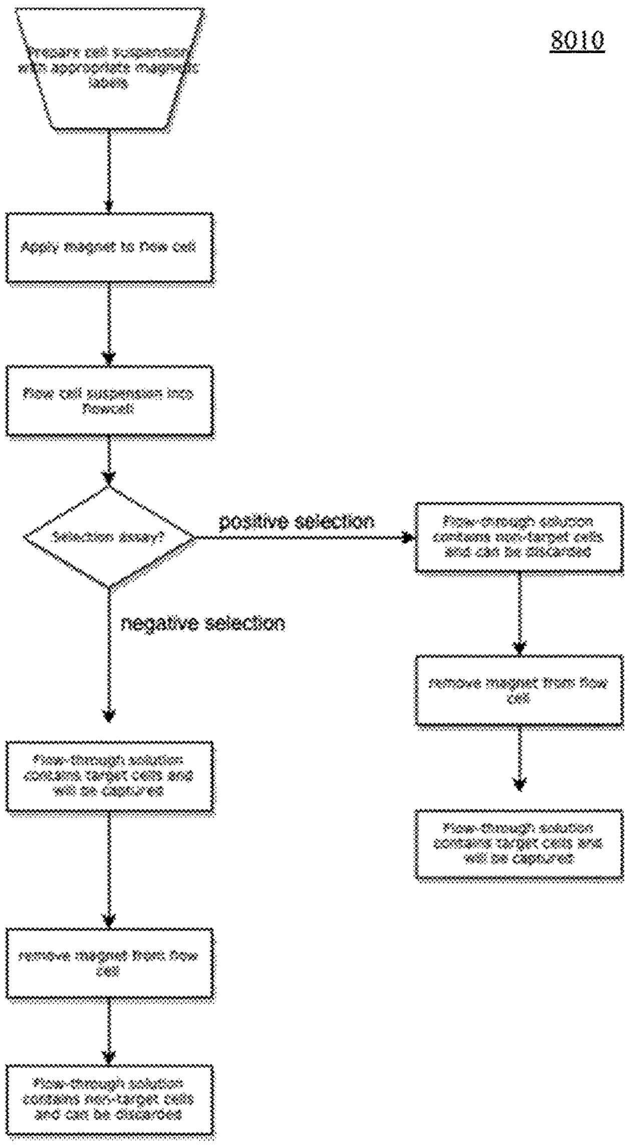
FIG. 80B is a flowchart of an illustrative variation of a method of selecting cells.

FIG. 80A is a flowchart of a method of separating cells 8000. FIG. 80B is a flowchart of a method of selecting cells 8010.

Figure 81:
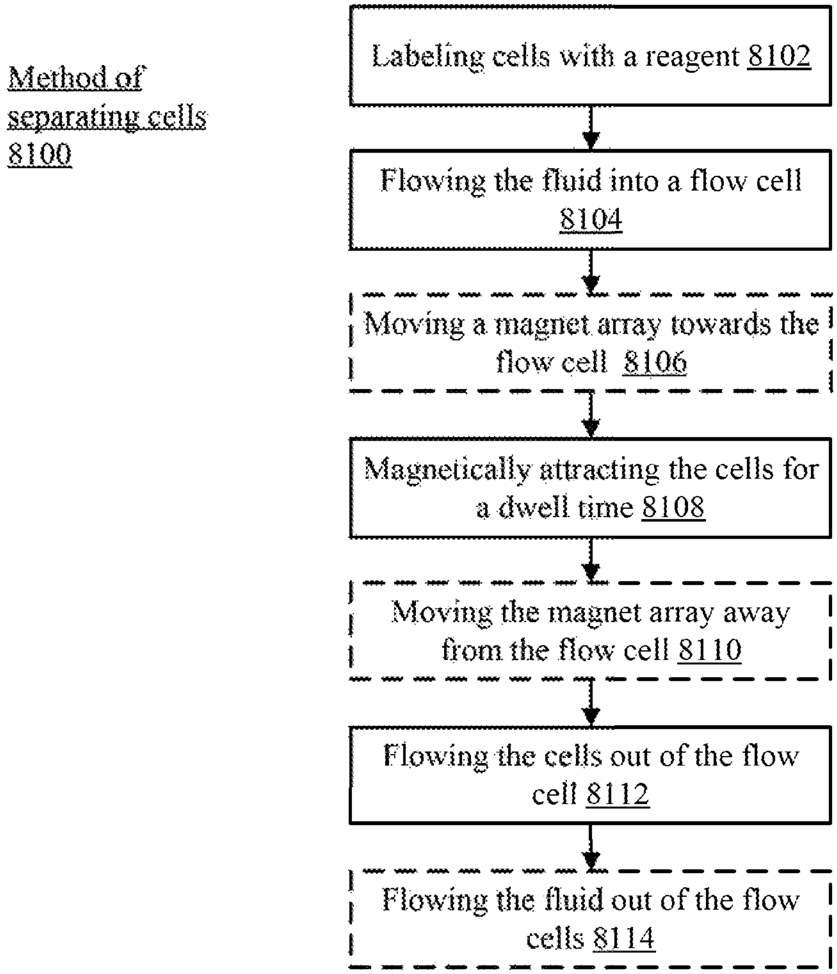
FIG. 81 is a flowchart of another illustrative variation of a method of separating cells.

FIG. 81 is a flowchart of a method of separating cells 8100. A method of magnetic-activated cell selection (MACS) may comprise labeling cells with a reagent 8102. In some variations, a magnetic-activated cell selection (MACS) reagent may be incubated with the input cells to label the set of cells with the MACS reagent. In some variations, incubating the MACS reagent comprises a temperature between about 1° C. and about 10° C. The fluid comprising input cells may be flowed into a flow cell 8104. A set of the cells are labeled with the MACS reagent. In some variations, the magnet array may optionally be moved relative to the flow cell 8106. In some variations, the set of cells may be magnetically attracted towards a magnet array for a dwell time 8108. In some variations, the dwell time may be at least about one minute. In some variations, the magnet array may be disposed external to the flow cell. In some variations, a longitudinal axis of the flow cell is perpendicular to ground. In some variations, the flow cell may be absent beads. In some variations, the magnet array may optionally be moved away from the flow cell to facilitate flowing the set of cells out of the flow cell 8110. The set of cells may be flowed out of the flow cell after the dwell time 8112. For example, flowing the set of cells out of the flow cell may comprise flowing a gas through the flow cell. The fluid without the set of cells may optionally be flowed out of the flow cell after the dwell time 8114.

Figure 82A:
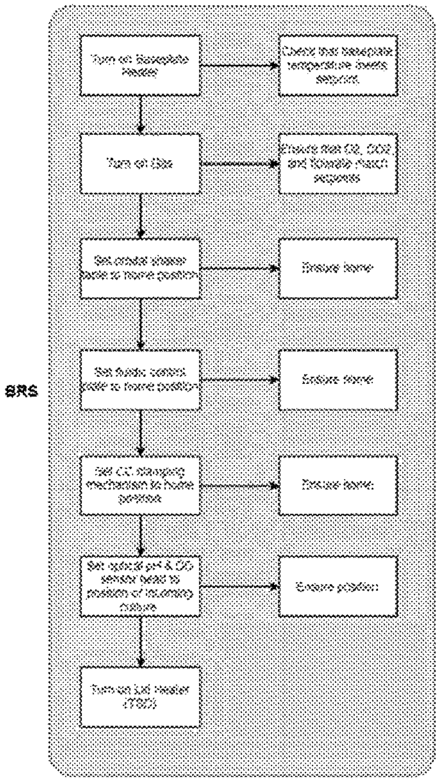
FIG. 82A is a flowchart of an illustrative variation of a method of preparing a bioreactor.
Figure 82B:
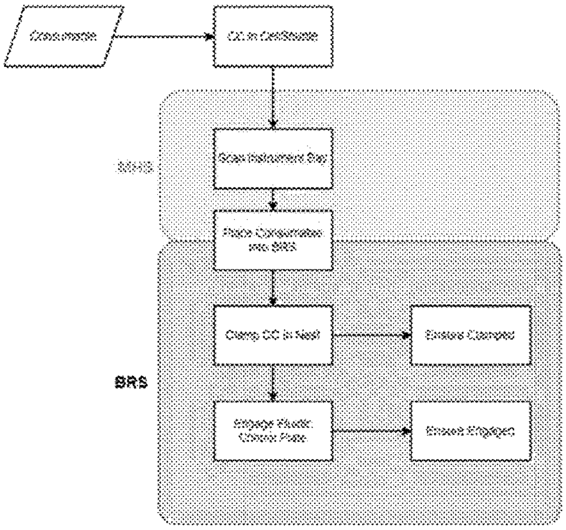
FIG. 82B is a flowchart of an illustrative variation of a method of loading a bioreactor.
Figure 82C:
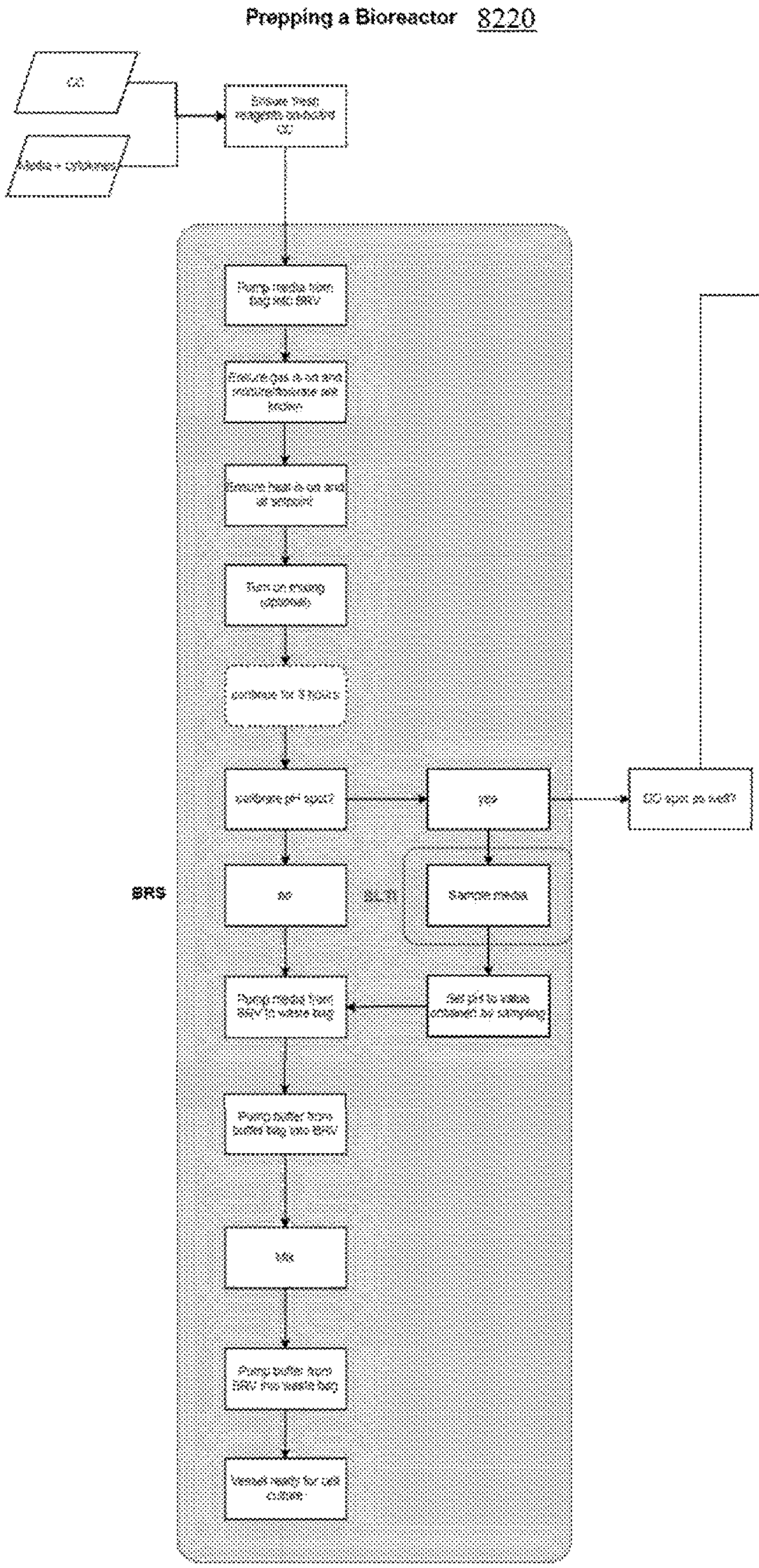
FIG. 82C is a flowchart of an illustrative variation of a method of preparing a bioreactor.
Figure 82D:
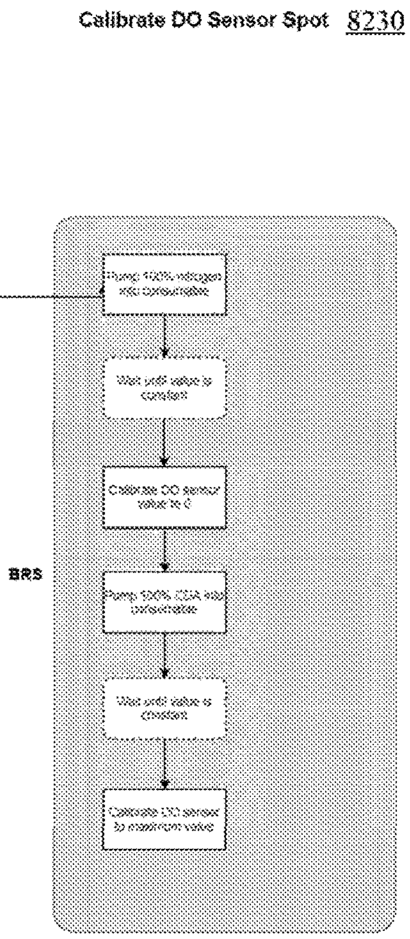
FIG. 82D is a flowchart of an illustrative variation of a method of calibration for a bioreactor.
Figure 82E:
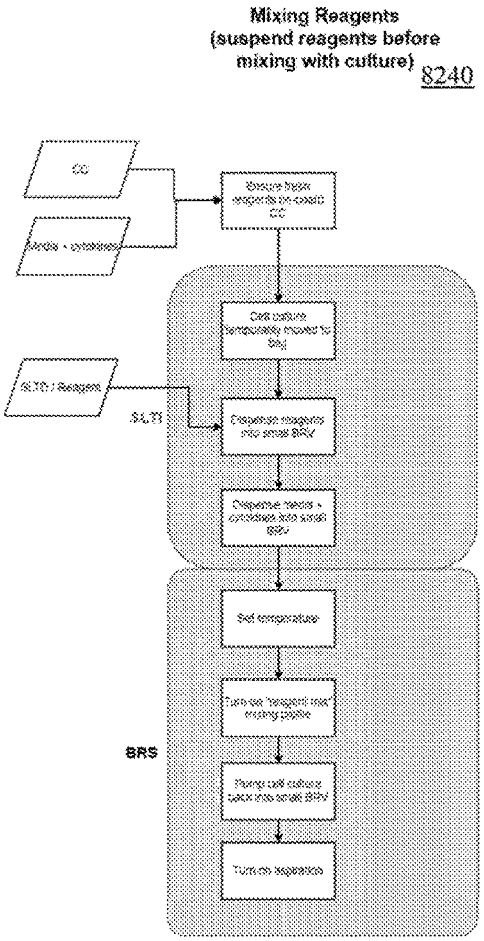
FIG. 82E is a flowchart of an illustrative variation of a method of mixing reagents.
Figure 82F:
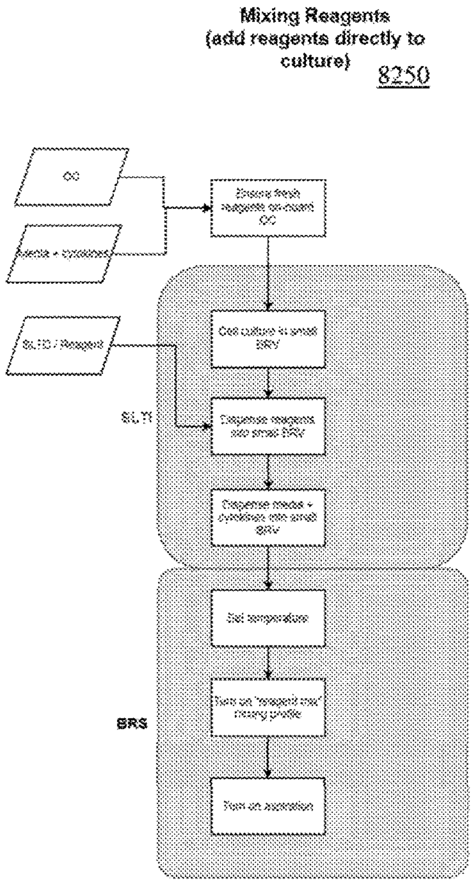
FIG. 82F is a flowchart of an illustrative variation of a method of mixing reagents.
Figure 82G:
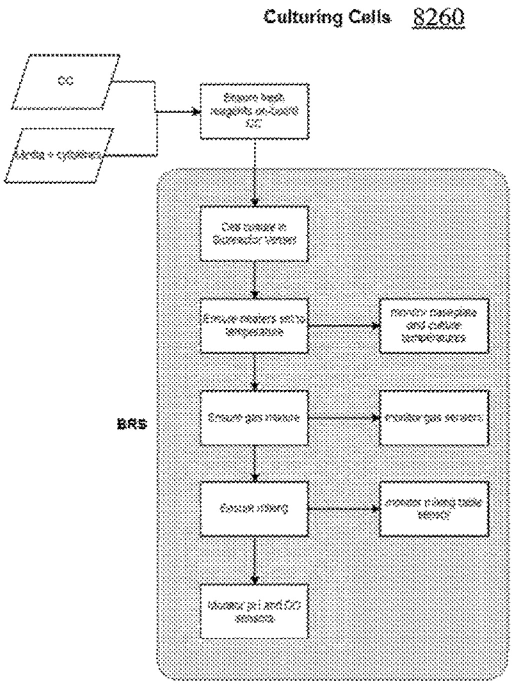
FIG. 82G is a flowchart of an illustrative variation of a method of culturing cells.
Figure 82H:
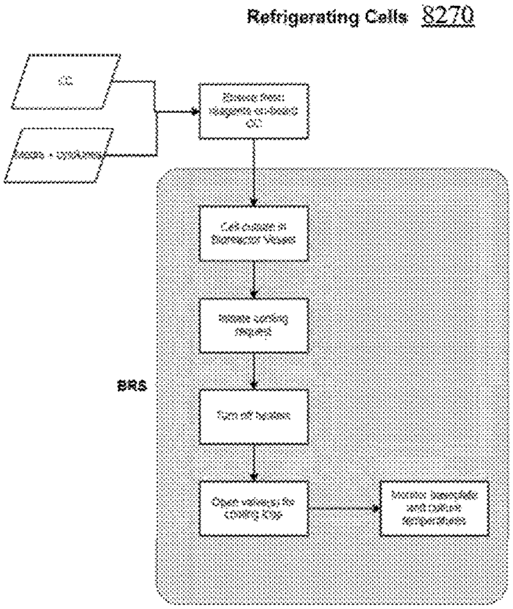
FIG. 82H is a flowchart of an illustrative variation of a method of refrigerating cells.
Figures 82I, 82J:
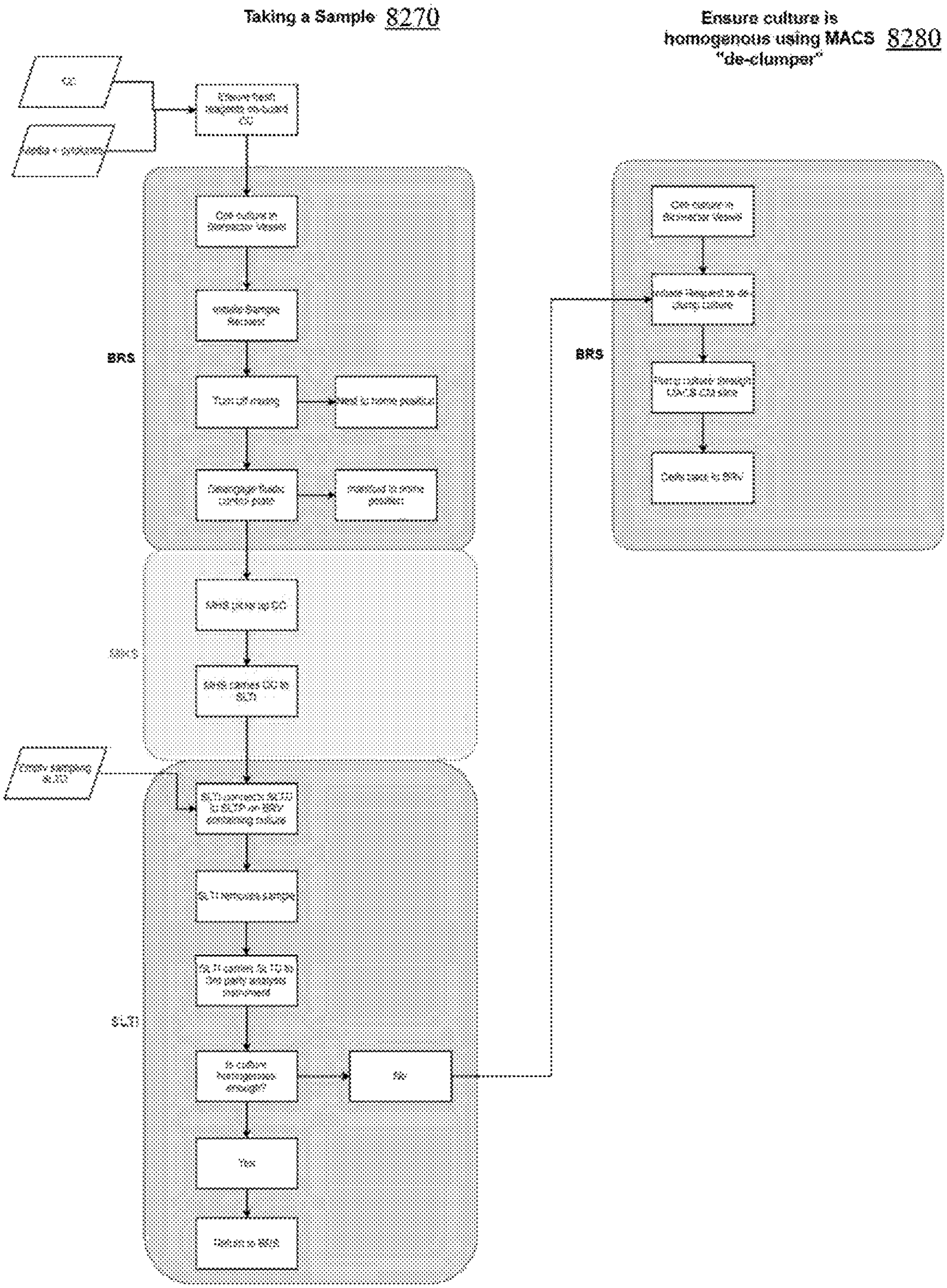
FIG. 82I is a flowchart of an illustrative variation of a method of taking a sample.
FIG. 82J is a flowchart of an illustrative variation of a method of culturing cells.
Figure 82K:
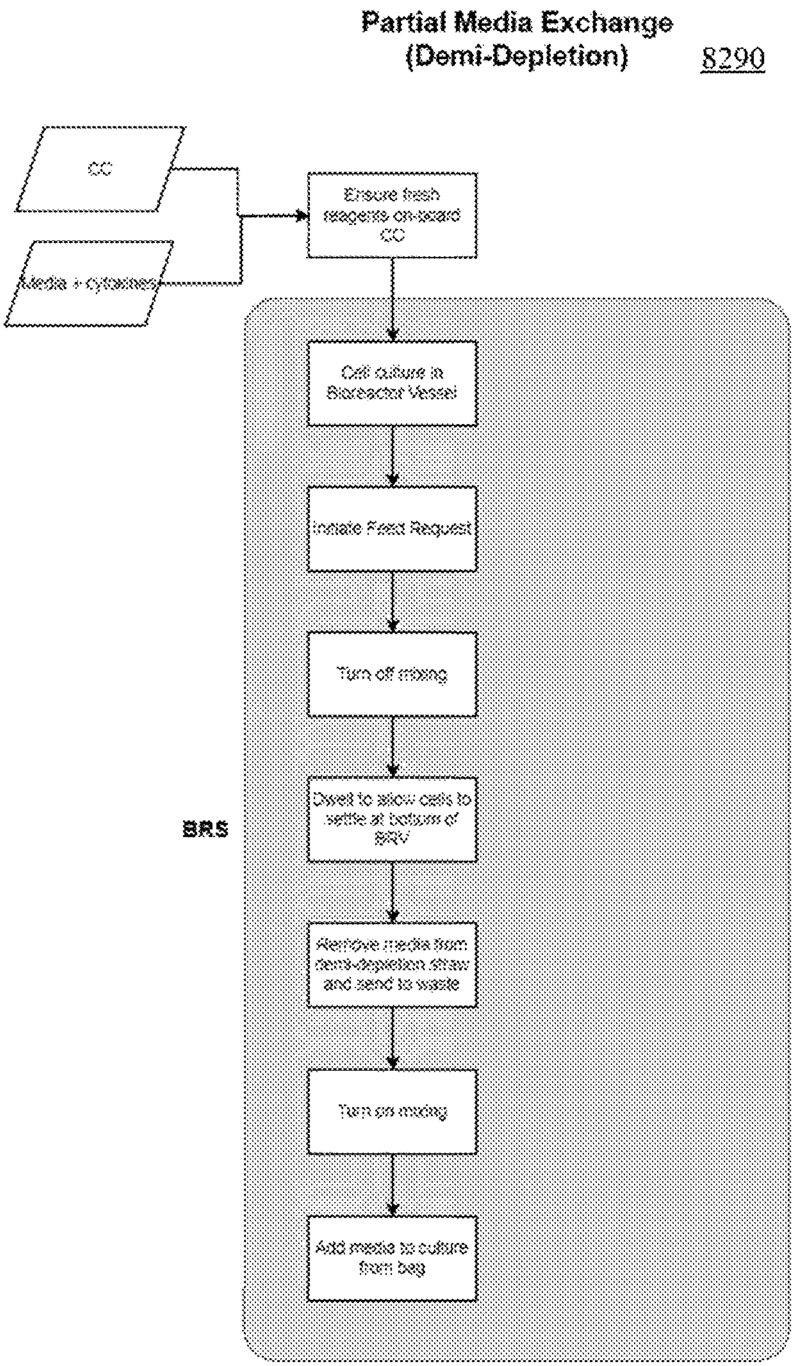
FIG. 82K is a flowchart of an illustrative variation of a method of media exchange.
Figure 82L:
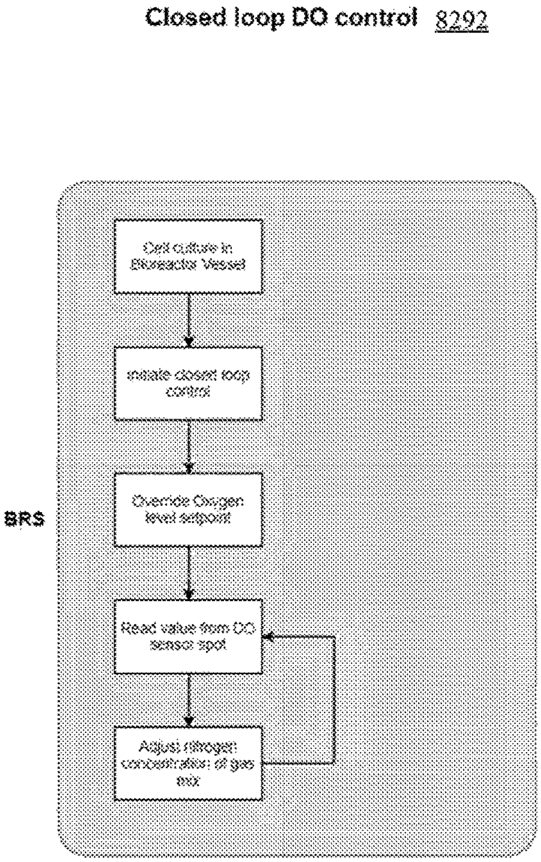
FIG. 82L is a flowchart of an illustrative variation of a method of controlling gas.
Figure 82M:
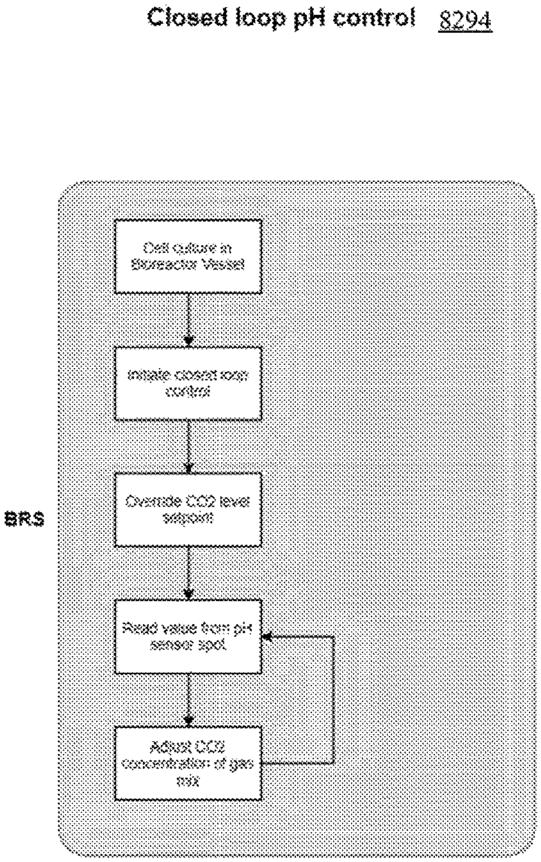
FIG. 82M is a flowchart of an illustrative variation of a method of controlling pH.

FIG. 82A is a flowchart of a method of preparing a bioreactor 8200. FIG. 82B is a flowchart of a method of loading a bioreactor 8210. FIG. 82C is a flowchart of a method of preparing a bioreactor 8220. FIG. 82D is a flowchart of a method of calibration for a bioreactor 8230. FIG. 82E is a flowchart of a method of mixing reagents 8240. FIG. 82F is a flowchart of a method of mixing reagents 8250. FIG. 82G is a flowchart of a method of culturing cells 8260. FIG. 82H is a flowchart of a method of refrigerating cells 8270. FIG. 82I is a flowchart of a method of taking a sample 8270. FIG. 82J is a flowchart of a method of culturing cells 8280. FIG. 82K is a flowchart of a method of media exchange 8290. FIG. 82L is a flowchart of a method of controlling gas 8292. FIG. 82M is a flowchart of a method of controlling pH 8294.

Figure 83:
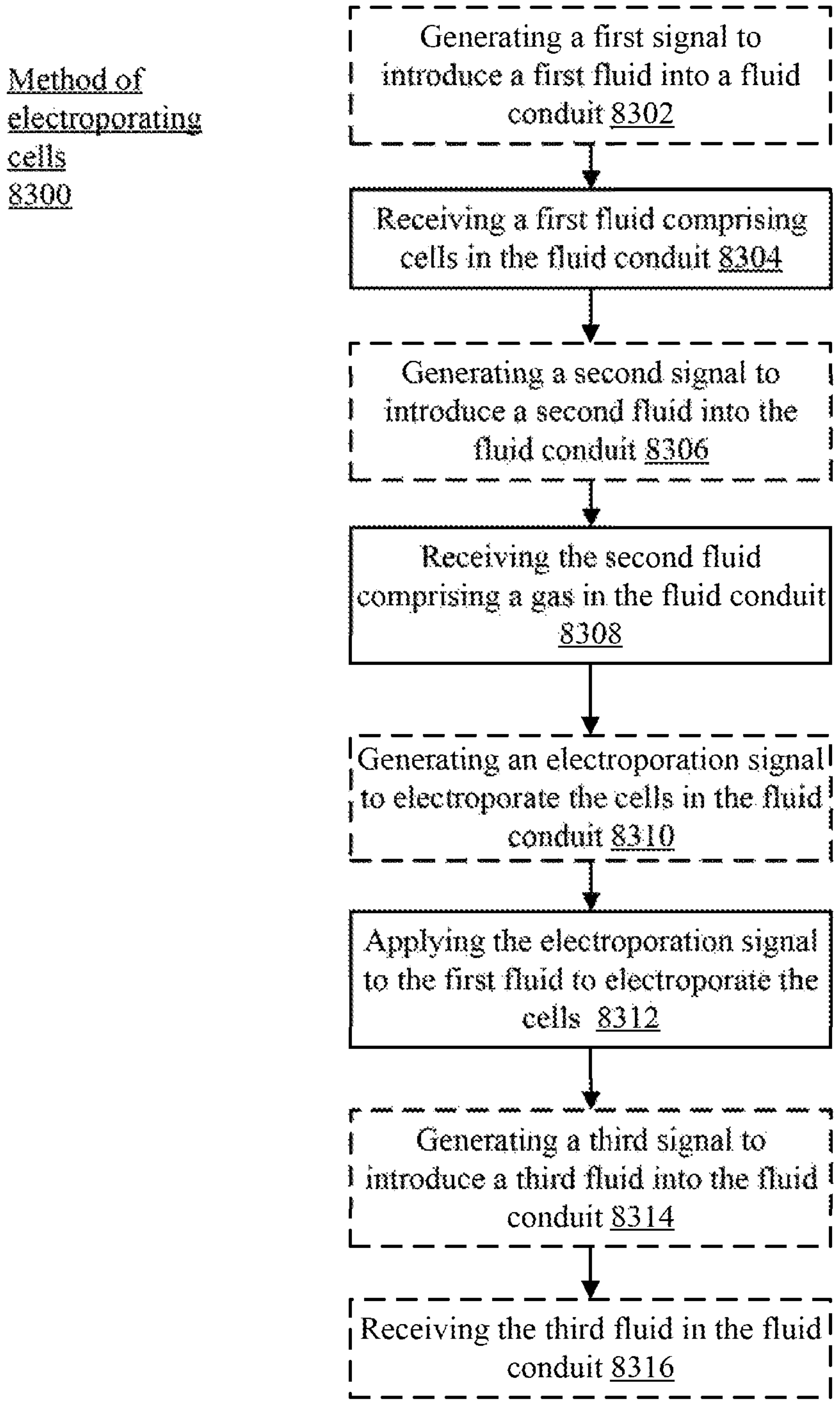
FIG. 83 is a flowchart of an illustrative variation of a method of electroporating cells.

FIG. 83 is a flowchart of a method of electroporating cells 8300 using an electroporation module. In some variations, an electroporation module may comprise a fluid conduit configured to receive a first fluid comprising cells and a second fluid, a set of electrodes coupled to the fluid conduit, a pump coupled to the fluid conduit, and a controller comprising a processor and memory.

A method of electroporating cells may optionally comprise generating a first signal to introduce the first fluid into the fluid conduit using the pump 8302. A first fluid comprising cells in a fluid conduit may be received 8304. In some variations, a second signal may optionally be generated to introduce the second fluid into the fluid conduit such that the second fluid separates the first fluid from a third fluid 8306. In some variations, the second fluid may comprise a gas or oil. A second fluid in the fluid conduit may be received to separate the first fluid from a third fluid 8308. An electroporation signal may optionally be generated to electroporate the cells in the fluid conduit using the set of electrodes 8310. An electroporation signal may be applied to the first fluid to electroporate the cells 8312. In some variations, the first fluid may be substantially static when applying the electroporation signal. In some variations, a third signal may optionally be generated to introduce the third fluid into the fluid conduit 8314. The third fluid may be separated from the first fluid by the second fluid. The third fluid may optionally be received in the fluid conduit separated from the first fluid by the second fluid 8316.

Figure 84:
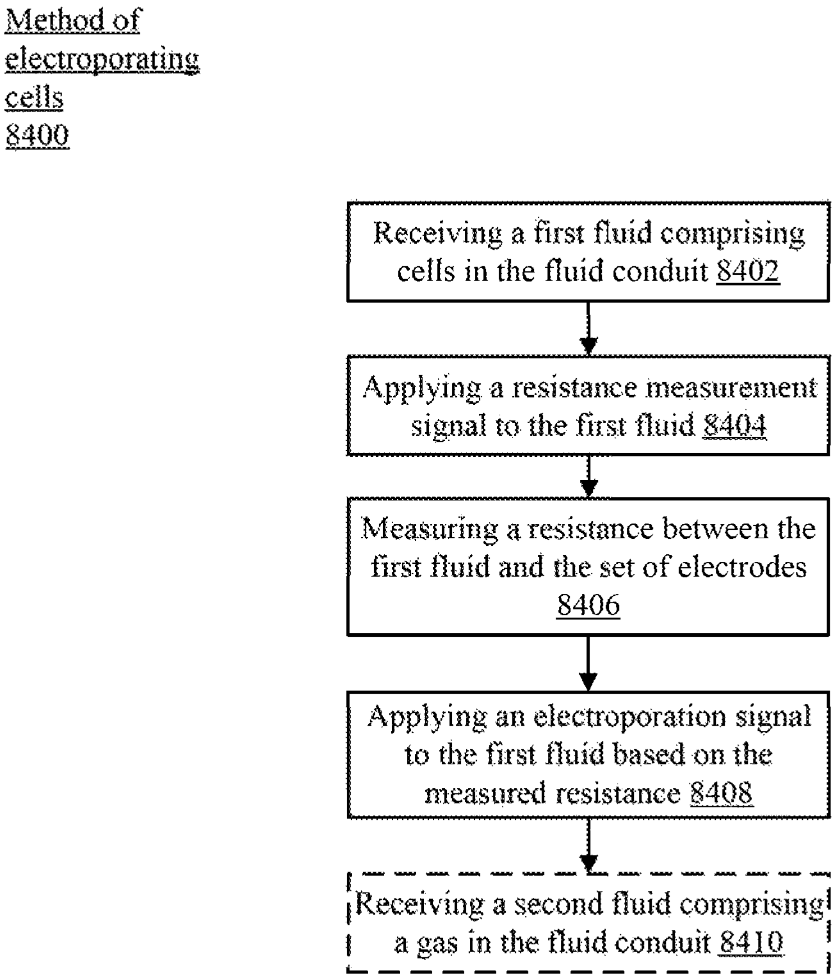
FIG. 84 is a flowchart of another illustrative variation of a method of electroporating cells.

FIG. 84 is a flowchart of a method of electroporating cells 8400. A method of electroporating cells may comprise receiving a first fluid comprising cells in a fluid conduit 8402. A resistance measurement signal may be applied to the first fluid using a set of electrodes 8404. A resistance may be measured between the first fluid and the set of electrodes 8406. An electroporation signal may be applied to the first fluid based on the measured resistance 8408. In some variations, a second fluid comprising a gas may optionally be received in the fluid conduit before applying the electroporation signal to the fluid. The first fluid may be separated from a third fluid by the second fluid.

Fluid Connector

Figure 27:
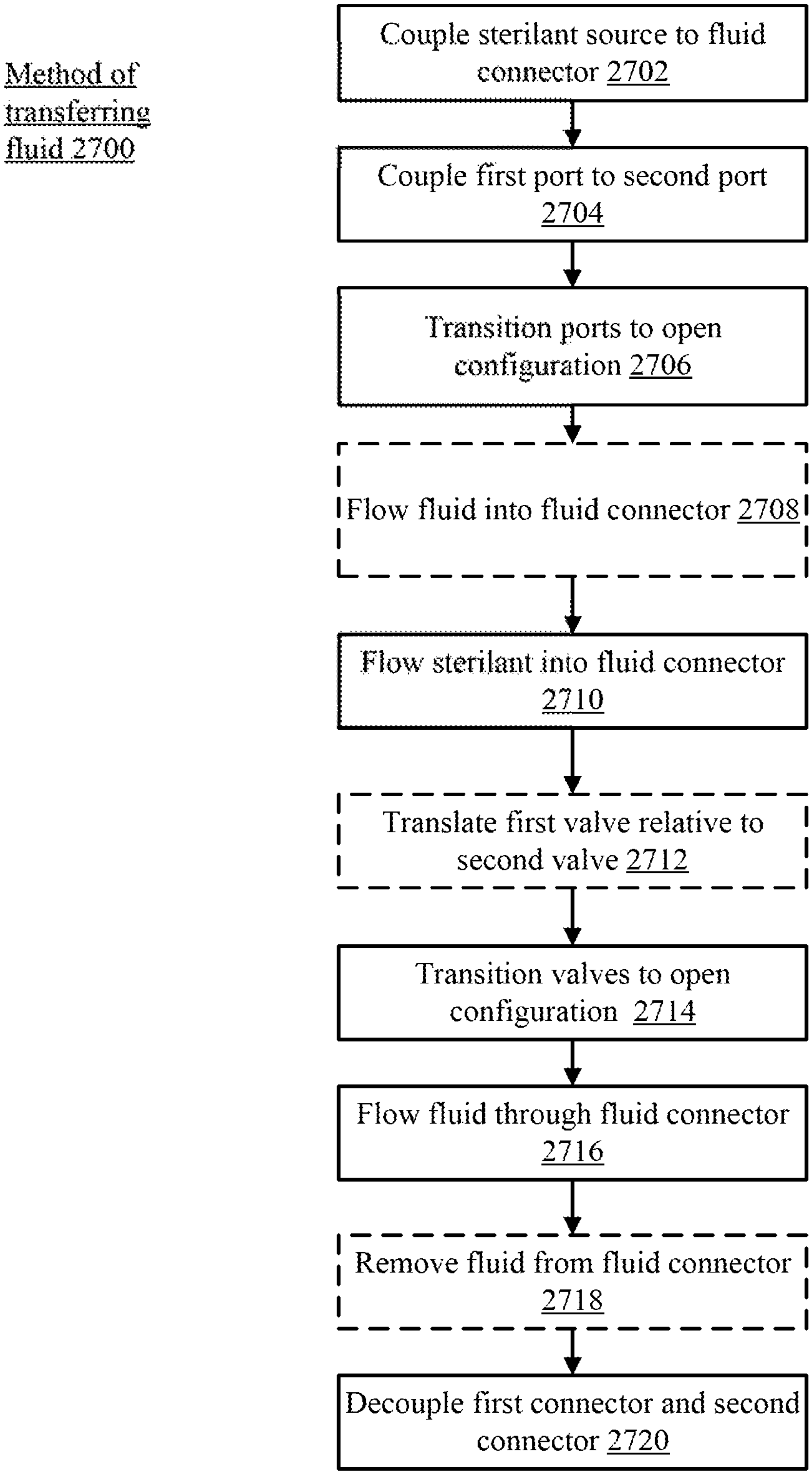
FIG. 27 is a flowchart of an illustrative variation of a method of transferring fluid using a fluid connector.

A method of transferring fluid using a fluid connector 2700 is described in the flowchart of FIG. 27 and illustrated schematically in the corresponding steps depicted in FIGS. 16B-16L. The method 2700 may comprise the step of coupling a sterilant source to a fluid connector 2702. For example, as shown in FIG. 16B, the inlet 1652 and outlet 1654 is coupled to a sterilant source to form a fluid pathway or connection. In some variations, a robot may be configured to couple and decouple the sterilant source to the sterilant port 1650 using a fluid conduit such as a tube. In some variations, the fluid connector 1600 may comprise a plurality of sterilant ports 1650. As described herein, in some variations, a sterilant port may optionally comprise one or more of a check valve and a particle filter configured to reduce ingress of debris (e.g., after disconnecting the fluid connector). In some variations, the sterilant source may comprise or be coupled to a pump configured to circulate a sterilant through the sterilant port 1650. In some variations, the sterilant port 1650 may be coupled to one or more of a sterilant source and a fluid source such as a heated air source. For example, a first sterilant port may be configured to couple to a first sterilant source, a second sterilant port may be configured to couple to a second sterilant source, and a third sterilant source may be configured to couple to an air source.

The separate portions of the fluid connector 1600 may be brought together and mated. The method 2700 may comprise coupling a first port of a first connector to a second port of a second connector 2704. FIG. 16C is a schematic diagram of the fluid connector 1600 where the first port 216 and second port 226 are in a coupled configuration (e.g. docked position) that forms a first seal. In some variations, the first connector 1610 and the second connector 1620 may be axially and/or rotationally aligned, and one or more of the connectors 1610, 1620 may be translated to couple the connectors 1610, 1620 together. In FIG. 16C, the first port 1616 and the second port 1626 are each in a closed configuration where the lumens of the respective first connector 1610 and second connector 1620 are sealed from the external environment to maintain sterility of the lumen of the fluid connector 1600. Furthermore, the first valve 1618 and the second valve 1628 are each in a closed configuration that seals the proximal and distal ends of the connectors from each other. For example, the first valve 1618 in the closed configuration forms a seal (e.g., barrier) between the first proximal end 1612 and the first distal end 1614. Similarly, the second valve 1628 in the closed configuration forms a seal between the second proximal end 1622 and the second distal end 1624. In this manner, even if a portion of a connector is contaminated (e.g., first distal end 1614), then the other portions of the fluid connector 1600 (e.g., first proximal end 1612, second connector 1620) may remain sterile by virtue of one or more of the port seals and valve seals.

The ports may be transitioned to an open configuration such that a distal end of the connectors may be in fluid communication. The method 2700 may comprise transitioning the ports to an open configuration 2706. FIG. 16D is a schematic diagram of the fluid connector 1600 where the first port 1616 and the second port 1626 are transitioned into an open port configuration to create a shared volume between the valves 1618, 1628 that is isolated from the external environment. In FIG. 16D, the first valve 1618 and the second valve 1628 are in the closed configuration such that the chamber 1615 defines the volume (e.g., cavity) of the fluid connector 1600 between the first valve 1618 and the second valve 1628. That is, the first distal end 1614 is in fluid communication with the second distal end 1624. The ports 1616, 1627 may be received and/or held in respective housings 1617, 1627 in the closed configuration. In some variations, a robot may be configured to transition the ports 1616, 1626 between the open configuration and the closed configuration as described in more detail herein. Additionally or alternatively, the first port 1616 and second port 1626 may automatically transition (e.g., mechanically actuate) from the closed configuration to the open configuration upon mating the first port 1616 to the second port 1626.

Figure 16E:
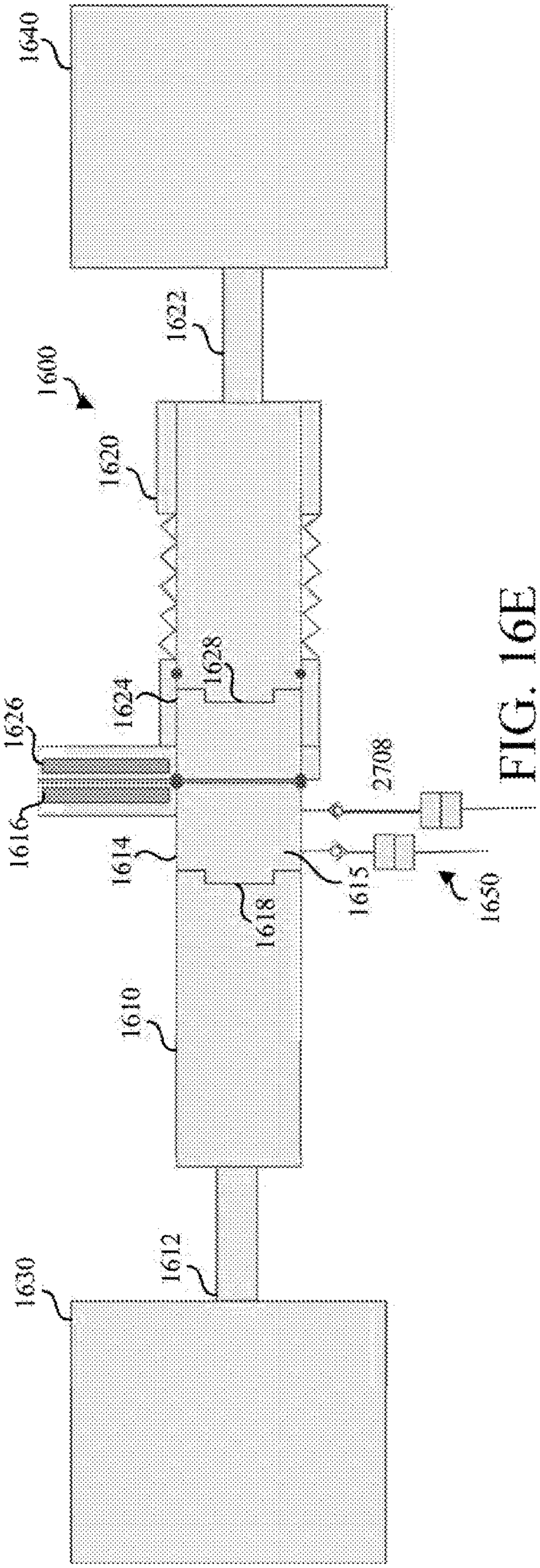
FIG. 16E is a schematic diagram of the fluid connector depicted in FIG. 16A receiving a gas.

In some variations, a fluid may be flowed into the fluid connector to aid sterilization. The method 2700 may comprise flowing fluid (e.g., liquid, gas) into the fluid connector through the sterilant port 2708. FIG. 16E is a schematic diagram of the fluid connector 1600 where the first chamber 1615 receives a fluid such as air at a predetermined temperature, pressure, and/or humidity. In some variations, one or more portions of the fluid connector 1600 may be dehumidified. For example, pressurized hot air may optionally be circulated within chamber 1615 in order to remove residual fluid, moisture, and raise a temperature of the inner surfaces of the chamber 1615. The circulated fluid may flow through housings 1617, 1627 and over inner and/or outer surfaces of the ports 1616, 1626.

Generally, sterilization of a fluid connector may comprise one or more steps of dehumidification, conditioning, decontamination, and aeration (e.g., ventilation). Dehumidification may include removing moisture from the fluid connector. Conditioning may include heating the surfaces of the fluid connector to be decontaminated in order to prevent condensation and aid sterilization. Decontamination may include circulating a sterilant through the fluid connector at a predetermined concentration, rate, and exposure time. Aeration may include removing the sterilant from the fluid connector by circulating a gas (e.g., sterile air) through the fluid connector.

Figure 16F:
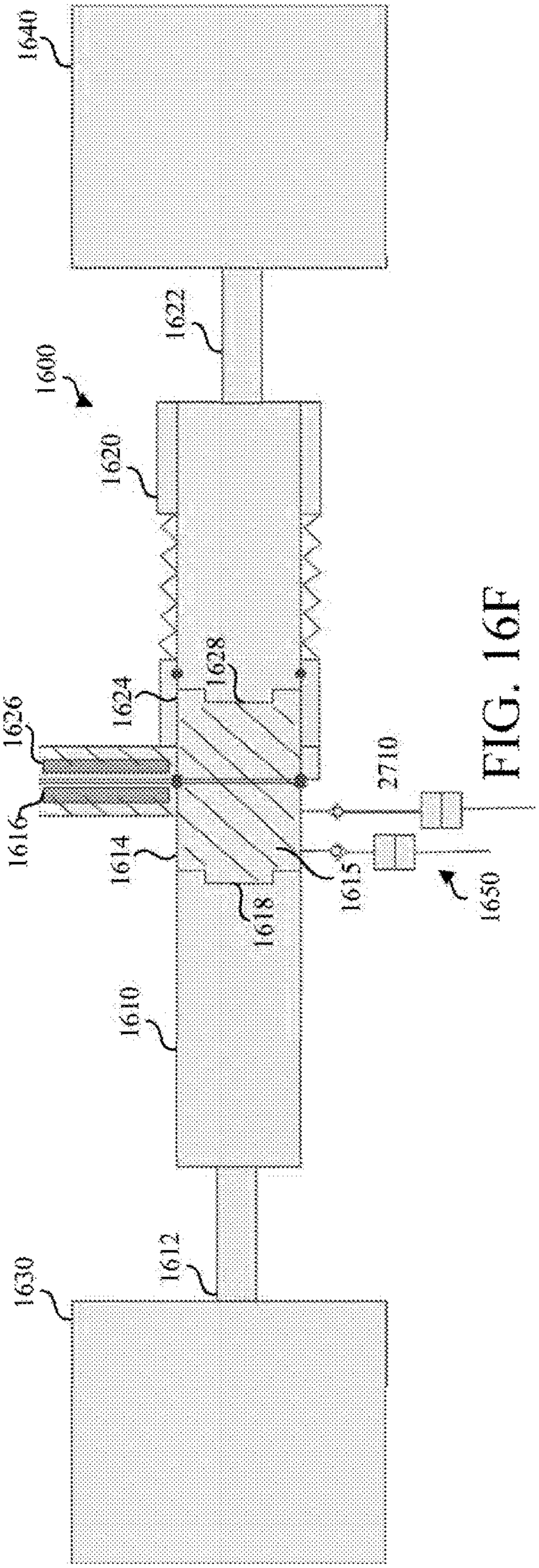
FIG. 16F is a schematic diagram of the fluid connector depicted in FIG. 16A receiving a sterilant.

A sterilant may be flowed into the fluid connector to sterilize one or more portions of the fluid connector. As described in more detail herein, the sterilant may be, for example, vaporized hydrogen peroxide (VHP) and/or ionized hydrogen peroxide (IHP). The method 2700 may comprise flowing a sterilant into the fluid connector through the sterilant port 2710. FIG. 16F is a schematic diagram of the fluid connector 1600 where the first chamber 1615 receives the sterilant for a predetermined amount of time (e.g., dwell time). For example, the sterilant may be circulated within the chamber 1615 to sterilize the chamber 1615 of the fluid connector 1600 and any contents disposed therein (e.g., other fluid, biological material). In some variations, the dwell time may be up to about 10 minutes, and between about 1 minute to about 10 minutes, including all ranges and sub-values in-between. In some variations, the vaporized hydrogen peroxide may comprise a concentration between about 50% and about 70%, including all ranges and sub-values in-between. Additionally or alternatively, one or more of the first valve 1618 and the second valve 1628 may be in the open configuration such that the sterilant may be circulated through other portions of the fluid connector 1600 such as first proximal end 1612 and second proximal end 1622.

Figure 16G:
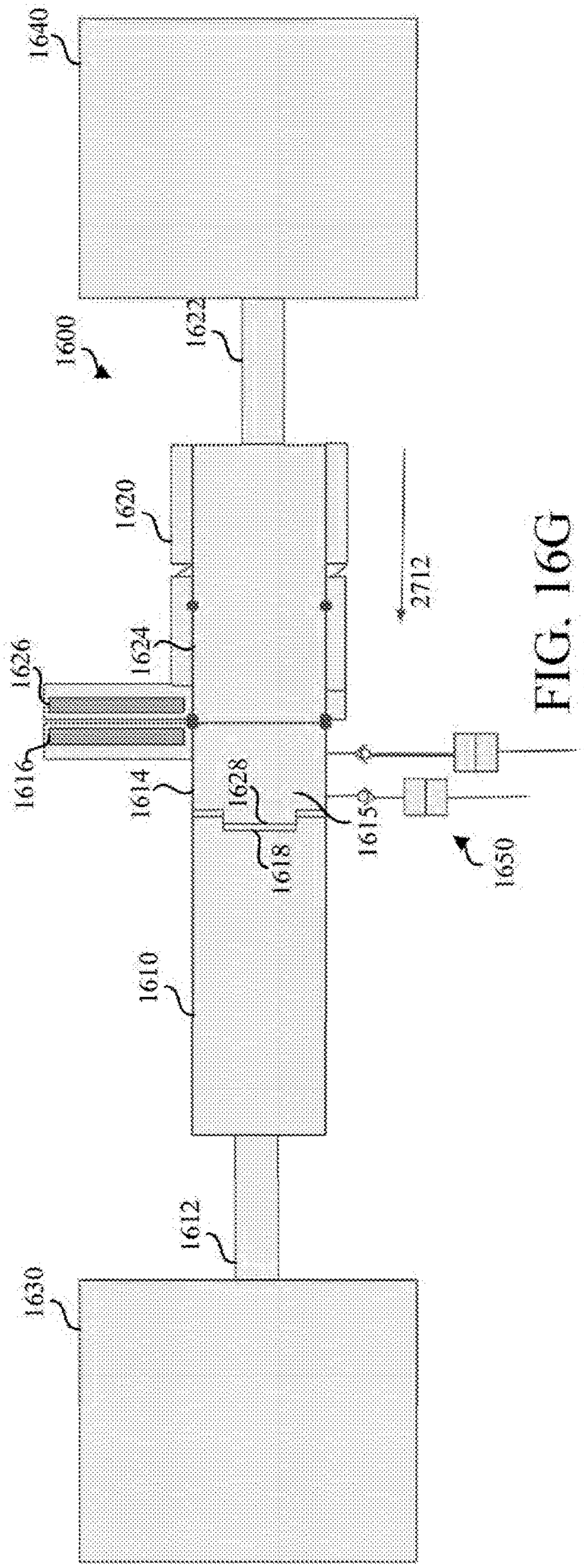
FIG. 16G is a schematic diagram of the fluid connector depicted in FIG. 16A in an open valve configuration.

In some variations, the valves may be translated relative to each other. The method 2700 may comprise translating a first valve relative to a second valve 2712. FIG. 16G is a schematic diagram of the fluid connector 1600 where the first valve 1618 and second valve 1628 are coupled to each other (e.g., transfer position). The first valve 1618 coupled to the second valve 1628 forms a second seal between the first connector 1610 and the second connector 1620.

The valves may be transitioned to an open configuration such that each end of the fluid connector is in fluid communication. The method 2700 may comprise transitioning the first valve and the second valve from a closed configuration to an open configuration 2714. In some variations, the first valve and the second valve may comprise a spring-loaded shutoff configured to actuate to the open configuration, thereby allowing for fluidic communication between the sterile lumens of the first connector 1610 and the second connector 1620. In some variations, each of the first valve 1618 of a first connector 1610 and the second valve 1628 of a second connector 1620 may comprise an engagement feature such as threading configured to facilitate coupling between the first valve 1618 and the second valve 1628. For example, once the second valve 1628 is translated to contact the first valve 1618, the engagement features of the valves 1618, 1628 may be coupled (e.g., locked) by rotating (e.g., twisting) one of the first valve 1618 and the second valve 1628 to engage their respective threads to each other. Conversely, one of the first valve 1618 and the second valve 1628 may be rotated in the opposite direction to uncouple (e.g., unlock) the first valve 1618 from the second valve 1628.

Figure 16H:
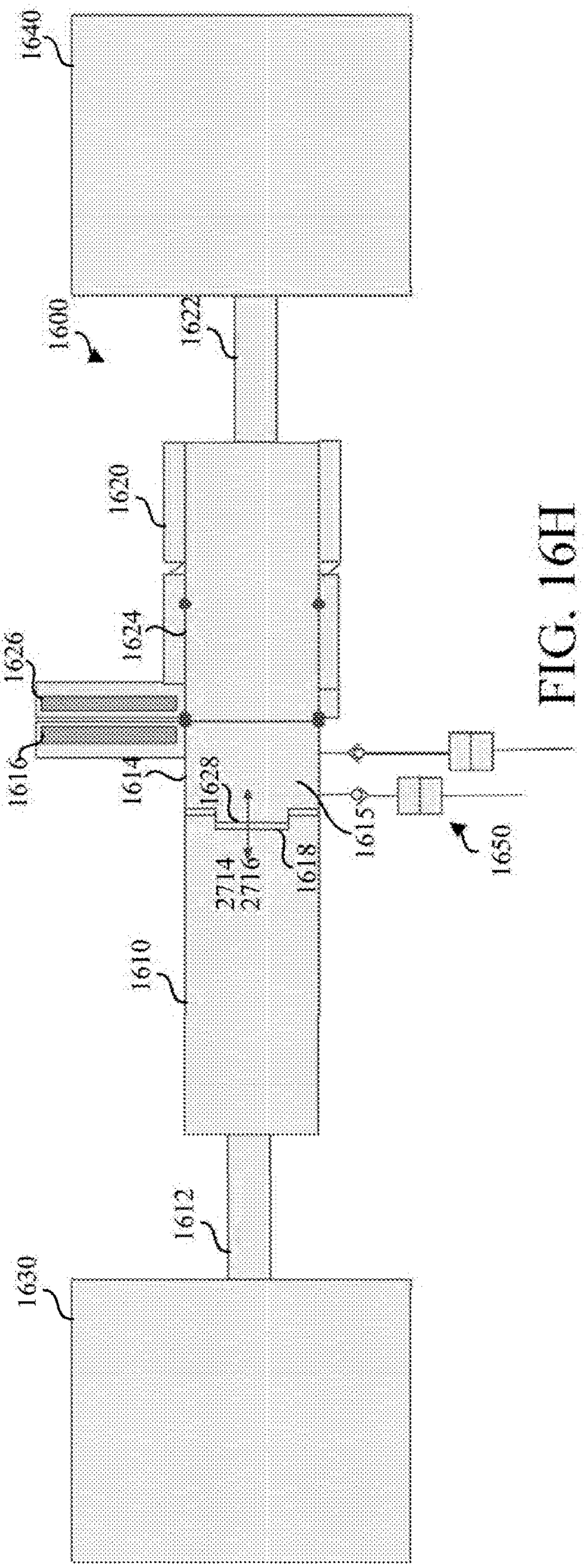
FIG. 16H is a schematic diagram of the fluid connector depicted in FIG. 16A transferring fluid between fluid devices coupled to the fluid connector.

In some variations, fluid may flow through the fluid connector 2716. FIG. 16H is a schematic diagram of the fluid connector depicted in FIG. 16A transferring fluid between fluid devices coupled to the fluid connector. For example, the contents (e.g., fluid, biological material) of the first fluid device 1630 and the second fluid device 1640 may be transferred through the fluid connector 1600. In some variations, one or more of a pump, gravity feed, and the like may aid transfer through the fluid connector 1600.

In some variations, another fluid may be flowed into the fluid connector after fluid transfer between a first fluid device and a second fluid device has been completed. The method 2700 may comprise flowing fluid (e.g., liquid, gas, sterilant) into the fluid connector through the sterilant port 2708 to remove a fluid and/or biological material from the fluid connector 2718. For example, flowing an inert gas into the fluid connector may reduce drops of liquid from forming when the first connector and second connector are separated. If a sterilant is flowed through the fluid connector, another fluid such as an inert gas may be flowed to aerate the fluid connector and ensure that the sterilant is removed.

Figure 16I:
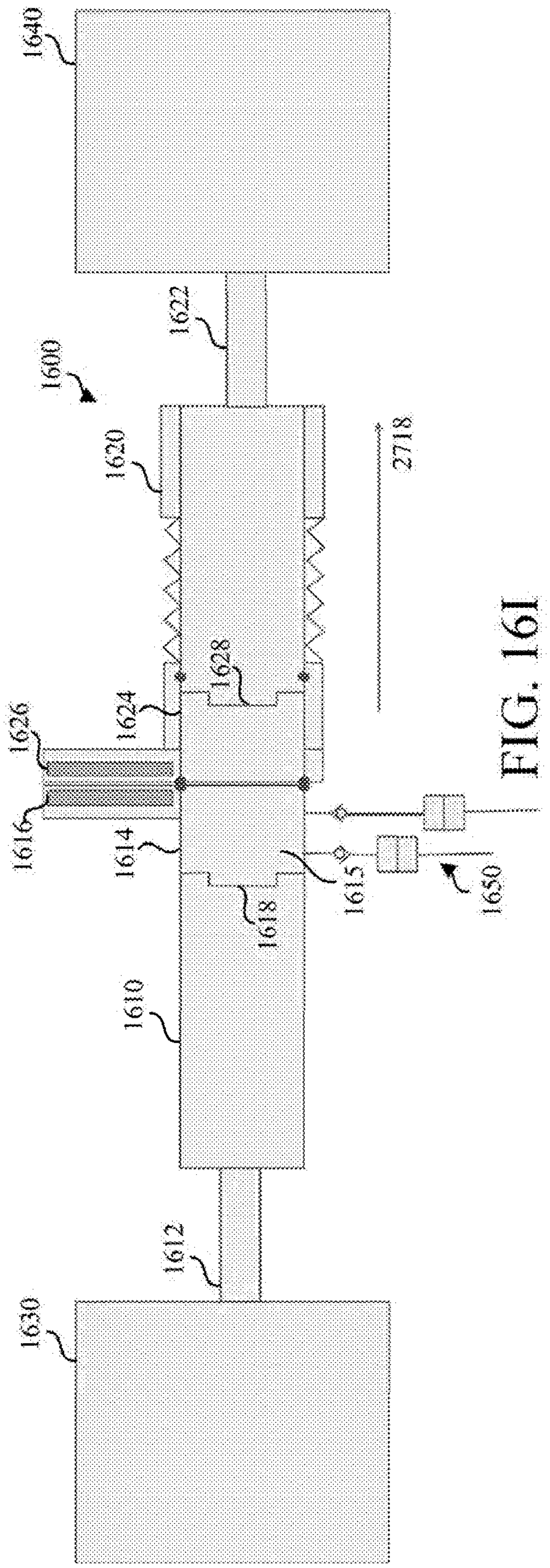
FIG. 16I is a schematic diagram of the fluid connector depicted in FIG. 16A in a closed valve configuration.

To begin decoupling the fluid connector, the valves may be translated away from each other. The method 2700 may comprise decoupling the first connector and the second connector 2720. In some variations, a robot may be configured to manipulate the fluid connector 1600 to transition the valves 1618, 1628 to a closed configuration and to translate the valves 1618, 1628 away from each other, which may occur simultaneously or independently. The valves 1618, 1628 in the closed configuration inhibit fluid flow between the first connector 1610 and the second connector 1620. FIG. 16I is a schematic diagram of the fluid connector 1600 in a closed valve configuration where the second valve 1628 is translated away from the first valve 1618. Accordingly, the fluid connector 1600 returns to the docked position. For example, the first valve 1618 and the second valve 1628 may be configured to engage their respective spring-loaded shutoff features to form a seal and reduce drips and/or leaks. In some variations, one or more of a fluid and sterilant may optionally be configured to circulate through the chamber 1615 to remove moisture and/or sterilize the chamber 1615.

Figure 16J:
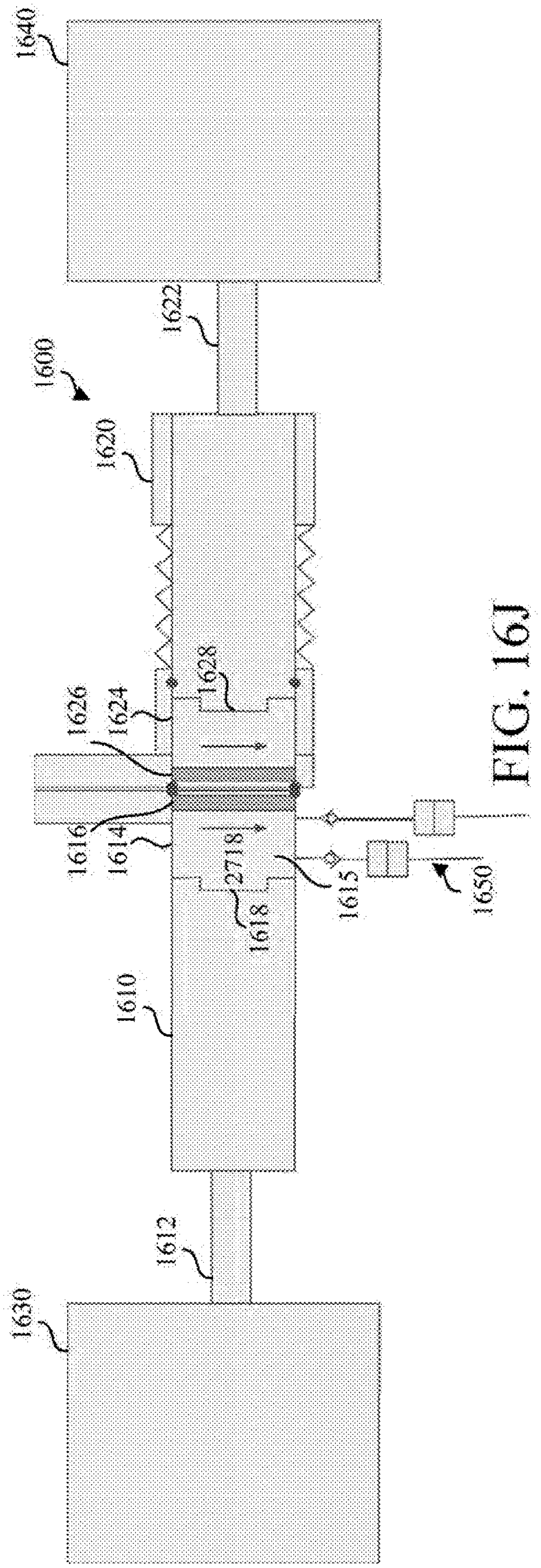
FIG. 16J is a schematic diagram of the fluid connector depicted in FIG. 16A in a closed port configuration.

FIG. 16J is a schematic diagram of the fluid connector 1600 where the first port 1616 and the second port 1626 are transitioned from the open port configuration to the closed port configuration. In some variations, a robot may be configured to manipulate the fluid connector 1600 to transition the ports 1616, 1626 to a closed position to seal a lumen of the first connector 1610 from a lumen of the second connector 1620. In some variations, the ports 1616, 1626 may be configured to automatically transition to the closed port configuration when the first valve 1618 separates from the second valve 1628.

Figure 16K:
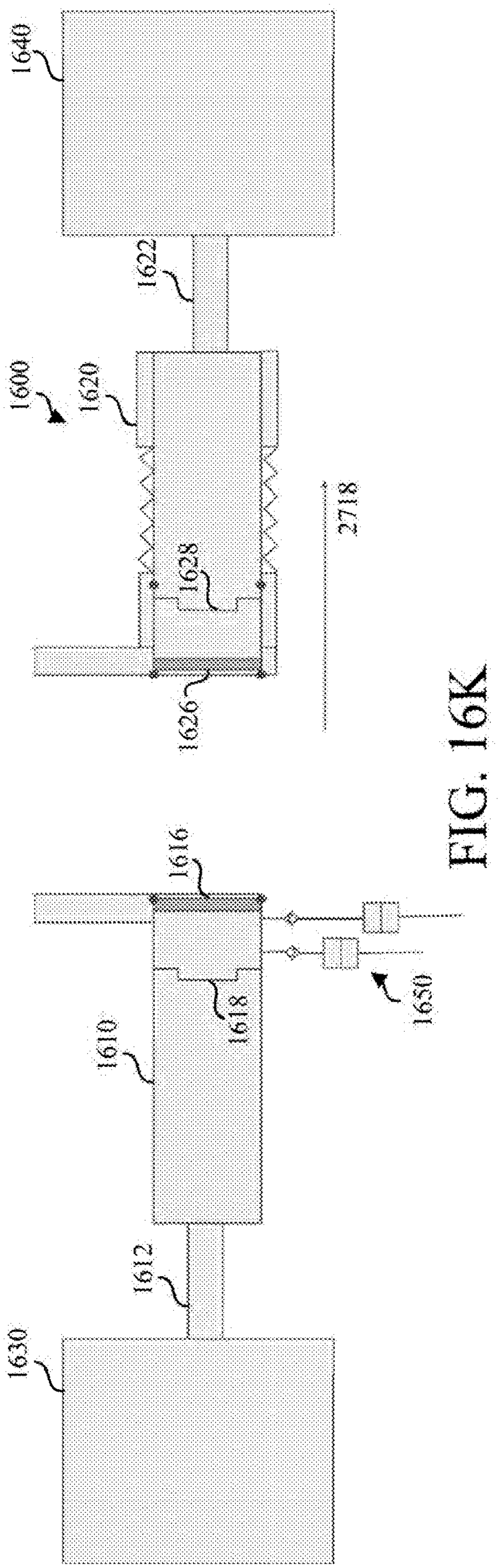
FIG. 16K is a schematic diagram of the fluid connector depicted in FIG. 16A in an uncoupled configuration.

FIG. 16K is a schematic diagram of the fluid connector 1600 where the second connector 1620 is translated away from the first connector 1610. In some variations, a robot may be configured to manipulate the fluid connector 1600 to separate the first connector 1610 from the second connector 1620. FIG. 16K depicts the fluid connector 1600 in a disengaged configuration.

Figure 16L:
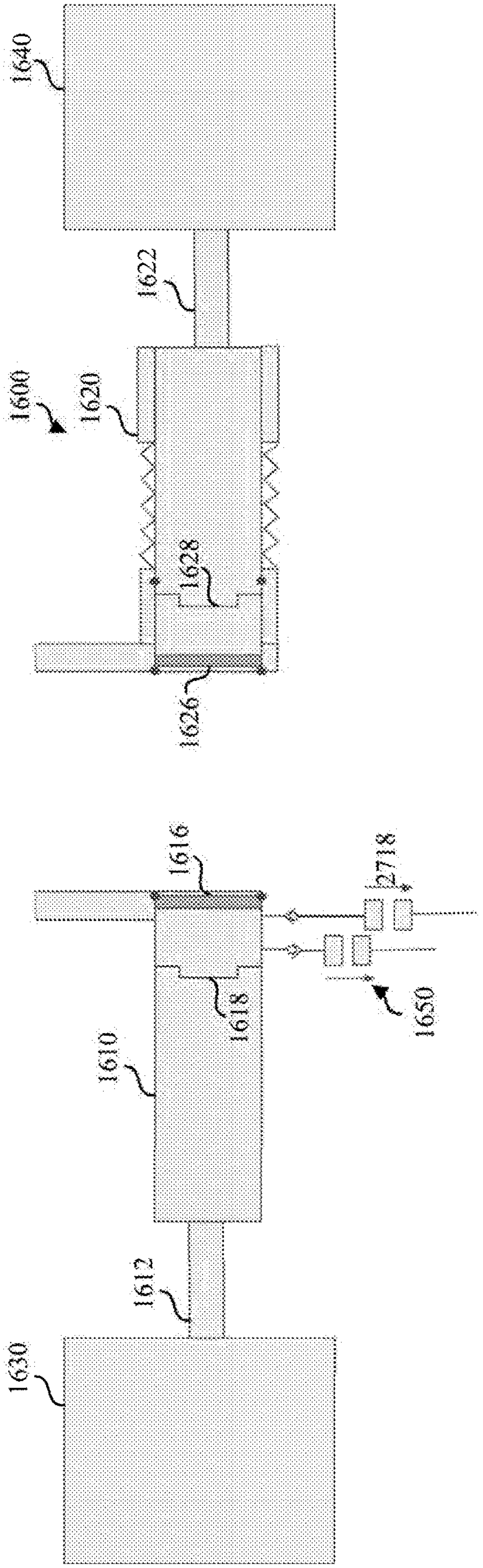
FIG. 16L is a schematic diagram of the fluid connector depicted in FIG. 16A uncoupled from a sterilant source.

FIG. 16L is a schematic diagram of the fluid connector 1600 decoupled from the sterilant source. In some variations, a robot may be configured to manipulate the fluid connector 1600 and/or sterilant source to separate the sterilant source 1650 from the sterilant source. In some variations, the sterilant source may be decoupled from the fluid connector 1600 at any point after completing a sterilization process.

In some variations, the cartridge comprises one or more Sterile Liquid Transfer Ports (SLTPs) configured for use with a Sterile Liquid Transfer Device (SLTD). In some variations, the SLTP comprises one or more of a cap, a fitting, and a tube fluidically coupled to the fitting. The cap may be removable or pierceable. The fitting may be a push-to-connect fitting (PTCF) or a threaded fitting. PTCF include male-to-female, female-to-male, and androgynous fittings. Illustrative SLTPs and SLTDs suitable for use in the systems of the disclosure may include, for example, AseptiQuik® S connectors, Lynx® CDR connectors, Kleenpak™ connectors, Intact™ connectors, GE LifeScience® ReadyMate connectors.

When the disclosure refers to sterile liquid transfer devices, sterile liquid transfer ports, and sterile liquid transfer, the word "sterile" should be understood as a non-limiting description of some variations—an optional feature providing advantages in operation of certain systems and methods of the disclosure. Maintaining sterility is typically desirable for cell processing but may be achieved in various ways, including but not limited to providing sterile reagents, media, cells, and other solutions; sterilizing cartridge(s) and/or cartridge component(s) after loading (preserving the cell product from destruction); and/or operating the system in a sterile enclosure, environment, building, room, or the like. Such operator performed or system performed sterilization steps may make the cartridge or cartridge components sterile and/or preserve the sterility of the cartridge or cartridge components.

III. Examples

Figure 85:
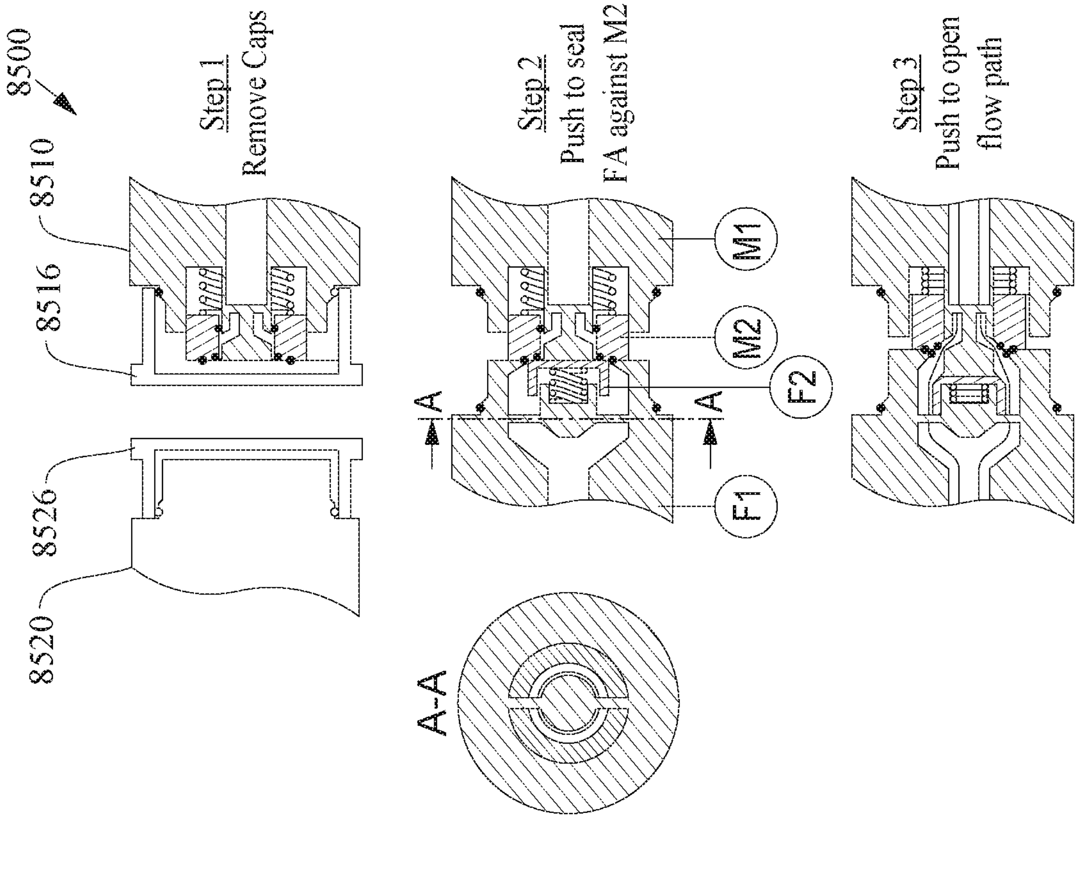
FIG. 85 are schematic diagrams of an illustrative variation of a fluid connector.

FIGS. 85-96D are diagrams of other variations of a fluid connector. FIG. 85 depicts a fluid connector 8500 comprising a first connector 8510 including a first cap 8516 and a second connector 8520 including a second cap 8526. Fluid connector 8500 may comprise a male connector and a female connector, each with a removable cap and internal self-shutoff valve configured to reduce leaks and drips. The first cap 8516 and the second cap 8526 may be removable from their respective connectors 8510, 8520.

Figure 86:
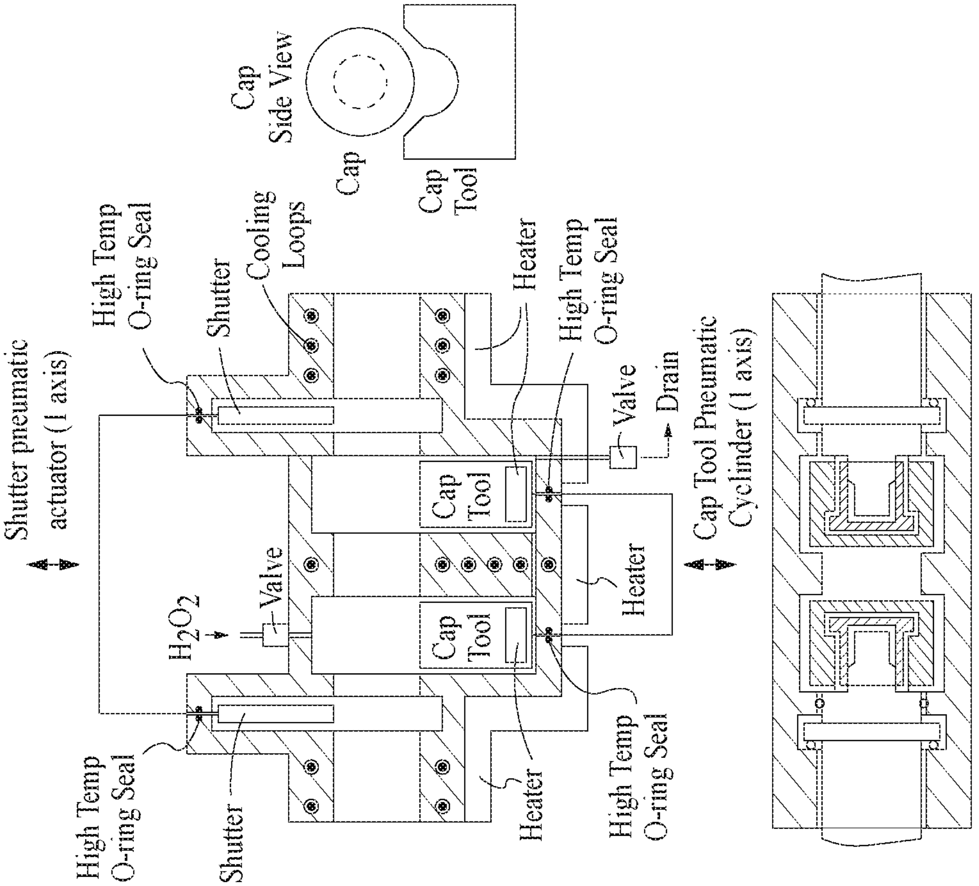
FIG. 86 are schematic diagrams of an illustrative variation of a fluid connector port.

In some variations, the fluid connector may be used with a self-sterilizing cap and decap tool 8600 depicted in FIG. 86. The cap/decap tool 8600 may be configured to facilitate a sterile environment (e.g., ISO5) where the caps may be removed and the connectors pressed together, first sealing the connectors to each other, and then pressed further to transition the internal self-shutoff valves to an open configuration.

In some variations, the tool 8600 may be configured to remove and re-apply caps to the fluid connector 8500, and to provide a sterile volume for aseptic connection and disconnection of the fluid connector 8500 pair. In some variations, a method of using the tool 8600 may comprise inserting both capped connectors in a first configuration (e.g., where the caps approach the closed shutters) such that the fluid connectors form a seal within a lumen of the decap tool 8600. In some variations the shutters may be opened to ensure a decap mechanism is retracted. Both capped connectors may be pushed to form a second configuration. The decap mechanism may be engaged to lock into features on the caps. Both capped connectors may be retracted to the first configuration where the caps are retained in the decap mechanism. The decap mechanism may be retracted such that the caps are held within a recess in the tool 8600. The internal volume may optionally be decontaminated with sterilant or heat. Both connectors may be advanced to connect and perform the transfer. The steps described herein may be sequentially reversed.

Figure 87:
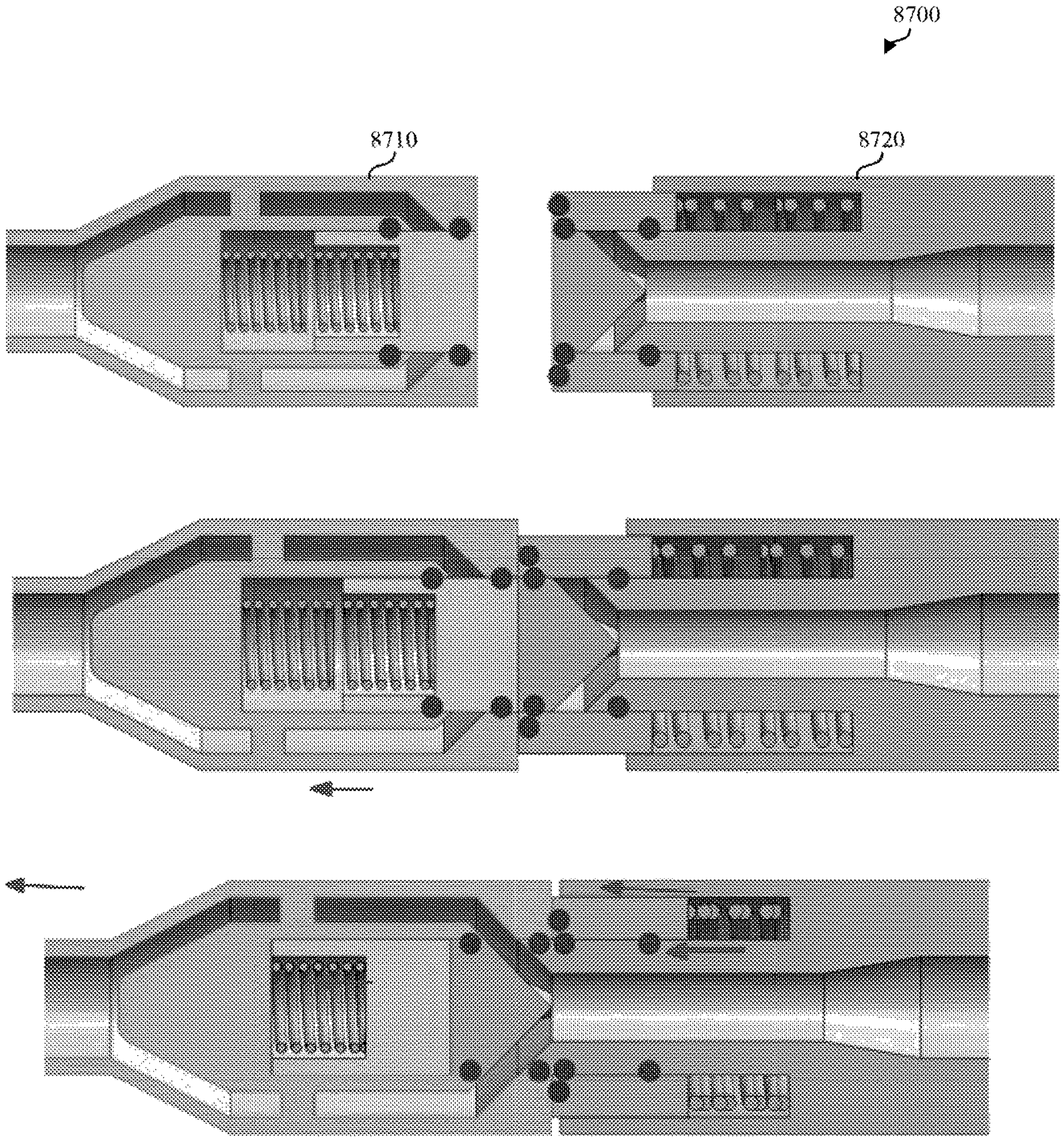
FIG. 87 is a schematic diagram of an illustrative variation of a fluid connector connection process.

FIG. 87 depict a coupling sequence for a self-sealing fluid connector 8700 comprising a first connector 8710 and a second connector 8720. The fluid connector 8700 may be configured to reduce leaks and drips and may facilitate smoother fluid flow path by removing spring elements from contact with fluid.

Figure 88:
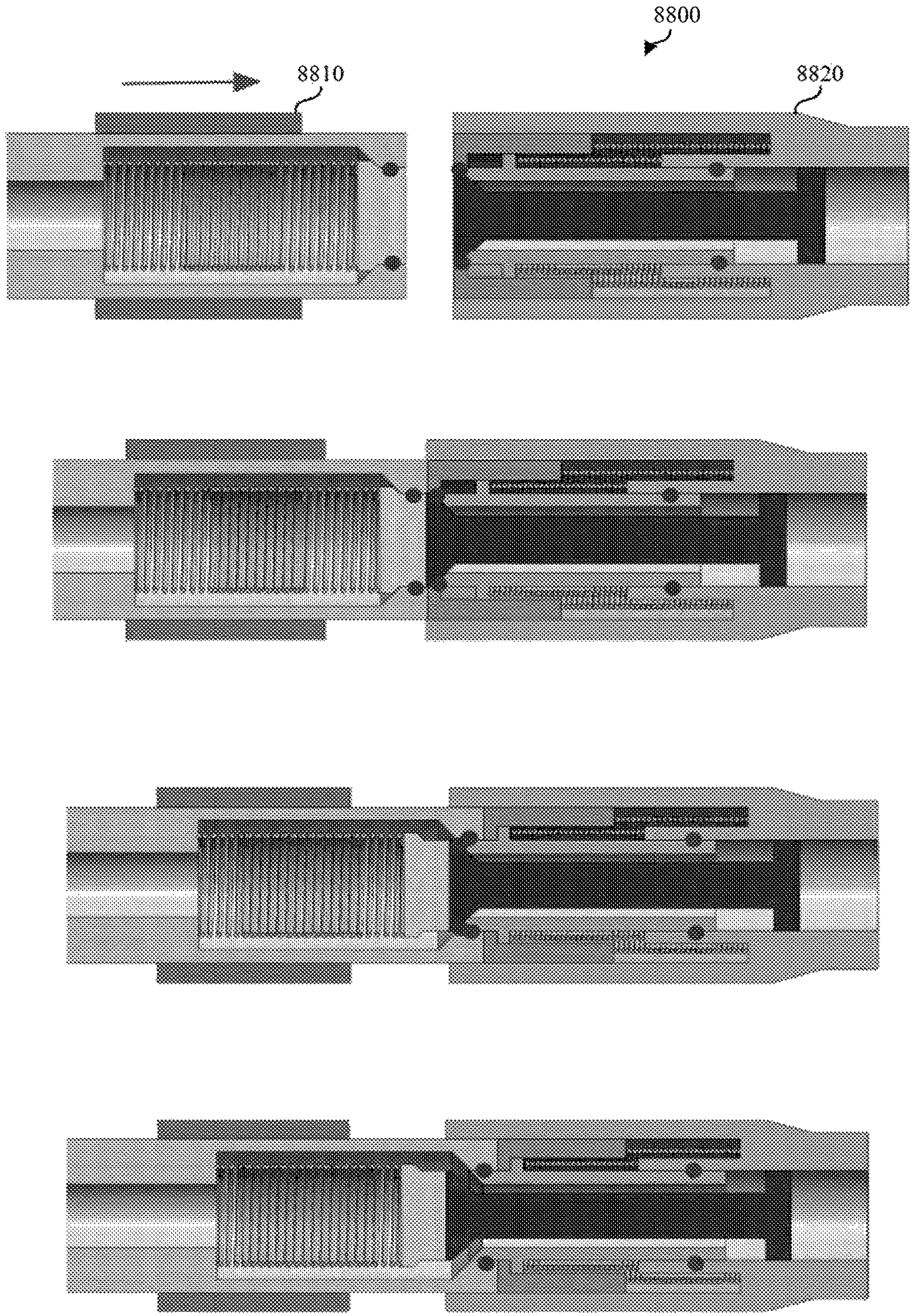
FIG. 88 is a schematic diagram of an illustrative variation of a fluid connector connection process.

FIG. 88 depict a coupling sequence for a self-sealing fluid connector 8800 comprising a first connector 8810 and a second connector 8820.

Figure 89:
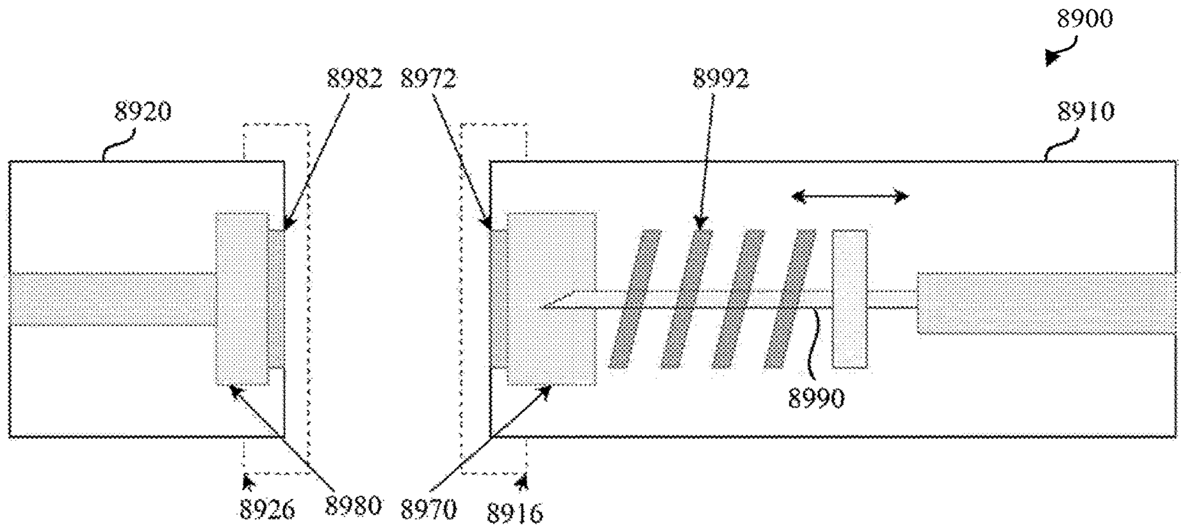
FIG. 89 is a schematic diagram of an illustrative variation of a fluid connector.

In some variations, a fluid connector may transfer fluids in a sterile manner using a retractable needle. FIG. 89 depicts a fluid connector 8900 comprising a first connector 8910 and a second connector 8920. The first connector 8910 may comprise a first cap 8916 configured to removably couple to a distal end of the first connector 8910. The first connector 8910 may comprise a first elastomeric member 8970 (e.g., sealing septum) and a first thermal member 8972 (e.g., thermally resealable septum) disposed at a distal end of the first connector 8910. The first connector 8910 may further comprise a needle 8990 and a spring 8992 coupled to the first elastomeric member 8970 and the needle 8990. The second connector 8920 may comprise a second cap 8926 configured to removably couple to a distal end of the second connector 8920. The second connector 8920 may comprise a second elastomeric member 8980 (e.g., sealing septum) and a second thermal member 8982 (e.g., thermally resealable septum) disposed at a distal end of the second connector 8920.

In some variations, the needle 8990 may be advanced through each of the first elastomeric member 8970, first thermal member 8972, second thermal member 8982, and second elastomeric member 8980 to form a fluid pathway between the first connector 8910 and the second connector 8920. Fluid may flow through the first connector 8910 and into the second connector 8920 via a lumen of needle 8990. Each of the elastomeric members 8970, 8980 and thermal members 8972, 8982 may seal once the needle 8990 is withdrawn from a distal end of the first connector 8910. For example, the thermal member 8972, 8982 may be configured to thermally seal at a predetermined temperature and the elastomeric members 8970, 8980 may self-seal once the needle 8990 has been withdrawn. In some variations, the fluid connector 8900 may be thermally decontaminated and resealed after fluid transfer. For example, the fluid connector 8900 (e.g., thermal members 8972, 8982) may be heated using one or more of a laser, contact heating, heated air, combinations thereof, and the like.

In some variations, a fluid connector may comprise a port comprising an actuator configured to transition the port between a closed port configuration and an open port configuration. In some variations, the actuator may comprise a spring such as an external spring, a rotary spring, and a linear spring, as described in more detail with respect to FIGS. 90A-96D.

Figure 90A:
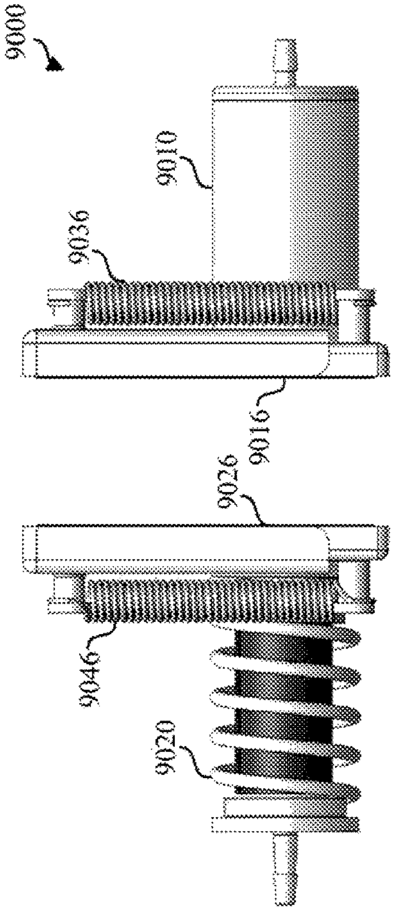
FIG. 90A is a side view of an illustrative variation of a fluid connector.
Figure 90B:
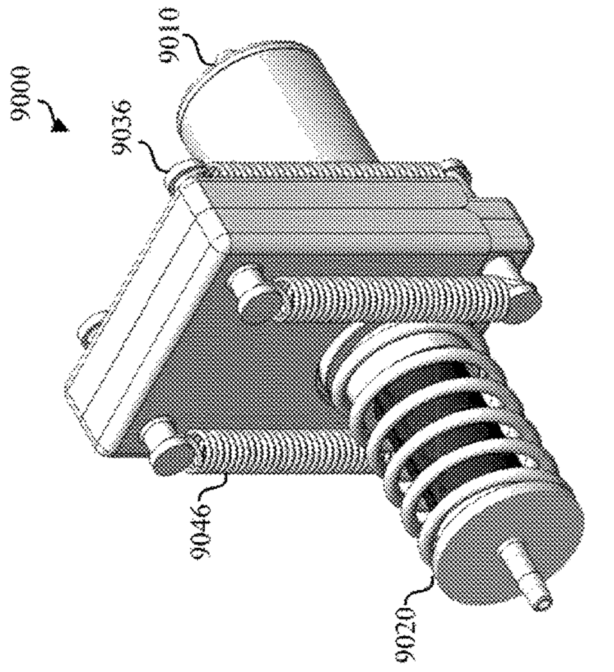
FIG. 90B is a perspective view of the fluid connector depicted in FIG. 90A.
Figure 90C:
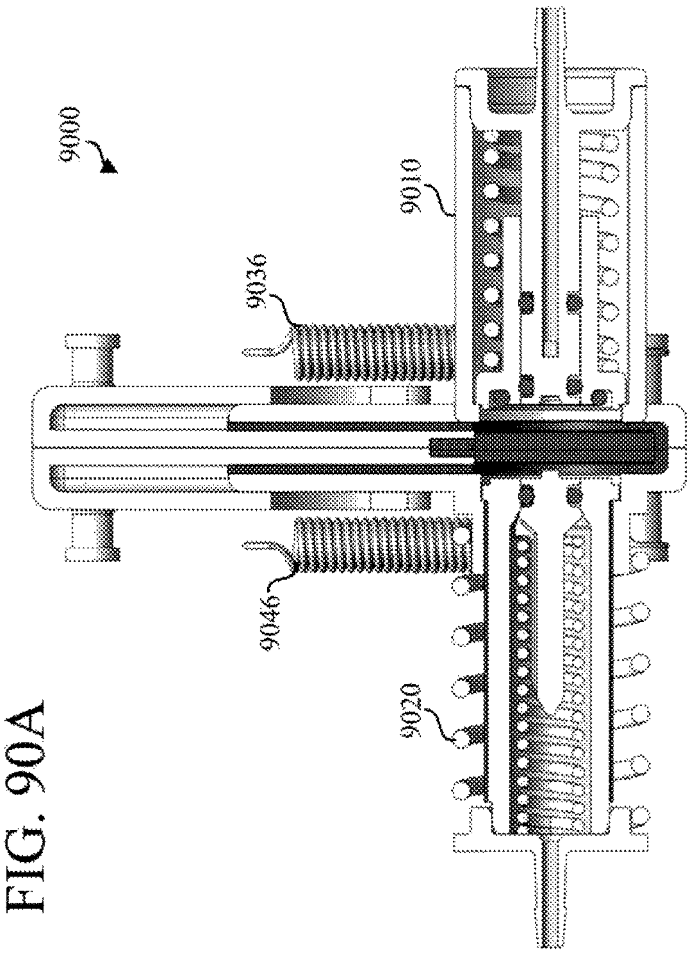
FIG. 90C is a cross-sectional side view of the fluid connector depicted in FIG. 90A.

FIGS. 90A-90C depict a fluid connector having an external spring actuator. FIG. 90A is a side view, FIG. 90B is a perspective view, and FIG. 90C is a cross-sectional side view of a fluid connector 9000 comprising a first connector 9010 and second connector 9020. The first connector 9010 may comprise a first port 9016 comprising a first spring 9036, and the second connector 9020 may comprise a second port 9026 comprising a second spring 9046. The springs 9036, 9046 may be configured to actuate respective ports 9016, 9026 between a closed port configuration and an open port configuration. Although not shown in FIG. 90C, springs 9036, 9046 may be coupled in an extended configuration to the pin in the open port configuration.

Figure 91A:
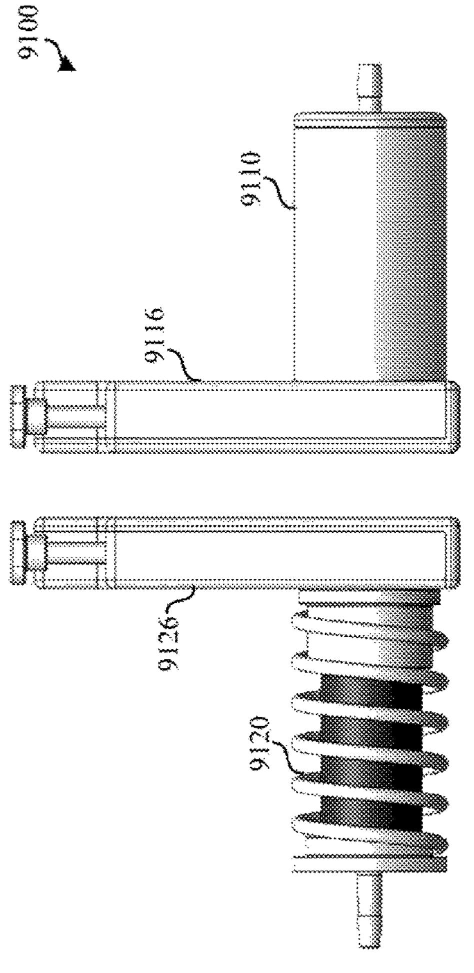
FIG. 91A is a side view of an illustrative variation of a fluid connector.
Figure 91B:
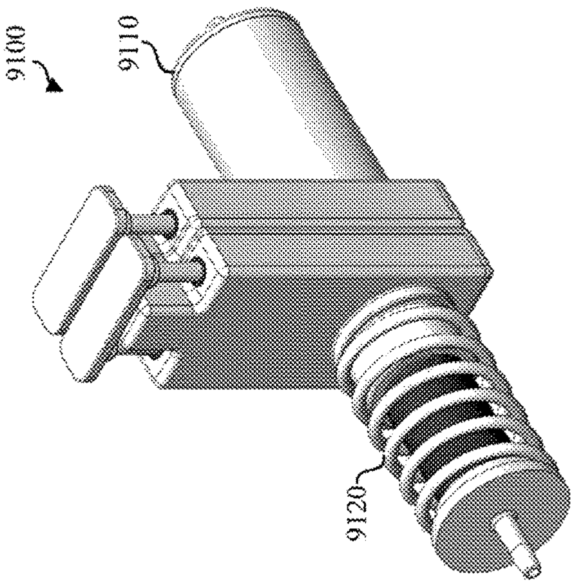
FIG. 91B is a perspective view of the fluid connector depicted in FIG. 91A.
Figure 91C:
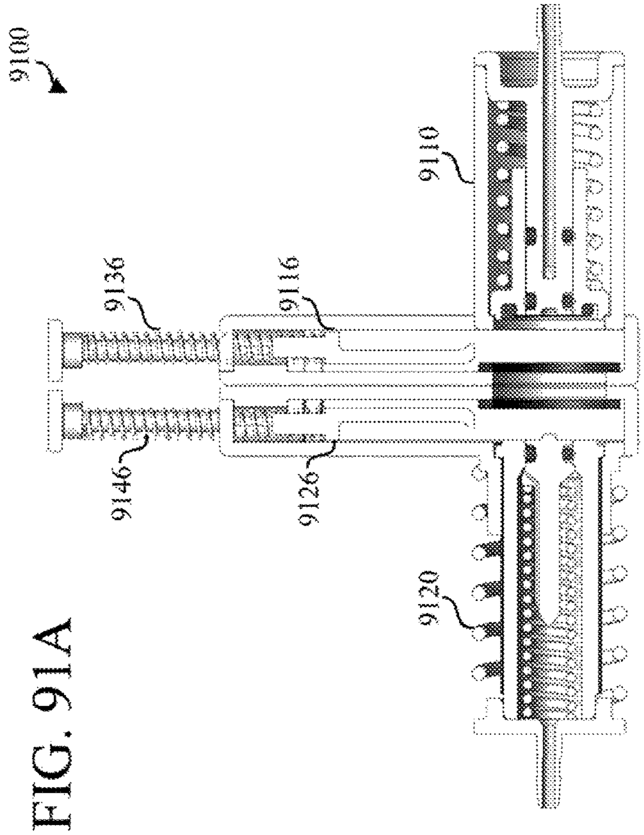
FIG. 91C is a cross-sectional side view of the fluid connector depicted in FIG. 91A.
Figure 91D:
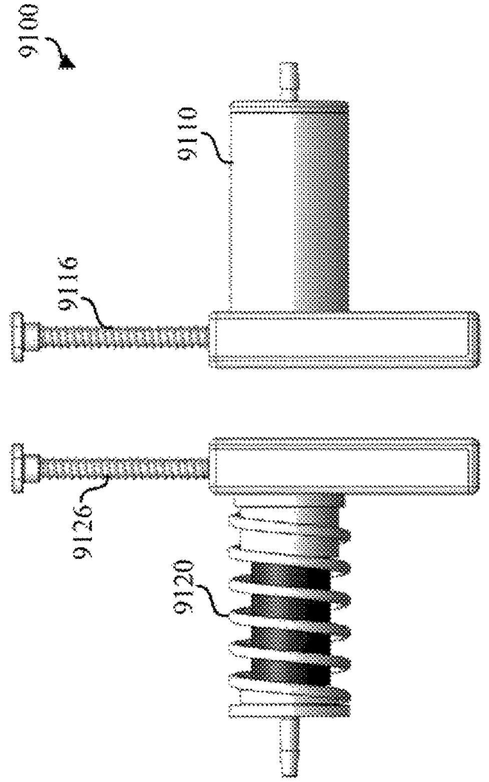
FIG. 91D is a side view of an illustrative variation of a fluid connector.
Figure 91F:
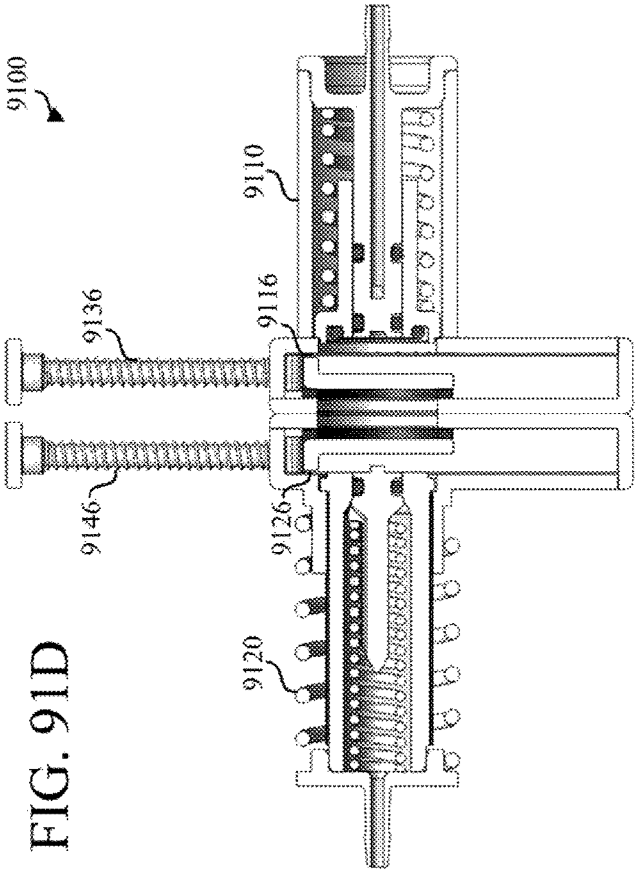
FIG. 91F is a cross-sectional side view of the fluid connector depicted in FIG. 91D.
Figure 91E:
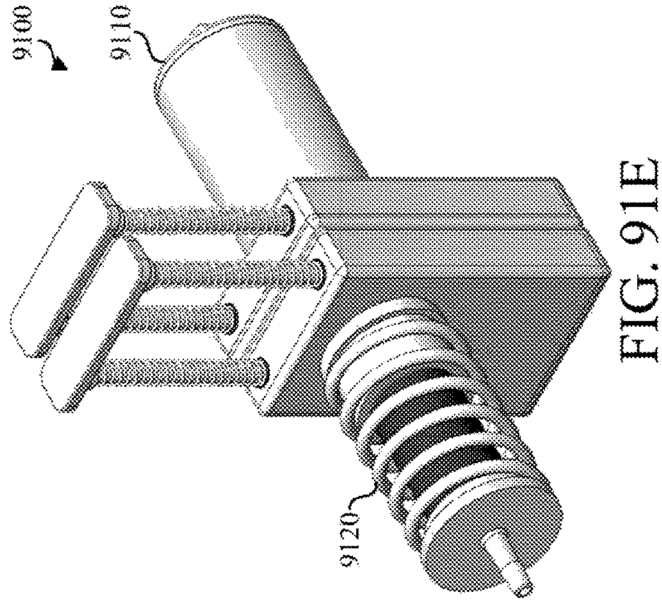
FIG. 91E is a perspective view of the fluid connector depicted in FIG. 91D.

FIGS. 91A-91F depict a fluid connector having a linear spring actuator. FIG. 91A is a side view, FIG. 91B is a perspective view, and FIG. 91C is a cross-sectional side view of the fluid connector 9100 in an open port configuration. The fluid connector 9100 may comprise a first connector 9110 and second connector 9120. The first connector 9110 may comprise a first port 9116 comprising a first spring 9136, and the second connector 9120 may comprise a second port 9126 comprising a second spring 9146. The springs 9136, 9146 may be configured to actuate respective ports 9116, 9126 between a closed port configuration and an open port configuration. FIG. 91D is a side view, FIG. 91E is a perspective view, and FIG. 91F is a cross-sectional side view of the fluid connector 9100 in a closed configuration.

Figure 92A:
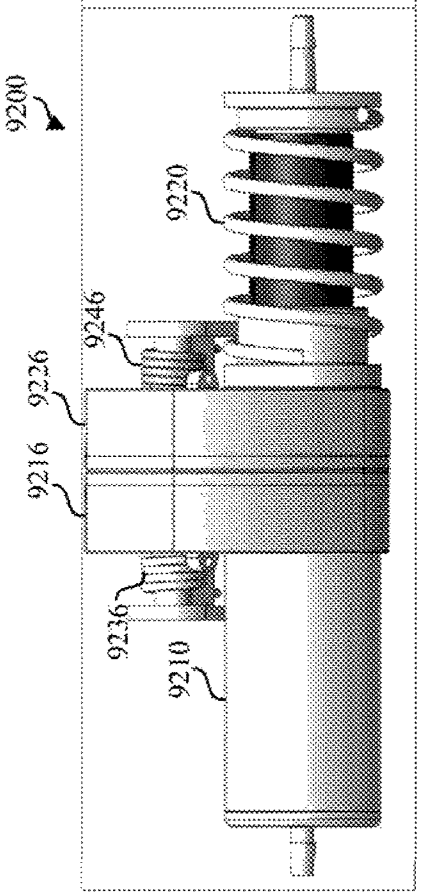
FIG. 92A is a side view of an illustrative variation of a fluid connector.
Figure 92B:
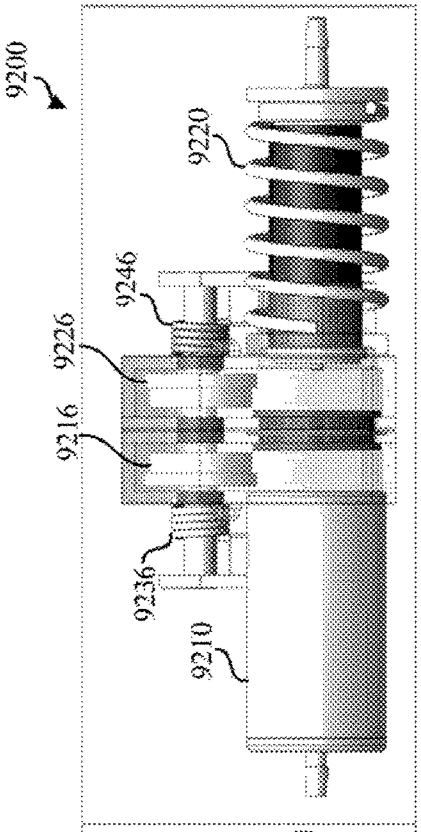
FIG. 92B is a transparent side view of the fluid connector depicted in FIG. 92A.
Figure 92C:
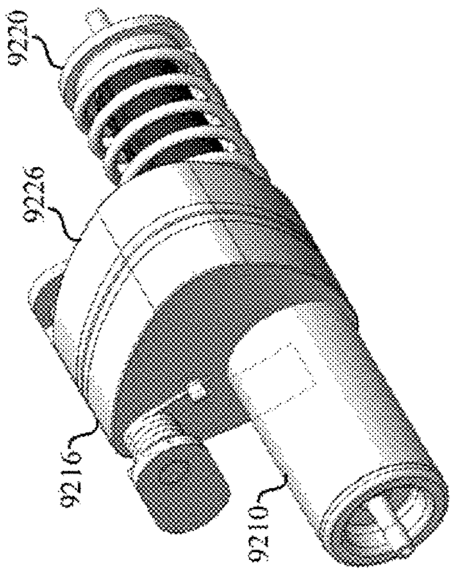
FIG. 92C is a perspective view of the fluid connector depicted in FIG. 92A.
Figure 92D:
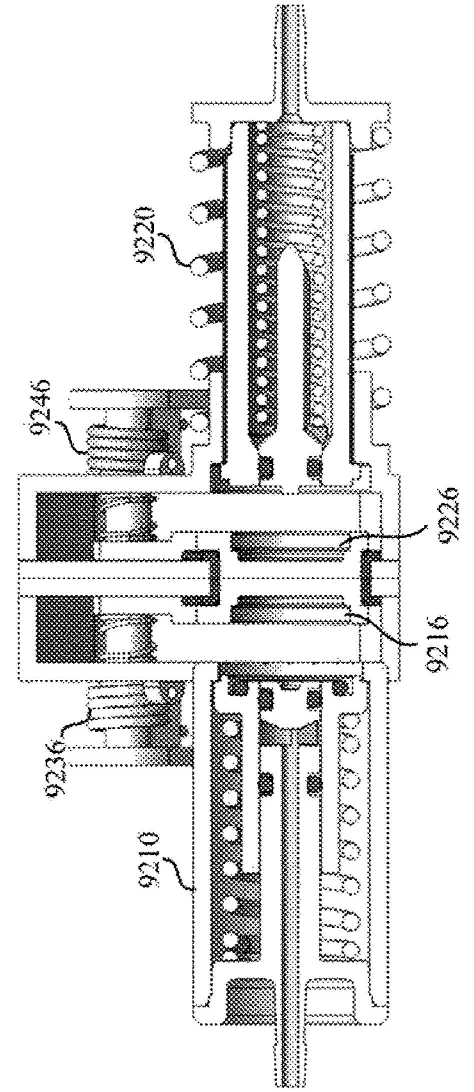
FIG. 92D is a cross-sectional side view of the fluid connector depicted in FIG. 92A.

FIGS. 92A-92D depict a fluid connector having a rotary spring actuator. FIG. 92A is a side view, FIG. 92B is a transparent side view, FIG. 92C is a perspective view, and FIG. 92D is a cross-sectional side view of a fluid connector 9200 comprising a first connector 9210 and second connector 9220. The first connector 9210 may comprise a first port 9216 comprising a first spring 9236, and the second connector 9220 may comprise a second port 9226 comprising a second spring 9246. The springs 9236, 9246 may be configured to actuate respective ports 9216, 9226 between a closed port configuration and an open port configuration. FIG. 92B shows the ports 9216, 9226 in an open port configuration and FIG. 92D shows the ports 9216, 9226 in a closed port configuration.

Figure 93A:
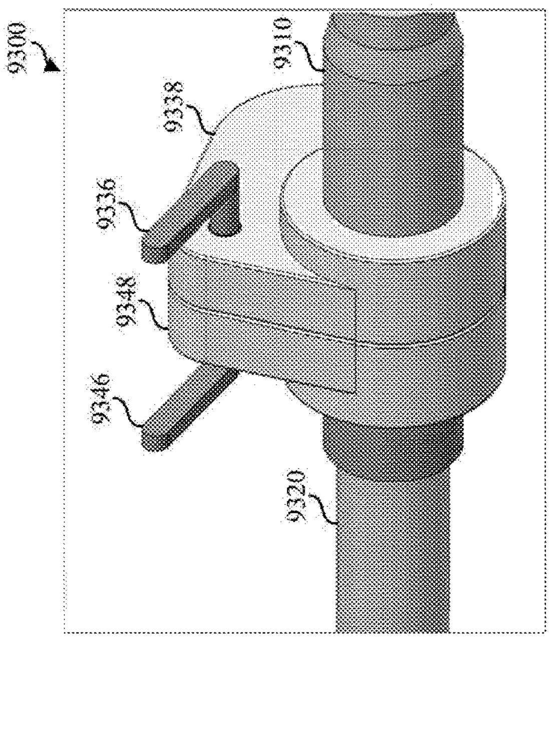
FIG. 93A is a perspective view of an illustrative variation of a fluid connector.
Figure 93B:
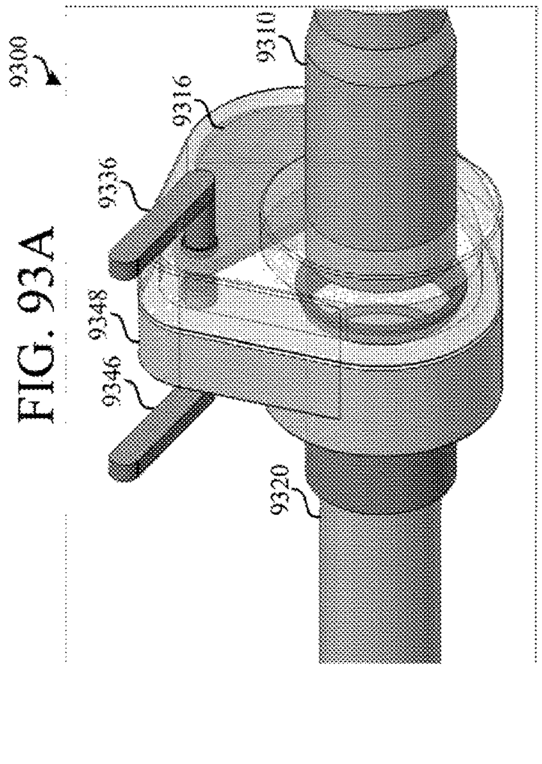
FIG. 93B is a transparent perspective view of the fluid connector depicted in FIG. 93A.

FIGS. 93A-94B depict fluid connectors having ports enclosed within a housing (e.g., enclosure). FIG. 93A is a perspective view and FIG. 93B is a transparent perspective view of a fluid connector 9300 comprising a first connector 9310 having a first housing 9338 and first actuator 9336, and a second connector 9320 having a second housing 9348 and a second actuator 9346. FIG. 93B shows a first port 9316 enclosed within first 9338 housing. The first port 9316 is coupled to the first actuator 9336 configured to transition the first port 9316 between an open port configuration (shown in FIG. 93B) and a closed port configuration.

Figure 94A:
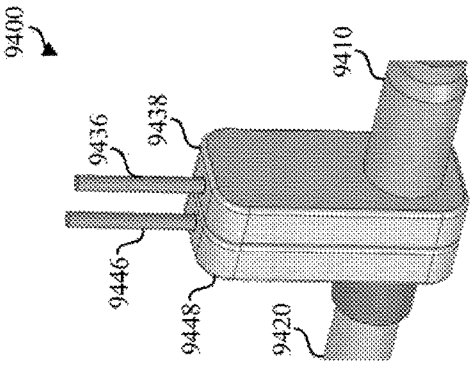
FIG. 94A is a perspective view of an illustrative variation of a fluid connector.
Figure 94B:
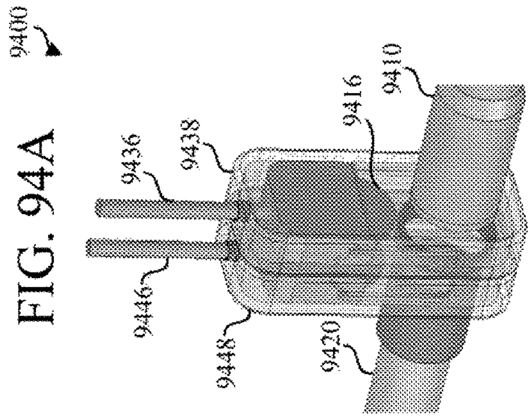
FIG. 94B is a transparent perspective view of the fluid connector depicted in FIG. 94A.

FIG. 94A is a perspective and FIG. 94B is a transparent perspective view of a fluid connector 9400 comprising a first connector 9410 having a first housing 9438 and a first actuator 9436, and a second connector 9420 having a second housing 9448 and a second actuator 9446. FIG. 94B shows a first port 9416 enclosed within first 9438 housing. The first actuator 9436 coupled to the first port 9416 may be configured to transition the first port 9416 between an open port configuration (shown in FIG. 94B) and a closed port configuration.

Figure 95A:
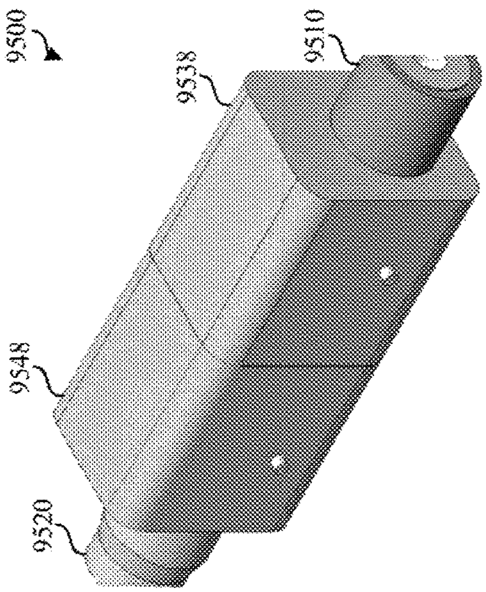
FIG. 95A is a perspective view of an illustrative variation of a fluid connector.
Figure 95B:
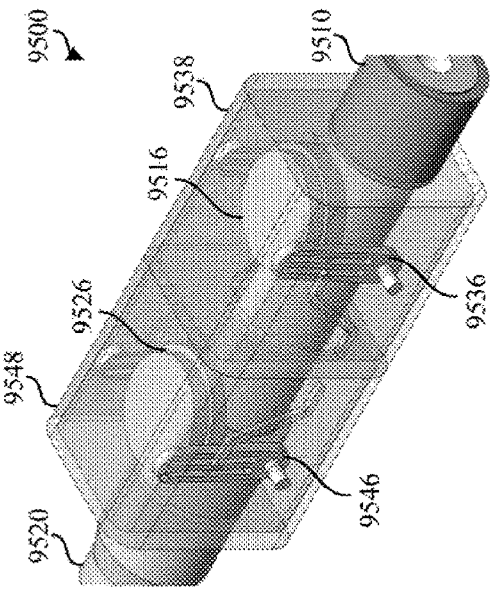
FIG. 95B is a transparent perspective view of the fluid connector depicted in FIG. 95A.
Figure 95C:
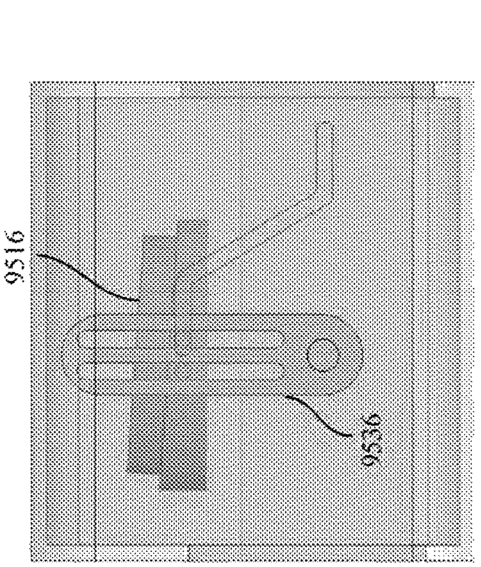
FIG. 95C is a detailed side view of a port in an open port configuration.
Figure 95D:
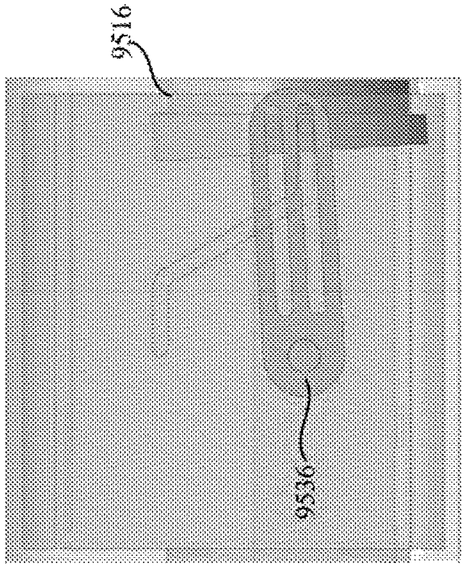
FIG. 95D is a detailed side view of a port in a closed port configuration.

FIG. 95A is a perspective view and FIG. 95B is a transparent perspective view of a fluid connector 9500 comprising a first connector 9510 having a first housing 9538, first port 9516, and a first actuator 9536. A second connector 9520 may comprise a second housing 9548, second port 9526, and a second actuator 9546. FIG. 95B shows the first port 9516 and the second port 9526 each in an open port configuration. For example, the first actuator 9536 coupled to the first port 9516 may be configured to transition the first port 9516 between an open port configuration and a closed port configuration. FIG. 95C is a detailed side view of the first port 9516 and first actuator 9536 in an open port configuration, and FIG. 95D is a detailed side view of the first port 9516 and first actuator 9536 in a closed port configuration.

Figure 97A:
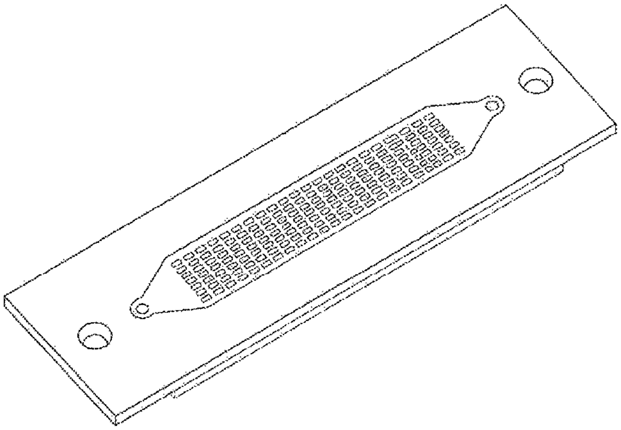
FIG. 97A is a perspective view of an illustrative variation of a MACS module.
Figure 97B:
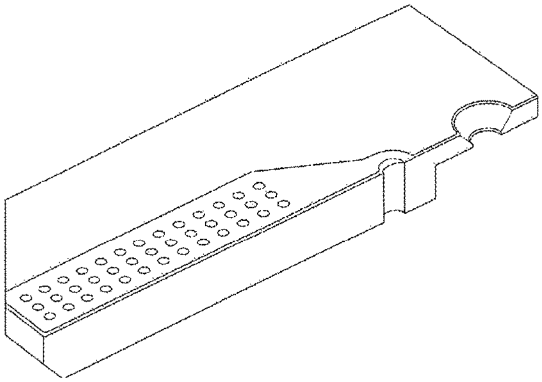
FIG. 97B is a cross-sectional perspective view of an illustrative variation of a MACS module.
Figure 97C:
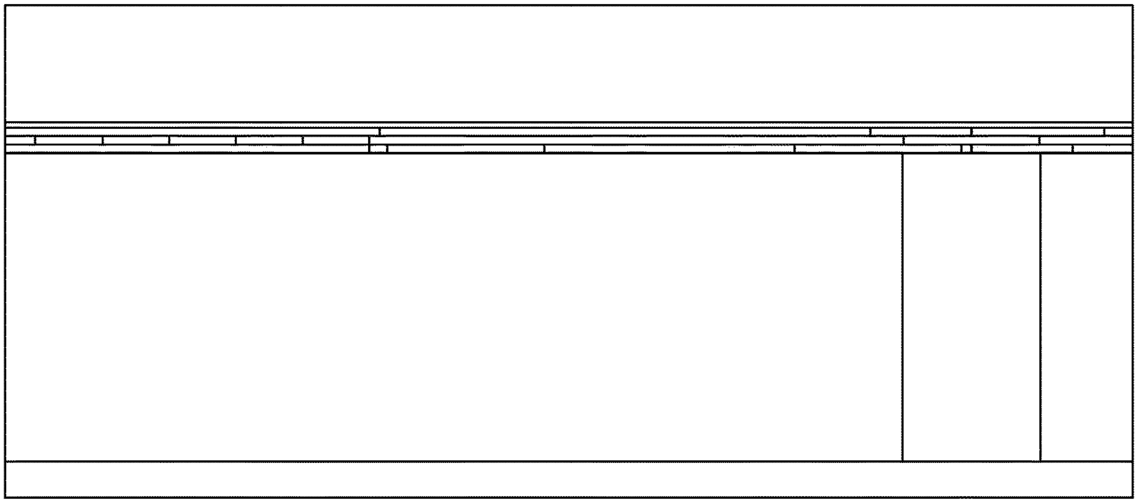
FIG. 97C is a cross-sectional side view of an illustrative variation of a MACS module.
Figure 98:
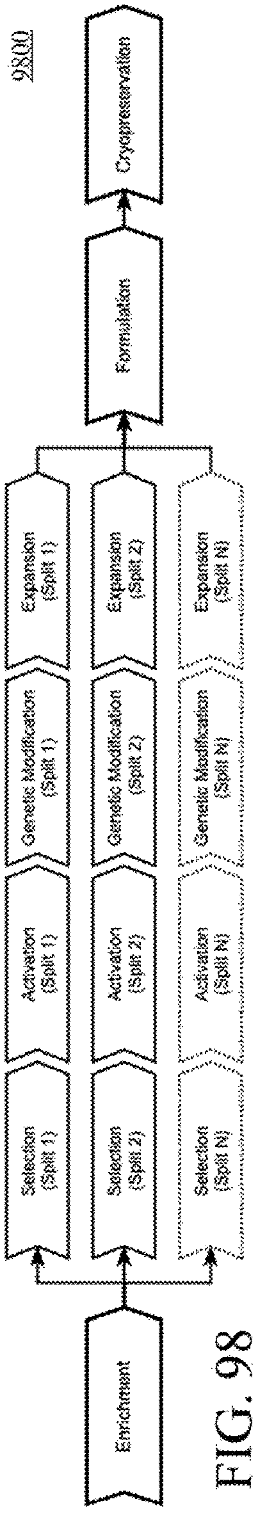
FIG. 98 is a flowchart of an illustrative variation of a method of cell processing.
Figure 99:
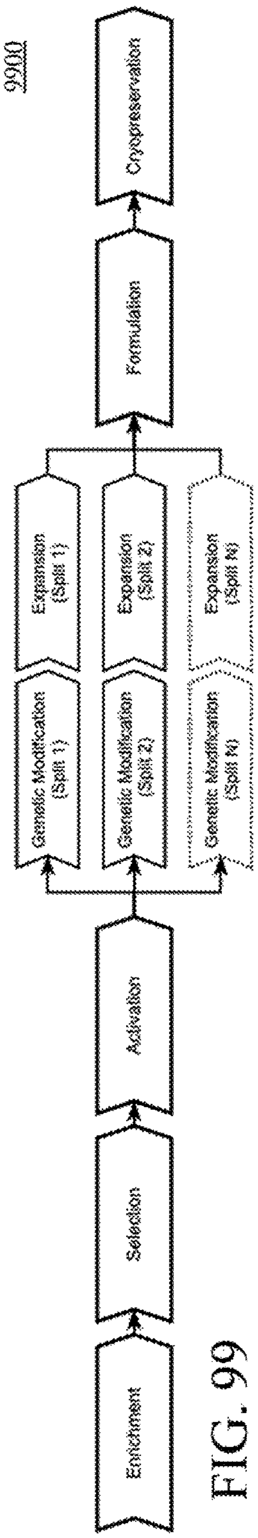
FIG. 99 is a flowchart of an illustrative variation of a method of cell processing.
Figure 100:
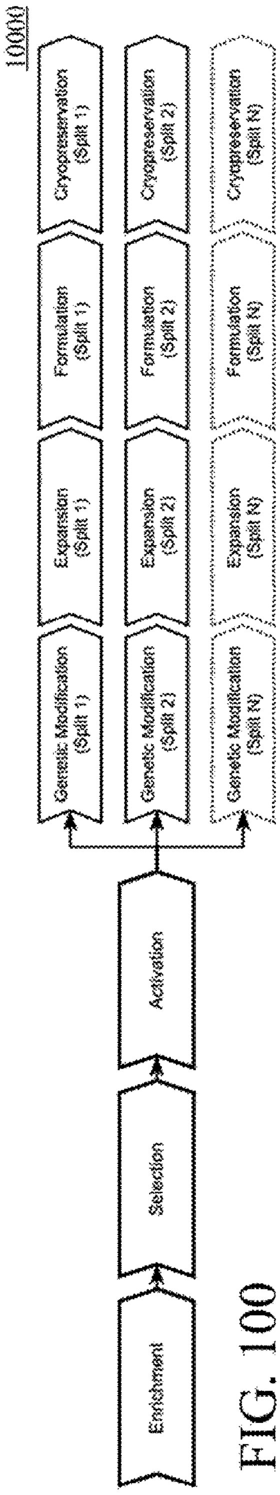
FIG. 100 is a flowchart of an illustrative variation of a method of cell processing.
Figure 101:
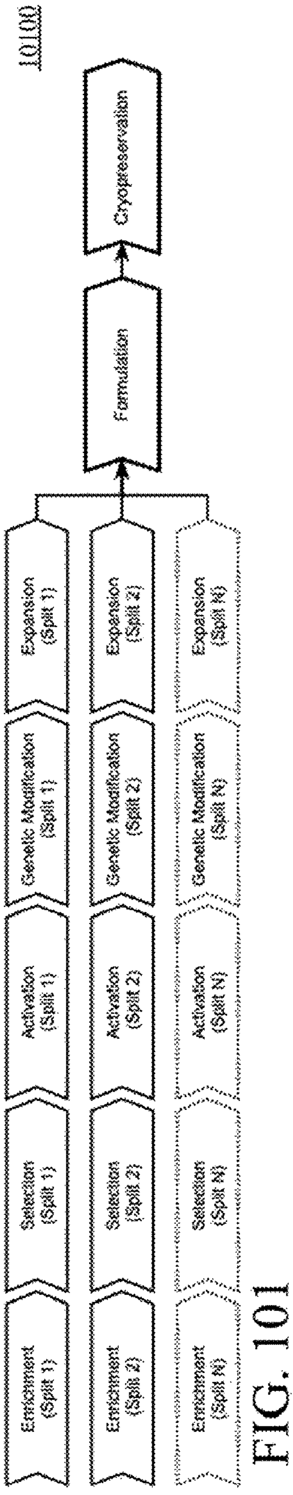
FIG. 101 is a flowchart of an illustrative variation of a method of cell processing.

FIG. 97A is a perspective view of a MACS module. FIG. 97B is a cross-sectional perspective view of a MACS module. FIG. 97C is a cross-sectional side view of a MACS module.

As used herein, sterile should be understood as a non-limiting description of some variations, an optional feature providing advantages in operation of certain systems and methods of the disclosure. Maintaining sterility is typically desirable for cell processing but may be achieved in various ways, including but not limited to providing sterile reagents, media, cells, and other solutions; sterilizing cartridge(s) and/or cartridge component(s) after loading (preserving the cell product from destruction); and/or operating the system in a sterile enclosure, environment, building, room, or the like. Such user or system performed sterilization steps may make the cartridge or cartridge components sterile and/or preserve the sterility of the cartridge or cartridge components.

All references cited are herein incorporated by reference in their entirety.

As used herein, the singular forms “a”, “an” and “the” include plural referents unless the context clearly dictates otherwise. “And” as used herein is interchangeably used with “or” unless expressly stated otherwise.

All embodiments of any aspect of the disclosure can be used in combination, unless the context clearly dictates otherwise.

Unless the context clearly requires otherwise, throughout the description and the claims, the words ‘comprise’, ‘comprising’, and the like are to be construed in an inclusive sense as opposed to an exclusive or exhaustive sense; that is to say, in the sense of “including, but not limited to”. Words using the singular or plural number also include the plural and singular number, respectively. Additionally, the words “herein,” “above,” “below,” and words of similar import, when used in this application, shall refer to this application as a whole and not to any particular portions of the application.

While embodiments of the present invention have been shown and described herein, those skilled in the art will understand that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed herein is:

1. A method for automated cell processing, the method comprising:

generating an ordered output list of cell processing steps based on an ordered input list of cell processing operations;

controlling a robot to retrieve a fluid device from a storage area based on the ordered output list;

controlling the robot to move the fluid device between a plurality of instruments in a sequence determined by the ordered output list, wherein the plurality of instruments performs the cell processing operations;

operating a fluid connector to couple the fluid device to at least one of the plurality of instruments; and transferring a fluid comprising cells through the fluid connector.

2. The method of claim 1, wherein the robot comprises an end effector configured to manipulate the fluid device.

3. The method of claim 2, wherein the end effector comprises a gripper configured to couple to one or more portions of the fluid device.

4. The method of claim 1, wherein controlling the robot comprises generating a robot signal using a controller comprising a processor and memory.

5. The method of claim 1, wherein the robot comprises a robotic arm.

6. The method of claim 1, wherein the robot is configured to move the fluid device without human intervention.

7. The method of claim 6, wherein the fluid device comprises a cavity configured to contain the fluid, and the fluid connector.

8. The method of claim 1, wherein the fluid device comprises an engagement feature configured to facilitate control of the fluid device by the robot.

9. The method of claim 1, wherein controlling the robot comprises controlling the robot to move a plurality of fluid devices in parallel.

10. The method of claim 1, wherein controlling the robot comprises controlling the robot to move the fluid device in three degrees of freedom.

11. The method of claim 1, wherein controlling the robot to retrieve the fluid device comprises instructing the robot to scan a barcode or read an RFID tag on the fluid device.

12. The method of claim 1, wherein the robot controlled to move within an enclosed area.

13. The method of claim 1, wherein the robot is configured for one or both of translation or rotation.

14. The method of claim 1, wherein the robot is configured to move the fluid device from a first to a second of the plurality of instruments.

* * * * *